(12) United States Patent
Kotian et al.

(10) Patent No.: US 9,580,428 B2
(45) Date of Patent: Feb. 28, 2017

(54) COMPOSITIONS AND METHODS FOR INHIBITING VIRAL POLYMERASE

(71) Applicants: Pravin L. Kotian, Birmingham, AL (US); Yarlagadda S. Babu, Birmingham, AL (US)

(72) Inventors: Pravin L. Kotian, Birmingham, AL (US); Yarlagadda S. Babu, Birmingham, AL (US)

(73) Assignee: BioCryst Pharmaceuticals, Inc., Durham, NC (US)

(*) Notice: Subject to any disclaimer, the term of this patent is extended or adjusted under 35 U.S.C. 154(b) by 0 days.

(21) Appl. No.: 14/395,355

(22) PCT Filed: Apr. 17, 2013

(86) PCT No.: PCT/US2013/036945
§ 371 (c)(1),
(2) Date: Oct. 17, 2014

(87) PCT Pub. No.: WO2013/158746
PCT Pub. Date: Oct. 24, 2013

(65) Prior Publication Data
US 2015/0191472 A1    Jul. 9, 2015

Related U.S. Application Data

(60) Provisional application No. 61/625,994, filed on Apr. 18, 2012.

(51) Int. Cl.
| | | |
|---|---|---|
| *C07D 487/04* | (2006.01) |
| *A61K 31/519* | (2006.01) |
| *A61P 31/14* | (2006.01) |
| *A61P 31/16* | (2006.01) |

(52) U.S. Cl.
CPC .......... *C07D 487/04* (2013.01); *A61K 31/519* (2013.01)

(58) Field of Classification Search
CPC ............................ C07D 487/04; A61K 31/519
See application file for complete search history.

(56) References Cited

U.S. PATENT DOCUMENTS

| | | | |
|---|---|---|---|
| 5,985,848 | A | 11/1999 | Furneaux et al. |
| 7,429,571 | B2 | 9/2008 | Chand et al. |
| 8,440,813 | B2 | 5/2013 | Babu et al. |
| 2004/0229839 | A1 | 11/2004 | Babu et al. |
| 2004/0242599 | A1 | 12/2004 | Chand et al. |
| 2005/0080053 | A1 | 4/2005 | Babu et al. |
| 2005/0187170 | A1 | 8/2005 | Bantia et al. |
| 2006/0122391 | A1 | 6/2006 | Babu et al. |
| 2007/0099942 | A1 | 5/2007 | Babu et al. |
| 2009/0227524 | A1 | 9/2009 | Babu et al. |
| 2009/0253648 | A1 | 10/2009 | Keicher et al. |
| 2009/0298863 | A1 | 12/2009 | Averett |
| 2010/0129317 | A1 | 5/2010 | Arterburn et al. |
| 2010/0143300 | A1 | 6/2010 | Babu et al. |
| 2010/0233120 | A1 | 9/2010 | Bachand et al. |
| 2013/0331404 | A1 | 12/2013 | Bantia et al. |

FOREIGN PATENT DOCUMENTS

| | | | |
|---|---|---|---|
| WO | WO-02/069903 A2 | | 9/2002 |
| WO | 2012051570 | * | 4/2012 |
| WO | WO 2012051570 | * | 4/2012 |

OTHER PUBLICATIONS

Pringle, C. R., Merk Manual Consumer Version, <https://www.merckmanuals.com/home/infections/viral-infections/overview-of-viral-infections>, downloaded Aug. 14, 2016.*
Kamath et al., 'Synthesis of analogs of forodesine HCI, a human purine nucleoside phosphorylase inhibitor—Part II', Bioorganic & Medicinal Chemistry Letters, vol. 19 pp. 2627-2629 (2009).
Zhang et al., "Syntheses of 2'-Deoxypsuedouridine, 2'-Deoxyformycin B, and 2',3'-Dideoxyformycin B by Palladium-Mediated Glycal-Aglycon Coupling", Journal Organic Chemistry' vol. 57, pp. 4690-4696 (1992).
Evans et al., "Addition of Lithiated 9-Deazapurine Derivatives to a Carbohydrate Cyclic Imine: Convergent Synthesis of the Aza-C-nucleoside Immucillins", Journal Organic Chemistry, vol. 66, pp. 5723-5730 (2001).
Evans et al., "Synthesis of Transition State Analogue Inhibitors for Purine Nucleoside Phosphorylase and N-Riboside Hydrolases", Tetrahedron, vol. 56, pp. 3053-3062 (2000).
Kuzuhara e tal., "Structural Basis of the Influenza A Virus RNA Polymerase PB2 RNA-binding Domain Containing the Pathogenicity-determinant Lysine 627 Residue", The Journal of Biological Chemistry, vol. 284, No. 11, pp. 6855-6860 (2009).
Boivin et al., "Influenza A Virus Polymerase: Structural Insights into Replication and Host Adaptation Mechanisms", The Journal of Biological Chemistry, 2010, 285, 28411-28417.

(Continued)

*Primary Examiner* — Susanna Moore
(74) *Attorney, Agent, or Firm* — Dana M. Gordon; Foley Hoag LLP

(57) ABSTRACT

Provided are compounds of Formula I:

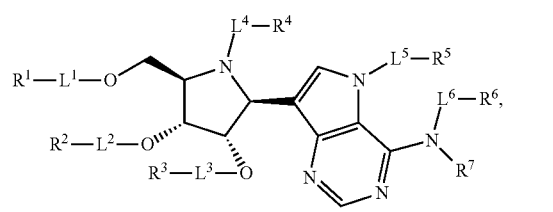

as described herein. Compounds of Formula I are useful in methods of inhibiting viral RNA polymerase activity and viral replication. Also provided are pharmaceutical compositions comprising compounds of Formula I, as well as methods of treating viral infections using compounds of Formula I.

16 Claims, 2 Drawing Sheets

(56) References Cited

OTHER PUBLICATIONS

Stone et al., "Pyrazolo[4,3-d] pyrimidines. Regioselectivity of N-Alkylation. Formation, Rearrangment, and Aldehyde Coupling Reactions of 3-Lithio Derivatives", Journal Organic Chemistry, vol. 44, No. 4, pp. 505-509 (1979).
Kiso et al., "T-705 (favipiravir) activity against lethal H5N1 influenza A viruses", PNAS, vol. 107, No. 2, pp. 882-887 (2010).
Priority Document U.S. Appl. No. 60/581,377 for PCT/US2005/022050.
Priority Document U.S. Appl. No. 60/880,278 for PCT/US2008/050929.
International Preliminary Report on Patentability from PCT/US2013/035945 dated Oct. 30, 2014.
International Search Report from PCT/US2013/035945 dated Aug. 6, 2013.
Evans et al., "Synthesis of a transition state analogue inhibitor of purine nucleoside phosphorylase via the Mannich reaction," Org Lett, 5(20):3639-40 (2003).

* cited by examiner

COMPOSITIONS AND METHODS FOR INHIBITING VIRAL POLYMERASE

RELATED APPLICATION

This application is the U.S. national phase of International Patent Application No. PCT/US13/036945, fled Apr. 17, 2013, which claims benefit of priority to U.S. Provisional Patent Application No. 61/625,994, filed Apr. 18, 2012.

BACKGROUND OF THE INVENTION

Viruses are responsible for many infectious diseases in animals, including mammals and humans in particular. Unlike infections with bacteria, relatively few agents are effective for the prevention and treatment of viral infections. The biology of viral diseases is now well understood, including viral genome transcription, translation, and replication. In RNA-containing viruses an important enzyme is RNA-dependent RNA polymerase, which is responsible for viral genome replication. RNA-dependent RNA polymerase is an essential protein encoded in the genomes of all RNA-containing viruses with no DNA stage that have negative-sense RNA. The enzyme catalyzes synthesis of the RNA strand complementary to a given RNA template. Because replication of the virus depends on RNA polymerase, this enzyme is a promising target in the development of new anti-viral compounds.

SUMMARY OF THE INVENTION

The invention provides compounds of Formula I, including pharmaceutically acceptable salts thereof, for use in inhibiting viral RNA polymerase activity or viral replication, and treating viral infections. The compounds are characterized, in part, by favorable pharmacokinetics for the active pharmaceutical ingredient, particularly in conjunction with enteral administration, including, in particular, oral administration. The invention also provides pharmaceutical compositions comprising one or more compounds of Formula I, or pharmaceutically acceptable salts thereof, as well as methods for preparing same. Also provided are methods for inhibiting viral RNA polymerase activity, viral replication, and treating viral infections.

DETAILED DESCRIPTION OF THE INVENTION

Figure 1:
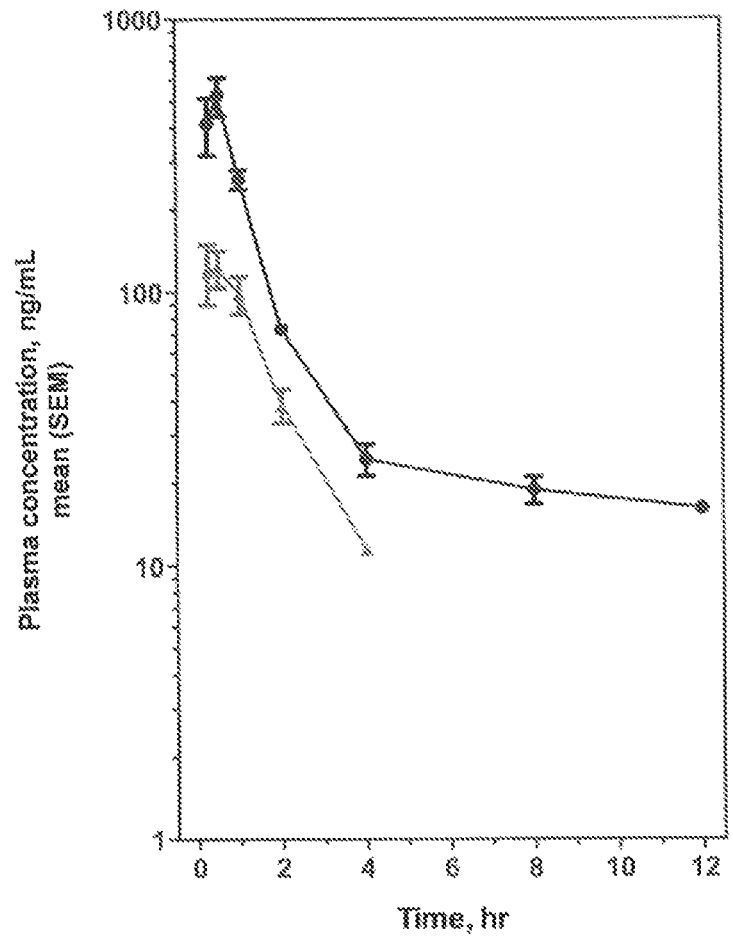
FIG. 1 is a graph depicting the plasma pharmacokinetics of compound 12i following single-dose oral administration of compound 12i (triangles, control) and compound 30f (circles, experimental) to rats. N=4 per group.

An aspect of the invention is a compound represented by Formula I, or a pharmaceutically acceptable salt thereof:

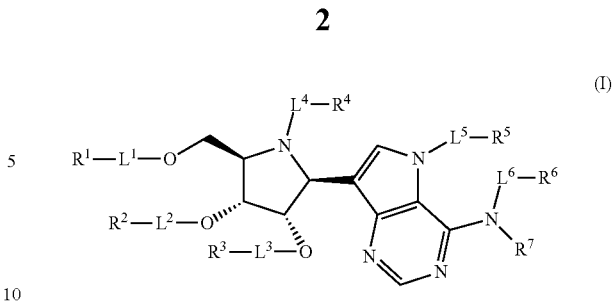

wherein:
$L^1$, $L^2$, $L^3$, $L^4$, $L^5$, and $L^6$, each independently, are a bond or a —C($R^0$)$_2$—O— linker;
$R^0$, independently for each occurrence, is H or ($C_1$-$C_6$)alkyl;
$R^1$, $R^2$, and $R^3$, each independently, are selected from the group consisting of H, aminoacyl, aminothionyl, acyl, $R^{10}$OC(O)—, phosphoryl, and aminophosphoryl; or $R^1$ and $R^2$, taken together, or $R^2$ and $R^3$, taken together, is selected from the group consisting of carbonyl, thiocarbonyl, phosphoryl, and ($C_1$-$C_6$)alkylphosphoryl;
$R^4$, $R^5$, and $R^6$, each independently, are selected from the group consisting of H, acyl, phosphoryl, alkylthio, $R^{10}$OC(O)—, and aminoalkyl;
$R^7$ is H; or $R^6$, $R^7$, and the nitrogen to which they are bonded, taken together, represent —N=C$R^{20}R^{21}$;
$R^{10}$, independently for each occurrence, is selected from the group consisting of H, ($C_1$-$C_6$)alkyl, aryl, heteroaryl, aralkyl, and heteroaralkyl;
$R^{20}$ and $R^{21}$, each independently, are selected from the group consisting of H, alkyl, amino, aryl, heteroaryl, aralkyl, and heteroaralkyl;
provided that the compound represented by Formula I is not

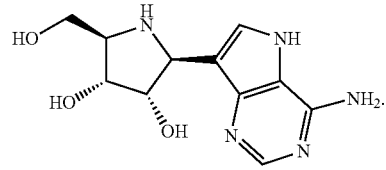

In certain embodiments the compound of Formula I is a compound represented by Formula IA, or a pharmaceutically acceptable salt thereof:

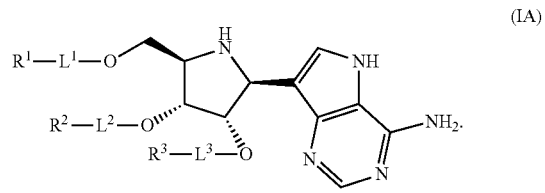

In certain embodiments in accordance with any one of the foregoing, $L^1$-$R^1$ is H.
In certain embodiments in accordance with any one of the foregoing, $L^2$-$R^2$ is H.
In certain embodiments in accordance with any one of the foregoing, $L^3$-$R^3$ is H.
Alternatively, in certain embodiments in accordance with any one of the foregoing, $L^2$-$R^2$ and $L^3$-$R^3$ are identical.
In certain embodiments in accordance with any one of the foregoing, each of $L^2$-$R^2$ and $L^3$-$R^3$ is H.

Alternatively, in certain embodiments in accordance with any one of the foregoing, $L^1$-$R^1$ and $L^3$-$R^3$ are identical.

In certain embodiments in accordance with any one of the foregoing, $L^1$-$R^1$ and $L^2$-$R^2$ are identical.

In certain embodiments in accordance with any one of the foregoing, each of $L^1$-$R^1$ and $L^2$-$R^2$ is H.

In certain embodiments in accordance with any one of the foregoing, each of $L^1$-$R^1$ and $L^3$-$R^3$ is H.

Alternatively, in certain embodiments in accordance with any one of the foregoing, $L^1$-$R^1$, $L^2$-$R^2$, and $L^3$-$R^3$ are identical; and none of $L^1$-$R^1$, $L^2$-$R^2$, and $L^3$-$R^3$ is H.

In certain embodiments in accordance with any one of the foregoing, independently for each occurrence aminoacyl is —C(=O)CH(NH$_2$)(CH$_2$)—CHR$^{30}$R$^{31}$, wherein n is 0 or 1; and R$^{30}$ and R$^{31}$ each independently are selected from the group consisting of H, (C$_1$-C$_6$)alkyl, aryl, heteroaryl, aralkyl, and heteroaralkyl.

In certain embodiments, R$^{30}$ and R$^{31}$ each independently are selected from the group consisting of H and (C$_1$-C$_6$) alkyl.

In certain embodiments, R$^{30}$ and R$^{31}$ each independently are (C$_1$-C$_6$)alkyl.

In certain embodiments, n is 0; and R$^{30}$ and R$^{31}$ each independently are methyl.

In certain embodiments in accordance with any one of the foregoing, independently for each occurrence aminothionyl is —C(=S)CH(NH$_2$)(CH$_2$)—CHR$^{30}$R$^{31}$, wherein n is 0 or 1; and R$^{30}$ and R$^{31}$ each independently are selected from the group consisting of H, (C$_1$-C$_6$)alkyl, aryl, heteroaryl, aralkyl, and heteroaralkyl.

In certain embodiments, R$^{30}$ and R$^{31}$ each independently are selected from the group consisting of H and (C$_1$-C$_6$) alkyl.

In certain embodiments, R$^{30}$ and R$^{31}$ each independently are (C$_1$-C$_6$)alkyl.

In certain embodiments, n is 0; and R$^{30}$ and R$^{31}$ each independently are methyl.

In certain embodiments in accordance with any one of the foregoing, independently for each occurrence acyl is —C(=O)R$^{40}$, wherein R$^{40}$ is selected from the group consisting of H, (C$_1$-C$_6$)alkyl, aryl, heteroaryl, aralkyl, and heteroaralkyl.

In certain embodiments, R$^{40}$ is H.

In certain embodiments, R$^{40}$ is (C$_1$-C$_6$)alkyl.

In certain embodiments in accordance with any one of the foregoing, independently for each occurrence R$^{10}$ is H.

Alternatively, in certain embodiments in accordance with any one of the foregoing, independently for each occurrence R$^{10}$ is (C$_1$-C$_6$)alkyl.

In certain embodiments in accordance with any one of the foregoing, independently for each occurrence aminophosphoryl is —P(=O)(OR$^{50}$)NR$^{51}$R$^{52}$, wherein R$^{50}$ is selected from the group consisting of H, (C$_1$-C$_6$) alkyl, aryl, arylalkyl, heteroaryl, heteroaralkyl, and —(CH$_2$)$_m$SC(=O)C(CH$_3$)$_2$CH$_2$OH;

m is 1 or 2;

R$^{51}$ is H or (C$_1$-C$_6$)alkyl; and

R$^{52}$ is selected from the group consisting of H, (C$_1$-C$_6$) alkyl, aryl, aralkyl, heteroaryl, heteroaralkyl, and —CR$^{60}$R$^{61}$C(=O)OR$^{62}$, wherein R$^{60}$ and R$^{61}$ each independently are H or (C$_1$-C$_6$)alkyl; and R$^{62}$ is selected from the group consisting of H, (C$_1$-C$_6$) alkyl, aryl, aralkyl, heteroaryl, heteroaralkyl.

In certain embodiments in accordance with any one of the foregoing, R$^{50}$ is H.

In certain embodiments in accordance with any one of the foregoing, R$^{50}$ is aryl.

In certain embodiments in accordance with any one of the foregoing, R$^{50}$ is —(CH$_2$)$_m$SC(=O)C(CH$_3$)$_2$CH$_2$OH.

In certain embodiments in accordance with any one of the foregoing, m is 2.

In certain embodiments in accordance with any one of the foregoing, R$^{51}$ is H.

In certain embodiments in accordance with any one of the foregoing, R$^{52}$ is aralkyl.

Alternatively, in certain embodiments in accordance with any one of the foregoing, R$^{52}$ is —CR$^{60}$R$^{61}$C(=O)OR$^{62}$.

In certain embodiments in accordance with any one of the foregoing, R$^{60}$ is H; R$^{61}$ is (C$_1$-C$_6$)alkyl; and R$^{62}$ is (C$_1$-C$_6$) alkyl.

In certain embodiments the compound of Formula I is a compound represented by Formula IB, or a pharmaceutically acceptable salt thereof:

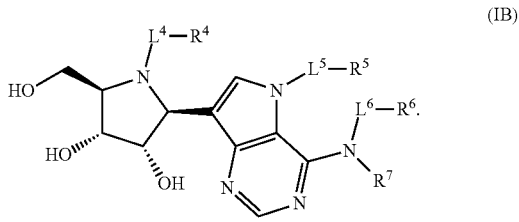

(IB)

In certain embodiments in accordance with any one of the foregoing, R$^7$ is H; each of L$^4$, L$^5$, and L$^6$ is a bond; and each of any two of R$^4$, R$^5$, and R$^6$ is H.

In certain embodiments in accordance with any one of the foregoing, each of R$^4$ and R$^5$ is H.

Alternatively, in certain embodiments in accordance with any one of the foregoing, each of R$^5$ and R$^6$ is H.

Alternatively, in certain embodiments in accordance with any one of the foregoing, each of R$^4$ and R$^6$ is H.

In certain embodiments in accordance with any one of the foregoing, R$^{10}$ of any R$^{10}$OC(O)— of R$^4$, R$^5$, and R$^6$ is H or (C$_1$-C$_6$)alkyl.

In certain embodiments in accordance with any one of the foregoing, any aminoalkyl of R$^4$, R$^5$, and R$^6$ is —CH$_2$N (CH$_3$)$_2$.

In certain embodiments, each of L$^4$, L$^5$, and L$^6$ is a bond; and R$^6$, R$^7$, and the nitrogen to which they are bonded, taken together, represent —N=CR$^{20}$R$^{21}$.

In certain embodiments in accordance with any one of the foregoing, R$^{20}$ is H and R$^{21}$ is amino.

In certain embodiments in accordance with any one of the foregoing, each of R$^4$ and R$^5$ is H.

Alternatively, in certain embodiments R$^7$ is H; at least one of L$^4$, L$^5$, and L$^6$ is a —C(R$^0$)$_2$—O— linker; and any R$^4$, R$^5$, or R$^6$ bonded to the at least one —C(R$^0$)$_2$—O— linker is phosphoryl.

Definitions

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., C$_1$-C$_{30}$ for straight chain, C$_3$-C$_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

The term "amino" is a term of art and as used herein refers to both unsubstituted and substituted amines, e.g., a moiety that may be represented by the general formulas:

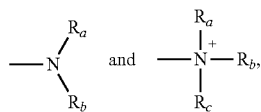

wherein $R_a$, $R_b$, and $R_c$ each independently represent a hydrogen, an alkyl, an alkenyl, —(CH$_2$)$_x$—R$_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or —(CH$_2$)$_x$—R$_d$.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "phosphoryl" is a term of art and as used herein may in general be represented by the formula:

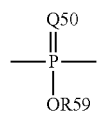

wherein Q50 represents S or O, and R59 represents hydrogen, a lower alkyl or an aryl; for example, —P(O)(OMe)- or —P(O)(OH)$_2$. When used to substitute, e.g., an alkyl, the phosphoryl group of the phosphorylalkyl may be represented by the general formulas:

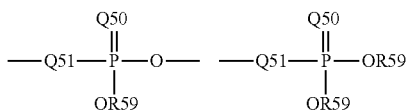

wherein Q50 and R59, each independently, are defined above, and Q51 represents 0, S or N; for example, —O—P(O)(OH)OMe or —NH—P(O)(OH)$_2$. When Q50 is S, the phosphoryl moiety is a "phosphorothioate."

The term "aminophosphoryl" as used herein refers to a phosphoryl group substituted with at least one amino group, as defined herein; for example, —P(O)(OH)NMe$_2$.

The term "carbonyl" as used herein refers to —C(O)—.

The term "thiocarbonyl" as used herein refers to —C(S)—.

The term "alkylphosphoryl" as used herein refers to a phosphoryl group substituted with at least one alkyl group, as defined herein; for example, —P(O)(OH)Me.

The term "alkylthio" as used herein refers to alkyl-S—.

The term "aryl" is a term of art and as used herein refers to includes monocyclic, bicyclic and polycyclic aromatic hydrocarbon groups, for example, benzene, naphthalene, anthracene, and pyrene. The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "heteroaryl" is a term of art and as used herein refers to a monocyclic, bicyclic and polycyclic aromatic group having one or more heteroatoms in the ring structure, for example, pyrrole, furan, thiophene, imidazole, oxazole, thiazole, triazole, pyrazole, pyridine, pyrazine, pyridazine and pyrimidine, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls.

The term "aralkyl" is a term of art and as used herein refers to an alkyl group substituted with an aryl group.

The term "heteroaralkyl" is a term of art and as used herein refers to an alkyl group substituted with a heteroaryl group.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of the invention, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

The term "protecting group" as used herein temporary substituents which protect a potentially reactive functional group from undesired chemical transformations. Examples of such protecting groups include esters of carboxylic acids and boronic acids, ethers of alcohols, and acetals and ketals of aldehydes and ketones. For instance, the phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as, to illustrate, formyl, dansyl, acetyl, benzoyl, trifluoroacetyl, succinyl, and methoxysuccinyl; aromatic urethane protecting groups as, for example, benzyloxycarbonyl (Cbz); and aliphatic urethane protecting groups such as t-butoxycarbonyl (Boc) or 9-Fluorenylmethoxycarbonyl (Fmoc).

The term "amino-protecting group" or "N-terminal protecting group" refers to those groups intended to protect the α-N-terminal of an amino acid or peptide or to otherwise protect the amino group of an amino acid or peptide against undesirable reactions during synthetic procedures. Commonly used N-protecting groups are disclosed in Greene, *Protective Groups In Organic Synthesis*, (John Wiley & Sons, New York (1981)), which is hereby incorporated by reference. Additionally, protecting groups can be used as pro-drugs which are readily cleaved in vivo, for example, by enzymatic hydrolysis, to release the biologically active parent. α-N-protecting groups comprise lower alkanoyl groups such as formyl, acetyl ("Ac"), propionyl, pivaloyl, t-butylacetyl and the like; other acyl groups include 2-chloroacetyl, 2-bromoacetyl, trifluoroacetyl, trichloroacetyl, phthalyl, o-nitrophenoxyacetyl, -chlorobutyryl, benzoyl, 4-chlorobenzoyl, 4-bromobenzoyl, 4-nitrobenzoyl and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-ethoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyoxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; arylalkyl groups such as benzyl, triphenylmethyl, benzyloxymethyl, 9-fluorenylmethyloxycarbonyl (Fmoc) and the like and silyl groups such as trimethylsilyl and the like. Still other examples include theyl, succinyl, methoxysuccinyl, subery, adipyl, azelayl, dansyl, benzyloxycarbonyl, methoxyazelayl, methoxyadipyl, methoxysuberyl, and 2,4-dinitrophenyl.

The term "carboxy protecting group" or "C-terminal protecting group" refers to a carboxylic acid protecting ester or amide group employed to block or protect the carboxylic acid functionality while the reactions involving other functional sites of the compound are performed. Carboxy protecting groups are disclosed in Greene, *Protective Groups in Organic Synthesis* pp. 152-186 (1981), which is hereby incorporated by reference. Additionally, a carboxy protecting group can be used as a pro-drug whereby the carboxy protecting group can be readily cleaved in vivo, for example by enzymatic hydrolysis, to release the biologically active parent. Such carboxy protecting groups are well known to those skilled in the art, having been extensively used in the protection of carboxyl groups in the penicillin and cephalosporin fields as described in U.S. Pat. Nos. 3,840,556 and 3,719,667, the disclosures of which are hereby incorporated herein by reference. Representative carboxy protecting groups are $C_1$-$C_8$ loweralkyl (e.g., methyl, ethyl or t-butyl and the like); arylalkyl such as phenethyl or benzyl and substituted derivatives thereof such as alkoxybenzyl or nitrobenzyl groups and the like; arylalkenyl such as phenylethenyl and the like; aryl and substituted derivatives thereof such as 5-indanyl and the like; dialkylaminoalkyl such as dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl such as benzoyloxymethyl, benzoyloxyethyl and the like; arylalkylcarbonyloxyalkyl such as benzylcarbonyloxymethyl, 2-benzylcarbonyloxyethyl and the like; alkoxycarbonylalkyl or cycloalkyloxycarbonylalkyl such as methoxycarbonylmethyl, cyclohexyloxycarbonylmethyl, 1-methoxycarbonyl-1-ethyl and the like; alkoxycarbonyloxyalkyl or cycloalkyloxycarbonyloxyalkyl such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl such as 2-(phenoxycarbonyloxy)ethyl, 2-(5-indanyloxycarbonyloxyl)ethyl and the like; alkoxyalkylcarbonyloxyalkyl such as 2-(1-methoxy-2-methylpropan-2-oyloxy)ethyl and like; arylalkyloxycarbonyloxyalkyl such as 2-(benzyloxycarbonyloxy)ethyl and the like; arylalkenyloxycarbonyloxyalkyl such as 2-(3-phenylpropen-2-yloxycarbonyloxy)ethyl and the like; alkoxycarbonylaminoalkyl such as t-butyloxycarbonylaminomethyl and the like; alkylaminocarbonylaminoalkyl such as methylaminocarbonylaminomethyl and the like; alkanoylaminoalkyl such as acetylaminomethyl and the like; heterocycliccarbonyloxyalkyl such as 4-methylpiperazinylcarbonyloxymethyl and the like; dialkylaminocarbonylalkyl such as dimethylaminocarbonylmethyl, diethylaminocarbonylmethyl and the like; (5-(loweralkyl)-2-oxo-1,3-dioxolen-4-yl)alkyl such as (5-t-butyl-2-oxo-1,3-dioxolen-4-yl)methyl and the like; and (5-phenyl-2-oxo-1,3-dioxolen-4-yl)alkyl such as (5-phenyl-2-oxo-1,3-dioxolen-4-yl)methyl and the like. Representative amide carboxy protecting groups are aminocarbonyl and loweralkylaminocarbonyl groups. For example, aspartic acid may be protected at the α-C-terminal by an acid labile group (e.g., t-butyl) and protected at the β-C-terminal by a hydrogenation labile group (e.g., benzyl) then deprotected selectively during synthesis. As mentioned above, the protected carboxy group may also be a loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester.

The term "amino acid" as used herein is a term of art and refers to alpha- and beta-aminocarboxylic acids, including so-called naturally occurring alpha-amino acids and non-naturally occurring amino acids. Naturally occurring alpha-amino acids specifically include alanine (Ala), arginine (Arg), asparagine (Asn), aspartic acid (Asp), cysteine (Cys), glutamic acid (Glu), glutamine (Gln), glycine (Gly), histidine (His), isoleucine (Ile), leucine (Leu), lysine (Lys), methionine (Met), ornithine (Orn), phenylalanine (Phe), proline (Pro), selenocysteine (Sec), serine (Ser), taurine, threonine (Thr), tryptophan (Trp), tyrosine (Tyr), and valine (Val). Polar naturally occurring alpha-amino acids include arginine, asparagine, aspartic acid, cysteine, glutamic acid, glutamine, histidine, lysine, ornithine, serine, threonine, and tyrosine. Nonpolar naturally occurring alpha-amino acids include alanine, glycine, isoleucine, leucine, methionine, phenylalanine, proline, tryptophan, and valine.

Non-naturally occurring amino acids include, but are not limited to, D-amino acids (i.e., an amino acid of an opposite chirality to the naturally occurring form), N-α-methyl amino acids, C-α-methyl amino acids, β-methyl amino acids, β-alanine (β-Ala), norvaline (Nva), norleucine (Nle), 4-aminobutyric acid (γ-Abu), 2-aminoisobutyric acid (Aib), 6-aminohexanoic acid (ε-Ahx), ornithine (orn), hydroxyproline (Hyp), sarcosine, citrulline, cysteic acid, cyclohexylalanine, α-amino isobutyric acid, t-butylglycine, t-butylalanine, 3-aminopropionic acid, 2,3-diaminopropionic acid (2,3-diaP), D- or L-phenylglycine, D- or L-2-naphthylalanine (2-Nal), 1,2,3,4-tetrahydroisoquinoline-3-carboxylic acid (Tic), D- or L-2-thienylalanine (Thi), D- or L-3-thienylalanine, D- or L-1-, 2-, 3- or 4-pyrenylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine, D- or L-p-methoxybiphenylalanine, methionine sulphoxide (MSO) and homoarginine (Har). Other examples include D- or L-2-indole(alkyl)alanines and D- or L-alkylalanines, wherein alkyl is substituted or unsubstituted methyl, ethyl, propyl, hexyl, butyl, pentyl, isopropyl, iso-butyl, or iso-pentyl, and phosphono- or sulfated (e.g., $-SO_3H$) non-carboxylate amino acids.

Other examples of non-naturally occurring amino acids include 3-(2-chlorophenyl)-alanine, 3-chloro-phenylalanine, 4-chloro-phenylalanine, 2-fluoro-phenylalanine, 3-fluoro-phenylalanine, 4-fluoro-phenylalanine, 2-bromo-phenylalanine, 3-bromo-phenylalanine, 4-bromo-phenylalanine, homophenylalanine, 2-methyl-phenylalanine, 3-methyl-phenylalanine, 4-methyl-phenylalanine, 2,4-dimethyl-phenylalanine, 2-nitro-phenylalanine, 3-nitro-phenylalanine, 4-nitro-phenylalanine, 2,4-dinitro-phenylalanine, 1,2,3,4-Tetrahydroisoquinoline-3-carboxylic acid, 1,2,3,4-tetrahydronorharman-3-carboxylic acid, 1-naphthylalanine, 2-naphthylalanine, pentafluorophenylalanine, 2,4-dichloro-phenylalanine, 3,4-dichloro-phenylalanine, 3,4-difluoro-phenylalanine, 3,5-difluoro-phenylalanine, 2,4,5-trifluoro-phenylalanine, 2-trifluoromethyl-phenylalanine, 3-trifluoromethyl-phenylalanine, 4-trifluoromethyl-phenylalanine, 2-cyano-phenylalanine, 3-cyano-phenylalanine, 4-cyano-phenyalanine, 2-iodo-phenyalanine, 3-iodo-phenylalanine, 4-iodo-phenylalanine, 4-methoxyphenylalanine, 2-aminoethyl-phenylalanine, 3-aminomethyl-phenylalanine, 4-aminomethyl-phenylalanine, 2-carbamoyl-phenylalanine, 3-carbamoyl-phenylalanine, 4-carbamoyl-phenylalanine, m-tyrosine, 4-amino-phenylalanine, styrylalanine, 2-amino-5-phenyl-pentanoic acid, 9-anthrylalanine, 4-tert-butyl-phenylalanine, 3,3-diphenylalanine, 4,4'-diphenylalanine, benzoylphenylalanine, α-methyl-phenylalanine, α-methyl-4-fluoro-phenylalanine, 4-thiazolylalanine, 3-benzothienylalanine, 2-thienylalanine, 2-(5-bromothienyl)-alanine, 3-thienylalanine, 2-furylalanine, 2-pyridylalanine, 3-pyridylalanine, 4-pyridylalanine, 2,3-diaminopropionic acid, 2,4-diaminobutyric acid, allylglycine, 2-amino-4-bromo-4-pentenoic acid, propargylglycine, 4-aminocyclopent-2-enecarboxylic acid, 3-aminocyclopentanecarboxylic acid, 7-amino-heptanoic acid, dipropylglycine, pipecolic acid, azetidine-3-carboxylic acid, cyclopropylglycine, cyclopropylalanine, 2-methoxy-phenylglycine, 2-thienylglycine, 3-thienylglycine, α-benzyl-proline, α-(2-fluoro-benzyl)-proline, α-(3-fluoro-benzyl)-proline, α-(4-fluoro-benzyl)-proline, α-(2-chloro-benzyl)-proline, α-(3-chloro-benzyl)-proline, α-(4-chloro-benzyl)-proline, α-(2-bromo-benzyl)-proline, α-(3-bromo-benzyl)-proline, α-(4-bromo-benzyl)-proline, α-phenethyl-proline, α-(2-methyl-benzyl)-proline, α-(3-methyl-benzyl)-proline, α-(4-methyl-benzyl)-proline, α-(2-nitro-benzyl)-proline, α-(3-nitro-benzyl)-proline, α-(4-nitro-benzyl)-proline, α-(1-naphthalenylmethyl)-proline, α-(2-naphthalenylmethyl)-proline, α-(2,4-dichloro-benzyl)-proline, α-(3,4-dichloro-benzyl)-proline, α-(3,4-difluoro-benzyl)-proline, α-(2-trifluoromethyl-benzyl)-proline, α-(3-trifluoromethyl-benzyl)-proline, α-(4-trifluoromethyl-benzyl)-proline, α-(2-cyano-benzyl)-proline, α-(3-cyano-benzyl)-proline, α-(4-cyano-benzyl)-proline, α-(2-iodo-benzyl)-proline, α-(3-iodo-benzyl)-proline, α-(4-iodo-benzyl)-proline, α-(3-phenyl-allyl)-proline, α-(3-phenyl-propyl)-proline, α-(4-tert-butyl-benzyl)-proline, α-benzhydryl-proline, α-(4-biphenylmethyl)-proline, α-(4-thiazolylmethyl)-proline, α-(3-benzo[b]thiophenylmethyl) -proline, α-(2-thiophenylmethyl)-proline, α-(5-bromo-2-thiophenylmethyl)-proline, α-(3-thiophenylmethyl)-proline, α-(2-furanylmethyl)-proline, α-(2-pyridinylmethyl)-proline, α-(3-pyridinylmethyl)-proline, α-(4-pyridinylmethyl)-proline, α-allyl-proline, α-propynyl-proline, γ-benzyl-proline, γ-(2-fluoro-benzyl)-proline, γ-(3-fluoro-benzyl)-proline, γ-(4-fluoro-benzyl)-proline, γ-(2-chloro-benzyl)-proline, γ-(3-chloro-benzyl)-proline, γ-(4-chloro-benzyl)-proline, γ-(2-bromo-benzyl)-proline, γ-(3-bromo-benzyl)-proline, γ-(4-bromo-benzyl)-proline, γ-(2-methyl-benzyl)-proline, γ-(3-methyl-benzyl)-proline, γ-(4-methyl-benzyl)-proline, γ-(2-nitro-benzyl)-proline, γ-(3-nitro-benzyl)-proline, γ-(4-nitro -benzyl)-proline, γ-(1-naphthalenylmethyl)-proline, γ-(2-naphthalenylmethyl)-proline, γ-(2,4-dichloro-benzyl)-proline, γ-(3,4-dichloro-benzyl)-proline, γ-(3,4-difluoro-benzyl) -proline, γ-(2-trifluoromethyl-benzyl)-proline, γ-(3-trifluoromethyl-benzyl)-proline, γ-(4-trifluoromethyl-benzyl)-proline, γ-(2-cyano-benzyl)-proline, γ-(3-cyano-benzyl)-proline, γ-(4-cyano-benzyl)-proline, γ-(2-iodo-benzyl)-proline, γ-(3-iodo-benzyl)-proline, γ-(4-iodo -benzyl)-proline, γ-(3-phenyl-allyl-benzyl)-proline, γ-(3-phenyl-propyl-benzyl)-proline, γ-(4-tert-butyl-benzyl)-proline, γ-benzhydryl-proline, γ-(4-biphenylmethyl)-proline, γ-(4-thiazolylmethyl)-proline, γ-(3-benzothioienylmethyl)-proline, γ-(2-thienylmethyl)-proline, γ-(3-thienylmethyl)-proline, γ-(2-furanylmethyl)-proline, γ-(2-pyridinylmethyl)-proline, γ-(3-pyridinylmethyl)-proline, γ-(4-pyridinylmethyl)-proline, γ-allyl-proline, γ-propynyl -proline, trans-4-phenyl-pyrrolidine-3-carboxylic acid, trans-4-(2-fluoro-phenyl) -pyrrolidine-3-carboxylic acid, trans-4-(3-fluoro-phenyl)-pyrrolidine-3-carboxylic acid, trans-4-(4-fluoro-phenyl)-pyrrolidine-3-carboxylic acid, trans-4-(2-chloro-phenyl) -pyrrolidine-3-carboxylic acid, trans-4-(3-chloro-phenyl)-pyrrolidine-3-carboxylic acid, trans-4-(4-chloro-phenyl)-pyrrolidine-3-carboxylic acid, trans-4-(2-bromo-phenyl) -pyrrolidine-3-carboxylic acid, trans-4-(3-bromo-phenyl)-pyrrolidine-3-carboxylic acid, trans-4-(4-bromo-phenyl)-pyrrolidine-3-carboxylic acid, trans-4-(2-methyl-phenyl) -pyrrolidine-3-carboxylic acid, trans-4-(3-methyl-phenyl)-pyrrolidine-3-carboxylic acid, trans-4-(4-methyl-phenyl)-pyrrolidine-3-carboxylic acid, trans-4-(2-nitro-phenyl) -pyrrolidine-3-carboxylic acid, trans-4-(3-nitro-phenyl)-pyrrolidine-3-carboxylic acid, trans-4-(4-nitro-phenyl)-pyrrolidine-3-carboxylic acid, trans-4-(1-naphthyl)-pyrrolidine-3-carboxylic acid, trans-4-(2-naphthyl)-pyrrolidine-3-carboxylic acid, trans-4-(2,5-dichloro -phenyl)-pyrrolidine-3-carboxylic acid, trans-4-(2,3-dichloro-phenyl)-pyrrolidine-3-carboxylic acid, trans-4-(2-trifluoromethyl-phenyl)-pyrrolidine-3-carboxylic acid, trans-4-(3-trifluoromethyl-phenyl)-pyrrolidine-3-carboxylic acid, trans-4-(4-trifluoromethyl -phenyl)-pyrrolidine-3-carboxylic acid, trans-4-(2-cyano-phenyl)-pyrrolidine-3-carboxylic acid, trans-4-(3-cyano-phenyl)-pyrrolidine-3-carboxylic acid, trans-4-(4-cyano-phenyl) -pyrrolidine-3-carboxylic acid, trans-4-(2-methoxy-phenyl)-pyrrolidine-3-carboxylic acid, trans-4-(3-methoxy-phenyl)-pyrrolidine-3-carboxylic acid, trans-4-(4-methoxy-phenyl) -pyrrolidine-3-carboxylic acid, trans-4-(2-hydroxy-phenyl)-pyrrolidine-3-carboxylic acid, trans-4-(3-hydroxy-phenyl)-pyrrolidine-3-carboxylic acid, trans-4-(4-hydroxy-phenyl) -pyrrolidine-3-carboxylic acid, trans-4-(2,3-dimethoxy-phenyl)-pyrrolidine-3-carboxylic acid, trans-4-(3,4-dimethoxy-phenyl)-pyrrolidine-3-carboxylic acid, trans-4-(3,5-dimethoxy-phenyl)-pyrrolidine-3-carboxylic acid, trans-4-(2-pyridinyl)-pyrrolidine-3-carboxylic acid, trans-4-(3-pyridinyl)-pyrrolidine-3-carboxylic acid, trans-4-(6-methoxy-3-pyridinyl)-pyrrolidine-3-carboxylic acid, trans-4-(4-pyridinyl)-pyrrolidine-3-carboxylic acid, trans-4-(2-thienyl)-pyrrolidine-3-carboxylic acid, trans-4-(3-thienyl)-pyrrolidine-3-carboxylic acid, trans-4-(2-furanyl)-pyrrolidine-3-carboxylic acid, trans-4-isopropyl -pyrrolidine-3-carboxylic acid, 4-phosphonomethyl-phenylalanine, benzyl -phosphothreonine, (1'-amino-2-phenylethyl)oxirane, (1'-amino-2-cyclohexyl -ethyl)oxirane, (1'-amino-2-[3-bromo-phenyl]ethyl)oxirane, (1'-amino-2-[4-(benzyloxy)phenyl]ethyl)oxirane, (1'-amino-2-[3,5-difluoro-phenyl]ethyl)oxirane, (1'-amino-2-[4-carbamoyl-phenyl]ethyl)oxirane, (1'-amino-2-[benzyloxy-ethyl])oxirane, (1'-amino-2-[4-nitro-phenyl]ethyl)oxirane, (1'-amino-3-phenyl-propyl)oxirane, (1'-amino-3-phenyl-propyl)oxirane, and/or salts and/or protecting group variants thereof.

Beta-amino acids include, without limitation, beta-alanine (3-aminopropanoic acid).

The term "compound of the invention" as used herein means a compound of Formula I and pharmaceutically acceptable salts thereof.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I. As another example, the salt may comprise less than one inorganic or organic acid molecule per molecule of base, such as two molecules of compound of Formula I per molecule of tartaric acid.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum *acacia*, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in *Remington's Pharmaceutical Sciences* by E. W. Martin, herein incorporated by reference in its entirety.

The term "treat" as used herein means prevent, halt or slow the progression of, or eliminate a disease or condition in a subject. In one embodiment "treat" means halt or slow the progression of, or eliminate a disease or condition in a subject. In one embodiment, "treat" means reduce at least one objective manifestation of a disease or condition.

The term "effective amount" as used herein refers to an amount that is sufficient to bring about a desired biological effect.

The term "inhibit" as used herein means decrease by an objectively measurable amount or extent. In various embodiments "inhibit" means decrease by at least 5, 10, 20, 30, 40, 50, 60, 70, 80, 90, or 95 percent compared to relevant control. In one embodiment "inhibit" means decrease 100 percent, i.e, halt or eliminate.

The term "subject" as used herein refers to a mammal. In various embodiments, a subject is a mouse, rat, rabbit, cat, dog, pig, sheep, horse, cow, or non-human primate. In one embodiment a subject is a human.

In certain embodiments, the compound represented by Formula I is selected from the group consisting of:

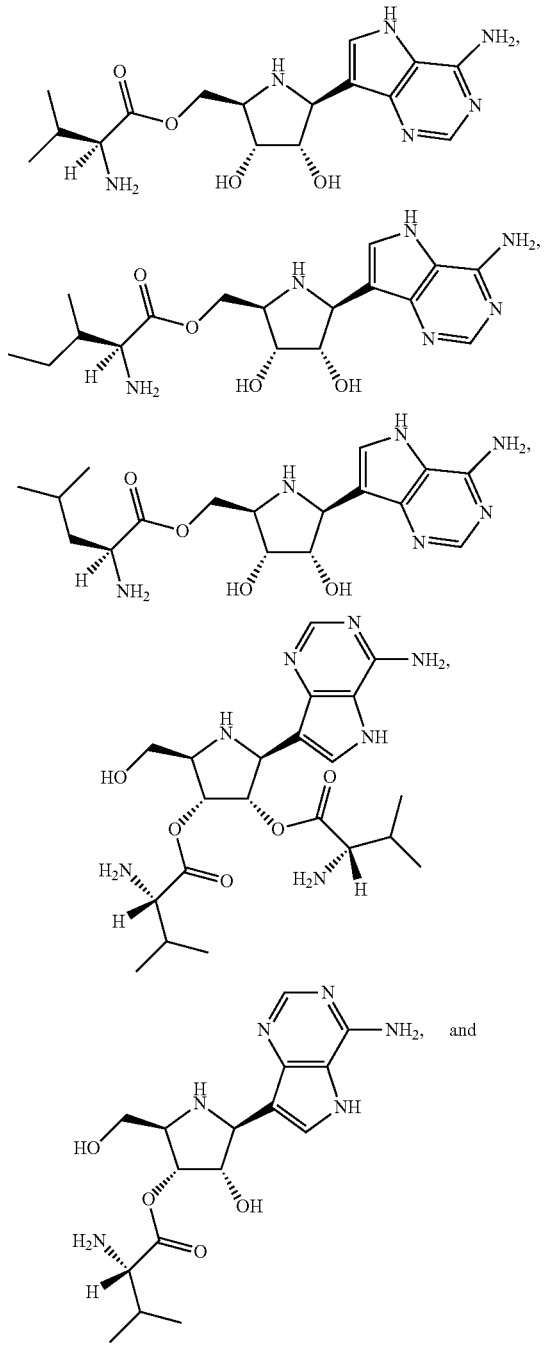

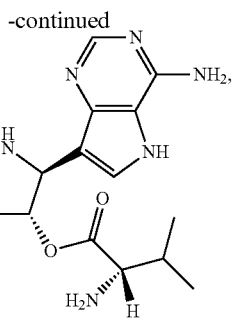

and pharmaceutically acceptable salts thereof.

In certain embodiments, the compound represented by Formula I is selected from the group consisting of (S)-((2R,3R,4S,5S)-5-(4-amino-5H-pyrrolo[3,2-d]pyrimidin-7-yl)-3,4-dihydroxypyrrolidin-2-yl)methyl 2-amino-3-methylbutanoate;

(2S,3S)-((2R,3R,4S,5S)-5-(4-amino-5H-pyrrolo[3,2-d]pyrimidin-7-yl)-3,4-dihydroxypyrrolidin-2-yl)methyl 2-amino-3-methylpentanoate;

(S)-((2R,3R,4S,5S)-5-(4-amino-5H-pyrrolo[3,2-d]pyrimidin-7-yl)-3,4-dihydroxypyrrolidin-2-yl)methyl 2-amino-4-methylpentanoate;

(2S,2'S)-(2S,3S,4R,5R)-2-(4-amino-5H-pyrrolo[3,2-d]pyrimidin-7-yl)-5-(hydroxymethyl)pyrrolidine-3,4-diylbis(2-amino-3-methylbutanoate);

(S)-(2R,3R,4S,5S)-5-(4-amino-5H-pyrrolo[3,2-d]pyrimidin-7-yl)-4-hydroxy-2-(hydroxymethyl)pyrrolidin-3-yl 2-amino-3-methylbutanoate;

(S)-(2S,3S,4R,5R)-2-(4-amino-5H-pyrrolo[3,2-d]pyrimidin-7-yl)-4-hydroxy-5-(hydroxymethyl)pyrrolidin-3-yl 2-amino-3-methylbutanoate; and pharmaceutically acceptable salts thereof.

General Methods of Preparation of Compounds of the Invention:

Heterocycles and heteroaryls can be prepared from known methods as reported in the literature (a. Ring system handbook, published by American Chemical Society edition 1993 and subsequent supplements. b. *The Chemistry of Heterocyclic Compounds;* Weissberger, A., Ed.; Wiley: New York, 1962. c. Nesynov, E. P.; Grekov, A. P. The chemistry of 1,3,4-oxadiazole derivatives. *Russ. Chem. Rev.* 1964, 33, 508-515. d. *Advances in Heterocyclic Chemistry;* Katritzky, A. R., Boulton, A. J., Eds.; Academic Press: New York, 1966. e. In *Comprehensive Heterocyclic Chemistry;* Potts, K. T., Ed.; Pergamon Press: Oxford, 1984. f. Eloy, F. A review of the chemistry of 1,2,4-oxadiazoles. *Fortschr. Chem. Forsch.* 1965, 4, pp 807-876. g. *Adv. Heterocycl. Chem.* 1976. h. *Comprehensive Heterocyclic Chemistry;* Potts, K. T., Ed.; Pergamon Press: Oxford, 1984. i. *Chem. Rev.* 1961 61, 87-127. j. 1,2,4-*Triazoles;* John Wiley & Sons: New York, 1981; Vol 37). Functional groups during the synthesis may need to be protected and subsequently deprotected. Examples of suitable protecting groups can be found in *Protective Groups in Organic Synthesis,* fourth edition, edited by Greene and Wuts.

Representative processes which can be used to prepare compounds of the invention and intermediates useful for preparing same are shown in the following Schemes.

Scheme 1
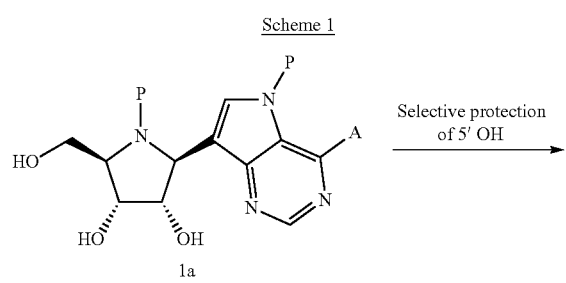
1a
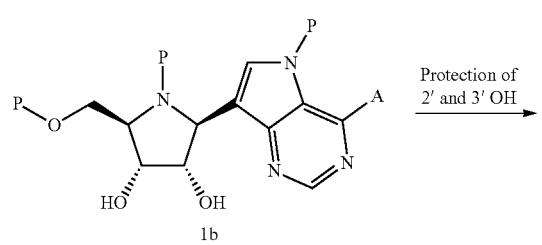
1b
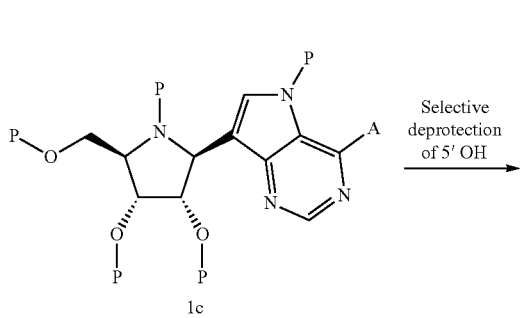
1c
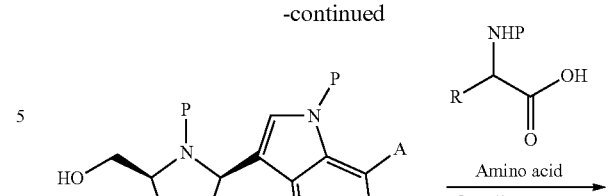
1d
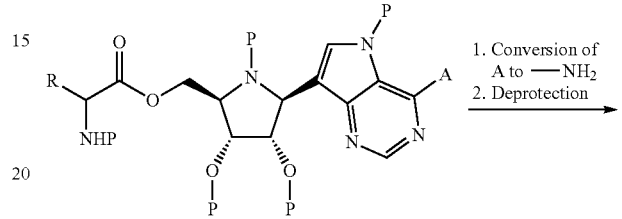
1e
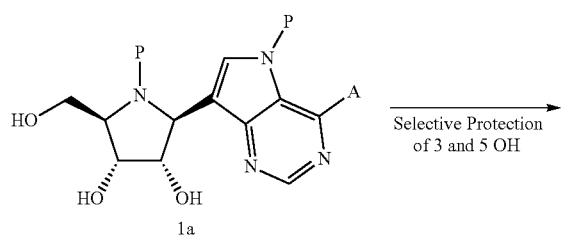
1f
P = Appropriate Protecting group
A = Cl, Br, I, OH, N₃, NHP, NP₂, OCH₃, —NH₂,
Scheme 2
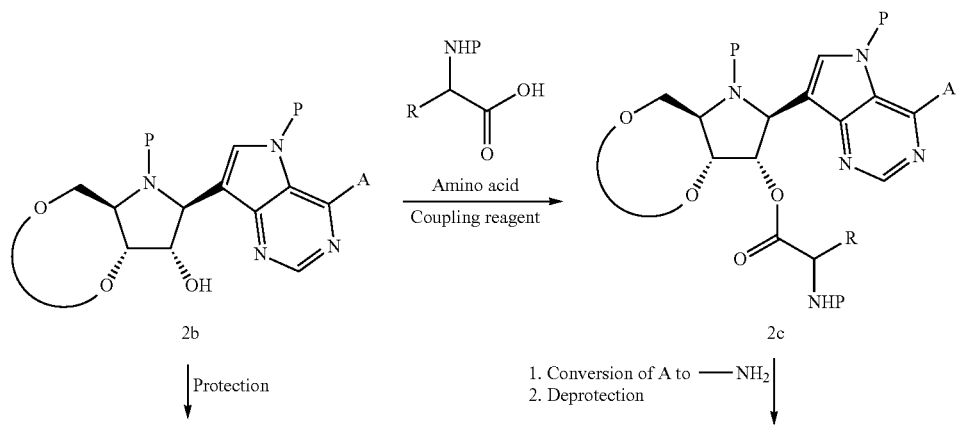

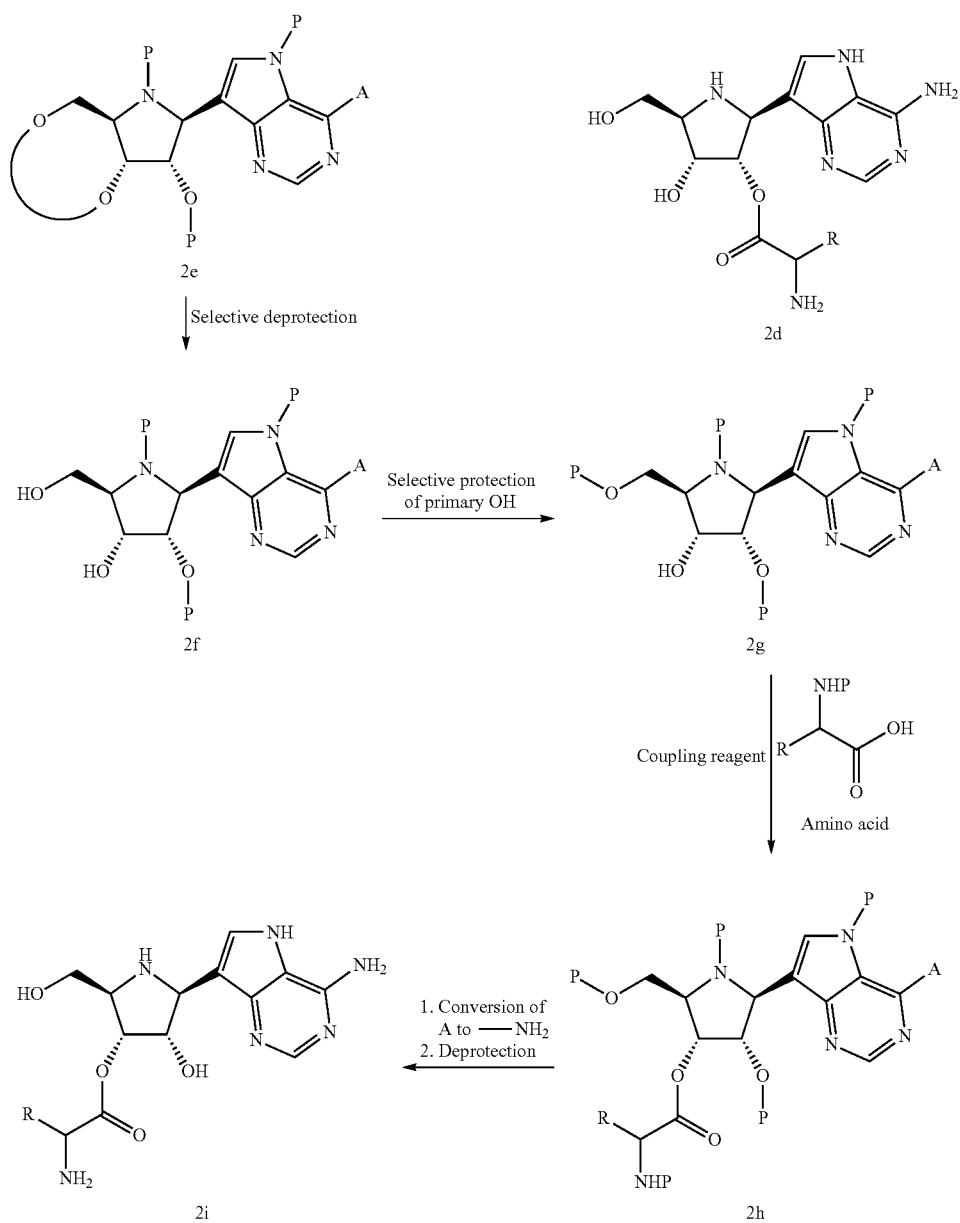
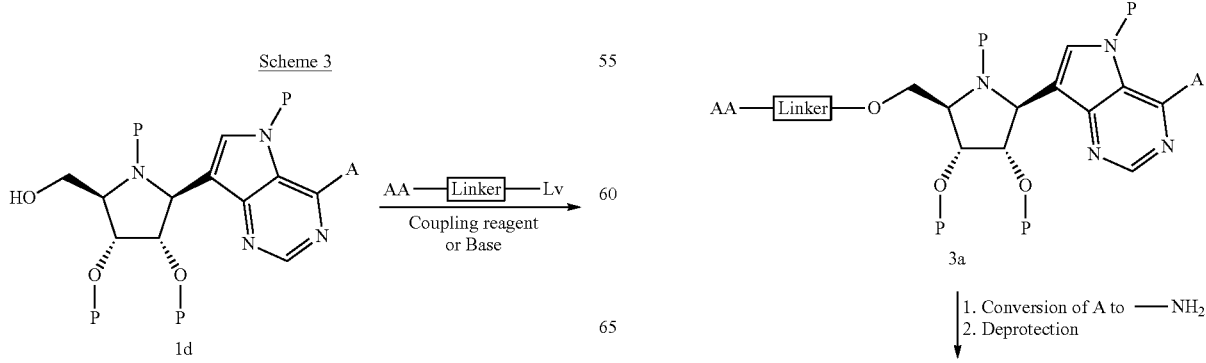
Scheme 3

-continued

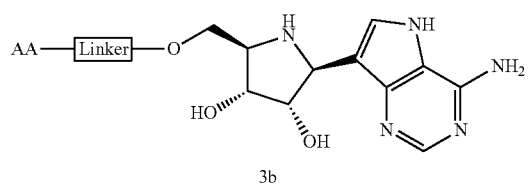

3b

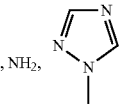

P = Appropriate Protecting group
A = Cl, Br, I, OH, N₃, NHP, NP₂, OCH₃, NH₂,
AA = Amino acid
Lv = leaving group Scheme 4

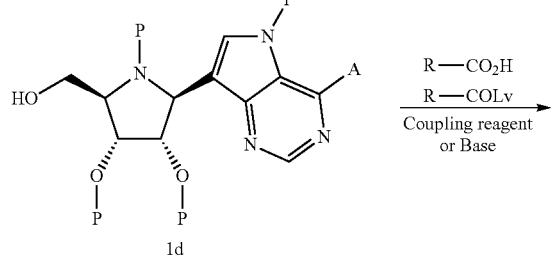

1d

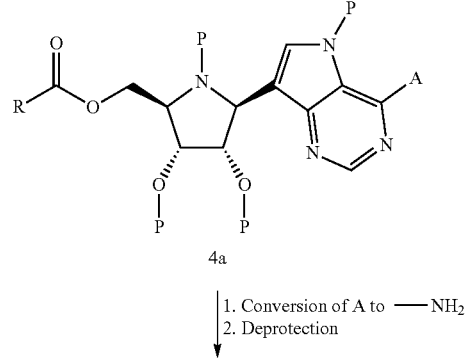

4a

1. Conversion of A to —NH₂
2. Deprotection

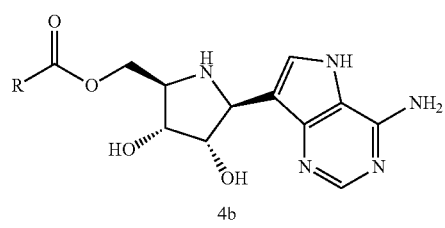

4b

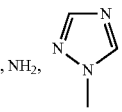

P = Appropriate Protecting group
A = Cl, Br, I, OH, N₃, NHP, NP₂, OCH₃, NH₂,
AA = Amino acid
Lv = leaving group Scheme 5

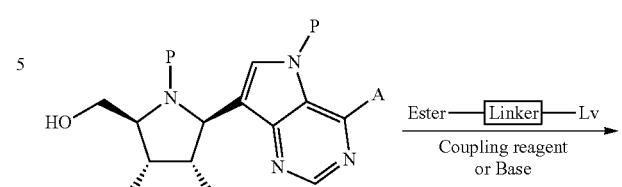

1d

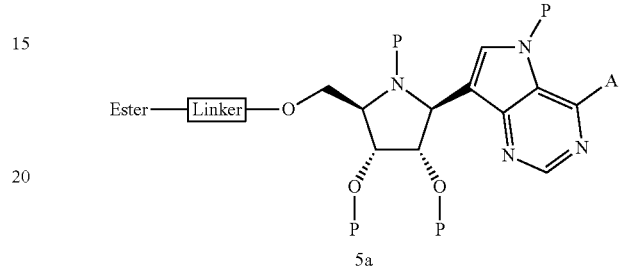

5a

1. Conversion of A to —NH₂
2. Deprotection

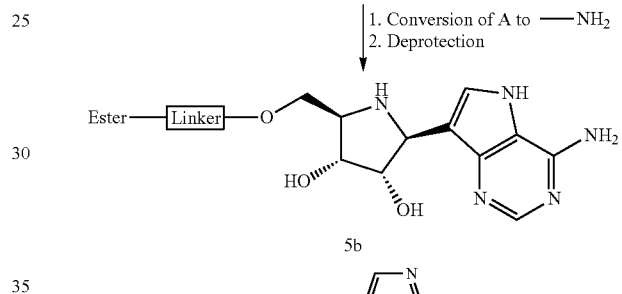

5b

P = Appropriate Protecting group
A = Cl, Br, I, OH, N₃, NHP, NP₂, OCH₃, NH₂,
AA = Amino acid
Lv = leaving group Scheme 6

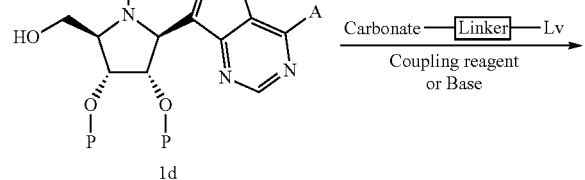

1d

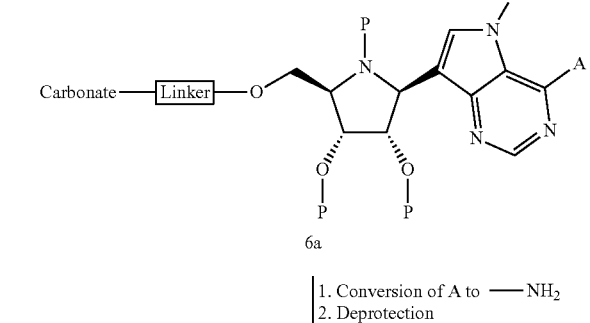

6a

1. Conversion of A to —NH₂
2. Deprotection

21
-continued
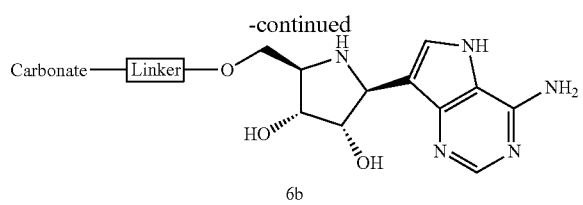
6b
22
-continued
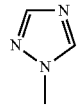
P = Appropriate Protecting group
A = Cl, Br, I, OH, N₃, NHP, NP₂, OCH₃, NH₂,
AA = Amino acid
Lv = leaving group
Scheme 7
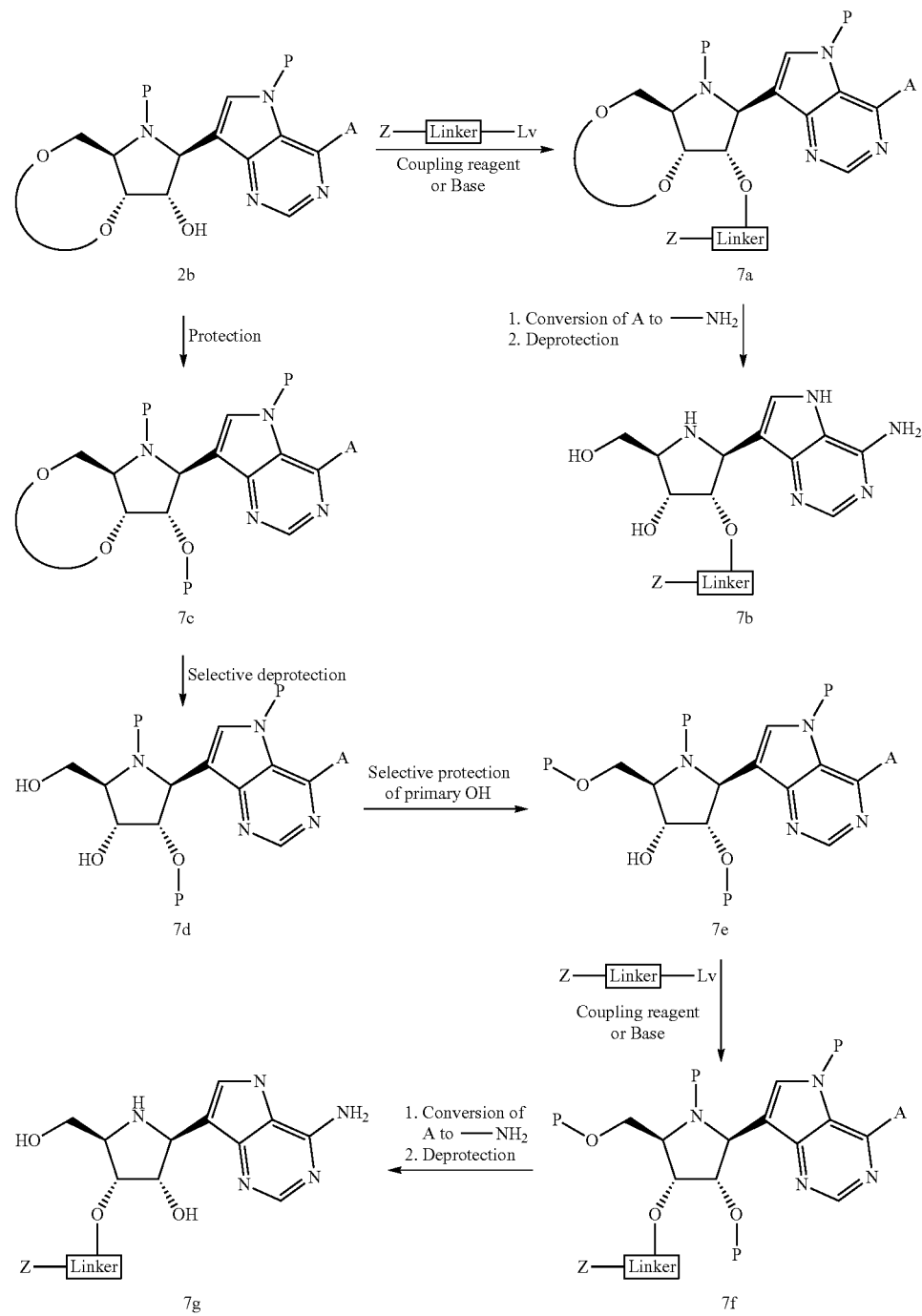
Z = amino acid or ester or carbonate

Scheme 8

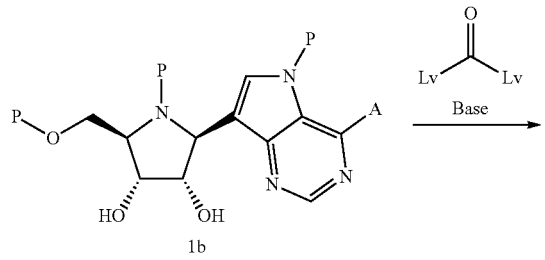

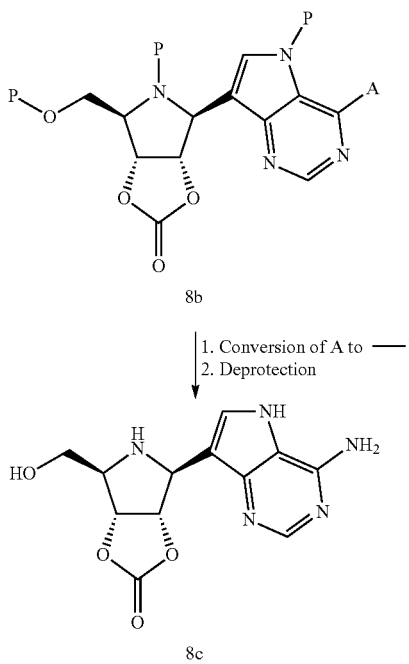

P = Appropriate Protecting group
A = Cl, Br, I, OH, N₃, NHP, NP₂, OCH₃, NH₂, 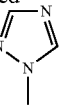
Lv = Leaving group References for Scheme 8:
1. WO 2011/123586 A1 (incorporated by reference).
2. WO 2010/135520 A1 (incorporated by reference).
3. WO 2009/069095 A2 (incorporated by reference).
4. WO 2009/029729 A1 (incorporated by reference).
5. WO 2008/082601 A2 (incorporated by reference).
6. WO 2007/022073 A2 (incorporated by reference).
7. Hecker, Scott J.; Reddy, K. Raja; van Poelje, Paul D.; Sun, Zhili; Huang, Wenjian; Varkhedkar, Vaibhav; Reddy, M. Venkat; Fujitaki, James M.; Olsen, David B.; Koeplinger, Kenneth A.; Boyer, Serge H.; Linemeyer, David L.; MacCoss, Malcolm; Erion, Mark D; Journal of Medicinal Chemistry (2007), 50(16), 3891-3896.
8. Yadava, Virendra Singh; Asian Journal of Chemistry (2005), 17(4), 2857-2859.
9. U.S. Pat. Appl. Publ. 2005/0182252 A1 (incorporated by reference).
10. U.S. Pat. Appl. Publ. 2005/0070556 A1 (incorporated by reference).
11. Reitz, Allen B.; Goodman, Michael G.; Pope, Barbara L.; Argentieri, Dennis C.; Bell, Stanley C.; Burr, Levelle E.; Chourmouzis, Erika; Come, Jon; Goodman, Jacquelyn H.; Klaubert, Dieter H.; Maryanoff, Bruce E.; McDonnell, Mark E.; Rampulla, Marianne S.; Schott, Mary R.; Chen, Robert; Journal of Medicinal Chemistry (1994), 37(21), 3561-78.

Scheme 9

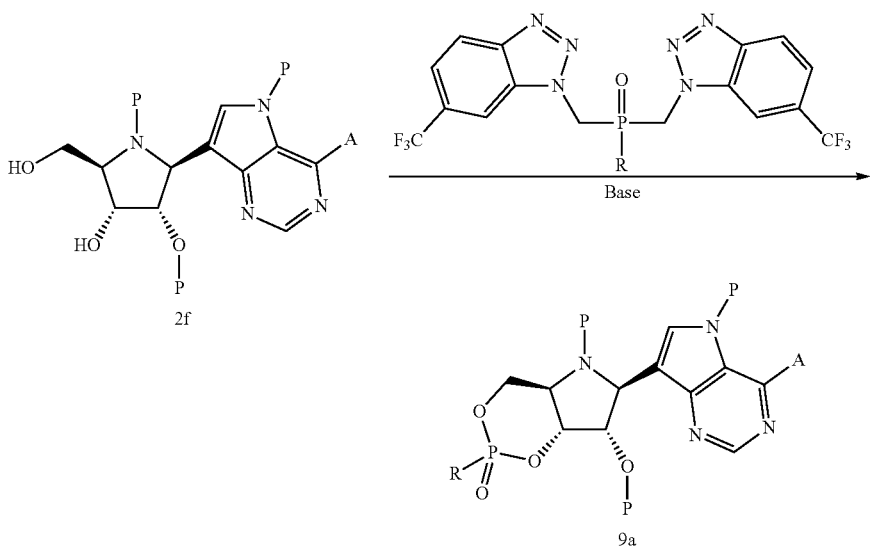

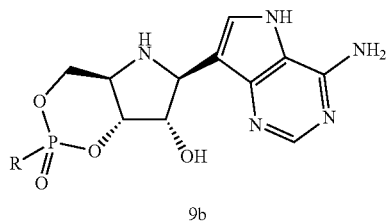
9b
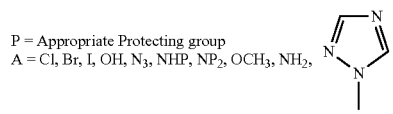
P = Appropriate Protecting group
A = Cl, Br, I, OH, N₃, NHP, NP₂, OCH₃, NH₂, 20
References for Scheme 9
1. Roelen, H. C. P. F.; De Vroom, E.; Wang, A. H. J.; Van der Marel, G. A.; Van Boom, J. H; Nucleosides & Nucleotides (1992), 11(1), 141-56.
2. Kaji, Akira (Japan) (1988), 5 pp. CODEN: JKXXAF JP 63135399 A 19880607 patent written in Japanese. Application: JP 1986-282021 19861128.
Scheme 10
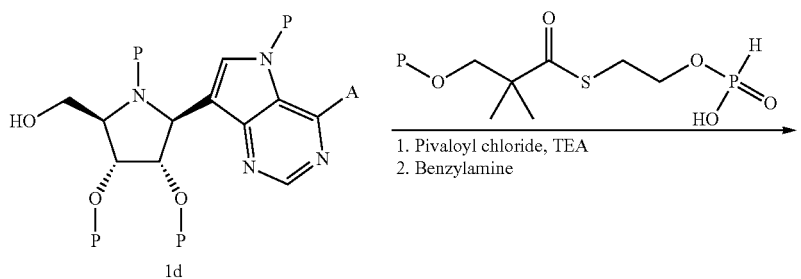
1d
1. Pivaloyl chloride, TEA
2. Benzylamine
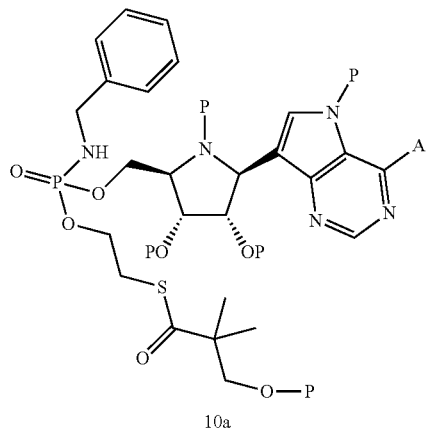
10a
1. Conversion of A to ——NH₂
2. Deprotection

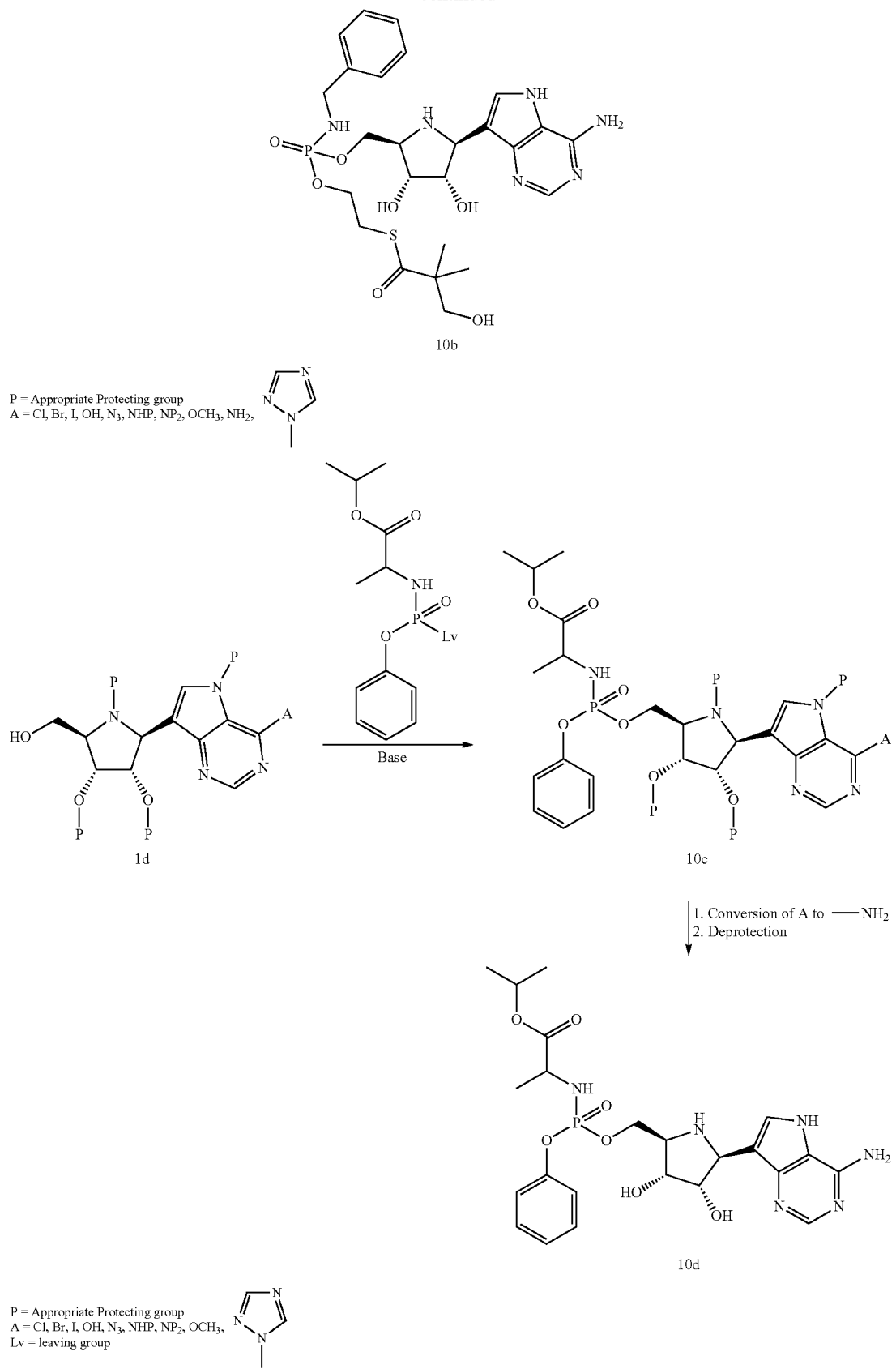

References for Scheme 10:
1. U.S. Pat. Appl. Publ. 2010/0203015 A1 (incorporated by reference).
2. WO 2009/132123 A1 (incorporated by reference).
3. Hatton, Wilfried; Hunault, Julie; Egorov, Maxim; Len, Christophe; Pipelier, Muriel; Blot, Virginie; Silvestre, Virginie; Fargeas, Valerie; Ane, Adjou; McBrayer, Tami; Detorio, Mervi; Cho, Jong-Hyun; Bourgougnon, Nathalie; Dubreuil, Didier; Schinazi, Raymond F.; Lebreton, Jacques; European Journal of Organic Chemistry (2011), 2011(36), 7390-7399.
4. Zhang, Hong-wang; Zhou, Longhu; Coats, Steven J.; McBrayer, Tamara R.; Tharnish, Phillip M.; Bondada, Lavanya; Detorio, Mervi; Amichai, Sarah A.; Johns, Melissa D.; Whitaker, Tony; Schinazi, Raymond F; Bioorganic & Medicinal Chemistry Letters (2011), 21(22), 6788-6792.
5. Ross, Bruce S.; Ganapati Reddy, P.; Zhang, Hai-Ren; Rachakonda, Suguna; Sofia, Michael J; Journal of Organic Chemistry (2011), 76(20), 8311-8319.
6. McGuigan, Christopher; Madela, Karolina; Aljarah, Mohamed; Gilles, Arnaud; Battina, Srinivas K.; Ramamurty, Changalvala V. S.; Srinivas Rao, C.; Vernachio, John; Hutchins, Jeff; Hall, Andrea; Kolykhalov, Alexander; Henson, Geoffrey; Chamberlain, Stanley; Bioorganic & Medicinal Chemistry Letters (2011), 21(19), 6007-6012.
7. Cho, Jong Hyun; Amblard, Franck; Coats, Steven J.; Schinazi, Raymond F; Tetrahedron (2011), 67(30), 5487-5493.
8. WO 2010/135520 A1 (incorporated by reference).
9. Perlikova, Pavla; Pohl, Radek; Votruba, Ivan; Shih, Robert; Birkus, Gabriel; Cihlar, Tomas; Hocek, Michal; Bioorganic & Medicinal Chemistry (2011), 19(1), 229-242.
10. WO 2010/108135 A1 (incorporated by reference).
11. WO 2010/130726 A1 (incorporated by reference).
12. WO 2010/030858 A1 (incorporated by reference).
13. WO 2010/108140 A1 (incorporated by reference).
14. WO 2010/026153 A1 (incorporated by reference).
15. WO 2010/081082 A2 (incorporated by reference).
16. McGuigan, Christopher; Madela, Karolina; Aljarah, Mohamed; Gilles, Arnaud; Brancale, Andrea; Zonta, Nicola; Chamberlain, Stanley; Vernachio, John; Hutchins, Jeff; Hall, Andrea; Ames, Brenda; Gorovits, Elena; Ganguly, Babita; Kolykhalov, Alexander; Wang, Jin; Muhammad, Jerry; Patti, Joseph M.; Henson, Geoffrey; Bioorganic & Medicinal Chemistry Letters (2010), 20(16), 4850-4854.
17. Derudas, Marco; Brancale, Andrea; Naesens, Lieve; Neyts, Johan; Balzarini, Jan; McGuigan, Christopher; Bioorganic & Medicinal Chemistry (2010), 18(7), 2748-2755.
18. Mehellou, Youcef; Valente, Rocco; Mottram, Huw; Walsby, Elisabeth; Mills, Kenneth I.; Balzarini, Jan; McGuigan, Christopher; Bioorganic & Medicinal Chemistry (2010), 18(7), 2439-2446.
19. McGuigan, Christopher; Gilles, Arnaud; Madela, Karolina; Aljarah, Mohamed; Holl, Sabrina; Jones, Sarah; Vernachio, John; Hutchins, Jeff; Ames, Brenda; Bryant, K. Dawn; Gorovits, Elena; Ganguly, Babita; Hunley, Damound; Hall, Andrea; Kolykhalov, Alexander; Liu, Yule; Muhammad, Jerry; Raja, Nicholas; Walters, Robin; Wang, Jin; Chamberlain, Stanley; Henson, Geoffrey; Journal of Medicinal Chemistry (2010), 53(13), 4949-4957.
20. Leisvuori, Anna; Aiba, Yuichiro; Loennberg, Tuomas; Poijaervi-Virta, Paeivi; Blatt, Laurence; Beigelman, Leo; Loennberg, Harri; Organic & Biomolecular Chemistry (2010), 8(9), 2131-2141.
21. Mehellou, Youcef; Balzarini, Jan; McGuigan, Christopher; Antiviral Chemistry & Chemotherapy (2010), 20(4), 153-160.
22. Rondla, Ramu; Coats, Steven J.; McBrayer, Tamara R.; Grier, Jason; Johns, Melissa; Tharnish, Phillip M.; Whitaker, Tony; Zhou, Longhu; Schinazi, Raymond F; Antiviral Chemistry & Chemotherapy (2009), 20(2), 99-106.
23. WO 2008/121941 A1 (incorporated by reference).
24. WO 2009/086192 A1 (incorporated by reference).
25. McGuigan, Christopher; Kelleher, Mary Rose; Perrone, Plinio; Mulready, Sinead; Luoni, Giovanna; Daverio, Felice; Rajyaguru, Sonal; Le Pogam, Sophie; Najera, Isabel; Martin, Joseph A.; Klumpp, Klaus; Smith, David B; Bioorganic & Medicinal Chemistry Letters (2009), 19(15), 4250-4254.
26. McGuigan, Christopher; Perrone, Plinio; Madela, Karolina; Neyts, Johan; Bioorganic & Medicinal Chemistry Letters (2009), 19(15), 4316-4320.

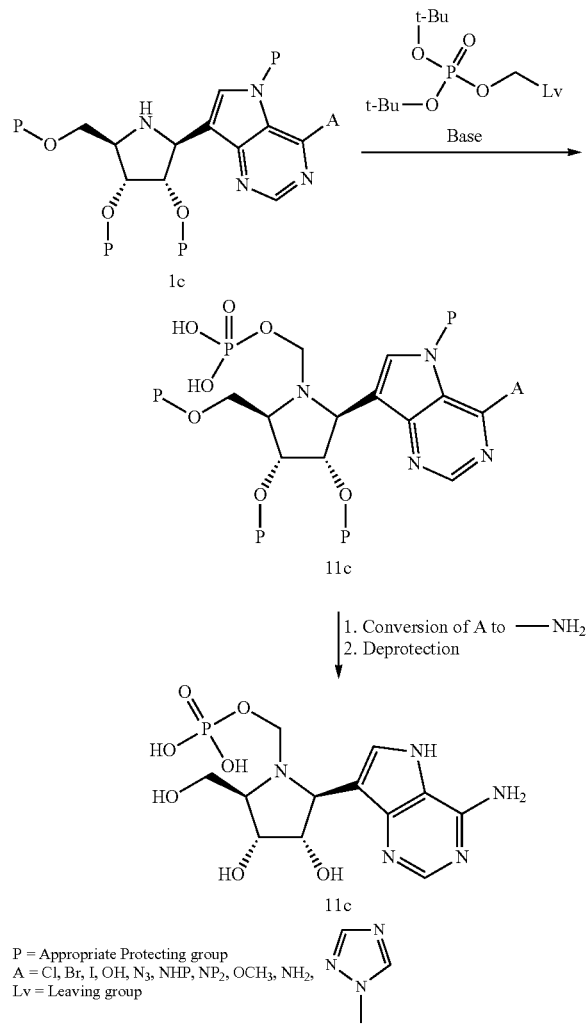

Scheme 11

P = Appropriate Protecting group
A = Cl, Br, I, OH, N$_3$, NHP, NP$_2$, OCH$_3$, NH$_2$,
Lv = Leaving group References for Scheme 11:
1. WO 2011/150016 A1 (incorporated by reference).
2. WO 2010/150761 A1 (incorporated by reference).
12. WO 2010/079443 A1 (incorporated by reference).
13. WO 2010/010017 A1 (incorporated by reference).
14. WO 2010/093789 A2 (incorporated by reference).

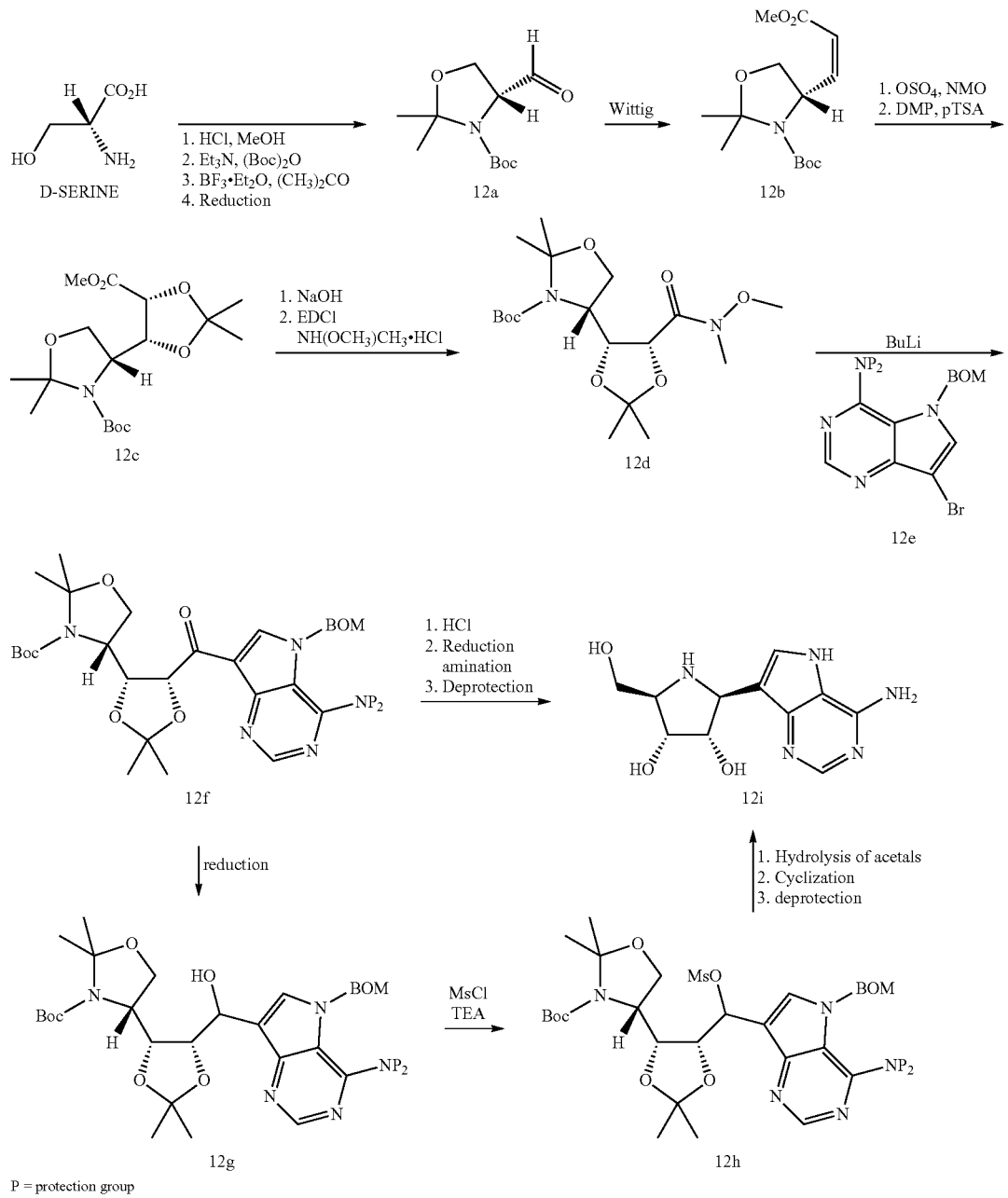

Scheme 12

3. WO 2011/068899 A1 (incorporated by reference).
4. WO 2011/084849 A1 (incorporated by reference).
5. U.S. Pat. Appl. Publ. 2011/0166128 A1 (incorporated by reference).
6. WO 2011/084846 A1 (incorporated by reference).
7. CN 102060874 A.
8. WO 2011/031979 A1 (incorporated by reference). 09. WO 2011/002999 A1 (incorporated by reference).
10. WO 2010/064735 A1 (incorporated by reference).
11. WO 2010/036638 A2 (incorporated by reference).

References for Garner's Aldehyde Compound 12a:
1. Upadhyay, Puspesh K.; Kumar, Pradeep; Synthesis (2010), (18), 3063-3066.
2. U.S. Pat. Appl. Publ. 2010/0152098 A1 (incorporated by reference).
3. Badarau, Eduard; Suzenet, Franck; Finaru, Adriana-Luminita; Guillaumet, Gerald; European Journal of Organic Chemistry (2009), (21), 3619-3627.

4. Belanger, Dominique; Tong, Xia; Soumare, Sadia; Dory, Yves L.; Zhao, Yue; Chemistry—A European Journal (2009), 15(17), 4428-4436.
5. Osada, Satoshi; Ishimaru, Takako; Kawasaki, Hiroshi; Kodama, Hiroaki; Heterocycles (2006), 67(1), 421-431.
6. Xin, Cong; Liao, Qing-Jiang; Yao, Zhu-Jun; Journal of Organic Chemistry (2004), 69(16), 5314-5321.
7. Dondoni, Alessandro; Perrone, Daniela; Organic Syntheses (2000), 77 64-77.
8. Campbell, Andrew D.; Raynham, Tony M.; Taylor, Richard J. K; Synthesis (1998), (12), 1707-1709.

References for Wittig reaction related to compound 12b:
1. Ma, Zhigiang; Lu, Jianming; Wang, Xiao; Chen, Chuo; Chemical Communications (Cambridge, United Kingdom) (2011), 47(1), 427-429.
2. Spangenberg, Thomas; Schoenfelder, Angele; Breit, Bernhard; Mann, Andre; European Journal of Organic Chemistry (2010), (31), 6005-6018.
3. Osman, Sami; Albert, Brian J.; Wang, Yanping; Li, Miaosheng; Czaicki, Nancy L.; Koide, Kazunori; Chemistry—A European Journal (2011), 17(3), 895-904,
4. Passiniemi, Mikko; Koskinen, An M. P; Synthesis (2010), (16), 2816-2822.
5. Thander, Latibuddin; Sarkar, Kaushik; Chattopadhyay, shital K; Tetrahedron: Asymmetry (2009), 20(11), 1213-1216.
6. Chiou, Wen-Hua; Schoenfelder, Angele; Mann, Andre; Ojima, Iwao; Pure and Applied Chemistry (2008), 80(5), 1019-1024.
7. Ribes, Celia; Falomir, Eva; Carda, Miguel; Marco, J. Alberto; Journal of Organic Chemistry (2008), 73(19), 7779-7782.
8. Mochizuki, Akiyoshi; Naito, Hiroyuki; Nakamoto, Yumi; Uoto, Kouichi; Ohta, Toshiharu; Heterocycles (2008), 75(7), 1659-1671.
9. Spangenberg, Thomas; Schoenfelder, Angele; Breit, Bernhard; Mann, Andre; Organic Letters (2007), 9(20), 3881-3884.
10. Lebel, Helene; Ladjel, Chehla; Organometallics (2008), 27(11), 2676-2678.
11. Liu, Fa; Hu, Tai-Shan; Yao, Zhu-Jun; Tetrahedron (2005), 61(21), 4971-4981.
12. Shigeki Sano, Tomoka Takehisa, Shiho Ogawa, Kenji yokoyama and Yoshimitsu Nagao Chem. Pharm. Bull. 50 (9) 1300-1302 (2002).
13. Raghavan, Sadagopan; Rajender, A.; Joseph, Suju C.; Rasheed, M. Abdul; Ravi Kumar, K; Tetrahedron: Asymmetry (2004), 15(2), 365-379.

References for Dihydroxylation for compounds related to 12c:
1. Dondoni, Alessandro; Merino, Pedro; Perrone, Daniela; Tetrahedron (1993), 49(14), 2939-56.
2. Ribes, Celia; Falomir, Eva; Carda, Miguel; Marco, J. Alberto; Journal of Organic Chemistry (2008), 73(19), 7779-7782.
3. Upadhyay, Puspesh K.; Kumar, Pradeep; Synthesis (2010), (18), 3063-3066.

Reference related to synthesis of base 12e:
Bambuch, Viterslav; Otmar, Miroslav; Pohl, Radek; Masojidkova, Milena; Holy, Antonin; Tetrahedron (2007), 63(7), 1589-1601.

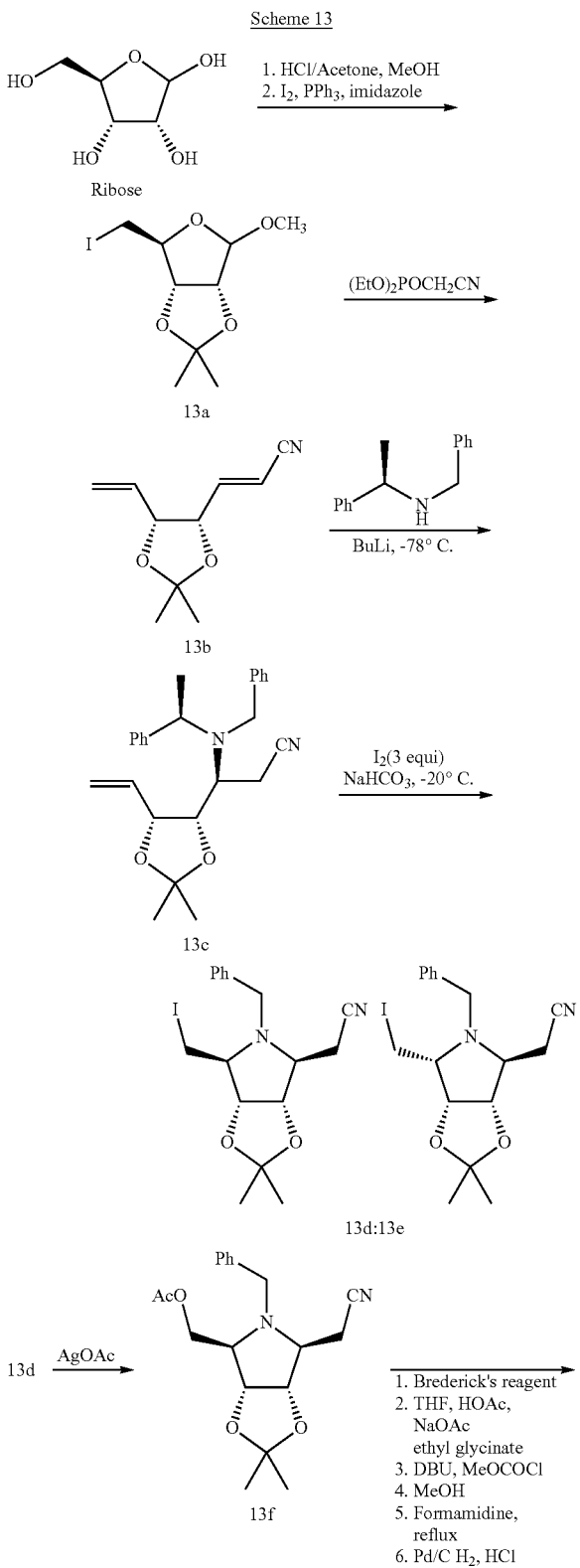

Scheme 13

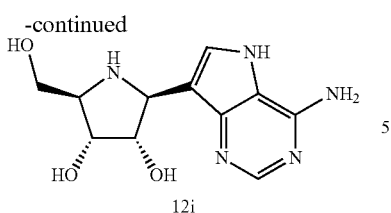

12i

References for preparation of compound 13a:
1. Mishra, Girija Prasad; Rao, Batchu Venkateswara; Tetrahedron: Asymmetry (2011), 22(7), 812-817.
2. Brock, E. Anne; Davies, Stephen G.; Lee, James A.; Roberts, Paul M.; Thomson, James E; Organic Letters (2011), 13(7), 1594-1597.
3. WO 2010/085377 A2 (incorporated by reference).
4. Yadav, J. S.; Reddy, P. Narayana; Reddy, B. V. Subba; Synlett (2010), (3), 457-461
5. Song, Kai; Zheng, Guo-jun; Huaxue Shiji (2010), 32(2), 171-172.
6. Prabhakar, Peddikotla; Rajaram, Singanaboina; Reddy, Dorigondla Kumar; Shekar, Vanam; Venkateswarlu, Yenamandra; Tetrahedron: Asymmetry (2010), 21(2), 216-221.
7. CN 101182342 A.
8. Baird, Lynton J.; Timmer, Mattie S. M.; Teesdale-Spittle, Paul H.; Harvey, Joanne E; Journal of Organic Chemistry (2009), 74(6), 2271-2277.
9. Wang, Xiang-cheng; Wang, Gang; Qu, Gang-lian; Huaxue Shijie (2008), 49(4), 226-228.
10. Ivanova, N. A.; Valiullina, Z. R.; shitikova, O. V.; Miftakhov, M. S; Russian Journal of Organic Chemistry (2007), 43(5), 742-746.
11. Braga, Fernanda Gambogi; Coimbra, Elaine Soares; Matos, Magnum de Oliveira; Lino Carmo, Arturene Maria; Cancio, Marisa Damato; da Silva, Adilson David; European Journal of Medicinal Chemistry (2007), 42(4), 530-537.
12. Wender, Paul A.; Bi, F. Christopher; Buschmann, Nicole; Gosselin, Francis; Kan, Cindy; Kee, Jung-Min; Ohmura, Hirofumi; Organic Letters (2006), 8(23), 5373-5376.
13. Fei, Xiangshu; Wang, Ji-Quan; Miller, Kathy D.; Sledge, George W.; Hutchins, Gary D.; Zheng, Qi-Huang; Nuclear Medicine and Biology (2004), 31(8), 1033-1041.
14. Abdel-Rahman, Adel A.-H.; Abdel-Megied, Ahmed E.-S.; Goda, Adel E.-S.; Zeid, Ibrahim F.; El Ashry, El Sayed H; Nucleosides, Nucleotides & Nucleic Acids (2003), 22(11), 2027-2038.
15. Palmer, Andreas M.; Jager, Volker; European Journal of Organic Chemistry (2001), (7), 1293-1308.
16. Paquette, Leo A.; Bailey, Simon; Journal of Organic Chemistry (1995), 60(24), 7849-56.
17. Classon, Bjoern; Liu, Zhengchun; Samuelsson, Bertil; Journal of Organic Chemistry (1988), 53(26), 6126-30.
18. Kissman, Henry M.; Baker, B. R; Journal of the American Chemical Society (1957), 79 5534-40.

References for cyclizations related to preparation of compounds of type 13d:
1. Davies, Stephen G.; Durbin, Matthew J.; Goddard, Euan C.; Kelly, Peter M.; Kurosawa, Wataru; Lee, James A.; Nicholson, Rebecca L.; Price, Paul D.; Roberts, Paul M.; Russell, Angela J.; Scott, Philip M.; Smith, Andrew D; Organic & Biomolecular Chemistry (2009), 7(4), 761-776.
2. Davies, Stephen G.; Nicholson, Rebecca L.; Price, Paul D.; Roberts, Paul M.; Russell, Angela J.; Savory, Edward D.; Smith, Andrew D.; Thomson, James E; Tetrahedron: Asymmetry (2009), 20(6-8), 758-772.
3. Davies, Stephen G.; Nicholson, Rebecca L.; Price, Paul D.; Roberts, Paul. M.; Smith, Andrew D; Synlett (2004), (5), 901-903.
4. Brock, E. Anne; Davies, Stephen G.; Lee, James A.; Roberts, Paul M.; Thomson, James E; Organic Letters (2011), 13(7), 1594-1597.
5. Gary B. Evans, Richard H. Furneaux, Andrzej Lewandowicz, Vern L. Schramm, and Peter C. Tyler, Journal of Medicinal Chemistry (2003), 46, 3412-3423.

Scheme 14

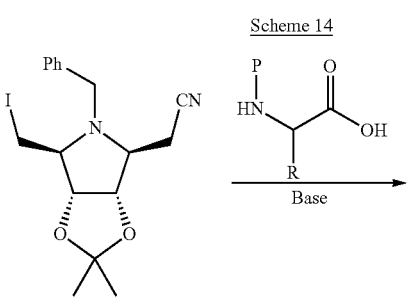

13d

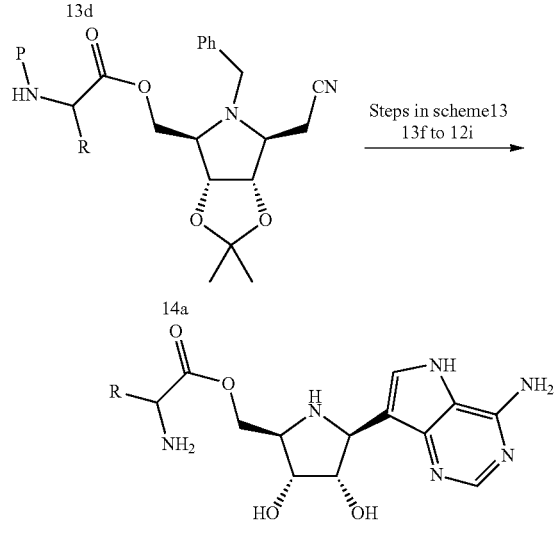

14a

14b

Scheme 15

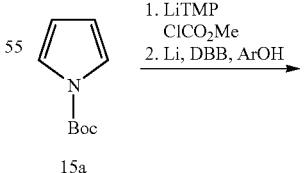

15a

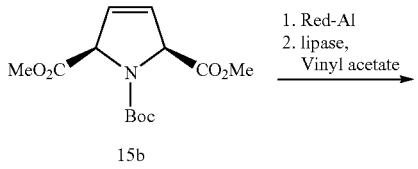

15b

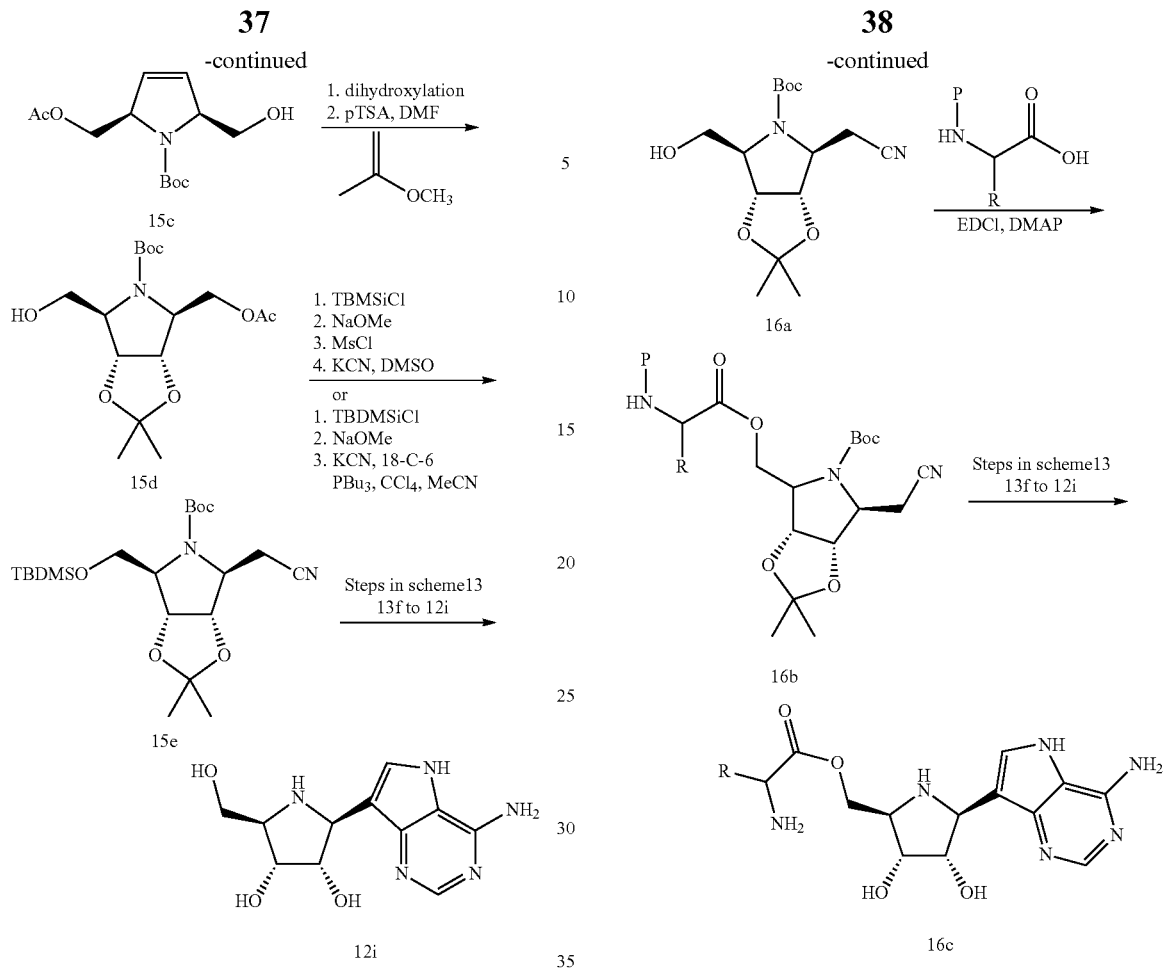

References for Scheme 15:
1. Chenevert, Robert; Jacques, Frederic; Giguere, Pascall; Dasser, Mohammed; Tetrahedron: Asymmetry (2008), 19(11), 1333-1338.
2. Donohoe, Timothy J.; Thomas, Rhian E.; Cheeseman, Matthew D.; Rigby, Caroline L.; Bhalay, Gurdip; Linney, Ian D; Organic Letters (2008), 10(16), 3615-3618.
3. Hanessian, Stephen; Therrien, Eric; Warrier, Jayakumar S.; Charron, Guillaume; Heterocycles (2006), 70 461-476.
4. Hamada, Yasumasa; Kawai, Akiyoshi; Kohno, Yasushi; Hara, Osamu; Shioiri, Takayuki; Journal of the American Chemical Society (1989), 111(4), 1524-5. (for Alcohol to Cyano).

Scheme 16A

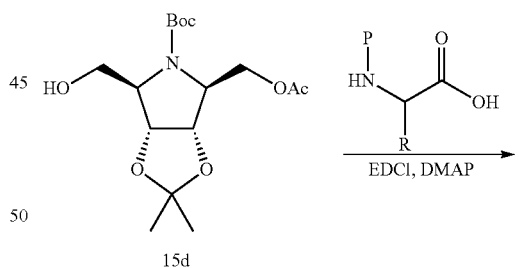

Scheme 16B

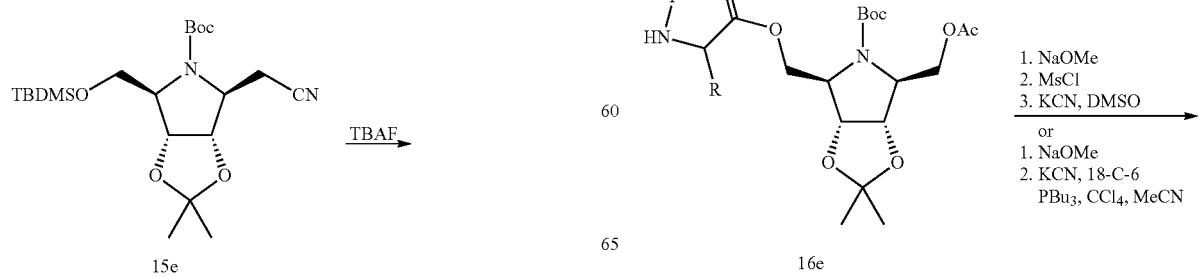

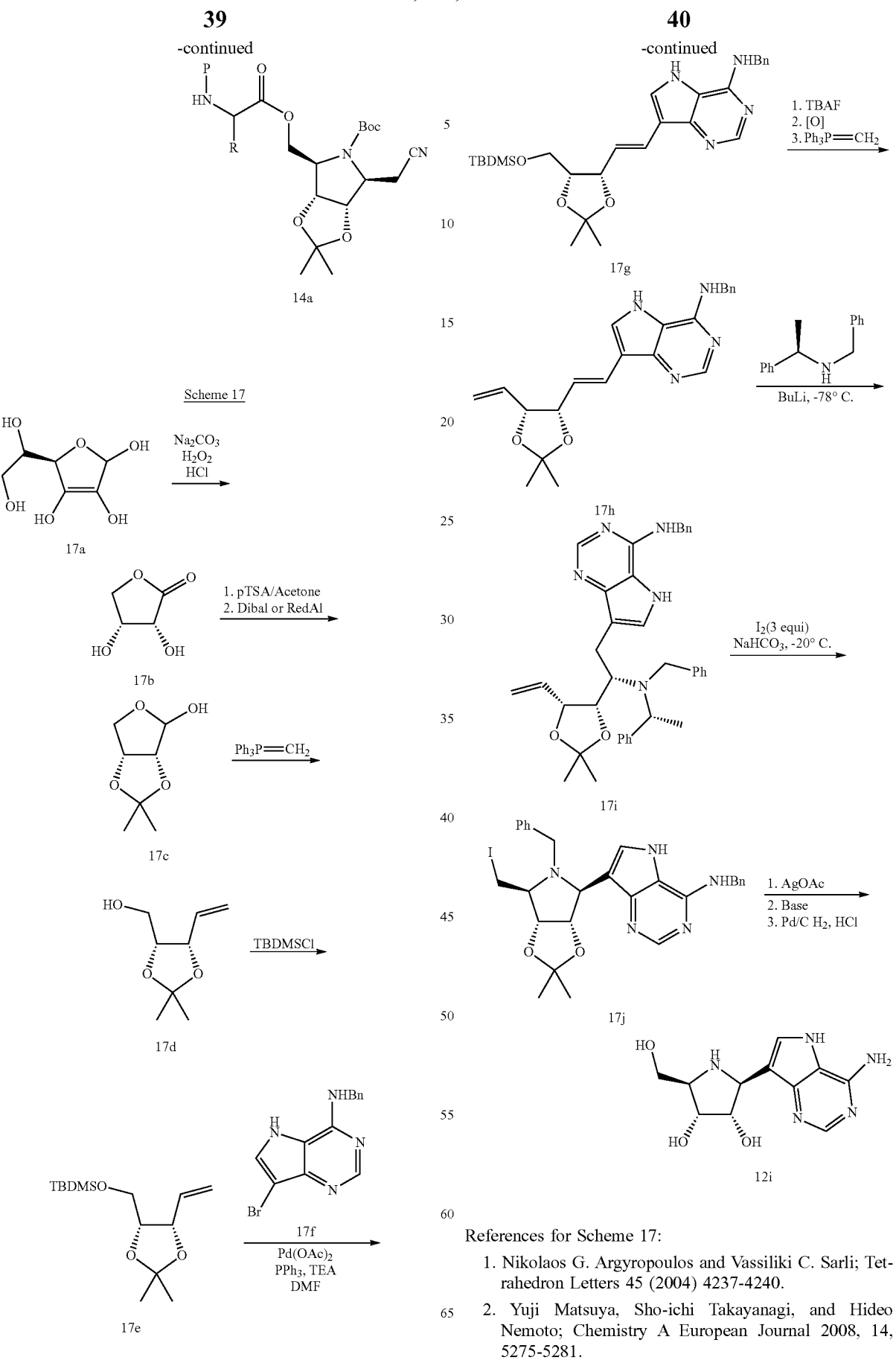
References for Scheme 17:
1. Nikolaos G. Argyropoulos and Vassiliki C. Sarli; Tetrahedron Letters 45 (2004) 4237-4240.
2. Yuji Matsuya, Sho-ichi Takayanagi, and Hideo Nemoto; Chemistry A European Journal 2008, 14, 5275-5281.

3. Hyo-Joong; Ricardo, Alonso; Illangkoon, Heshan I.; Kim, Myong Jung; Carrigan, Matthew A.; Frye, Fabianne; Benner, Steven A; Journal of the American Chemical Society (2011), 133(24), 9457-9468.
4. Paudyal, Mahesh P.; Rath, Nigam P.; Spilling, Christopher D; Organic Letters (2010), 12(13), 2954-2957.
5. Scarpi, Dina; Occhiato, Ernesto G.; Guarna, Antonio. Dipartimento di Chimica Organica 'U. Schiff; Tetrahedron: Asymmetry (2009), 20(3), 340-350.
6. WO 2008/108508 A1 (incorporated by reference).
7. WO 2008/010776 A1 (incorporated by reference).
8. U.S. Pat. Appl. Publ. 2007/0265333 A1 (incorporated by reference).
9. Vu, Nguyen Quang; Chai, Christina L. L.; Lim, Kok Peng; Chia, Sze Chen; Chen, Anqi; Tetrahedron (2007), 63(30), 7053-7058.
10. WO 99/21858 A1 (incorporated by reference).
11. Bambuch, Viterslav; Otmar, Miroslav; Pohl, Radek; Masojidkova, Milena; Holy, Antonin; Tetrahedron (2007), 63(7), 1589-1601.

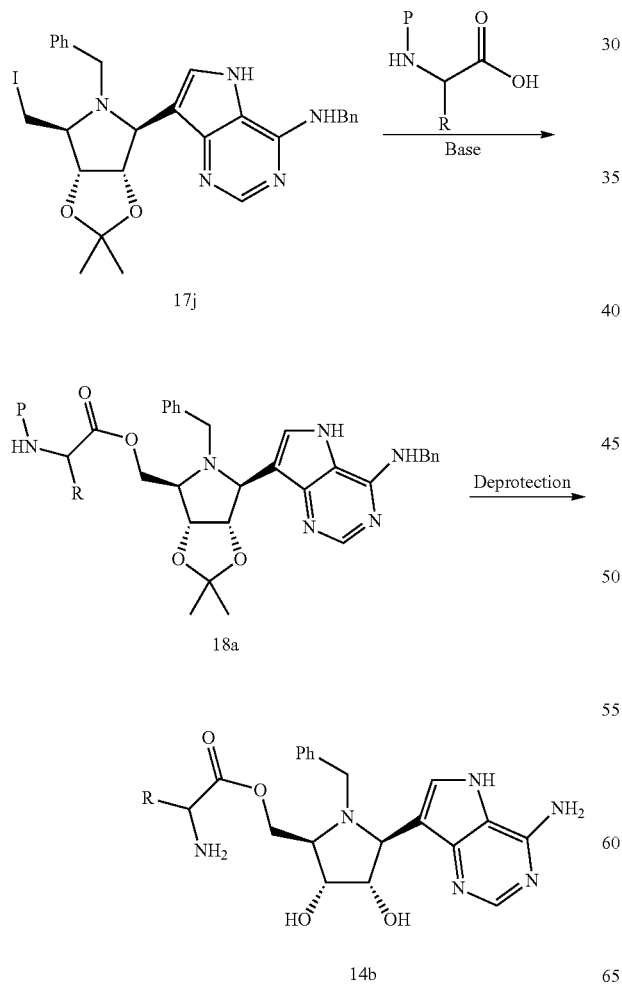

Scheme 18

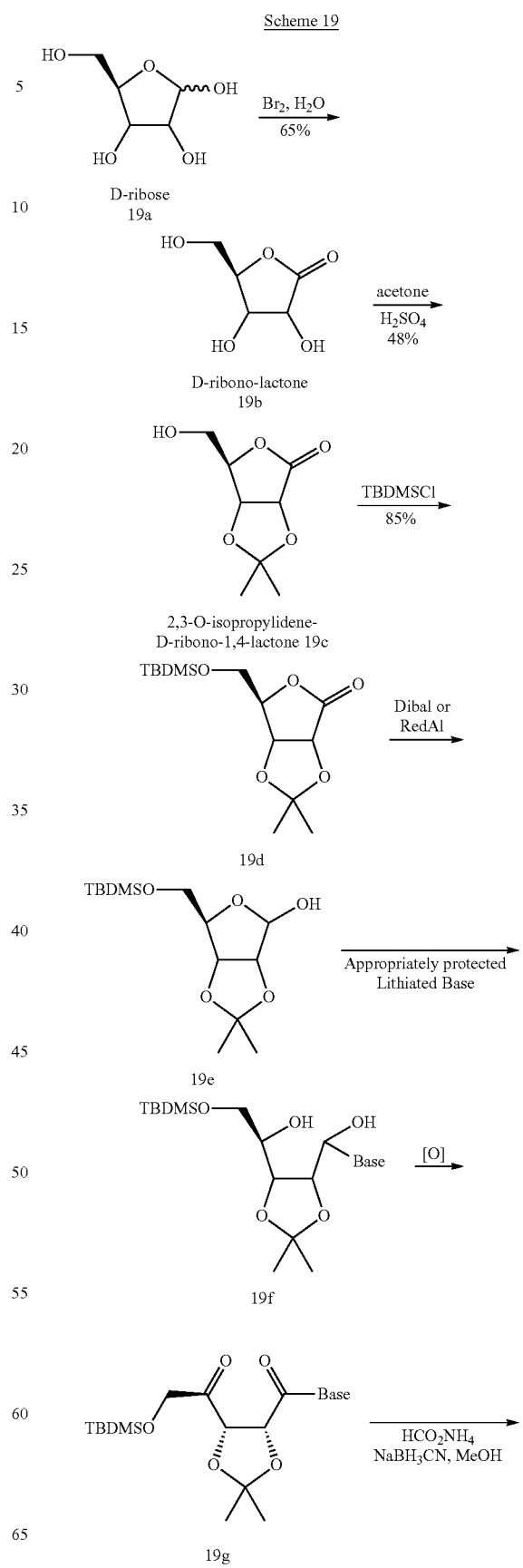

Scheme 19

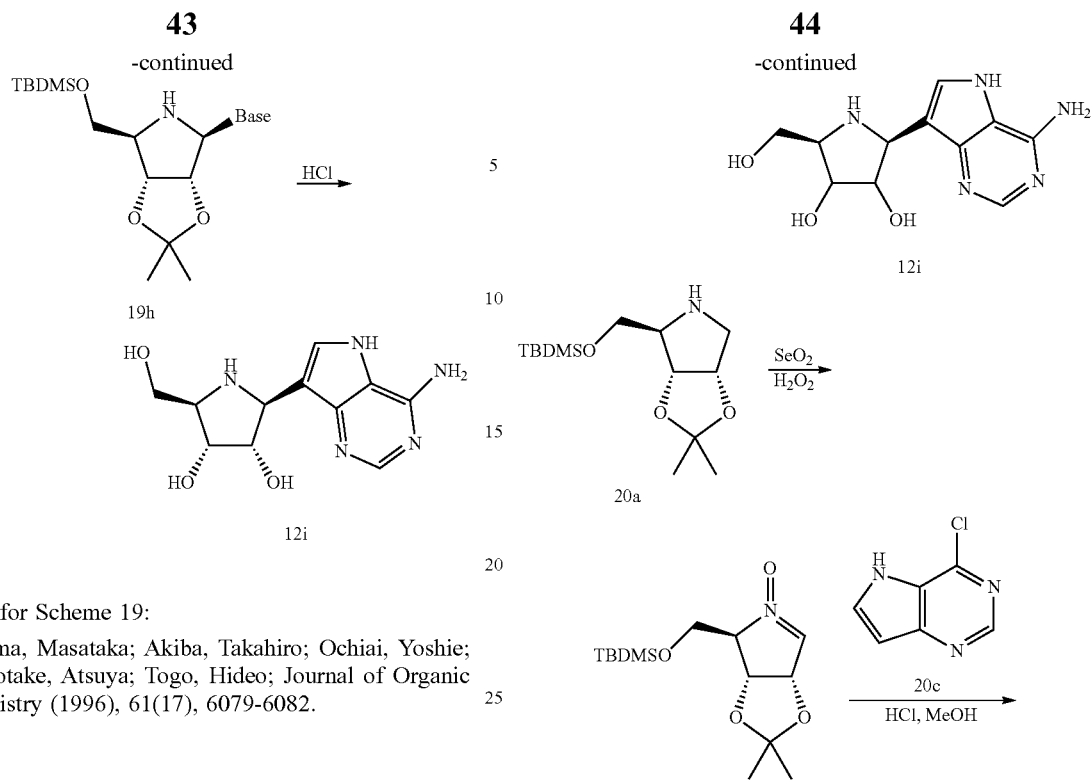
Reference for Scheme 19:
Yokoyama, Masataka; Akiba, Takahiro; Ochiai, Yoshie; Momotake, Atsuya; Togo, Hideo; Journal of Organic Chemistry (1996), 61(17), 6079-6082.
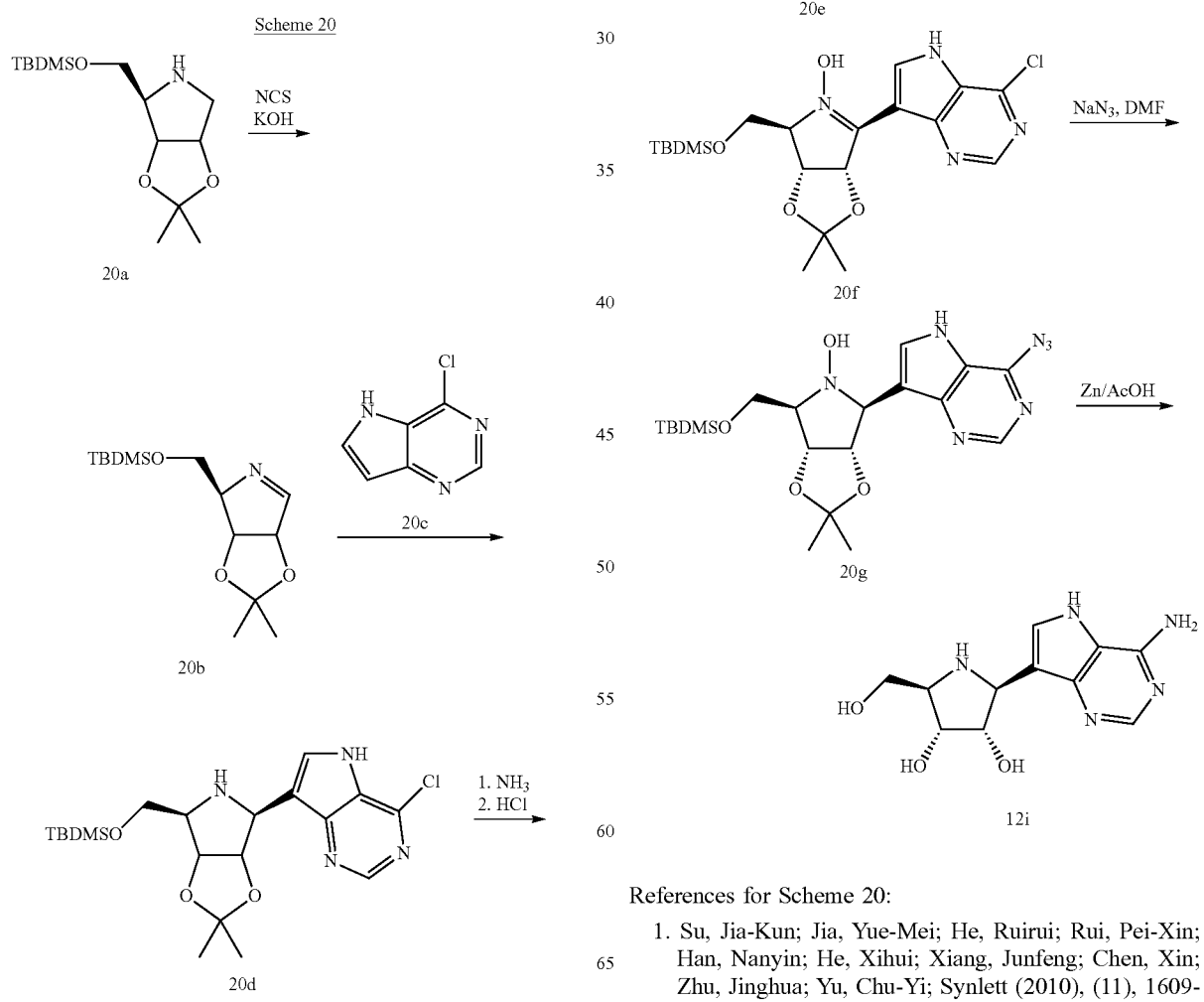
References for Scheme 20:
1. Su, Jia-Kun; Jia, Yue-Mei; He, Ruirui; Rui, Pei-Xin; Han, Nanyin; He, Xihui; Xiang, Junfeng; Chen, Xin; Zhu, Jinghua; Yu, Chu-Yi; Synlett (2010), (11), 1609-1616.

2. Li, Xiao-Liu; Qin, Zhan-Bin; Wang, Rui; Chen, Hua; Zhang, Ping-Zhu; Tetrahedron (2011), 67(10), 1792-1798.
Scheme 21
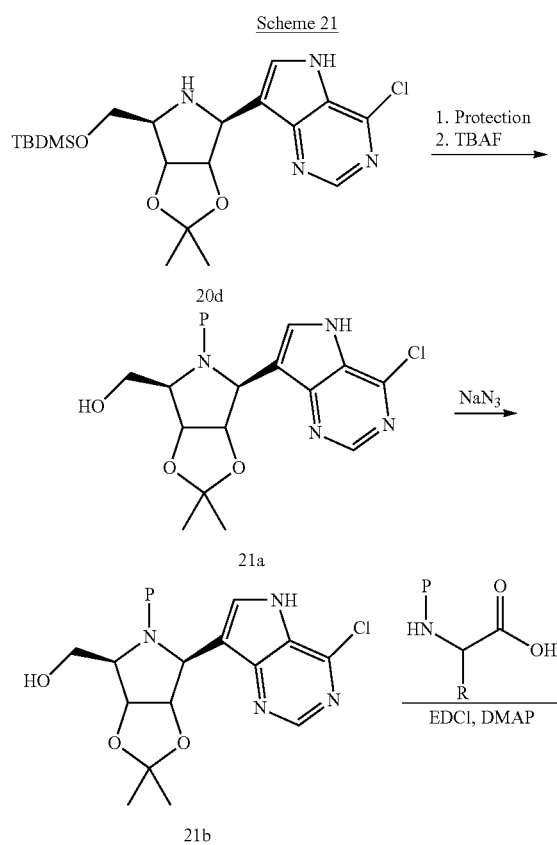
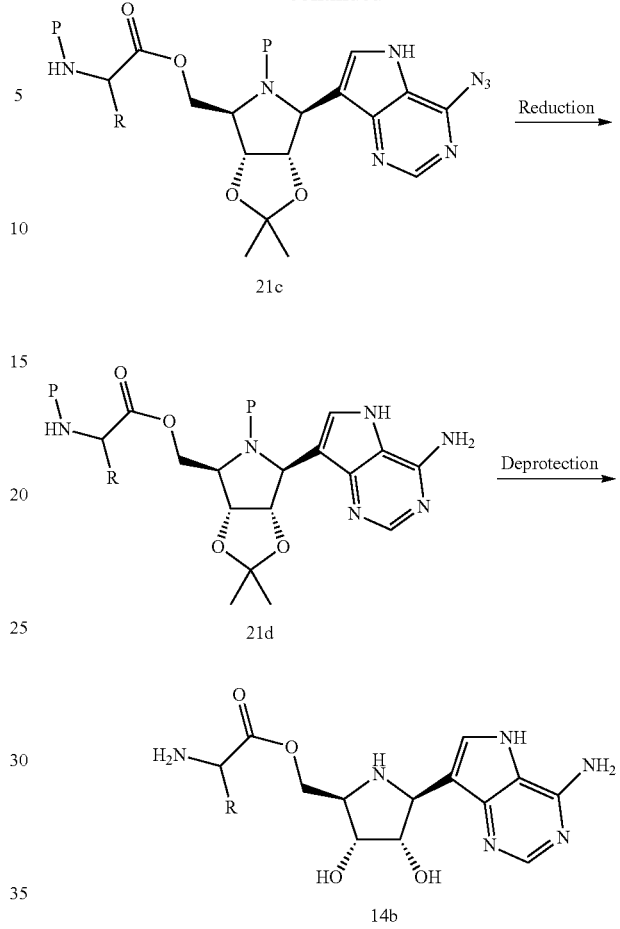
Scheme 22

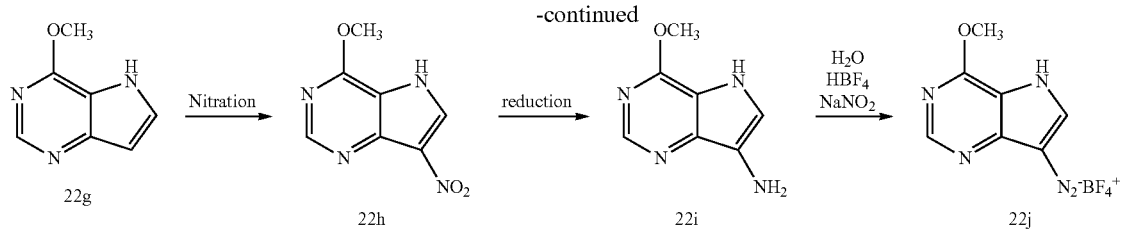

Reference for 7-nitro-3H-pyrrolo[3,2-d]pyrimidin-4-(5H)-one:
1. WO 2008/063669 A1 (incorporated by reference).
2. U.S. Pat. Appl. Publ. 2007/0155738 A1 (incorporated by reference).

Reference for Heck coupling related to preparation of compounds 23g and 23h:
Severino, Elias A.; Costenaro, Edson R.; Garcia, Ariel L. L.; Correia, Carlos Roque D; Organic Letters (2003), 5(3), 305-308.

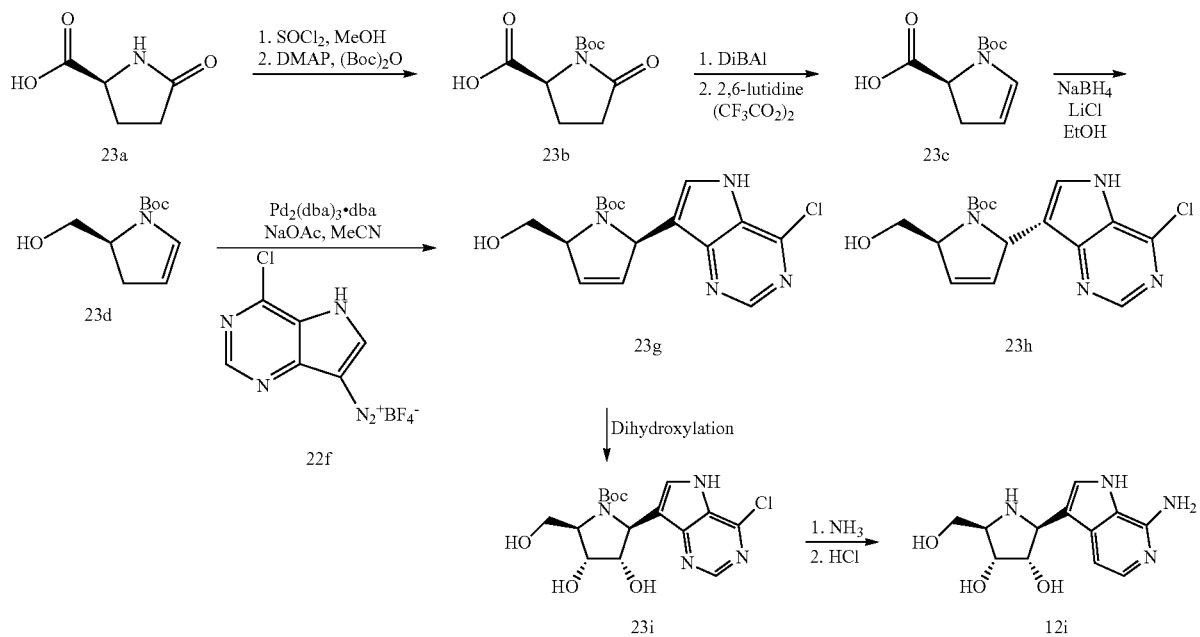

References to make (S)-1-tert-butyl 2-methyl 5-oxopyrrolidine-1,2-dicarboxylate (23c):
1. U.S. Pat. Appl. Publ. 2011/0237636 A1 (incorporated by reference).
2. WO 2011/015537 A1 (incorporated by reference).
References to make (S)-tert-butyl 2-(hydroxymethyl)-2,3-dihydro-1H-pyrrole-1-carboxylate (23d):
1. Oliveira, Denilson F.; Miranda, Paulo C. M. L.; Correia, Carlos R. D; Journal of Organic Chemistry (1999), 64(18), 6646-6652.
2. Schumacher, Kelly K.; Jiang, Jianjun; Joullie, Madeleine M; Tetrahedron: Asymmetry (1998), 9(1), 47-53.
3. Dormoy, Jean Robert; Castro, Bertrand; Chappuis, Georges; Fritschi, Ulrich Stefan; Grogg, Peter; Angewandte Chemie (1980), 92(9), 761.
4. Woo, Grace H. C.; Kim, Se-Ho; Wipf, Peter; Tetrahedron (2006), 62(45), 10507-10517.
5. Moro, Angelica Venturini; Rodrigues dos Santos, Marcelo; Correia, Carlos Roque D; European Journal of Organic Chemistry (2011), 2011(36), 7259-7270.

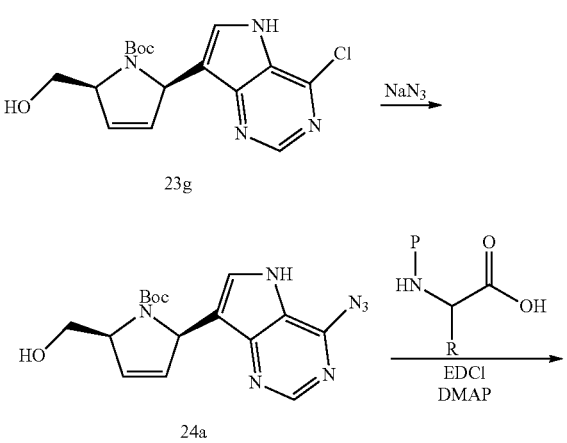

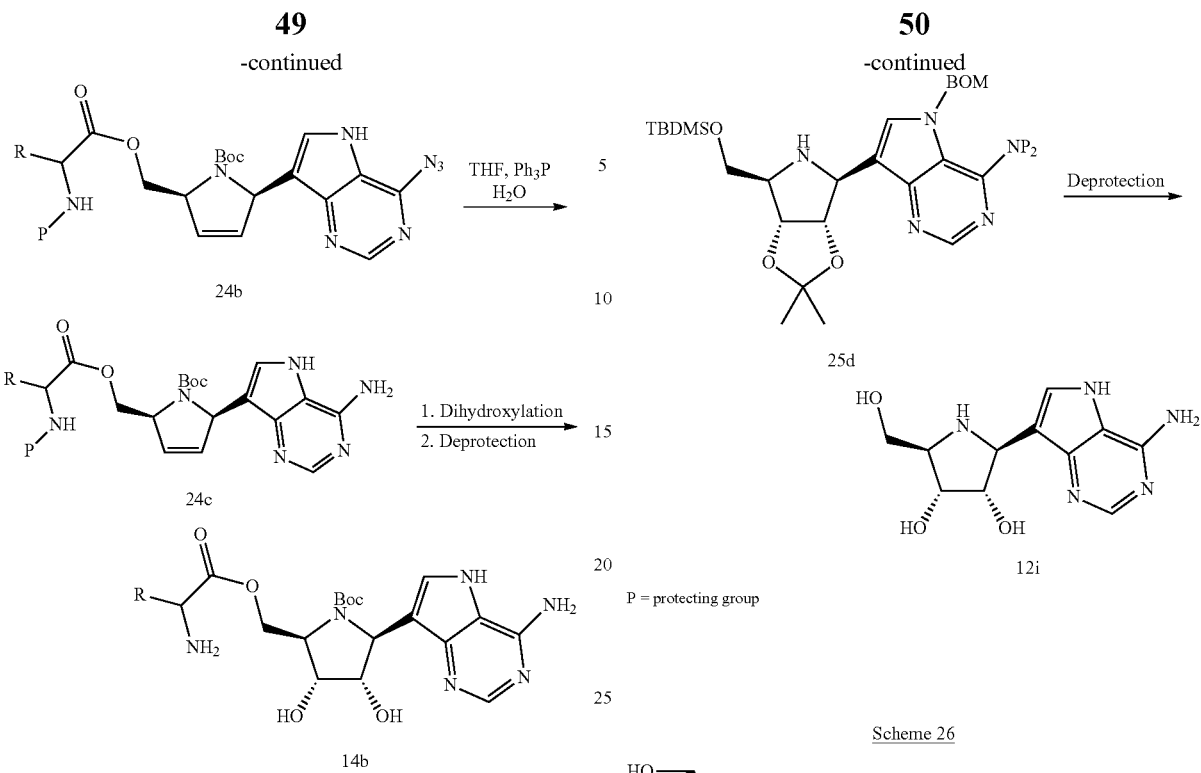
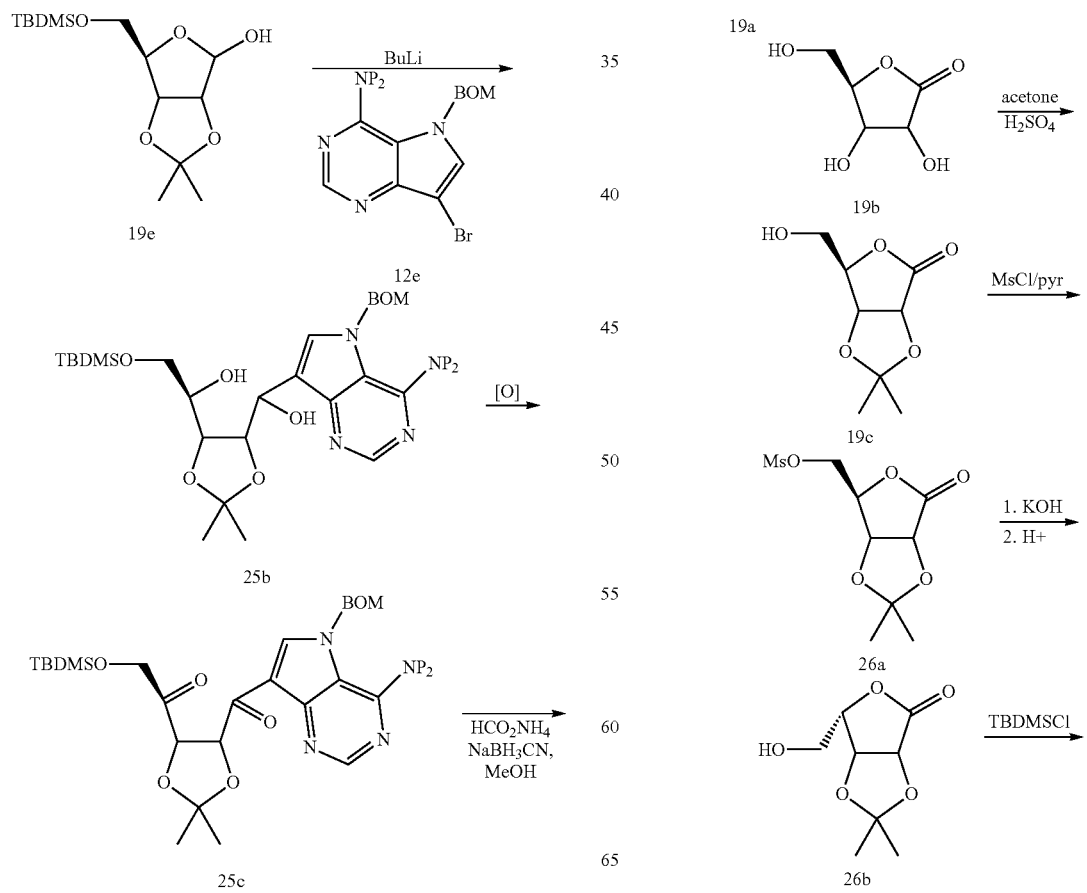

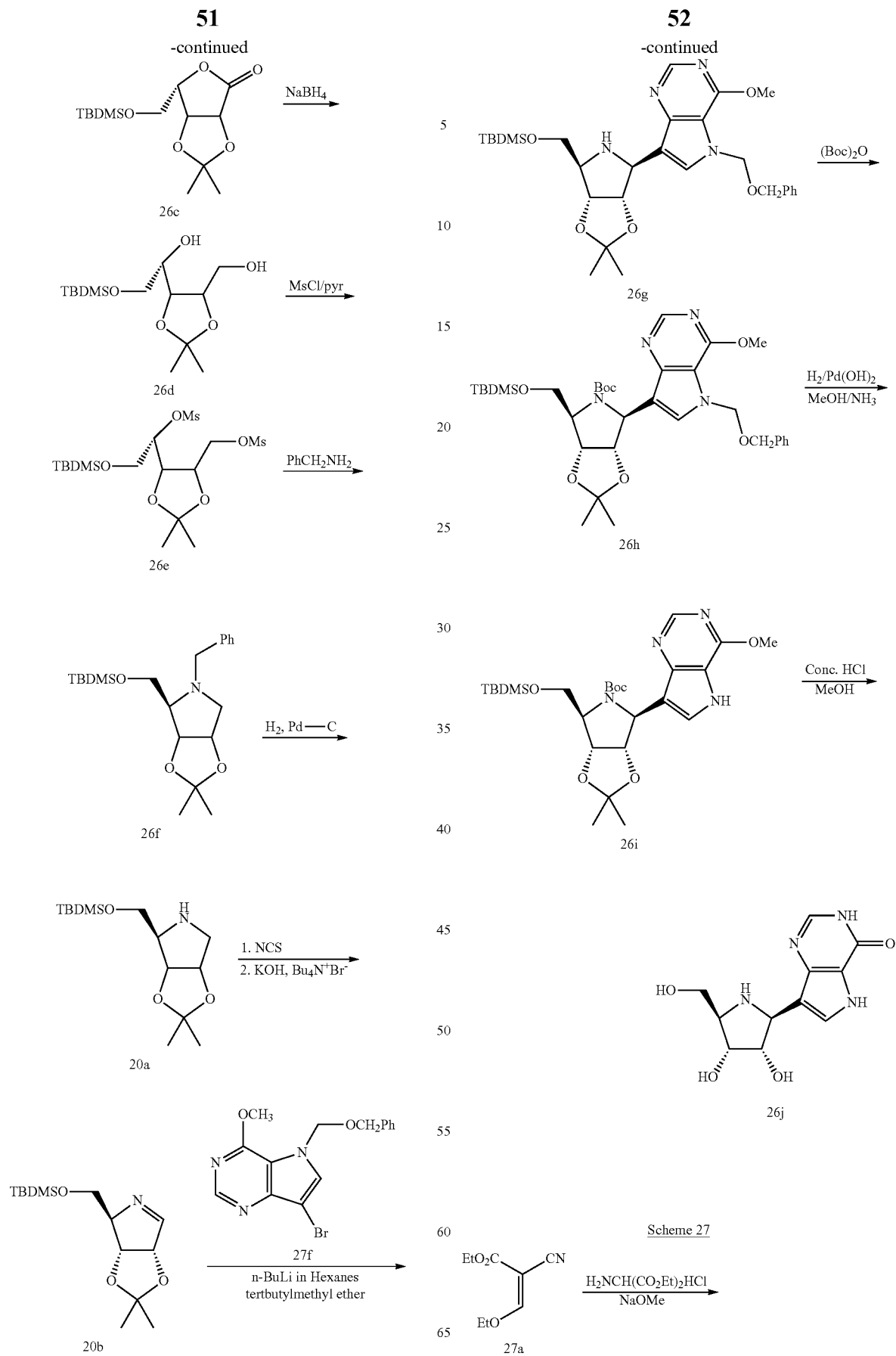

53
-continued
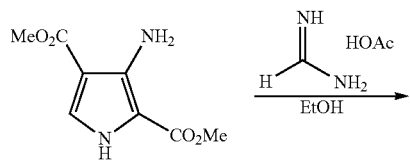
27b
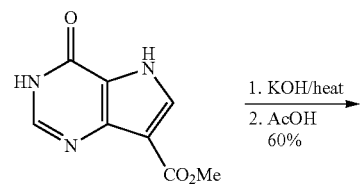
27c
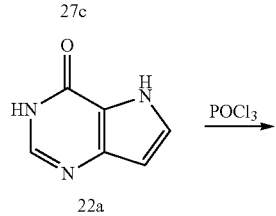
22a
Scheme 28
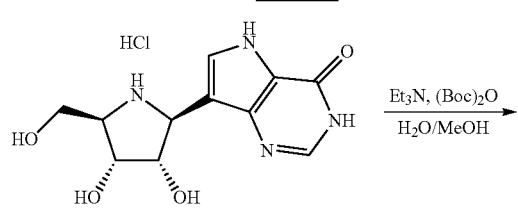
26j
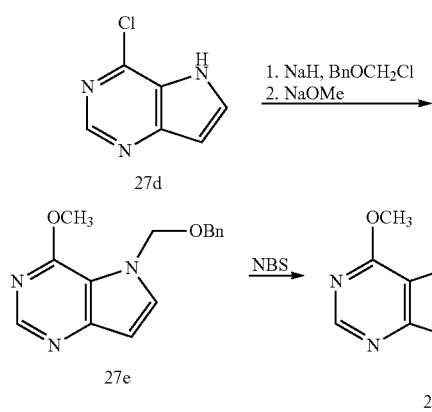
28a
54
-continued
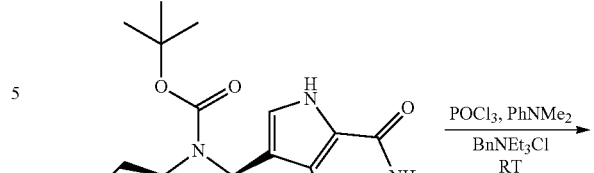
28b
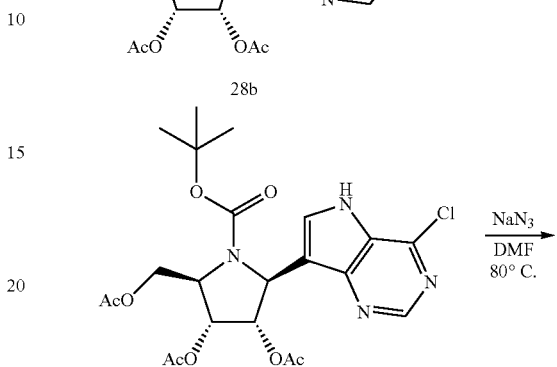
28c
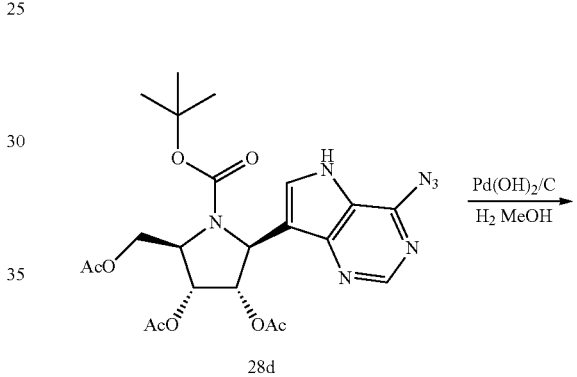
28d
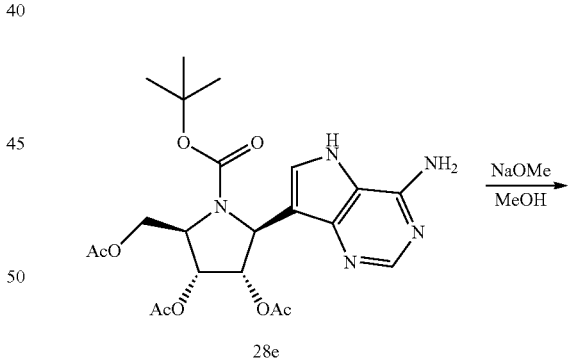
28e
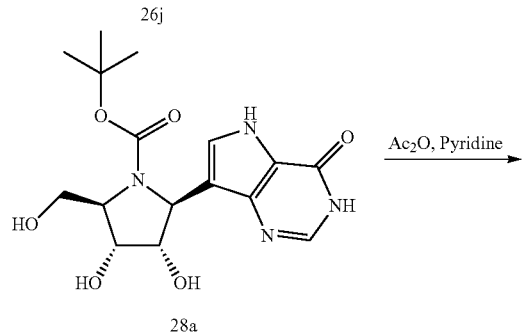
28f

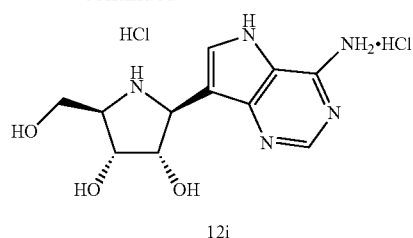
12i
Scheme 29
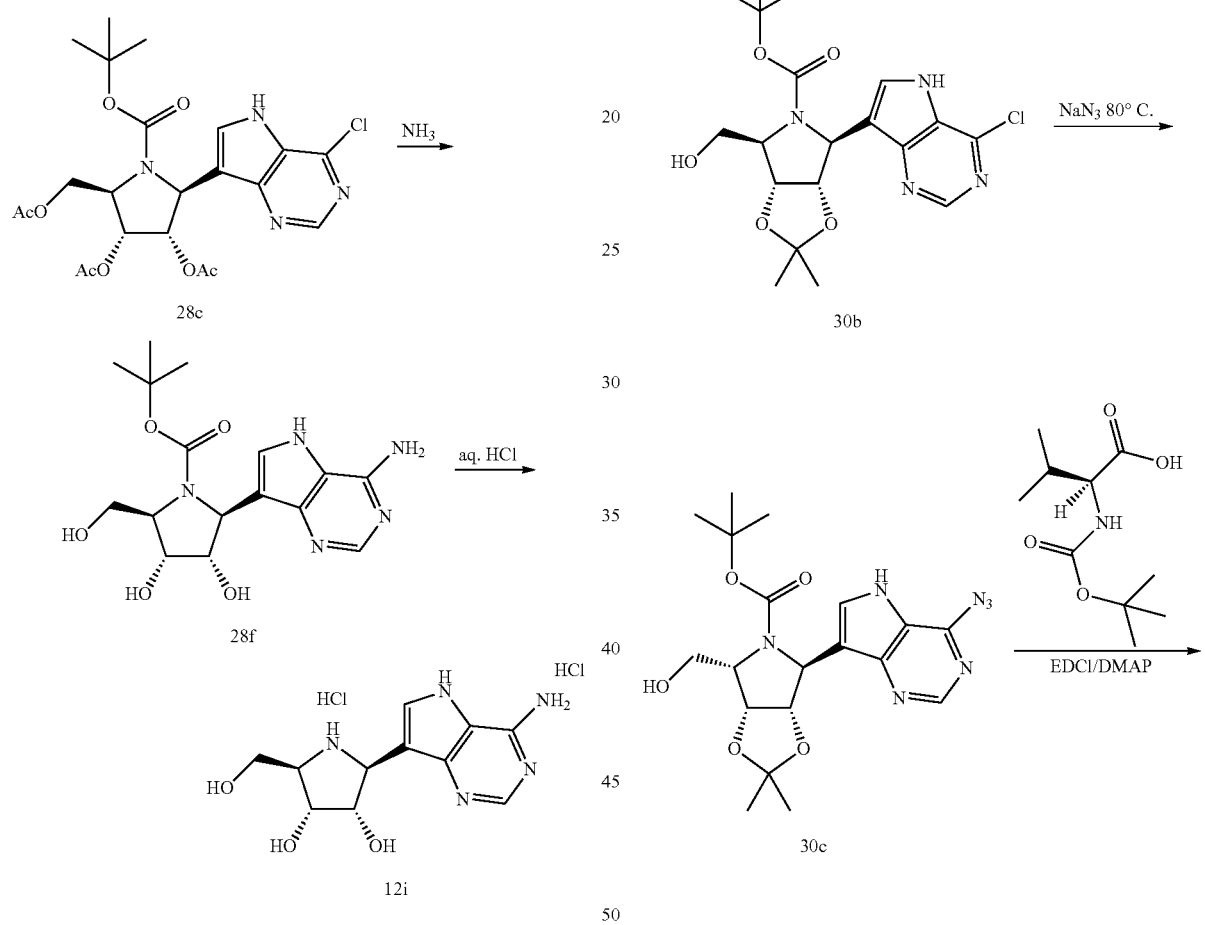
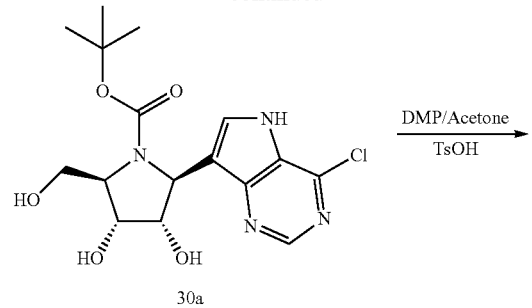
30a
Scheme 30
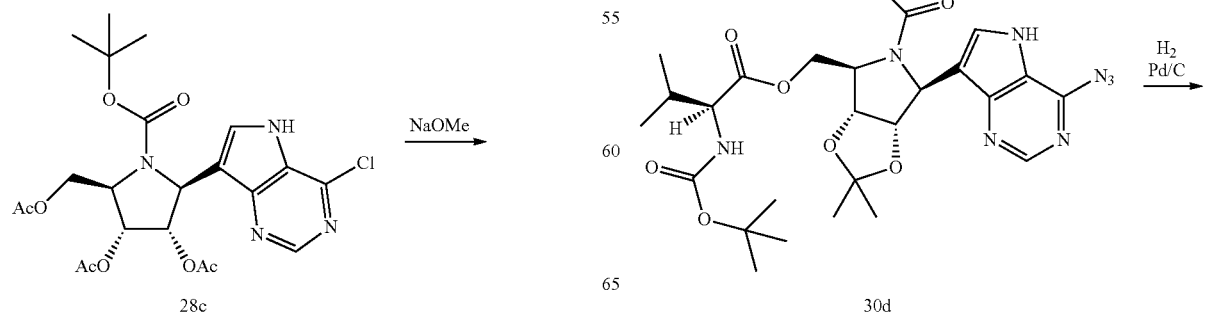

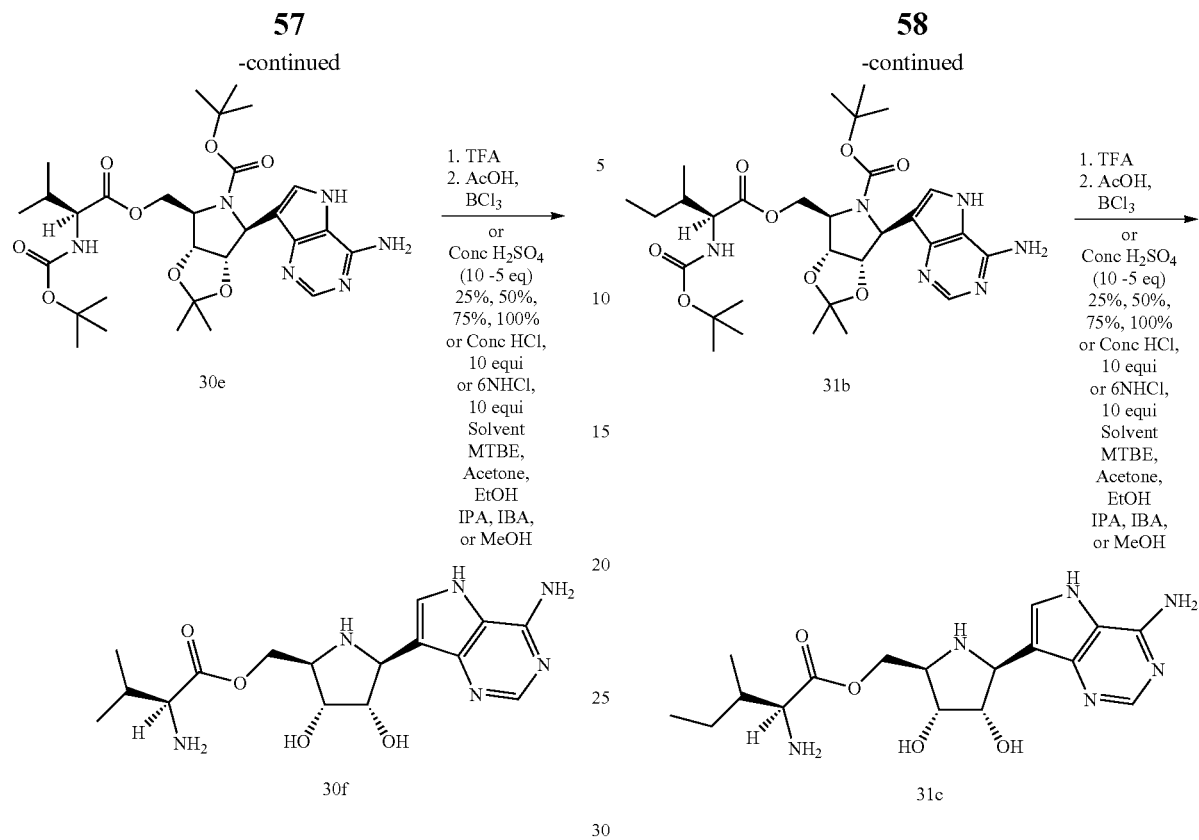
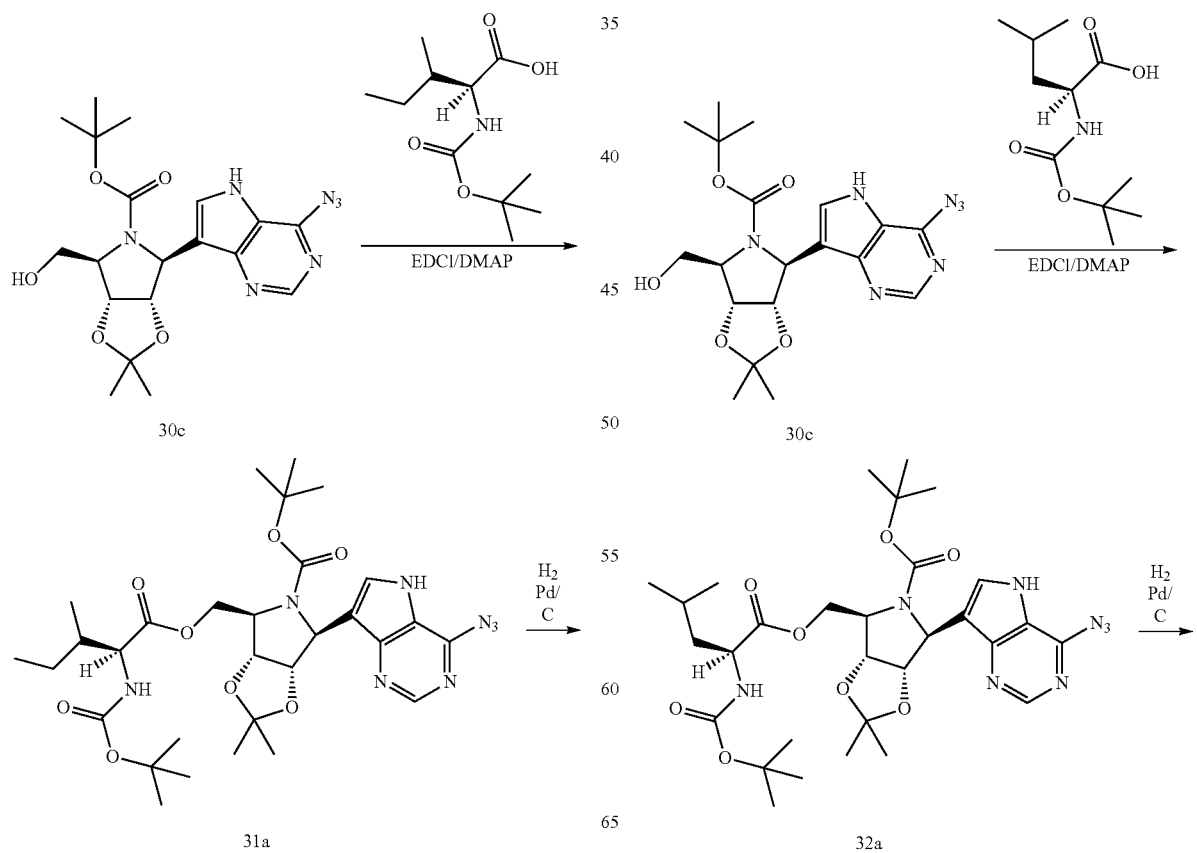
Scheme 31
Scheme 32

59
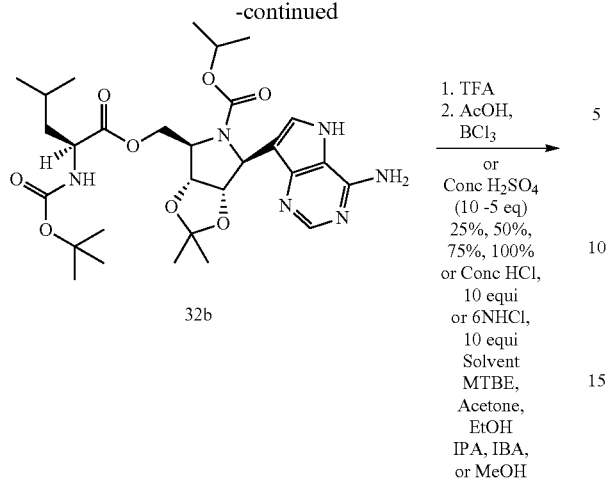
32b
1. TFA
2. AcOH, BCl₃
or
Conc H₂SO₄
(10-5 eq)
25%, 50%, 75%, 100%
or Conc HCl, 10 equi
or 6NHCl, 10 equi
Solvent
MTBE, Acetone, EtOH
IPA, IBA, or MeOH
60
-continued
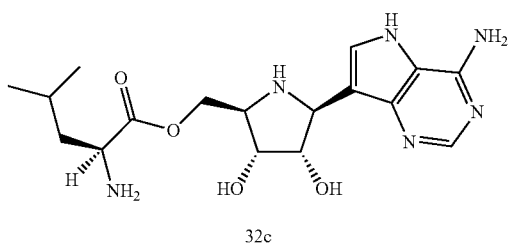
32c
Scheme 33
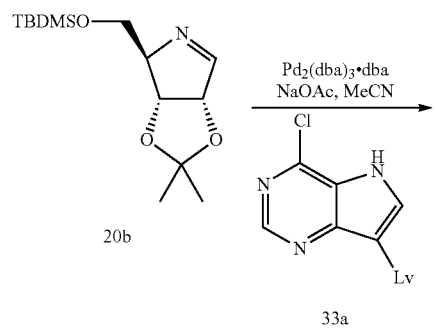
20b
Pd₂(dba)₃·dba
NaOAc, MeCN
33a
Lv = leaving group
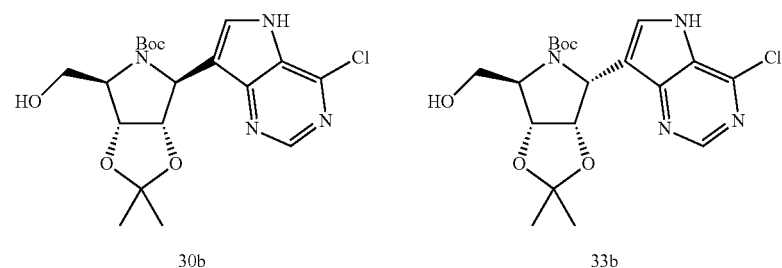
30b            33b
1. NH₃
2. HCl
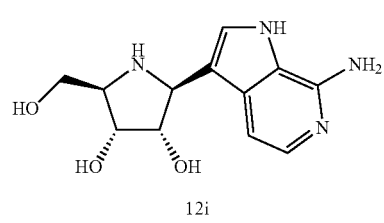
12i Scheme 34
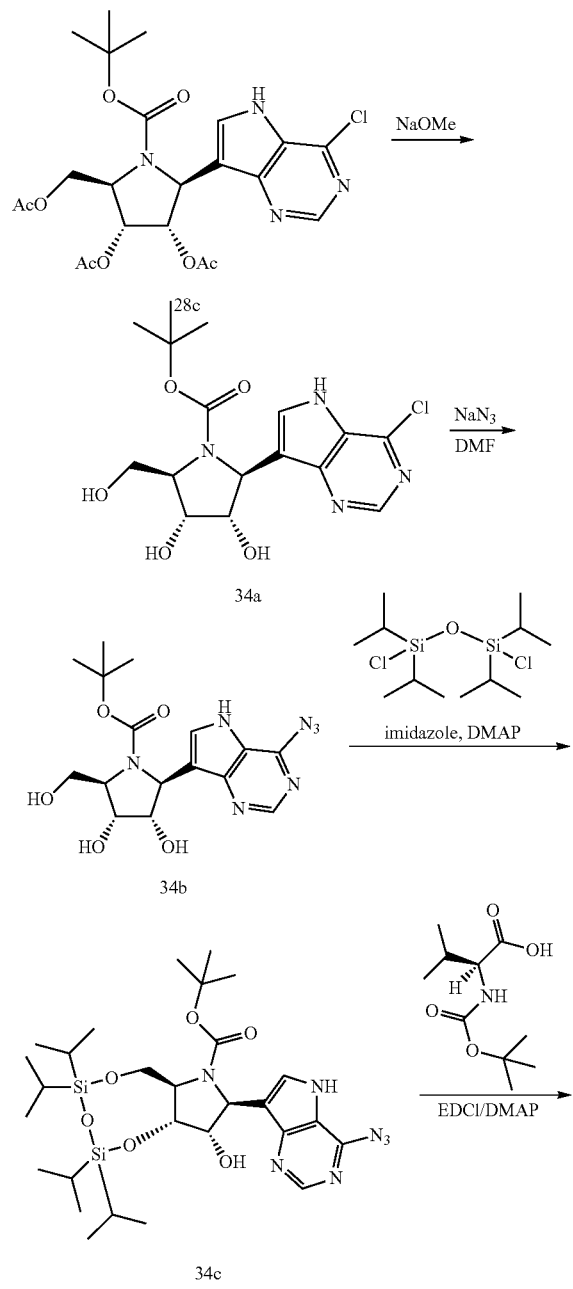
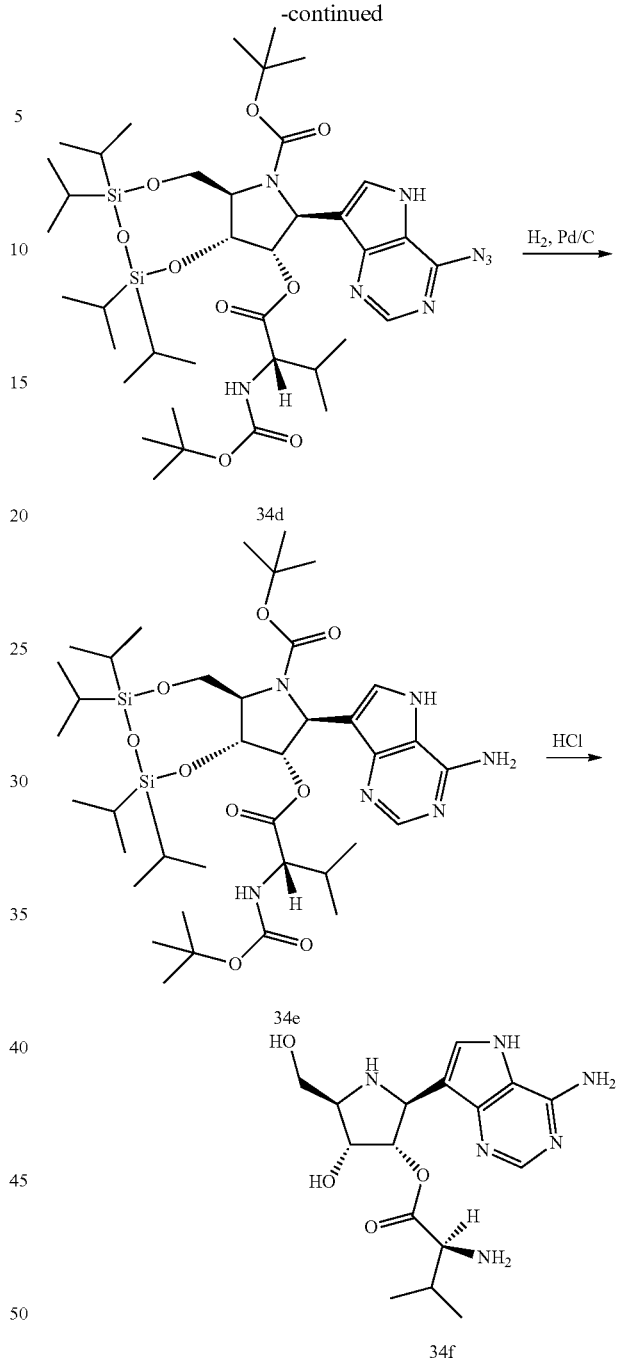
Scheme 35
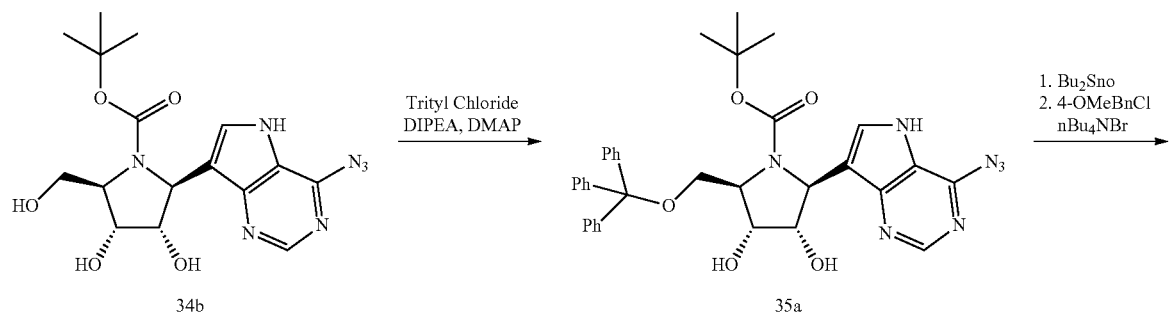

-continued
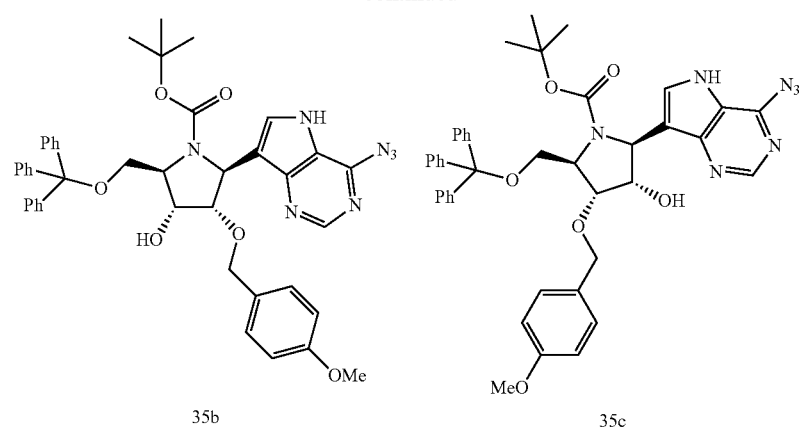
35b      35c
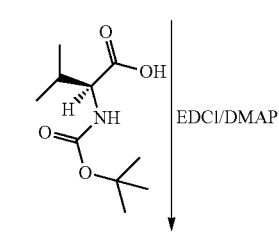
EDCl/DMAP
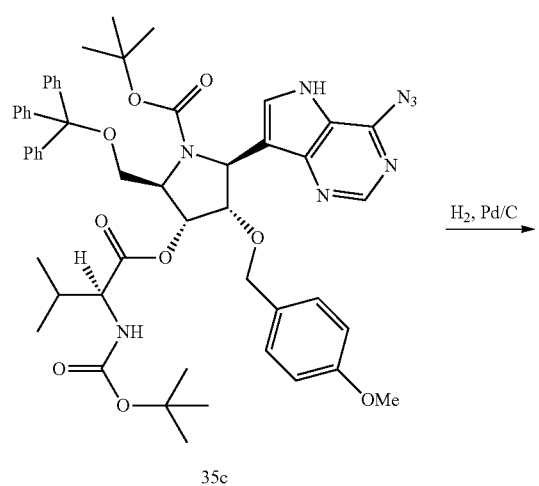
35c
H₂, Pd/C
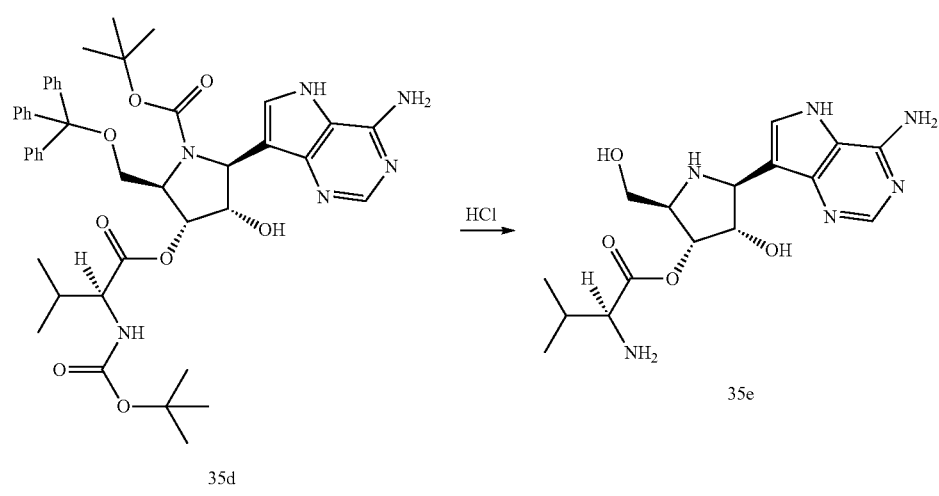 [SMILES: CC(C)[C@H](NC(=O)OC(C)(C)C)C(=O)O[C@H]1[C@@H](O)[C@H](c2c[nH]c3c(N)ncnc23)N(C(=O)OC(C)(C)C)[C@@H]1COC(c1ccccc1)(c1ccccc1)c1ccccc1 ; Cl ; CC(C)[C@H](N)C(=O)O[C@H]1[C@@H](O)[C@H](c2c[nH]c3c(N)ncnc23)N[C@@H]1CO]
35d     HCl     35e Scheme 36
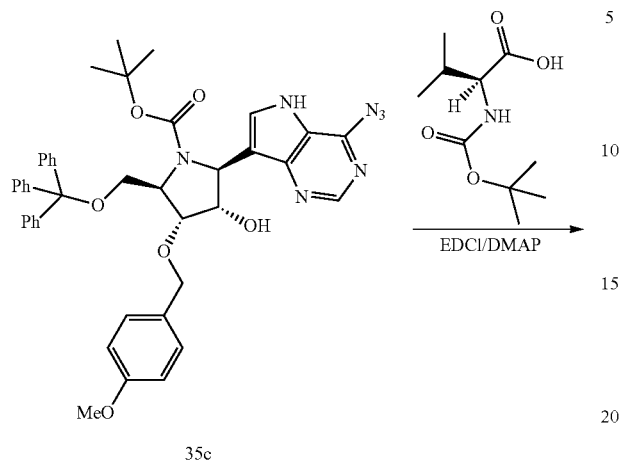
35c
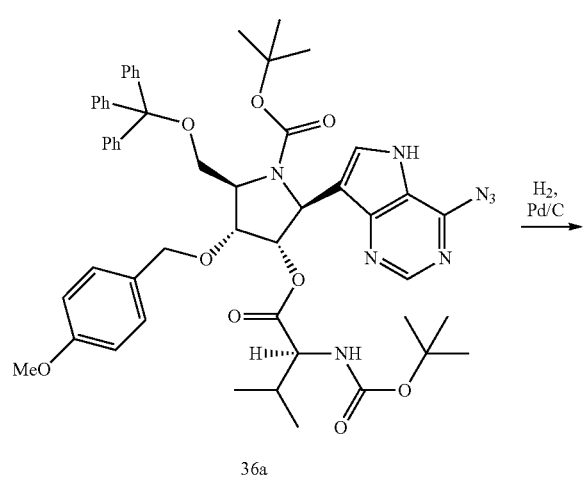
36a
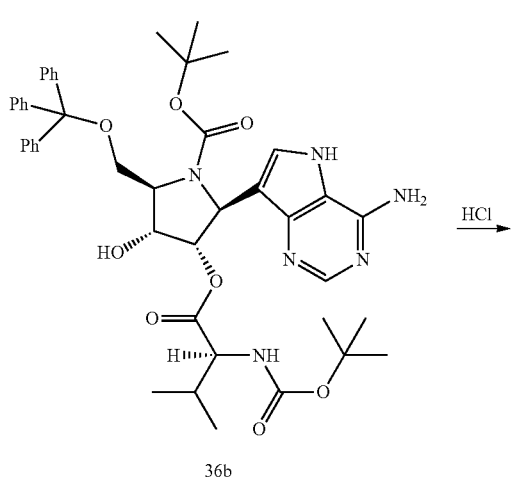
36b
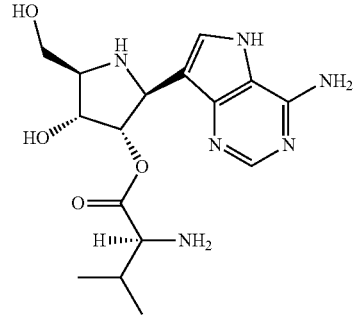
34f
Scheme 37
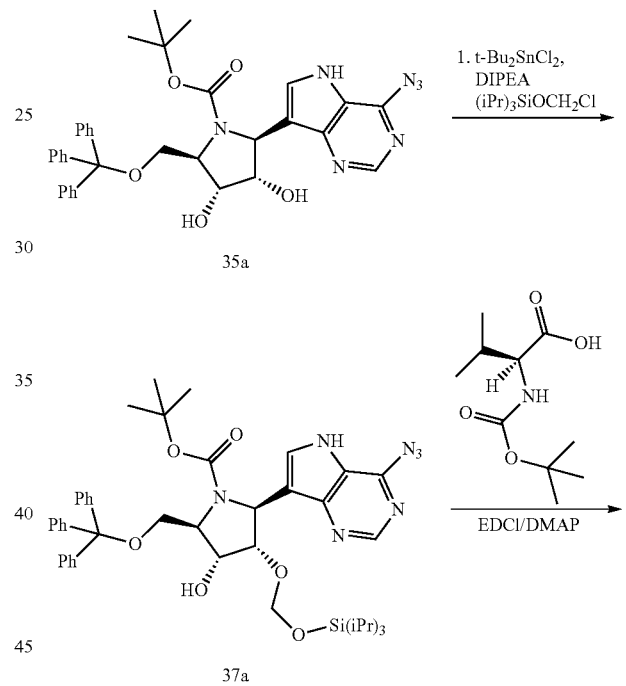
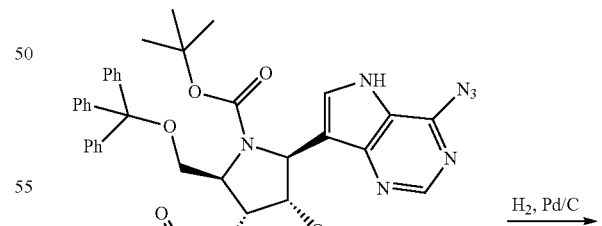
37b

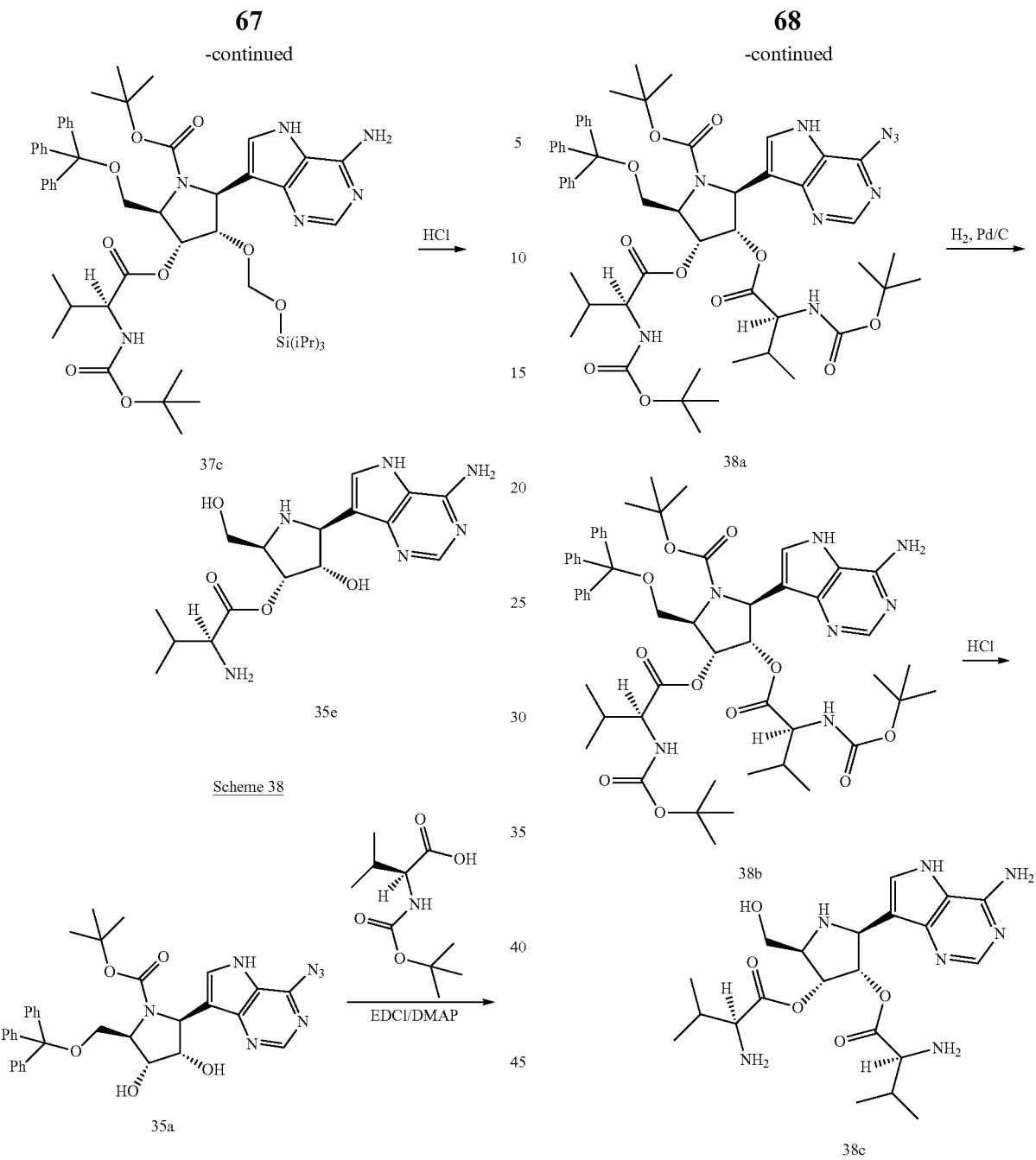
Scheme 38
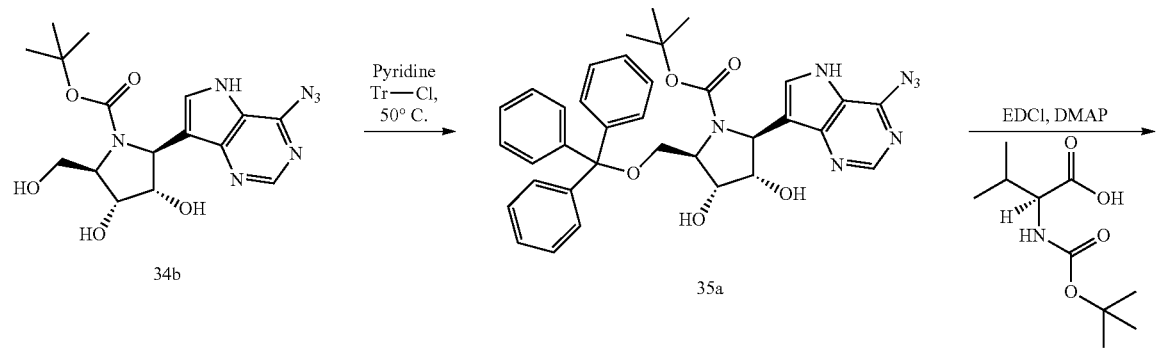
Scheme 39A

69
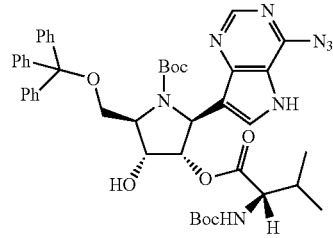
39a
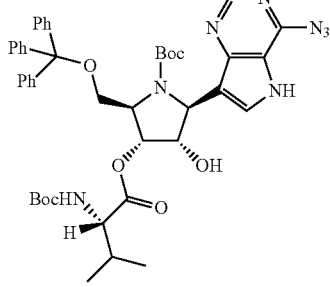
39b
70
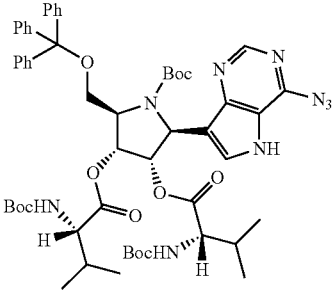
38a
| Pd/C EtOH H₂ | Pd/C EtOH H₂ | Pd/C EtOH H₂ |
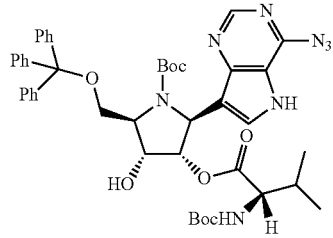
39d
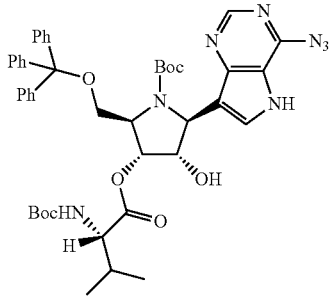
39e
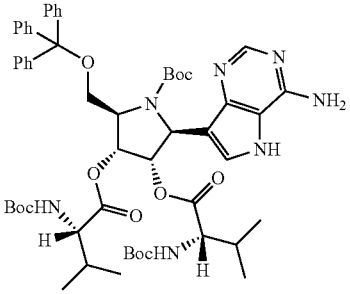
38b
Scheme 39B
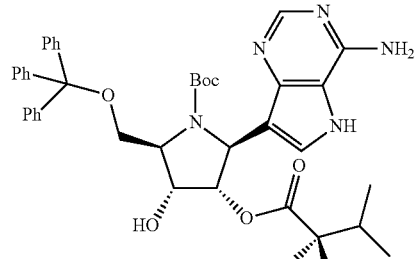
39d
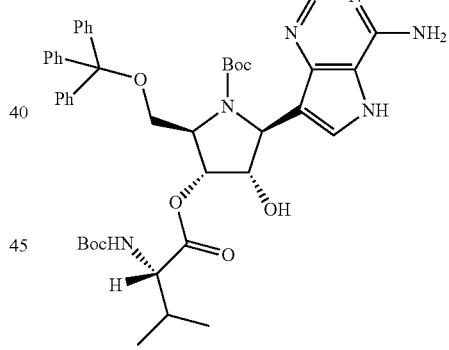
39e
TFA or Conc H₂SO₄ or Conc HCl →
TFA or Conc H₂SO₄ or Conc HCl →
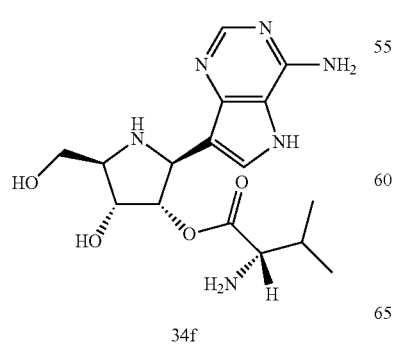
34f
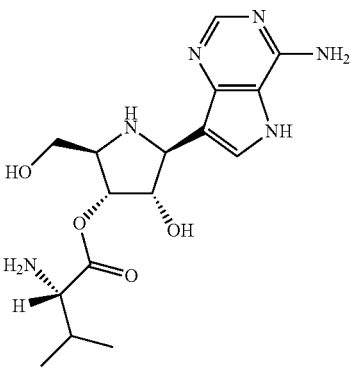
35e

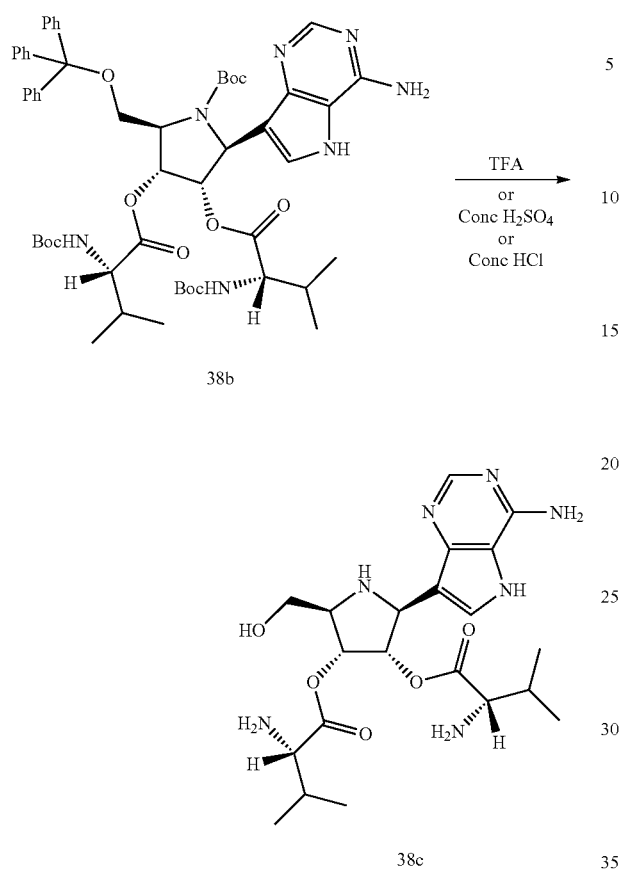

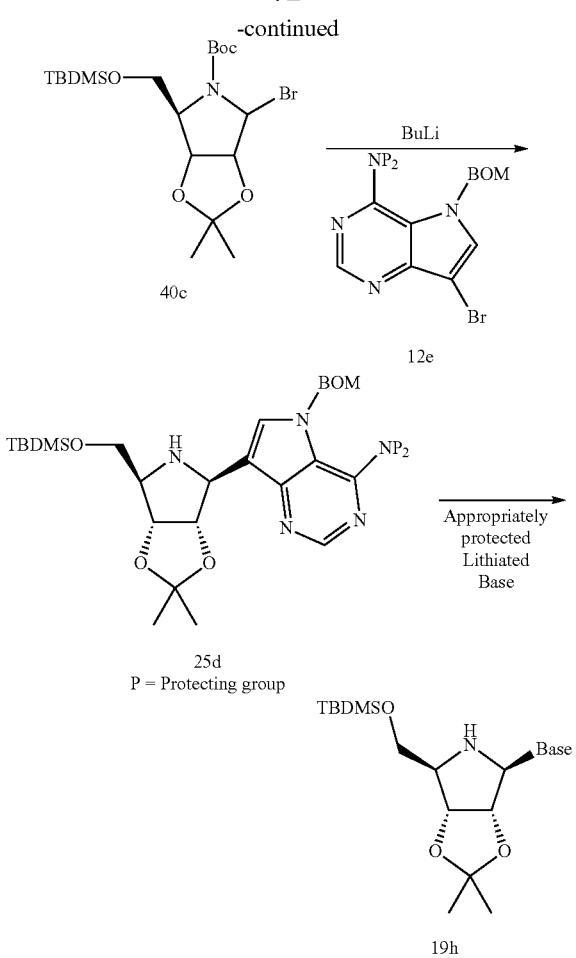

Scheme 40

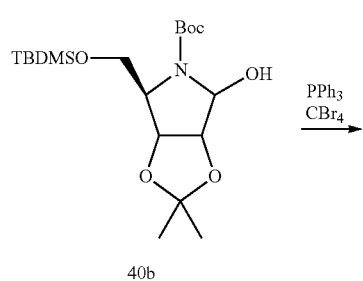

References for preparation of (3aR,4R,6aR)-tert-butyl 4-(((tert-butyldimethylsilyl)oxy)methyl)-2,2-dimethyl-6-oxodihydro-3aH-[1,3]dioxolo[4,5-c]pyrrole-5(4H)-carboxylate (40a):
1. Malladi, Venkata L. A.; Sobczak, Adam J.; Meyer, Tiffany M.; Pei, Dehua; Wnuk, Stanislaw F; Bioorganic & Medicinal Chemistry (2011), 19(18), 5507-5519.
2. Fiaux, Helene; Kuntz, Douglas A.; Hoffman, Daniela; Janzer, Robert C.; Gerber-Lemaire, Sandrine; Rose, David R.; Juillerat-Jeanneret; Bioorganic & Medicinal Chemistry (2008), 16(15), 7337-7346.
3. Yokoyama, Masataka; Ikenogami, Taku; Togo, Hideo. Inage-ku, Yayoi-cho; Perkin 1 (2000), (13), 2067-2071.
4. Zanardi, Franca; Battistini, Lucia; Nespi, Marika; Rassu, Gloria; Spanu, Pietro; Cornia, Mara; Casiraghi, Giovanni; Tetrahedron: Asymmetry (1996), 7(4), 1167-1180.

References for reduction of Lactone (40a) to Lactol (40b):
1. Malladi, Venkata L. A.; Sobczak, Adam J.; Meyer, Tiffany M.; Pei, Dehua; Wnuk, Stanislaw F; Bioorganic & Medicinal Chemistry (2011), 19(18), 5507-5519.
2. Wang, Xiao-Ling; Huang, Wen-Feng; Lei, Xin-Sheng; Wei, Bang-Guo; Lin, Guo-Qiang; Tetrahedron (2011), 67(26), 4919-4923
3. Liu, Xue-Kui; Qiu, Shi; Xiang, Yong-Gang; Ruan, Yuan-Ping; Zheng, Xiao; Huang, Pei-Qiang; Journal of Organic Chemistry (2011), 76(12), 4952-4963.
4. Hulme, Alison N.; Montgomery, Charles H; Tetrahedron Letters (2003), 44(41), 7649-7653.

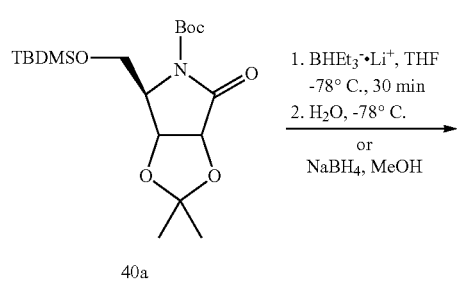

References for Lactol to Bromo compound (40c):

1. Reddy, P. Ganapati; Chun, Byoung-Kwon; Zhang, Hai-Ren; Rachakonda, Suguna; Ross, Bruce S.; Sofia, Michael J; Journal of Organic Chemistry (2011), 76(10), 3782-3790.
2. Chatterjee, Abhishek; Hazra, Amrita B.; Abdelwahed, Sameh; Hilmey, David G.; Begley, Tadhg P; Angewandte Chemie, International Edition (2010), 49(46), 8653-8656.
3. WO 2010075549 A2 (incorporated by reference).
4. WO 2010075517 A2 (incorporated by reference).
5. WO 2009152095 A2 (incorporated by reference).
6. Castro, Bertrand R. Ecole Nationale Superieure de Chimie de Montpellier, Montpellier, Fr. Organic Reactions (Hoboken, N.J., United States) (1983), 29 Publisher: John Wiley & Sons, Inc.

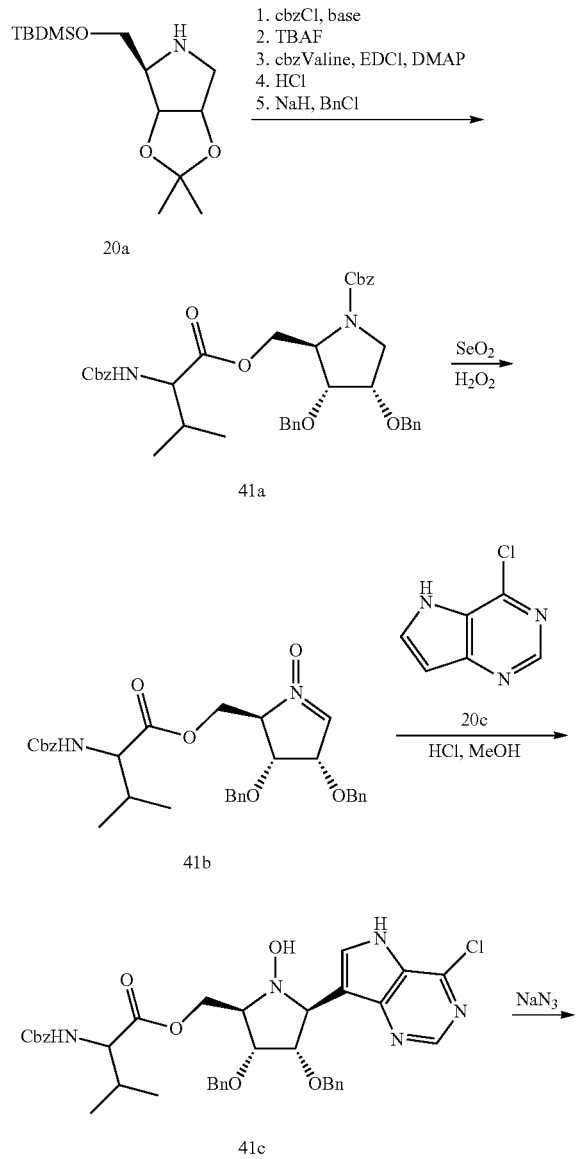

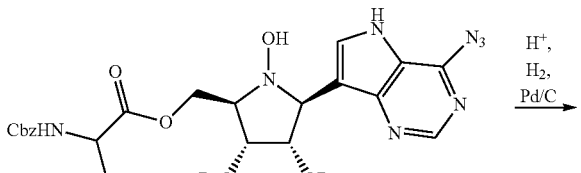

In an embodiment, the compound of Formula I is selected from the group consisting of

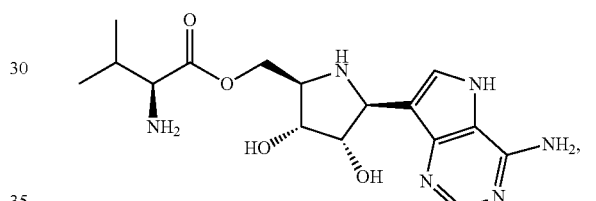

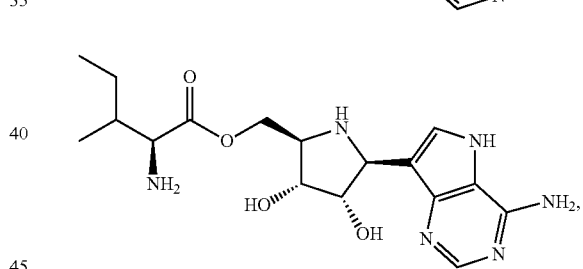

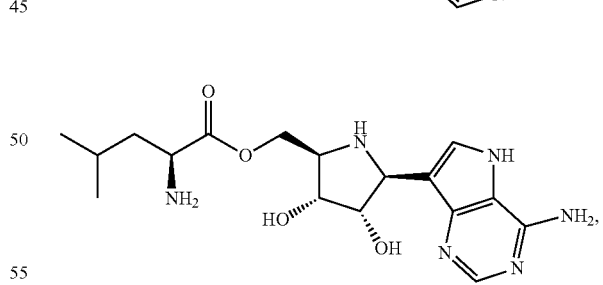

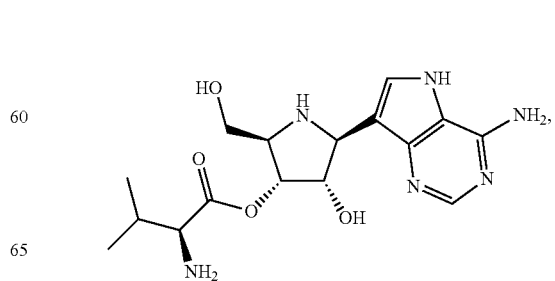

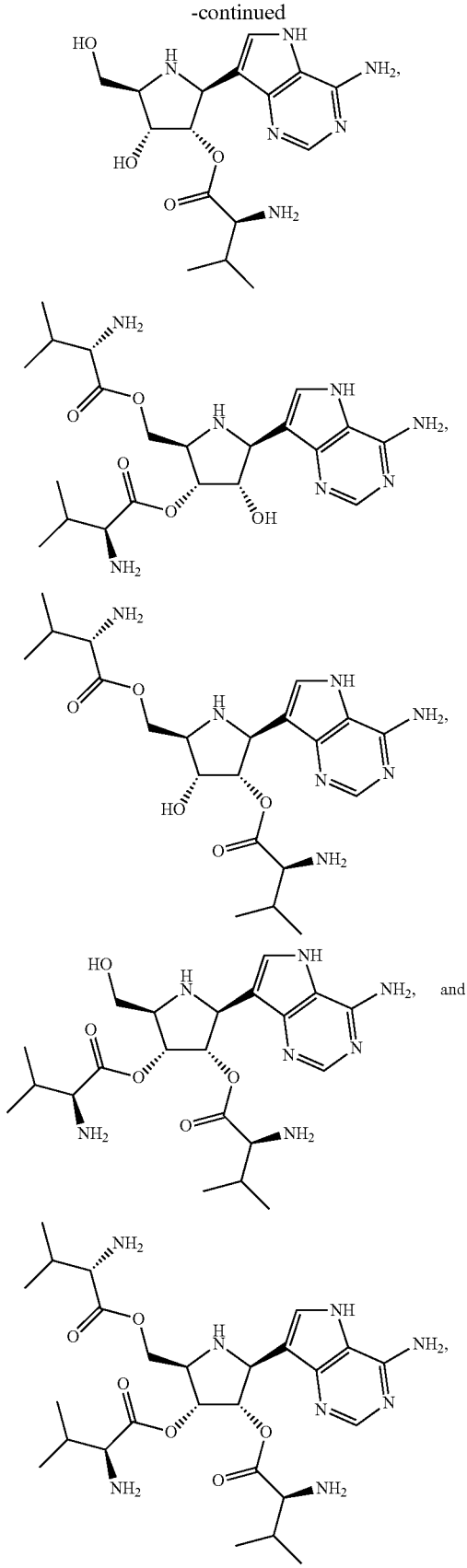

and pharmaceutically acceptable salts thereof.

In an embodiment, the compound of Formula I is

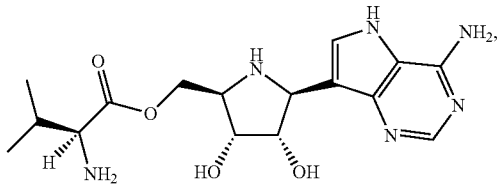

or a pharmaceutically acceptable salt thereof.

In an embodiment, the compound of Formula I is selected from the group consisting of

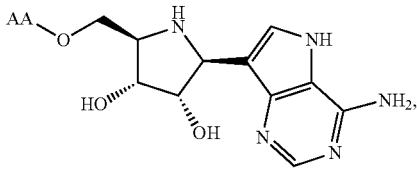

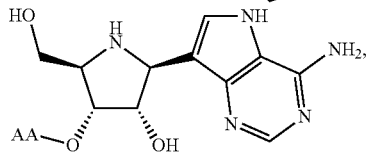

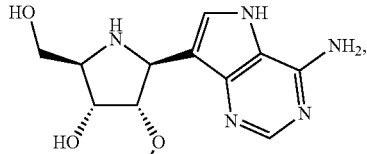

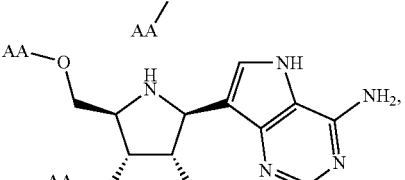

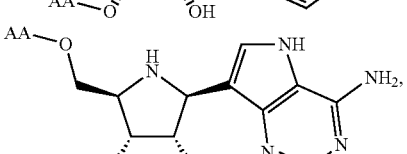

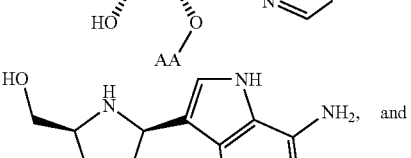

and

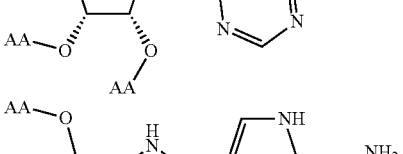

and pharmaceutically acceptable salts thereof, wherein in each instance "AA" represents an aminoacyl group of an amino acid, e.g. alanyl, leucyl, methionyl, or valinyl.

In an embodiment, the compound of Formula I is selected from the group consisting of

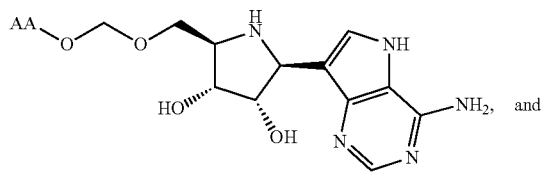

and

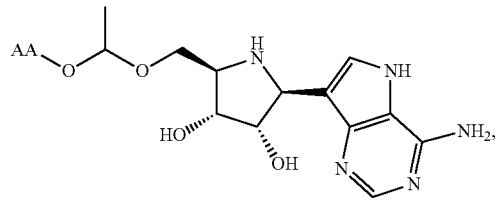

and pharmaceutically acceptable salts thereof, wherein in each instance "AA" represents an aminoacyl group of an amino acid, e.g. alanyl, leucyl, methionyl, or valinyl.

In an embodiment, the compound of Formula I is selected from the group consisting of

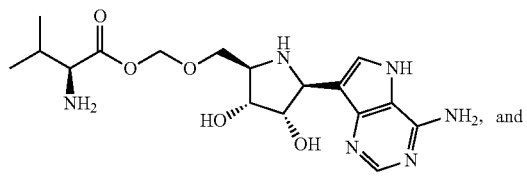

and

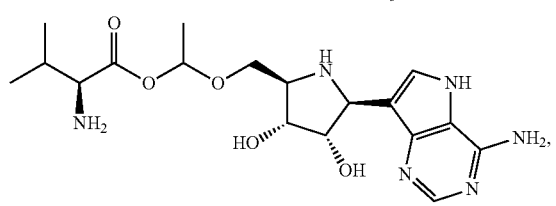

and pharmaceutically acceptable salts thereof.

In an embodiment, the compound of Formula I is selected from the group consisting of

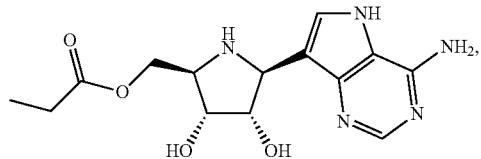

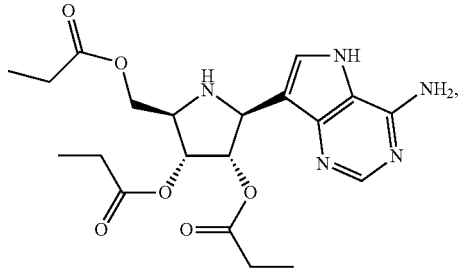

-continued

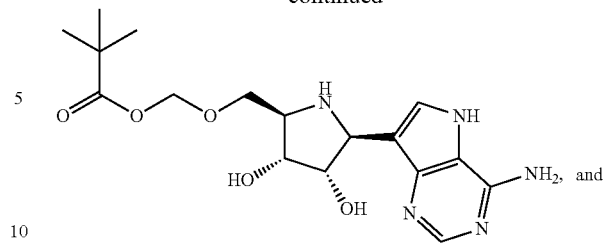

and

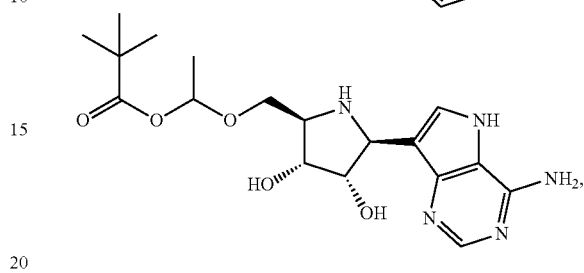

and pharmaceutically acceptable salts thereof.

In an embodiment, the compound of Formula I is selected from the group consisting of

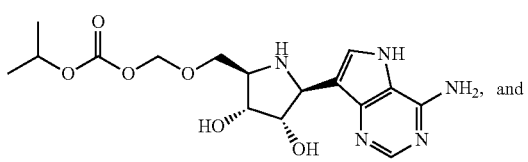

and

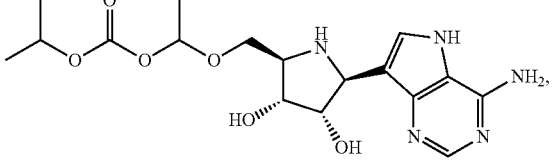

and pharmaceutically acceptable salts thereof

In an embodiment, the compound of Formula I is

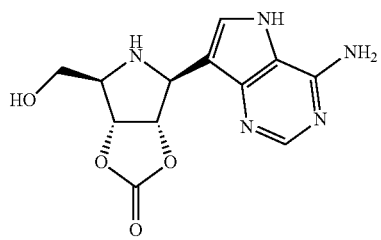 [SMILES: Nc1ncnc2c([C@@H]3N[C@H](CO)[C@H]4OC(=O)O[C@H]43)c[nH]c12]

or a pharmaceutically acceptable salt thereof

In an embodiment, the compound of Formula I is

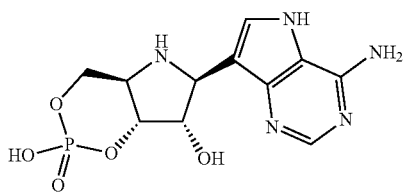

or a pharmaceutically acceptable salt thereof.

In an embodiment, the compound of Formula I is selected from the group consisting of

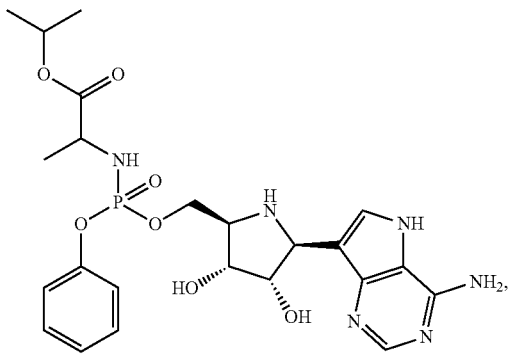

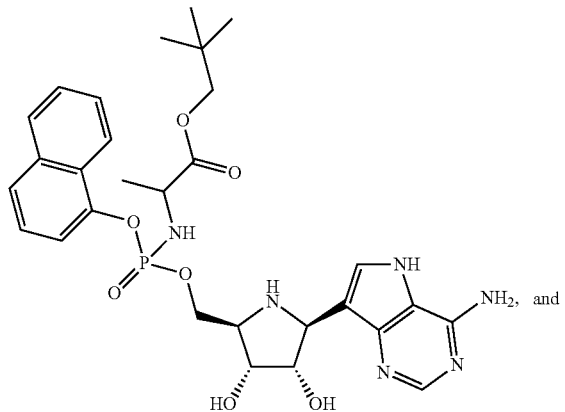

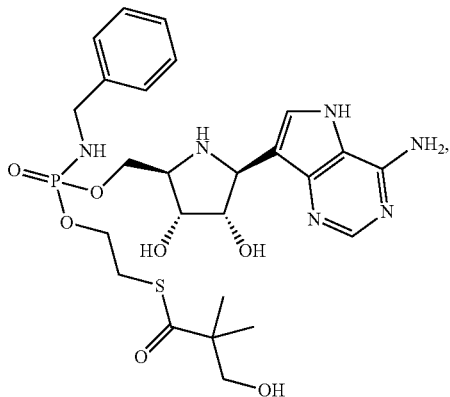

and pharmaceutically acceptable salts thereof.

In an embodiment, the compound of Formula I is selected from the group consisting of

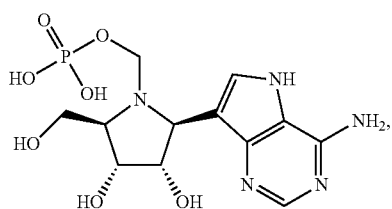

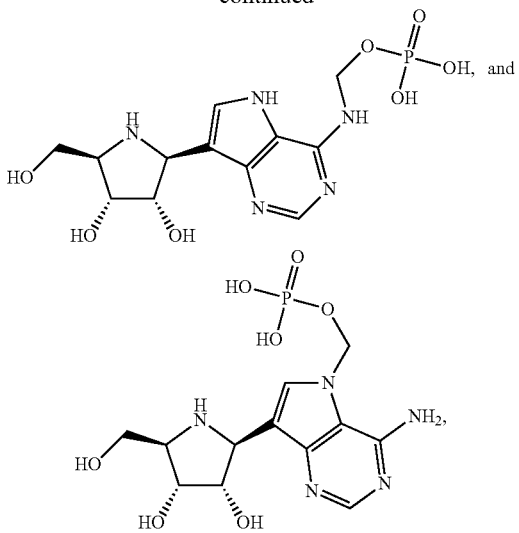

and pharmaceutically acceptable salts thereof.

In an embodiment, the compound of Formula I is selected from the group consisting of

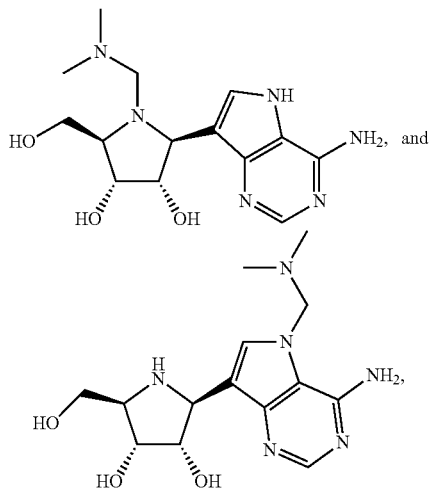

and pharmaceutically acceptable salts thereof

In an embodiment, the compound of Formula I is

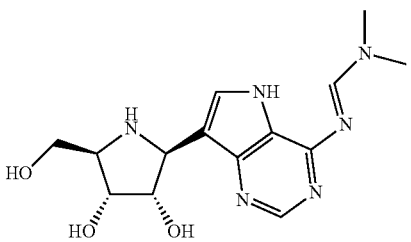 [SMILES: CN(C)/C=N/c1ncnc2c([C@@H]3N[C@H](CO)[C@@H](O)[C@H]3O)c[nH]c12]

or a pharmaceutically acceptable salt thereof.

An aspect of the invention is a pharmaceutical composition comprising a compound of the invention, or a pharmaceutically acceptable salt thereof, and a pharmaceutically acceptable carrier.

An aspect of the invention is a method of preparing a pharmaceutical composition. The method includes the step of combining a compound of the invention, or a pharmaceutically acceptable salt thereof, with a pharmaceutically acceptable carrier.

Compounds of the invention are useful for inhibiting nucleic acid polymerase activity of certain viruses. Compounds of the invention are also useful for inhibiting viral replication or treating viral infections.

Animal RNA viruses are classified into three distinct groups based on their genome and mode of replication (and the numerical groups based on the older Baltimore classification):

Double-stranded (ds) RNA viruses (Baltimore classification Group III) contain from one to a dozen different RNA molecules, each of which codes for one or more viral proteins. Examples of dsRNA viruses include reoviridae.

Positive-sense single-stranded (ss) RNA viruses (Baltimore classification Group IV) have their genome directly utilized as if it were mRNA, producing a single protein which is modified by host and viral proteins to form the various proteins needed for replication. One of these includes RNA-dependent RNA polymerase, which copies the viral RNA to form a double-stranded replicative form, which in turn directs the formation of new virions. Examples of positive-sense ssRNA viruses include togaviridae, flaviviridae, calciviridae, coronaviridae, picornaviridae, and togaviridae.

Negative-sense ssRNA viruses (Baltimore classification Group V) must have their genome copied by an RNA polymerase to form positive-sense RNA. This means that the virus must bring along with it the RNA-dependent RNA polymerase enzyme. The positive-sense RNA molecule then acts as viral mRNA, which is translated into proteins by the host ribosomes. The resultant protein goes on to direct the synthesis of new virions, such as capsid proteins and RNA replicase, which is used to produce new negative-sense RNA molecules. Negative-sense ssRNA viruses include bornaviridae, filoviridae, orthomyxoviridae, paramyxoviridae, rhabdoviridae, arenaviridae, and bunyaviridae.

Retroviruses (Baltimore classification Group VI) have a single-stranded RNA genome but are generally not considered RNA viruses because they use DNA intermediates to replicate. Reverse transcriptase, a viral enzyme that comes from the virus itself after it is uncoated, converts the viral RNA into a complementary strand of DNA, which is copied to produce a double stranded molecule of viral DNA. After this DNA is integrated, expression of the encoded genes may lead the formation of new virions. Retroviruses include without limitation HIV-1 and HIV-2.

An aspect of the invention is a method of inhibiting viral nucleic acid polymerase activity of a virus. The method includes the step of contacting a viral nucleic acid polymerase of the virus with an effective amount of a compound of the invention, or a pharmaceutically acceptable salt thereof.

In one embodiment, the viral nucleic acid polymerase is a DNA polymerase.

In one embodiment the viral nucleic acid polymerase is an RNA polymerase.

In one embodiment, the virus is selected from the group consisting of RNA viruses.

In one embodiment, the virus is selected from the group consisting of orthomyxoviridae, paramyxoviridae, arenaviridae, bunyaviridae, flaviviridae, filoviridae, togaviridae, picornaviridae, and coronaviridae.

In one embodiment, the virus is selected from the group consisting of adenovirus, rhinovirus, hepatitis A virus, hepatitis C virus, polio virus, measles virus, Ebola virus, Coxsackie virus, West Nile virus, smallpox virus, yellow fever virus, Dengue Fever virus, influenza A virus, influenza B virus, lassa virus, lymphocytic choriomeningitis virus, Junin virus, machuppo virus, guanarito virus, hantavirus, Rift Valley Fever virus, La Crosse virus, California encephalitis virus, Crimean-Congo virus, Marburg virus, Japanese encephalitis virus, Kyasanur Forest virus, Venezuelan equine encephalitis virus, Eastern equine encephalitis virus, Western equine encephalitis virus, severe acute respiratory syndrome (SARS) virus, parainfluenza virus, respiratory syncytial virus, Punta Toro virus, Tacaribe virus, and Pichinde virus.

In one embodiment, the virus is selected from the group consisting of adenovirus, Dengue Fever virus, Ebola virus, Marburg virus, influenza A virus, influenza B virus, Junin virus, measles virus, parainfluenza virus, Pichinde virus, Punta Toro virus, respiratory syncytial virus, rhinovirus, Rift Valley Fever virus, SARS virus, Tacaribe virus, Venezuelan equine encephalitis virus, West Nile virus, and yellow fever virus.

In one embodiment, the virus is selected from the group consisting of Ebola virus, yellow fever virus, Marburg virus, influenza A virus, and influenza B virus.

An aspect of the invention is a method of inhibiting replication of a virus. The method includes the step of contacting a virus with an effective amount of a compound of the invention, or a pharmaceutically acceptable salt thereof: so as to inhibit replication of the virus.

In one embodiment, the virus is selected from the group consisting of RNA viruses.

In one embodiment, the virus is selected from the group consisting of orthomyxoviridae, paramyxoviridae, arenaviridae, bunyaviridae, flaviviridae, filoviridae, togaviridae, picornaviridae, and coronaviridae.

In one embodiment, the virus is selected from the group consisting of adenovirus, rhinovirus, hepatitis A virus, hepatitis C virus, polio virus, measles virus, Ebola virus, Coxsackie virus, West Nile virus, smallpox virus, yellow fever virus, Dengue Fever virus, influenza A virus, influenza B virus, lassa virus, lymphocytic choriomeningitis virus, Junin virus, machuppo virus, guanarito virus, hantavirus, Rift Valley Fever virus, La Crosse virus, California encephalitis virus, Crimean-Congo virus, Marburg virus, Japanese encephalitis virus, Kyasanur Forest virus, Venezuelan equine encephalitis virus, Eastern equine encephalitis virus, Western equine encephalitis virus, severe acute respiratory syndrome (SARS) virus, parainfluenza virus, respiratory syncytial virus, Punta Toro virus, Tacaribe virus, and Pichinde virus.

In one embodiment, the virus is selected from the group consisting of adenovirus, Dengue Fever virus, Ebola virus, Marburg virus, influenza A virus, influenza B virus, Junin virus, measles virus, parainfluenza virus, Pichinde virus, Punta Toro virus, respiratory syncytial virus, rhinovirus, Rift Valley Fever virus, SARS virus, Tacaribe virus, Venezuelan equine encephalitis virus, West Nile virus, and yellow fever virus.

In one embodiment, the virus is selected from the group consisting of Ebola virus, yellow fever virus, Marburg virus, influenza A virus, and influenza B virus.

An aspect of the invention is a method of treating a viral infection in a subject. The method includes the step of administering to a subject in need thereof an effective amount of a compound of the invention, or a pharmaceutically acceptable salt thereof.

In one embodiment, the virus is selected from the group consisting of RNA viruses.

In one embodiment, the virus is selected from the group consisting of orthomyxoviridae, paramyxoviridae, arenaviridae, bunyaviridae, flaviviridae, filoviridae, togaviridae, picornaviridae, and coronaviridae.

In one embodiment, the virus is selected from the group consisting of adenovirus, rhinovirus, hepatitis A virus, hepatitis C virus, polio virus, measles virus, Ebola virus, Coxsackie virus, West Nile virus, smallpox virus, yellow fever virus, Dengue Fever virus, influenza A virus, influenza B virus, lassa virus, lymphocytic choriomeningitis virus, Junin virus, machuppo virus, guanarito virus, hantavirus, Rift Valley Fever virus, La Crosse virus, California encephalitis virus, Crimean-Congo virus, Marburg virus, Japanese encephalitis virus, Kyasanur Forest virus, Venezuelan equine encephalitis virus, Eastern equine encephalitis virus, Western equine encephalitis virus, severe acute respiratory syndrome (SARS) virus, parainfluenza virus, respiratory syncytial virus, Punta Toro virus, Tacaribe virus, and Pichinde virus.

In one embodiment, the virus is selected from the group consisting of adenovirus, Dengue Fever virus, Ebola virus, Marburg virus, influenza A virus, influenza B virus, Junin virus, measles virus, parainfluenza virus, Pichinde virus, Punta Toro virus, respiratory syncytial virus, rhinovirus, Rift Valley Fever virus, SARS virus, Tacaribe virus, Venezuelan equine encephalitis virus, West Nile virus, and yellow fever virus.

In one embodiment, the virus is selected from the group consisting of Ebola virus, yellow fever virus, Marburg virus, influenza A virus, and influenza B virus.

The compounds of the invention can be formulated as pharmaceutical compositions and administered to a mammalian host, such as a human patient, in a variety of forms adapted to the chosen route of administration, e.g., orally or parenterally, by intravenous, intraperitoneal, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following diluents and carriers: binders such as gum tragacanth, *acacia*, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or physiologically acceptable aqueous solution, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of Formula I to the skin are known to the art; for example, see Jacquet et al. (U.S. Pat. No. 4,608,392; incorporated herein by reference), Geria (U.S. Pat. No. 4,992,478; incorporated herein by reference), Smith et al. (U.S. Pat. No. 4,559,157; incorporated herein by reference), and Wortzman (U.S. Pat. No. 4,820,508; incorporated herein by reference).

Useful dosages of the compounds of the invention can be determined by comparing their in vitro activity and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular compound or salt selected but also with the route of administration, the nature of the condition being treated, and the age and condition of the patient and will be ultimately at the discretion of the attendant physician or clinician.

In general, however, a suitable dose will be in the range of from about 0.5 to about 100 mg/kg body weight of the recipient per day, e.g., from about 3 to about 90 mg/kg of body weight per day, from about 6 to about 75 mg per kilogram body weight per day, from about of 10 to about 60 mg/kg/day, or from about 15 to about 50 mg/kg/day.

Compounds of the invention can be conveniently formulated in unit dosage form; for example, containing 5 to 1000 mg, 10 to 750 mg, or 50 to 500 mg of active ingredient per unit dosage form. In one embodiment, the invention provides a composition comprising a compound of the invention formulated in such a unit dosage form. The desired dose may conveniently be presented in a single dose or as divided doses to be administered at appropriate intervals, for example, as two, three, four or more sub-doses per day. The sub-dose itself may be further divided, e.g., into a number of discrete loosely spaced administrations, such as multiple inhalations from an insufflator or by application of a plurality of drops into the eye.

Compounds of the invention can also be administered in combination with other therapeutic agents, for example, other agents that are useful for treating a viral infection.

The invention also provides a kit comprising a compound of the invention, or a pharmaceutically acceptable salt thereof; at least one other therapeutic agent, packaging material, and instructions for administering the compound of the invention or the pharmaceutically acceptable salt thereof and the other therapeutic agent or agents to a mammal to treat a viral infection in the mammal. In one embodiment, the mammal is a human.

The invention will now be illustrated by the following non-limiting Examples.

EXAMPLES

Example 1

(2S,3S,4R,5R)-2-(4-amino-5H-pyrrolo[3,2-d]pyrimidin-7-yl)-5-(hydroxymethyl)pyrrolidine-3,4-diol dihydrochloride (12i)

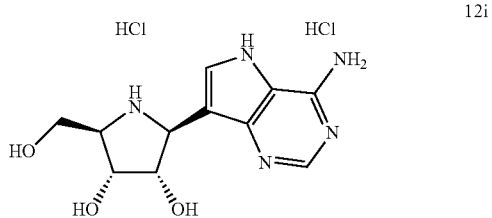 [SMILES: Cl ; Cl ; Nc1ncnc2c([C@@H]3N[C@H](CO)[C@@H](O)[C@H]3O)c[nH]c12]

12i (2S,3S,4R,5R)-tert-butyl 2-(4-amino-5H-pyrrolo[3,2-d]pyrimidin-7-yl)-3,4-dihydroxy-5-(hydroxymethyl)pyrrolidine-1-carboxylate (28f) was treated as follows in three batches.

Batch 1. (28f) was dissolved in aq. HCl (1658.8 mmol, 118 mL of conc. HCl and 293 mL of water).

Batch 2. (28f) was dissolved in aq. HCl (239.6 mmol, 169 mL of conc. HCl and 421 mL of water).

Batch 3. (28f) was dissolved in aq. HCl (263.5 mmol, 186 mL of conc. HCl and 468 mL of water).

The reaction mixtures were stirred at room temperature for 30 min (strong evolution of $CO_2$ gas) and then each batch was concentrated in vacuum to dryness (80-90° C.). Batches 2 and 3 were pooled to give 226 g of damp clear yellow product. Batch 1 gave 91.4 g of a dark grayish product. The crystallization was done as follows: For batches 2 and 3 wet product: 226 mL of water were added to the product then heated to 50° C. at which point hot ethanol was slowly added until crystallization started. The mixture was kept at 50° C. for 10 minutes then allowed to reach 25° C. with strong stirring before filtration to give light yellow colored powder of (2S,3S,4R,5R)-2-(4-amino-5H-pyrrolo[3,2-d]pyrimidin-7-yl)-5-(hydroxymethyl)pyrrolidine-3,4-diol (12i) (88 g, 52%). Batch 1 was purified the same way to give 33.0 g (59%) light grayish colored product. The total yield was 121.0 g (53.5%) after drying at 55° C. at high vacuum. The mother liquor from the recrystallization of batches 1 and 2 was reprocessed to give 15.0 g of light yellowish powder product (12i); MP: 238° C. $^1$H NMR (300 MHz, DMSO-$d_6$) δ 14.60 (s, 1H), 13.25 (s, 1H), 10.23 (s, 1H), 9.13 (s, 2H), 8.84 (s, 1H), 8.63 (s, 1H), 8.11 (d, J=3.1 Hz, 1H), 5.55 (s, 2H), 4.78 (d, J=4.4 Hz, 1H), 4.44 (dd, J=8.8, 5.0 Hz, 1H), 4.14-4.02 (m, 1H), 3.73 (d, J=5.1 Hz, 2H), 3.52 (s, 1H); $^1$H NMR (300 MHz, $D_2O$) δ 8.33 (s, 1H), 7.94 (s, 1H), 4.90 (d, J=8.9 Hz, 1H), 4.65 (s, 1H), 4.37 (dd, J=4.8, 3.4 Hz, 1H), 3.89 (s, 1H), 3.88 (s, 1H), 3.81 (dd, J=8.1, 4.5 Hz, 1H); MS (ES+) 266.3 (M+1); Optical rotation −52.69; ($H_2O$, C=1.15); Analysis: Calculated for $C_{11}H_{15}N_5O_3 \cdot 2HCl \cdot 0.25H_2O$: C, 38.55; H, 5.15; Cl, 20.44; N, 20.69; Found: C, 38.67; H, 5.05; Cl, 20.45; N, 20.42.

Alternative method for preparation of (2S,3S,4R,5R)-2-(4-amino-5H-pyrrolo[3,2-d]pyrimidin-7-yl)-5-(hydroxymethyl)pyrrolidine-3,4-diol dihydrochloride (12i) from (2R,3R,4S,5S)-2-(acetoxymethyl)-1-(tert-butoxycarbonyl)-5-(4-chloro-5H-pyrrolo[3,2-d]pyrimidin-7-yl)pyrrolidine-3,4-diyl diacetate (28c).

To a clear solution of (2R,3R,4S,5S)-2-(acetoxymethyl)-1-(tertbutoxy carbonyl)-5-(4-chloro-5H-pyrrolo[3,2-d]pyrimidin-7-yl)-pyrrolidine-3,4-diyl diacetate (28c) (40 g, 78.29 mmol) in ethanol (400 mL) was purged ammonia (35% volume with respect to ethanol) at −50° C. The chilled solution was poured carefully into autoclave and heated for 16 h at 100-105° C. TLC was checked to ensure the completion of reaction. Mixture was allowed to cool to room temperature. The solvent was distilled to furnish (2S,3S,4R,5R) -tert-butyl 2-(4-amino-5H-pyrrolo[3,2-d]pyrimidin-7-yl)-3,4-dihydroxy-5-(hydroxymethyl)pyrrolidine-1-carboxylate (28f) 38 g as dark brown sticky mass.

To a stirred solution of tert-butyl (2S,3R,4S,5S)-5-(hydroxymethyl)-2-(4-amino-5H -pyrrolo[3,2-d]pyrimidin-7-yl)-pyrrolidine-3,4-dihydroxy carboxylate (28f) (292 g, 799.16 mmol) in deionized water (584 mL) was added conc. HCl (423 mL). The resulting clear solution was stirred for 30 min at room temperature. Then it was concentrated to dryness (water bath 80-90° C.) to get a damp yellow solid. The wet cake was then diluted with deionized water (475 mL) and allowed to heat at 70° C. to get a clear solution and cooled to 50° C. Hot ethanol (1.6 L) was added slowly to get partial precipitation. The mixture was stirred for 10 min at 60° C. Mixture was allowed to cool to room temperature and cooled to 10° C. and stirred for 1 h at same temperature. The solid obtained was collected by filtration, dried at 55-60° C. until constant weight was obtained to furnish (2S,3S,4R,5R)-2-(4-amino-5H-pyrrolo[3,2-d]pyrimidin-7-yl)-5-(hydroxymethyl)pyrrolidine-3,4-diol dihydrochloride (12i) (65 g) as pale yellow to off-white solid; MP: 255.5° C. $^1$H NMR (300 MHz, DMSO-d$_6$) δ 14.64 (s, 1H), 13.19 (s, 1H), 10.20 (s, 1H), 9.11 (s, 2H), 8.83 (s, 1H), 8.64 (s, 1H), 8.11 (d, J=3.1 Hz, 1H), 5.99-5.20 (bs, 2H), 4.78 (s, 1H), 4.43 (dd, J=8.9, 4.9 Hz, 1H), 4.11 (t, J=4.2 Hz, 1H), 3.73 (d, J=5.1 Hz, 2H), 3.51 (s, 2H); MS (ES+) 266.1 (M+1); Optical rotation −51.74 (H$_2$O, C=0.545); Analysis: Calculated for C$_{11}$H$_{15}$N$_5$O$_3$.2HCl.0.25H$_2$O: C, 38.55; H, 5.15; Cl, 20.69; N, 20.44; Found: C, 38.51; H, 5.11; Cl, 20.57; N, 20.31.

Preparation of (2R,3R,4S,5S)-2-(acetoxymethyl)-1-(tert-butoxycarbonyl)-5-(4-chloro-5H-pyrrolo[3,2-d] pyrimidin-7-yl)pyrrolidine-3,4-diyl diacetate (28c) and tert-butyl (2S,3R,4S,5S)-5-(hydroxymethyl)-2-(4-amino-5H-pyrrolo[3,2-d]pyrimidin-7-yl)-pyrrolidine-3,4-dihydroxy carboxylate (28f).

Step 1: Preparation of D-Ribono Lactone (19b)

A 22-L three-neck flask fitted with a mechanical stirrer, a 1 L pressure-equalizing addition funnel, and an efficient condenser was charged with D-ribose (19a) (2.0 kg, 13.33 mol) solid sodium bicarbonate (2.24 kg, 26.66 mole) and water (12 L). The reaction mixture was stirred at room temperature for 1 h at which time most of the solid disappeared. The reaction vessel was placed in an ice bath with the internal temperature maintained at 5±1° C. The addition funnel was filled with bromine (710 mL, 13.86 mol) and the bromine was added to the vigorously stirred aqueous solution at a rate of about 5 mL/min such that the temperature was maintained between 5-10° C. When the addition was completed (about 2.5 h) the resulting orange solution was stirred for an additional 3 h. To the reaction mixture was added solid sodium hydrogen sulfite (~75 g) in small lots until the orange color was completely discharged. The clear aqueous solution was transferred to a 20-L evaporating flask and evaporated to dryness on a rotary evaporator (80° C., 10 mm Hg) over a period of 4 h, to leave a semi-solid residue.

To the residue was added ethyl alcohol (~4 L) and stirred at 40° C. for 1 h. The mixture was cooled down and filtered over a funnel to remove most of the insoluble inorganic salts. The solid residue was washed with ethyl alcohol (1 L). The filtrate was transferred to a 20-L evaporating flask and concentrated to dryness on a rotary evaporator (50° C., 10 mm Hg) to furnish a solid residue. To this residue was added ethyl alcohol (~3 L) and the slurry was stirred at room temperature for 12 h. The solid was collected by filtration and washed with ethyl alcohol (750 mL). The product D-Ribono lactone (19b) was dried in a vacuum oven at 40° C. (0.1 mmHg). Yield 1.28 kg (65%); M.P. 77-80° C.; $^1$H NMR (D$_2$O) δ 4.72 (d, 1 H), 4.57 (t, 1 H), 4.42 (d, 1 H), 3.80 (m, 2 H).

Step 2: Preparation of 2,3-O-isopropylidene D-Ribono-1,4-lactone (19c)

A 50-L jacketed reaction vessel was charged with D-ribono-1,4-lactone (19b) (3.0 kg, 20.27 mol), and 30 L of ACS grade acetone. The reaction mixture was stirred at room temperature for 1 h. The internal temperature of the reaction vessel was lowered to 10° C. and conc. sulfuric acid (49 mL) was added slowly to the reaction mixture. Upon addition of the sulfuric acid the internal reaction temperature was allowed to warm up slowly. The reaction mixture was stirred at this temperature for 2.5-3 h. The reaction was monitored by TLC (TLC; 9:1, methylenechloride:methyl alcohol, R$_f$=0.75). The reaction mixture was neutralized by addition of solid sodium bicarbonate (~500 g) until the pH was neutral. The reaction mixture was filtered over a funnel. The solid residue containing inorganic salts was washed with acetone (3 L). The filtrate was transferred to a 20-L evaporation flask and evaporated to dryness (50° C., 10 mmHg) to give a semi-solid compound. The residue was taken in ethyl acetate (3 L) and stirred at room temperature for 4 h on rotary evaporator. The solid 2,3-O-isopropylidene D-Ribono-1,4-lactone (19c) was collected by filtration and dried in a vacuum oven for 16 h at 40° C. (0.1 mm Hg). Yield: 1.819 kg (48%); MP 136-140° C.; $^1$H NMR (CDCl$_3$) δ 4.8 (dd, 2 H), 4.6 (s, 1 H), 3.85 (dd, 2 H), 1.5 (s, 3 H), 1.4 (s, 3 H).

Step 3: Preparation of 2,3-O-isopropylidene 5-O-methanesulfonyl D Ribono-1,4-lactone (26a)

A solution of 2,3-O-isopropylidene D-Ribono-1,4-lactone (19c) (4.3 kg, 22.96 mol) in ACS grade pyridine (20 L) was stirred in a 50 L reaction vessel at room temperature for 15 min until complete dissolution. The internal temperature of the reaction vessel was lowered to −15° C. followed by slow addition of methane sulfonylchloride (1.96 L, 25.26 mol) over a period of 2 h. The internal temperature was maintained at 0-5° C. The reaction was stirred at 0° C. for ~2 h under inert atmosphere until the reaction TLC showed no SM (TLC; 7:3 ethyl acetate:hexane, R$_f$=0.85). Upon completion of the reaction DCM (10 L) was added and extracted with 3N HCl (4 times, pH=3), [Back extract the aqueous layer with DCM (5 L) each time] followed by quick saturated NaHCO$_3$ wash. The organic fraction was dried over sodium sulfate, filtered and evaporated to syrup. Yield: 4.89 kg (80%). The product 2,3-O-isopropylidene 5-O-methanesulfonyl D Ribono-1,4-lactone (26a) was taken to the next step without any further purification; $^1$H NMR (CDCl$_3$) δ 4.8 (m, 3H), 4.5 (m, 2H), 3.08 (s, 3H), 1.5 (s, 3H), 1.4 (s, 3H).

Step 4: Preparation of 2,3-O-isopropylidene L Lyxono-1,4-lactone (26b)

To 2,3-O-isopropylidene 5-O-methanesulfonyl D Ribono-1,4-lactone (26a) (3.04 kg, 11.37 mol) was added water (10 L), followed by slow addition of solid KOH (1.83 kg, 32.77 mol). (Caution: The compound goes into solution upon addition of solid KOH. The reaction is exothermic while adding KOH so the reaction vessel has to be placed in an ice bath.) By the time the addition of KOH was complete the reaction temperature had reached 45° C. The reaction mixture was stirred at ~ room temperature (RT) for 3 h. The solution was again cooled down in ice bath and then acidified to pH=3 (exact) using conc. HCl solution. The reaction mixture was evaporated to give a solid brown residue. The residue was stirred twice with boiling acetone (~5 L) for 1 h and the organics was decanted. The remaining salts were then dissolved in minimum amount of water and pH adjusted to 3 using conc. HCl (~200 mL). The aqueous solution was concentrated and the solid residue was extracted with acetone (~5 L). The organic layer was dried, filtered, and evaporated to give white needles of 2,3-O-isopropylidene L Lyxono-1,4-lactone (26b). Crystallization can be carried out in hot acetone. Yield: 1.60 kg (75%); $^1$H NMR (D$_2$O) δ 5.00 (m, 2H), 3.8 (m, 3H), 1.5 (s, 3H), 1.4 (s, 3H).

Step 5: Preparation of 2,3-O-isopropylidene 5-O-tertbutyldimethylsilyl L Lyxono-1,4-lactone (26c)

A 22-L 3-neck flask fitted with mechanical stirrer was added 2,3-O-isopropylidene L Lyxono-1,4-lactone (26b) (2.0 kg, 10.63 mol), DMAP (~25 g), Imidazole (1.60 kg, 23.40 mol, 2.2 equiv.) and stirred in ACS grade DMF (8 L) for 1 h. The reaction temperature was lowered to 0° C. using ice bath. To the reaction mixture was added TBDMSCl (2.08 kg, 13.81 mol, 1.3 equiv.) slowly over a period of 2 h. The reaction mixture was stirred at room temperature under inert atmosphere for 14 h. Upon completion of the reaction as indicated by TLC (7:3, EtOAc: hexane, R$_f$=0.80), the reaction mixture was poured in ice water and extracted with EtOAc (×2). The organic layer was separated, dried and filtered to give an oily residue. The reaction vessel, which contains the product, was placed in an ice bath followed by addition of hexanes (~3 L). The compound does crystallize in hexane. Filter the crystals and wash the crystals with minimal amount of hexanes and place the product in vacuum oven at 40° C. overnight to furnish 2,3-O-isopropylidene 5-O-tertbutyldimethylsilyl L Lyxono-1,4-lactone (26c) 3.01 kg (93%); $^1$H NMR (CDCl$_3$) δ 4.8 (s, 2H), 4.5 (m, 1H), 3.9 (m, 2H), 1.5 (s, 3H), 1.4 (s, 3H), 0.9 (s, 9H), 0.0 (s, 6H).

Step 6: Preparation of 2-(tert-Butyldimethylsilanoxy)-1-(5-hydroxymethyl-2,2-dimethyl-[1,3]dioxolano-4-yl)-ethanol (26d)

A solution of 2,3-O-isopropylidene 5-O-tertbutyldimethylsilyl L Lyxono-1,4-lactone (26c) (3.00 kg, 9.93 mol) in THF:MeOH (9:1 v/v mixture, 15 L) was stirred at RT for 0.5 h until complete dissolution was observed. The internal temperature of the reaction vessel was lowered to −5° C. Sodium borohydride (751 g, 19.86 mol, 2 eq) was added in small portions such that the temperature did not exceed 15-17° C. Addition of the reagent was completed over a period of 1 h. The reaction was allowed to attain room temperature over a period of 3 h and then continued stirring at this temperature for 18 h. The reaction mixture was monitored by TLC (3:7, ethylacetate:hexane, R$_f$=0.15). Upon completion of the reaction the solution was diluted with EtOAc (5 L), and washed with 1 N HCl solution (2 times). The organic layer was washed with water, dried and evaporated to give an oily residue. To this add ~3 L of hexanes and cool the evaporating flask in ice bath. The crystals will crash out of the solution. Filter the crystals and wash with ~250 mL of hexanes. Dry in vacuum oven at 40° C. for 24 h, to furnish 2-(tert-Butyldimethylsilanoxy)-1-(5-hydroxymethyl-2,2-dimethyl-[1,3]dioxolano-4-yl)-ethanol (26d). Yield: 2.32 kg (77%); $^1$H NMR (CDCl$_3$) δ 4.2 (m, 2H), 3.7 (m, 5H), 1.5 (s, 3H), 1.4 (s, 3H), 0.9 (s, 9H), 0.0 (s, 6H).

Step 7: Preparation of Methanesulfonic acid 2-(tert-butyldimethylsilayloxy)-1-1(5-methanesulfonyloxymethyl-2,2-dimethyl-[1,3]dioxolan-4-yl)-ethyl ester (26e)

A 500 mL 3-neck flask was charged with dry pyridine (20 mL), catalytic amount of DMAP followed by addition of methane sulfonyl chloride (4.98 mL, 64.4 mmol, 4.0 eq) at 0° C. 2-(tert-Butyldimethylsilanoxy)-1-(5-hydroxymethyl-2,2-dimethyl-[1,3]dioxolano-4-yl)-ethanol (26d) (5.0 g, 16.3 mmol) dissolved in dry pyridine (20 mL) was added slowly to the reaction vessel. The reaction was stirred under inert atmosphere for 4 h at this temperature. (TLC; 1:9 ethylacetate:hexane, R$_f$=0.85). Upon completion of the reaction, add 1 ml of water and 100 mL EtOAc and stir. Extract the organic layer with water, dry and evaporate to give syrup of methanesulfonic acid 2-(tertbutyldimethylsilayloxy)-1-1(5-methanesulfonyloxymethyl-2,2-dimethyl-[1,3]dioxolan-4-yl)-ethyl ester (26e). Yield: 8.7 g (90%). The crude was taken to the next step without any further purification.

Step 8: Preparation of 5-O-tertbutyldimethylsilyl-1,4-N-benzylimino-2,3-O-ispropylidene-D-ribitol (26f)

To methanesulfonic acid 2-(tertbutyldimethylsilayloxy)-1-1(5-methanesulfonyloxymethyl-2,2-dimethyl-[1,3]dioxolan-4-yl)-ethyl ester (26e) (8.6 g) was added neat benzylamine (10 mL) and the reaction was heated to 70° C. for 48 h. TLC (4:1 hexane:EtOAc, R$_f$=0.68) showed that the reaction was complete. The reaction mixture was cooled down and brine was added to the reaction mixture. Extract the reaction mixture with dichloromethane, wash with water, dry and evaporate to furnish syrup which contained a lot of the amine reagent. The residue was taken up in toluene and to that dry ice chips were added so as to precipitate out the salts. Filter the solid and evaporate the filtrate to furnish the desired product 5-O-tertbutyldimethylsilyl-1,4-N-benzylimino-2,3-O-ispropylidene-D-ribitol (26f) (5.6 g, 92%). This was taken directly to the next step without any further purification. $^1$H NMR (CDCl$_3$) δ 7.2-7.4 (m, 5H), 4.65 (m, 1H), 4.55 (dd, 1H), 4.0 (d, 1H), 3.6-3.8 (m, 3H), 3.1 (dd, 1H), 3.0 (m, 1H), 2.75 (dd, 1H), 1.5 (s, 3H), 1.34 (s, 3H), 0.9 (s, 9H), 0.0 (s, 6H).

Step 9: Preparation of 5-O-tertbutyldiemthylsilyl-1,4-imino-2,3-O-ispropylidene-D-ribitol (20a)

To 5-O-tertbutyldimethylsilyl-1,4-N-benzylimino-2,3-O-ispropylidene-D-ribitol (26f) (5.93 g, 15.74 mmol) in EtOH (15 mL) was added Pd/C (50 mg) and the reaction was hydrogenated at 80 psi for 5 h, or until TLC (3:2, hexane:

EtOAc, $R_f$=0.18) showed the reaction to be complete. The reaction mixture was filtered over Celite pad and the Celite pad was washed with EtOH (25 mL). The filtrate was passed through a Millipore filter (0.25 μm) to remove traces of the catalyst and evaporated to furnish 5-O-tertbutyldiemthylsilyl-1,4-imino-2,3-O-ispropylidene-D-ribitol (20a) as a syrup. Yield: 3.5 g (75%-steps); $^1$H NMR (CDCl$_3$) δ 4.65 (m, 2H), 3.60 (dd, 2H), 3.24 (t, 1H), 3.00 (d, 2H), 1.5 (s, 3H), 1.34 (s, 3H), 0.9 (s, 9H), 0.0 (s, 6H).

Step 10: Preparation of (3aR,4R,6aS)-4-(((tert-butyldimethylsilyl)oxy)methyl)-2,2-dimethyl-4,6a-dihydro-3aH-[1,3]dioxolo[4,5-c]pyrrole (20b)

A solution of 5-O-tertbutyldiemthylsilyl-1,4-imino-2,3-O-ispropylidene-D-ribitol (20a) (94 g, 327 mmol) in toluene (470 mL) is added to a suspension of N-Chlorosuccinimide (54.6 g, 408.8 mmol) in toluene (470 mL) at 17 to 23° C. over a period of 60 to 90 minutes. The reaction mixture was stirred at 17 to 23° C. for 1 hour, chilled to −3 to 3° C. and stirred for additional hour The succinimide by-product is removed by filtration and the filtered solution charged directly to a 60% potassium hydroxide solution (458 g, 8175 mmol in 305 mL of water) containing tetrabutylammonium bromide (10.53 g, 32.7 mmol). The reaction mixture is stirred at −5 to 5° C. for 17 h. Water (700 mL) is then added to the two-phase mixture to dissolve inorganic precipitates and the toluene product solution is washed with an ammonium acetate buffer (pH ~4.5), buffered brine solution (700 mL) and stabilized with triethylamine prior to drying by circulation through magnesium sulphate and then by charging magnesium sulphate to the reactor. The dried solution containing (3aR,4R,6aS)-4-(((tert-butyldimethylsilyl)oxy)methyl)-2,2-dimethyl-4,6a-dihydro-3aH-[1,3]dioxolo[4,5-c]pyrrole (20b) in toluene is used as such immediately for the next step.

Step 11: Preparation of 1S-5-O-tert-butyldimethylsilyl-1,4-dideoxy-1-C-[(4-methyoxypyrrolo[3,2-d]pyrimidin-9-N-(benzyloxomethyl)-7-yl)]-1,4-imino-2,3-O-isopropylidine-D-ribitol (26g)

6-Methoxy-N-(benzyloxymethyl)-9-deazahypoxanthine (27f) (271.0 g, 0.775 mole) was added to a 22 L 3-neck round-bottom flask containing anhydrous anisole (1.7 L) under a N$_2$ atmosphere. This mixture was heated gently until the mixture became homogenous (≈45° C.). The mixture was cooled to ambient temperature and anhydrous ether (2.9 L) was added. The reaction flask was placed into a cooling bath and cooled to −70° C. using dry ice/acetone. At ≈−20° C., the bromide started precipitating as a fine white solid. To the suspension was added nBuLi (1.6 N, 486 mL, 0.778 mol) over a 1.2 h period via a dropping funnel such that the internal temperature was maintained <−50° C. After the last addition, TLC (30% EtOAc/hexane) analysis indicated <2% of the bromide remained. (3aR,4R,6aS)-4-(((tert-butyldimethylsilyl)oxy)methyl)-2,2-dimethyl-4,6a-dihydro-3aH-[1,3]dioxolo[4,5-c]pyrrole (20b) (183 g, 0.642 mole) in toluene was added over a 15 minute period via an addition funnel maintaining the internal temperature below −50° C. The reaction mixture was a pale-amber color. The reaction flask was removed from the cooling bath and allowed to warm. The reaction mixture was allowed to warm to −2° C. and TLC (40% EtOAc/hexane, visualized with Ehrlichs reagent) showed no remaining (3aR,4R,6aS)-4-(((tert-butyldimethylsilyl)oxy)methyl)-2,2-dimethyl-4,6a-dihydro-3aH-[1,3]dioxolo[4,5-c]pyrrole (20b). The reaction was quenched with H$_2$O (2 L) and extracted with ether (2×2 L). The combined organic layers were dried (MgSO$_4$) and concentrated in vacuo (high vacuum at 60° C. was used to remove anisole) to give a crude dark oil of 1S-5-O-tert-butyldimethylsilyl-1,4-dideoxy-1-C-[(4-methyoxypyrrolo[3,2-d]pyrimidin-9-N-(benzyloxomethyl)-7-yl)]-1,4-imino-2,3-O-isopropylidine-D-ribitol (26g) which was suitable for use in the next step. Yield 284 g (79%). A small amount (5 g) of the crude mixture was purified by flash column chromatography (silica gel, eluting with 0-40% ethylacetate in hexane) to furnish 1S-5-O-tert-butyldimethylsilyl-1,4-dideoxy-1-C-[(4-methyoxypyrrolo[3,2-d]pyrimidin-9-N-(benzyloxomethyl)-7-yl)]-1,4-imino-2,3-O -isopropylidine-D-ribitol (26g) as an orange syrup (3.4 g); $^1$H NMR (DMSO-d$_6$) δ 0.02 (s, 3 H), 0.03 (s, 3 H), 0.8 (s, 9 H), 1.25 (s, 3 H), 1.48 (s, 3 H), 3.11-3.20 (m, 1 H), 3.60-3.71 (m, 2 H), 4.05 (s, 3 H), 4.26 (d, 1 H, J=4.7 Hz), 4.49 (s, 2 H), 4.52-4.56 (m, 1 H), 4.81-4.85 (m, 1 H), 5.71 (s, 2 H), 7.21-7.32 (m, 5 H), 7.80 (s, 1 H), 8.40 (s, 1 H); $^{13}$C NMR (CDCl$_3$) δ −5.46, −5.43, 18.30, 25.53, 25.88, 27.63, 53.43, 61.59, 62.54, 66.14, 70.14, 76.93, 82.32, 86.40, 114.43, 116.22, 116.56, 127.67, 127.93, 128.43, 130.55, 136.93, 149.61, 149.82, 156.16; IR 3420, 1610 cm$^{-1}$; MS (ES+) m/z 555.3; Analysis: Calculated for C$_{29}$H$_{42}$N$_4$O$_5$Si: C, 62.79; H, 7.63; N, 10.10; Found: C, 62.95; H, 7.59; N, 9.95.

Step 12: Preparation of 1S—N-tert-butoxycarbonyl-5-O-tert-butyldimethylsilyl-1,4-dideoxy-1-C-[(4-methyoxypyrrolo[3,2-d]pyrimidin-9-N-(benzyloxomethyl)-7-yl)]-1,4-imino-2,3-O-isopropylidine-D-ribitol (26h)

Crude 1S-5-O-tert-butyldimethylsilyl-1,4-dideoxy-1-C-[(4-methyoxypyrrolo[3,2-d]pyrimidin-9-N-(benzyloxomethyl)-7-yl)]-1,4-imino-2,3-O-isopropylidine-D-ribitol (26g) (275 g, 0.496 mole) was taken up in CH$_2$Cl$_2$ (1.4 L) and cooled to 5° C. in an ice/water bath. To this cooled mixture was added Boc$_2$O (168.5 g, 0.772 mole) in 4 portions such that the reaction mixture temperature was maintained <10° C. After 30 min, TLC (40% ethylacetate/hexane) showed no starting material remained. The crude mixture was absorbed on SiO$_2$ (700 g) and purified by flash chromatography (silica gel 1.5 kg, eluting with 10% ethylacetate in hexane). The appropriate fractions were pooled and concentrated in vacuum to give 1S—N-tert-butoxycarbonyl-5-O-tert-butyldimethylsilyl-1,4-dideoxy-1-C-[(4-methyoxypyrrolo[3,2-d]pyrimidin-9-N-(benzyloxomethyl)-7-yl)]-1,4-imino-2,3-O -isopropylidine-D-ribitol (26h) (272 g, 84%) as a yellow syrup; $^1$H NMR (CDCl$_3$) δ 0.02 (s, 3 H), 0.03 (s, 3 H), 0.82 (s, 9 H), 1.31-1.58 (m, 15 H) 2.05-2.09 (m, 1 H); 3.58-3.80 (m, 2 H), 4.08 (s, 3 H), 4.17-4.32 (m, 1 H), 4.44 (s, 2 H), 4.84-5.71 (m, 4 H), 7.19-7.33 (m, 5 H), 7.46 (s, 1 H), 8.51 (s, 1 H); $^{13}$C NMR (CDCl$_3$) δ −5.31, −5.20, 14.10, 14.20, 18.32, 21.01, 22.64, 25.56, 25.93, 27.46, 28.46, 31.58, 53.44, 60.34, 62.48, 70.08, 76.96, 79.84, 111.69, 115.89, 127.67, 127.93, 128.43, 136.90, 148.62, 149.90, 154.38, 156.19; IR 1692, 1608 cm$^{-1}$; MS (ES+) m/z 655.3; Analysis: Calculated for C$_{34}$H$_{50}$N$_4$O$_7$Si: C, 62.43; H, 7.65; N, 8.56. Found: C, 62.79; H, 7.89; N, 8.47.

Step 13: Preparation of (3aR,4R,6S,6aS)-tert-butyl 4-(((tert-butyldimethylsilyl)oxy)methyl)-6-(4-methoxy-5H-pyrrolo[3,2-d]pyrimidin-7-yl)-2,2-dimethyldihydro-3aH-[1,3]dioxolo[4,5-c]pyrrole-5(4H)-carboxylate (26i)

Palladium hydroxide on charcoal (120 g, 50% wet type) was charged to a 2 L conical flask. Methanol (7.60 kg) was weighed out into a 20 L polydrum. 0.80 kg of this methanol was used to transferred to the conical flask containing the palladium hydroxide catalyst and the conical flask swirled to prepare a homogeneous mixture. This suspension was then poured into a 20 L hydrogenation vessel, which had been purged with nitrogen. Residual palladium hydroxide on charcoal was rinsed from the conical flask to the hydrogenation vessel with methanol (25 mL). 1S—N-tert-butoxycarbonyl-5-O-tert-butyldimethylsilyl-1,4-dideoxy-1-C-[(4-methyoxypyrrolo[3,2-d]pyrimidin-9-N-(benzyloxomethyl)-7-yl)]-1,4-imino-2,3-O-isopropylidine-D-ribitol (26h) (380 g) was charged into a 10 L polydrum followed by 1.32 kg of the methanol from the 20 L polydrum. This methanolic solution of 1S—N-tert-butoxycarbonyl-5-O-tert-butyldimethylsilyl-1,4-dideoxy-1-C-[(4-methyoxypyrrolo[3,2-d]pyrimidin-9-N-(benzyloxomethyl)-7-yl)]-1,4-imino-2,3-O-isopropylidine-D-ribitol (26h) was charged to the 20 L hydrogenation vessel. The remainder of the methanol in the 20 L polydrum was charged to the vessel, via the 10 L polydrum, as a rinse. A solution of ammonia in methanol (7.0 M, 0.68 kg) was measured out into the 10 L polydrum and transferred to the hydrogenation vessel. The vessel was pressurized to 5 bar with hydrogen gas and the contents heated to 35° C. with agitation. These reaction conditions were maintained for 20 h, with the hydrogen topped up as required. After this time, HPLC analysis indicated that approximately 2% starting material remained, which suggested that the reaction was sufficiently complete. The contents of the vessel were transferred to a 20 L polydrum then filtered through a bed of Celite. Nitrogen was purged over the filter funnel during this operation, and methanol (1.50 kg) was used to wash the filter cake. The filtrate and washings were transferred to a rotary evaporator and concentrated under reduced pressure to a weight of 0.48 kg. Methanol (2.50 kg) was added to the rotary evaporator flask and the solution concentrated to a constant mass (0.340 kg, approximately quantitative yield). Additional methanol (1.0 kg) was added to the product (3aR,4R,6S,6aS)-tert-butyl 4-(((tert-butyldimethylsilyl)oxy)methyl)-6-(4-methoxy-5H-pyrrolo[3,2-d]pyrimidin-7-yl)-2,2-dimethyldihydro-3aH-[1,3]dioxolo[4,5-c]pyrrole-5(4H)-carboxylate (26i) to prepare a solution for use in the next step.

Step 14: Preparation of 7-((2S,3S,4R,5R)-3,4-dihydroxy-5-(hydroxymethyl)pyrrolidin-2-yl)-3H-pyrrolo[3,2-d]pyrimidin-4-(5H)-one hydrochloride (26j)

The solution of (3 aR,4R,6S,6aS)-tert-butyl 4-(((tert-butyldimethylsilyl)oxy)methyl)-6-(4-methoxy-5H-pyrrolo[3,2-d]pyrimidin-7-yl)-2,2-dimethyldihydro-3aH-[1,3]dioxolo[4,5-c]pyrrole-5(4H)-carboxylate (26i) was diluted with methanol to produce a total volume of 2.5 L and charged to a 5 L multi-necked round bottom flask fitted with a mechanical stirrer, a reflux condenser and internal thermometer. The solution was heated using an oil bath and simultaneously, concentrated hydrochloric acid (37%, 2.18 L or 2.62 kg) was charged over 40 minutes (the internal temperature increased from 43° C. to 58° C. during this time). Heating was continued for another 6 h, with the internal temperature reaching 68° C., at which point the solution was allowed to cool to room temperature and stirred for further 15 h. The brown solution was concentrated on a rotary evaporator to a volume of 1.5-2.0 L then water (0.5 L) was added. The suspension was transferred back to the 5 L flask and heated to re-dissolve the solids. This was achieved at 50° C. after additional water (0.50 L) had been added. Charcoal (95 g) was added, and the suspension was stirred at 50° C. for 1 h. The charcoal was removed by filtration through a pad of Celite, washing with water (1.0 L approximately). The filtrate and washings, now partially decolorized, were concentrated on a rotary evaporator to a volume of 0.95 L. The ambient temperature solution was transferred to a 10 L flask and cooled in an ice bath with agitation. Ethanol (7.90 L) was charged portion-wise to the solution, causing the product to crystallize. Over a further 2 h stirring, the internal temperature was reduced to 5° C. The solid product was collected by filtration under a blanket of nitrogen, and was washed with pre-chilled ethanol (3×250 mL). The product was pulled dry on the filter funnel for 30 minutes then transferred to a drying tray. The product was oven dried at 70° C. overnight to afford 7-((2S,3S,4R,5R)-3,4-dihydroxy-5-(hydroxymethyl)pyrrolidin-2-yl)-3H-pyrrolo[3,2-d]pyrimidin-4-(5H)-one hydrochloride (26j) as an off-white solid (101.2 g, 58%). 7-((2S,3S,4R,5R)-3,4-dihydroxy-5-(hydroxymethyl)pyrrolidin-2-yl)-3H-pyrrolo[3,2-d]pyrimidin-4-(5H)-one hydrochloride (26j) (101.2 g) was charged to a 20 L jacketed vessel. Water (1.52 L) was added and the suspension agitated until the solids dissolved. Concentrated hydrochloric acid (37%, 63.6 mL) was charged and the solution stirred at 25° C. Once homogeneous, the solution was run off to a polydrum and the vessel was rinsed clean with water (506 mL). As a clarification step, the solution of 7-(2S,3S,4R,5R)-3,4-dihydroxy-5-(hydroxymethyl)pyrrolidin-2-yl)-3H-pyrrolo[3,2-d]pyrimidin-4-(5H)-one hydrochloride (26j) was filtered through filter paper on a polypropylene filter funnel and then charged back to the vessel. The wash was also filtered in this manner, then charged back to the vessel. The solution was stirred at approximately 15° C. for 45 minutes. Ethanol (1.0 L) was added to the stirred solution, over 15 minutes. 7-((2S,3S,4R,5R)-3,4-dihydroxy-5-(hydroxymethyl)pyrrolidin-2-yl)-3H-pyrrolo[3,2-d]pyrimidin-4-(5H)-one hydrochloride (26j) seed crystals (2.0 g) were added to induce crystallization. After 70 minutes, ethanol (1.0 L) was added and the suspension was stirred at 15° C. for a further 19.5 h. Additional ethanol (8.0 L) was added to the suspension, and stirring at 15° C. was continued for a further 5 h. The jacket temperature was set to 0° C. and the stirring continued for an additional 2 h. At which point, the suspension was run off to a polydrum and filtered through filter papers in a polypropylene filter funnel. The filter cake was washed with chilled ethanol (1.0 L then 0.5 L) and pulled dry on the filter funnel for 30 minutes. The solid was then transferred to a drying tray and oven dried at 70° C. overnight to afford 7-((2S,3S,4R,5R)-3,4-dihydroxy-5-(hydroxymethyl)pyrrolidin-2-yl)-3H-pyrrolo[3,2-d]pyrimidin-4-(5H)-one hydrochloride (26j) as an off-white solid (176.9 g, 87% recovery).

Step 15: Preparation of (2R,3R,4S,5S)-tert-butyl 3,4-dihydroxy-2-(hydroxymethyl)-5-(4-oxo-4,5-dihydro-3H-pyrrolo[3,2-d]pyrimidin-7-yl)pyrrolidine-1-carboxylate (28a)

To a suspension of 7-((2S,3S,4R,5R)-3,4-dihydroxy-5-(hydroxymethyl)pyrrolidin-2-yl)-3H-pyrrolo[3,2-d]pyrimidin-4-(5H)-one (26j) (446.19 gm, 1.47 mol) in a water:methanol mixture (1:1, 10.4 L) was added triethylamine (621 mL, 4.42 mol, 3.0 eq) at room temperature followed by (Boc)$_2$O (987 g, 4.53 mol, 3.1 eq). The reaction mixture became a clear colored solution after the addition of (Boc)$_2$O with slight increase of the internal temperature from 28° C. to 33° C. The solution started showing some turbidity after 1 hour of stirring. The solution was stirred at room temperature overnight. The solid product was collected by filtration and washed with water (5.0 L), dried at high vacuum at 50° C. to furnish (2R,3R,4S,5S)-tert-butyl 3,4-dihydroxy-2-(hydroxymethyl)-5-(4-oxo-4,5-dihydro-3H-pyrrolo[3,2-d]pyrimidin-7-yl)pyrrolidine-1-carboxylate (28a) (482 g, 89%) as an off-white solid; $^1$H NMR (300 MHz, DMSO-d$_6$) δ 11.92 (s, 2H), 7.81 (s, 1H), 7.32 (d, J=22.7 Hz, 1H), 5.73-5.20 (m, 1H), 5.05-4.91 (m, 1H), 4.87-4.76 (m, 1H), 4.74-4.49 (m, 1H), 4.33-4.17 (m, 1H), 4.09-3.86 (m, 2H), 3.64-3.48 (m, 2H), 1.39-1.00 (m, 9H); MS (ES+) 755.1 (2M+Na), (ES−) 731.7 (2M−1); Analysis: Calculated for $C_{16}H_{22}N_4O_6$: C, 52.45; H, 6.05; N, 15.29; Found: C, 52.24; H, 6.02; N, 15.05.

Step 16: Preparation of (2R,3R,4S,5S)-2-(acetoxymethyl)-1-(tert-butoxycarbonyl)-5-(4-oxo-4,5-dihydro-3H-pyrrolo[3,2-d]pyrimidin-7-yl)pyrrolidine-3,4-diyl diacetate (28b)

To a suspension of (2R,3R,4S,5S)-tert-butyl 3,4-dihydroxy-2-(hydroxymethyl)-5-(4-oxo-4,5-dihydro-3H-pyrrolo[3,2-d]pyrimidin-7-yl)pyrrolidine-1-carboxylate (28a) (482 g, 1.32 mole, 1.0 equiv.) in pyridine (740 mL, 9.21 mole, 7 equiv.) was added DMAP (3.22 g, 26.32 mmol, 0.02 equiv.) and acetic anhydride (435 mL, 4.61 mmol, 3.5 eq) at room temperature. The internal temperature started rising upon the addition of the acetic anhydride, therefore ice-water bath cooling was required. Upon the total addition of the anhydride the temperature rose to 67° C. then decreased to room temperature. The ice-water bath was removed after the reaction reached 25° C. The suspension did not give a clear solution but a lighter suspension was observed. The reaction mixture was stirred at room temperature for 14 h to yield a non-clear solution. A worked aliquot shows that there is no more starting material and there are only two major spots by TLC (9:1 chloroform: methanol), MS shows two majors peaks at (493.0, M+1) for product and tetraacetylated product (M+1=535). The reaction mixture was diluted with 3.0 L of chloroform, stirred for 10 minutes then added 2.0 L of deionized water. A waxy white unknown product was formed in the aqueous organic phase interface. This unknown product remained in the aqueous phase after the partition was done. The organic phase was separated and washed again with 2.0 L of water. The combined water layers were back extracted with 1.0 L of chloroform. The combined organic phases were washed with aqueous 2.0 N HCl (2×1.0 L), water (2×1.0 L), saturated sodium bicarbonate (2×1.0 L) and brine (2×1.0 L). The organic layer was dried over MgSO$_4$, filtered and concentrated to dryness under vacuum and 50-55° C. water bath. The vacuum was switched to a high vacuum oil pump until no more distillate was seen to furnish a dense syrupy product. The round bottom flask was left at high vacuum oil pump for 14 h to minimize the residual pyridine. A combination of solid foam which turns into a nice white solid and a dense residue of (2R,3R,4S,5S)-2-(acetoxymethyl)-1-(tert-butoxycarbonyl)-5-(4-oxo-4,5-dihydro-3H-pyrrolo[3,2-d]pyrimidin-7-yl)pyrrolidine-3,4-diyl diacetate (28b) was obtained (715, 110% yield). This percentage reflects the amount of tetraacetylated compound. The product was pure enough to be used as is for next step. An analytical sample was prepared by purification of the mixture using flash column chromatography (silica gel, eluting with 0-100% (9:1) ethyl acetate/methanol in hexane) to furnish (2R,3R,4S,5S)-2-(acetoxymethyl)-1-(tert-butoxycarbonyl)-5-(4-oxo-4,5-dihydro-3H-pyrrolo[3,2-d]pyrimidin-7-yl)pyrrolidine-3,4-diyl diacetate (28b) as a white solid; $^1$H NMR (300 MHz, DMSO-d$_6$) δ 12.13 (s, 1H, D$_2$O exchangeable), 11.98 (s, 1H, D$_2$O exchangeable), 7.82 (s, 1H), 7.29 (s, 1H), 5.76 (s, 1H), 5.37 (t, J=4.5 Hz, 1H), 4.99 (s, 1H), 4.55 (dd, J=11.3, 6.6 Hz, 1H), 4.34 (d, J=8.3 Hz, 1H), 4.03 (q, J=7.1 Hz, 1H), 2.01 (d, J=12.6 Hz, 9H), 1.23 (dd, J=39.9, 32.8 Hz, 9H); MS (ES+) 493.0 (M+1); (ES−) 526.7 (M+Cl); Analysis: Calculated for $C_{22}H_{28}N_4O_9$: C, 53.65; H, 5.73; N, 11.38; Found: C, 53.18; H, 5.89; N, 11.10.

Step 17: Preparation of (2R,3R,4S,5S)-2-(acetoxymethyl)-1-(tert-butoxycarbonyl)-5-(4-chloro-5H-pyrrolo[3,2-d]pyrimidin-7-yl)pyrrolidine-3,4-diyl diacetate (28c)

To a solution of (2R,3R,4S,5S)-2-(acetoxymethyl)-1-(tert-butoxycarbonyl)-5-(4-oxo-4,5-dihydro-3H-pyrrolo[3,2-d]pyrimidin-7-yl)pyrrolidine-3,4-diyl diacetate (28b) (622 g, 1.26 mol, 1.0 eq) in acetonitrile (2.75 L) was added benzyltriethylammonium chloride (575 g, 2.5 mol, 2.0 eq), dimethylaniline (240 mL, 1.9 mol, 1.5 eq), followed by POCl$_3$ (706 mL, 7.58 mol, 6.0 eq) at room temperature. A clear, light yellow colored solution was obtained. The reaction mixture was slowly heated up to 80° C. and held at this temperature for 10 minutes. TLC in 9:1 chloroform:methanol shows that the reaction is >98% completed. The black homogeneous solution was cooled down to 50.0° C. and concentrated under vacuum (water bath 70-73° C.) to remove POCl$_3$; the residue was put under oil pump high vacuum until no more distillate was seen. The residue was dissolved in 3.0 L of chloroform and quickly washed carefully with aqueous saturated sodium bicarbonate until a neutral pH was obtained. The organic layer was separated washed with water (2 L), brine (2 L), dried over MgSO$_4$, filtered and concentrated in vacuum to dryness (water bath at 50-53° C.). The black product of (2R,3R,4S,5S)-2-(acetoxymethyl)-1-(tert-butoxycarbonyl)-5-(4-chloro-5H-pyrrolo[3,2-d]pyrimidin-7-yl)pyrrolidine-3,4-diyl diacetate (28c) was used as is in the next step without purification. An analytical sample was prepared by purifying 0.5 g using flash column chromatography (silica gel 12 g, eluting with 0 to 50% ethyl acetate/methanol (9:1) in hexanes) relevant product obtained was dissolved in ether/hexanes left overnight, crystals formed (301 mg) were collected by filtration to furnish (2R,3R,4S,5S)-2-(acetoxymethyl)-1-(tert-butoxycarbonyl)-5-(4-chloro-5H-pyrrolo[3,2-d]pyrimidin-7-yl)pyrrolidine-3,4-diyl diacetate (28c) as a white solid; $^1$H NMR (300 MHz, DMSO-d$_6$) δ 12.55 (s, 1H, D$_2$O exchangeable), 8.65 (s, 1H), 7.87 (bs, 1H), 5.79 (bs, 1H), 5.44 (t, J=4.0 Hz, 1H), 5.10 (bs, 1H), 4.56 (dd, J=11.5, 6.8 Hz, 1H), 4.38 (dd, J=11.4, 4.1 Hz, 1H), 4.08 (bs, 1H), 2.07 (s, 3H), 2.00 (s, 6H), 1.38 (s, 4H), 1.13 (s, 5H); MS (ES+) 510.865 (M+1), (ES−) 508.717 (M−1); Analysis: Calculated for $C_{22}H_{27}ClN_4O_8$: C, 51.72; H, 5.33; Cl, 6.94; N, 10.97; Found: C, 51.91; H, 5.32; Cl, 6.76; N, 10.90.

Step 18: Preparation of (2R,3R,4S,5S)-2-(acetoxymethyl)-5-(4-azido-5H-pyrrolo[3,2-d]pyrimidin-7-yl)-1-(tert-butoxycarbonyl)pyrrolidine-3,4-diyl diacetate (28d)

To a solution of (2R,3R,4S,5S)-2-(acetoxymethyl)-1-(tert-butoxycarbonyl)-5-(4-chloro-5H-pyrrolo[3,2-d]pyrimidin-7-yl)pyrrolidine-3,4-diyl diacetate (28c) (622 g, 1.26 mol, 1 eq) in DMF (1.5 L) was added sodium azide (411 g, 6.32 mol, 5 equiv.) and heated with stirring at 60° C. for 10 h at which time the reaction has gone to completion (TLC in 9:1 chloroform methanol and 1:1 hexane: ethyl acetate).

The reaction was cooled to 25° C., dumped in ice (2 L) and extracted with chloroform (2×1 L). The chloroform layers were combined washed with water (2×2 L), brine (2 L), dried, filtered and concentrated in vacuum (water bath 70-80° C.) to yield a black sludge. Purification of the sludge was achieved by column chromatography (987 g of black sludge, 8×30 inch column, ½ full silica gel, elution profile hexane:ethylacetate; 9:1 (40.0 L); 7:3 (20.0 L); 6:4 (20.0 L); 1:1 (20 L); 4:6 (20.0 L) and 2:8 (20.0 L). The appropriate fractions were pooled and concentrated in vacuum (water bath 50.0° C.) to furnish (2R,3R,4S,5S)-2-(acetoxymethyl)-5-(4-azido-5H-pyrrolo[3,2-d]pyrimidin-7-yl)-1-(tert-butoxycarbonyl)pyrrolidine-3,4-diyl diacetate (28d) (407.05 g, 62.3% yield for two steps) as a dense reddish colored honey-like product. An analytical sample was prepared by purification of the mixture by flash column chromatography (0-100% ethyl acetate in hexane) to furnish (2R,3R,4S,5S)-2-(acetoxymethyl)-5-(4-azido-5H-pyrrolo[3,2-d]pyrimidin-7-yl)-1-(tert -butoxycarbonyl)pyrrolidine-3,4-diyl diacetate (28d) as an orange solid. $^1$H NMR (300 MHz, DMSO-d$_6$) δ 13.08 (d, J=155.6 Hz, 1H, D$_2$O exchangeable), 9.86 (s, 1H), 7.61 (d, J=76.8 Hz, 1H), 5.78 (t, J=4.5 Hz, 1H), 5.41 (t, J=4.3 Hz, 1H), 5.21 (s, 1H), 4.55 (dd, J=11.4, 6.4 Hz, 1H), 4.41 (dd, J=11.4, 3.9 Hz, 1H), 4.07 (d, J=16.5 Hz, 1H), 2.06 (s, 3H), 2.01 (d, J=9.9 Hz, 6H), 1.23 (dd, J=39.8, 32.7 Hz, 9H); MS (ES+) 518.0 (M+1), 540 (M+23); (ES−) 516.4 (M−1); Analysis: Calculated for C$_{22}$H$_{27}$N$_7$O$_8$: C, 51.06; H, 5.26; N, 18.95; Found: C, 50.97; H, 5.30; N, 18.62.

Step 19: Preparation of (2R,3R,4S,5S)-2-(acetoxymethyl)-5-(4-amino-5H-pyrrolo[3,2-d]pyrimidin-7-yl)-1-(tert-butoxycarbonyl) pyrrolidine-3,4-diyl diacetate (28e)

(2R,3R,4S,5S)-2-(acetoxymethyl)-5-(4-azido-5H-pyrrolo[3,2-d]pyrimidin-7-yl)-1-(tert-butoxycarbonyl)pyrrolidine-3,4-diyl diacetate (28d) was reduced in three different batches as follows.

Batch 1: To a 2.0 L Parr hydrogenator, Teflon insert was added (2R,3R,4S,5S)-2-(acetoxymethyl)-5-(4-azido-5H-pyrrolo[3,2-d]pyrimidin-7-yl)-1-(tert -butoxycarbonyl)pyrrolidine-3,4-diyl diacetate (28d) (108.01 g, 300 mmol in methanol, 800 mL), Pd(OH)$_2$ (21.6 g, 20% w/w).

Batch 2: To a 2.0 L Parr hydrogenator, Teflon insert was added (2R,3R,4S,5S)-2-(acetoxymethyl)-5-(4-azido-5H-pyrrolo[3,2-d]pyrimidin-7-yl)-1-(tert -butoxycarbonyl)pyrrolidine-3,4-diyl diacetate (28d) (140.70 g, 271.9 mmol in methanol, 1.0 L), Pd(OH)$_2$ (28.14 g, 20% w/w).

Batch 3: To a 2.0 L Parr hydrogenator, Teflon insert was added (2R,3R,4S,5S)-2-(acetoxymethyl)-5-(4-azido-5H-pyrrolo[3,2-d]pyrimidin-7-yl)-1-(tert -butoxycarbonyl)pyrrolidine-3,4-diyl diacetate (28d) (140.7 g, 271.9 mmol in methanol, 1.0 L), Pd(OH)$_2$ (28.14 g, 20% w/w).

The reaction mixtures were hydrogenated at 150 psi for 15-18 h. The reaction mixture was filtered to remove the catalyst through Celite. The filtrate was concentrated in vacuum (water bath 60-70° C.) until constant weight to furnish a dark colored product (2R,3R, 4S, 5S)-2-(acetoxymethyl)-5-(4-amino-5H-pyrrolo[3,2-d]pyrimidin-7-yl)-1-(tert -butoxycarbonyl) pyrrolidine-3,4-diyl diacetate (28e) (328.8 g, 89%). The product was pure enough to be used as is for the next step. An analytical sample was prepared by purification of the mixture using flash column chromatography (0-10% methanol in chloroform). $^1$H NMR (300 MHz, DMSO-d$_6$) δ 11.06 (s, 1H), 8.12 (s, 1H), 7.49 (s, 1H), 6.94 (s, 2H), 5.86 (s, 1H), 5.44 (t, J=4.2 Hz, 1H), 5.02 (s, 1H), 4.56 (dd, J=11.3, 6.9 Hz, 1H), 4.40 (dd, J=11.3, 4.2 Hz, 1H), 4.16-3.98 (m, 1H), 2.09-1.94 (m, 9H), 1.48-1.14 (m, 9H); MS (ES+) 492.1 (M+1); (ES−) 526.4 (M+Cl); Analysis: Calculated for C$_{22}$H$_{29}$N$_5$O$_8$.1.25H$_2$O: C, 51.41; H, 6.18; N, 13.62; Found: C, 51.24; H, 5.92; N, 13.33.

Step 20: Preparation of (2S,3S,4R,5R)-tert-butyl 2-(4-amino-5H-pyrrolo[3,2-d]pyrimidin-7-yl)-3,4-dihydroxy-5-(hydroxymethyl)pyrrolidine-1-carboxylate (28f)

Batch 1. To (2R,3R,4S,5S)-2-(acetoxymethyl)-5-(4-amino-5H-pyrrolo[3,2-d]pyrimidin-7-yl)-1-(tert-butoxycarbonyl)pyrrolidine-3,4-diyl diacetate (28e) (81.5 g, 165.8 mmol), was added anhydrous methanol (370 mL) followed by the addition of NaOMe (sodium methoxide, 25 wt. % solution in methanol, 4.49 g, 20.76 mmol) at room temperature. The reaction mixture was stirred at room temperature until TLC (chloroform:methanol 9:1) shows that all the starting material has reacted.

Batch 2. To (2R,3R,4S,5S)-2-(acetoxymethyl)-5-(4-amino-5H-pyrrolo[3,2-d]pyrimidin-7-yl)-1-(tert-butoxycarbonyl)pyrrolidine-3,4-diyl diacetate (28e) (117.8 g, 239.6 mmol), was added anhydrous methanol (530 mL) followed by the addition of NaOMe (sodium methoxide, 25 wt. % solution in methanol, 6.58 g, 30.45 mmol) at room temperature. The reaction mixture was stirred at room temperature until TLC (chloroform:methanol 9:1) shows that all the starting material has reacted.

Batch 3. To (2R,3R,4S,5S)-2-(acetoxymethyl)-5-(4-amino-5H-pyrrolo[3,2-d]pyrimidin-7-yl)-1-(tert-butoxycarbonyl)pyrrolidine-3,4-diyl diacetate (28e) (129.5 g, 263.5 mmol) was added anhydrous methanol (584 mL) followed by the addition of NaOMe (sodium methoxide, 25 wt. % solution in methanol, 6.99g, 32.35 mmol) at room temperature. The reaction mixture was stirred at room temperature until TLC (chloroform:methanol 9:1) shows that all the starting material has reacted (7-8 h).

The above solutions were concentrated (water bath 65-75° C.) to furnish (2S,3S,4R,5R)-tert-butyl 2-(4-amino-5H-pyrrolo[3,2-d]pyrimidin-7-yl)-3,4-dihydroxy-5-(hydroxymethyl)pyrrolidine-1-carboxylate (28f) which was pure enough to be used as is for the next step. An analytical sample was prepared by purification of the mixture using flash column chromatography (0-10% methanol in chloroform). $^1$H NMR (300 MHz, DMSO-d$_6$) δ 10.77 (s, 1H), 8.01 (s, 1H), 7.40 (s, 1H), 6.82 (s, 3H), 5.04-4.91 (m, 1H), 4.87-4.74 (m, 1H), 4.56-4.35 (m, 2H), 4.04-3.90 (m, 2H), 3.72-3.63 (m, 1H), 3.59-3.41 (m, 1H), 1.15 (2s, 9H); MS (ES+) 366.1 (M+1); (ES−) 400.3 (M+Cl); Analysis: Calculated for C$_{16}$H$_{23}$N$_5$O$_5$0.25H$_2$O: C, 51.33; H, 6.46; N, 18.71; Found: C, 51.04; H, 6.43; N, 18.48.

Preparation of Methoxy-N-(benzyloxymethyl)-9-bromo-9-deazahypoxanthine (27f)

Step 1: Preparation of Dimethyl 3-amino-1H-pyrrole-2,4-dicarboxylate (27b)

To a solution of diethyl aminomalonate (370.4 g, 1.75 mol) in methanol (3.6 L) at room temperature was added a 5.4 M solution of NaOMe (975 mL, 5.25 mol) in one portion (the reaction mixture was light brown in color). To the reaction mixture was added ethyl (ethoxymethylene)cyanoacetate (27a) (296 g, 1.75 mol) in three portions (not much temperature change was observed during the addition −1° C. change, the reaction color changes from light brown to dark brown). The reaction mixture was heated at refluxed for 48 h (TLC analysis 50% ethylacetate in hexane was done to check disappearance of starting material). The reaction mixture was neutralized by the addition of AcOH (210 mL, 3.5 mole) to pH 6. The reaction mixture was concentrated in vacuo to furnish brown residue. Residue was triturated with water (3 L), filtered, washed with water (500 mL) and hexanes. It was air-dried for 48 h and in vacuo oven at 60° C. to furnish dimethyl 3-amino-1H-pyrrole-2,4-dicarboxylate (27b) 287 g (83%) as a brown solid. It was used as such for the next step.

Step 2: Preparation of
3H,5H-Pyrrolo[3,2-d]pyrimidin-4-one (27c)

A mixture of dimethyl 3-amino-1H-pyrrole-2,4-dicarboxylate (27b) (286 g, 1.44 mole) and formamidine acetate (451g, 4.33 mole) in ethanol (2.8 L, 2 mL/mmole) was heated at reflux overnight. The reaction mixture was not homogenous initially but after couple of h of reflux seems homogenous and dark brown in color (the stirring becomes difficult as solid starts falling out of solution). TLC analysis of an aliquot (50% ethyl acetate in hexane) indicates still some unreacted starting material was present. The reaction mixture was continued to heat at reflux for additional 24 h and cooled to room temperature. The solid obtained was collected by filtration washed with water and hexane and dried in vacuo to furnish 3H,5H-Pyrrolo[3,2-d]pyrimidin-4-one (27c) (223 g, 80%) as a light brown solid. The material was used as such without purification.

Step 3: Preparation of
3H,5H-Pyrrolo[3,2-d]pyrimidin-4-one (22a)

A mixture of 3H,5H-Pyrrolo[3,2-d]pyrimidin-4-one (27c) (130.4 g, 0.675 mole) in 2 N KOH (1.35 L, 2.7 mole) was heated at gentle reflux for 40 h. The reaction mixture was cooled to 60° C. and cautiously neutralized with glacial acetic acid (162 mL, 2.7 mole) to pH 6 (foaming due to decarboxylation was observed and the color of the reaction mixture was black). The reaction mixture was cooled to room temperature and the solid obtained was collected by filtration washed with water (2×250 mL) air dried and the dried in high vacuo over $P_2O_5$ to furnish product as a blackish gray solid (145 g, 159%). NMR of the product indicates lot of acetic acid or its salt so the yield is higher TLC shows clean product plus some product in the baseline using CMA-80 as solvent system). The product was triturated with water (400 mL) and neutralized with saturated aqueous NaHCO3 until no effervescence and pH is around 7-8). The blackish gray solid was collected by filtration and washed with water to furnish on air drying for 48 h, 67.62 g (74%) of product. The product was further dried in vacuo at ethanol reflux temperature to give 3H,5H-Pyrrolo[3,2-d]pyrimidin-4-one (22a) as a blackish gray powder; MP of an analytically pure sample >250° C.; $^1$H NMR (360 MHz, DMSO-$d_6$) δ 12.05 (s, $D_2O$ exchangeable, 1H), 11.82 (s, $D_2O$ exchangeable, 1H), 7.77 (s, 1H), 7.36 (s, 1H), 6.35 (s, 1H). $^{13}$C-NMR (DMSO-$d_6$) 153.88, 144.80, 141.66, 127.51, 117.92, 103.10; IR (KBr) 3107, 3030 and 1674 cm$^{-1}$; MS (ES+) 136.2 (M+1); Analysis: Calculated for $C_6H_5N_3O$: C, 53.33; H, 3.73; N, 31.10; Found: C, 53.38; H, 3.77; N, 31.11.

Step 4: Preparation of
4-Chloropyrrolo[3,2-d]pyrimidine (27d)

To a sample of 3H,5H-Pyrrolo[3,2-d]pyrimidin-4-one (22a) (31.08 g, 230 mmol) under $N_2$ was added phosphorus oxychloride (60 mL, 644 mol, 2.8 eq). The mixture was heated at reflux for 1 h during which time the reaction became black homogenous. The reaction was cooled in an ice-water bath and then poured into chipped ice (775 mL) with stirring. The pH of the aqueous solution was slowly adjusted to ~pH 8 with concentrated NH$_4$OH (225 mL) with continued cooling of the mixture. The resulting precipitate was collected by vacuum filtration and washed with water. The solid was transferred to a drying tray and dried in vacuo at 110° C. to furnish 4-Chloropyrrolo[3,2-d]pyrimidine (27d) (31.48 g, 89%) as a dark gray solid. An analytical sample was obtained by column chromatography (silica gel, EtOAc-hexanes, 35:65) followed by evaporation of the relevant fractions. Trituration of the solid with EtOAc-MeOH afforded 4-Chloropyrrolo[3,2-d]pyrimidine (27d) as an off-white solid, MP >150° C. (dec); $^1$H NMR (DMSO-$d_6$) δ 12.43 (s, $D_2O$ exchangeable, 1H), 8.61 (s, 1H), 7.97 (dd, J=2.8, 2.8 Hz; $D_2O$ exchange collapse to d, 1H), 6.72 (dd, J=1.7, 3.5 Hz; $D_2O$ exchange collapse to d, 1H). $^{13}$C-NMR (DMSO-$d_6$) 151.30, 149.58, 142.12, 134.83, 124.32, 102.70; IR (neat) 3128, 3078, 2979, 1621 cm$^{-1}$; MS (ES+) 154.01 (100%, M+1) and 156.01 (33%); Analysis: Calculated for $C_6H_4N_3Cl$: C, 46.93; H, 2.63; N, 27.36; Cl, 23.09; Found: C, 47.10; H, 2.79; N, 27.15; Cl, 22.93.

Step 5: Preparation of
6-Methoxy-N-(benzyloxymethyl)-9-deazahypoxanthine (27e)

To the suspension of pre-washed NaH (20 g, 500 mmol, 1.25 eq, 60% oil dispersion, washed with hexanes 2 times) in anhydrous THF (1.0 L) cooled to 4° C. was added portion wise solid 4-Chloropyrrolo[3,2-d]pyrimidine (27d) (61.4 g, 400 mmol) cautiously with stirring under $N_2$ in portions over 10-15 min such that $H_2$ gas evolution was controlled. After about an hour gas evolution ceased and benzyl chloromethyl ether (61 mL, 440 mmol, 1.1 eq) was added drop wise over 45 min at 4° C. (additional gas evolution was observed). The resulting mixture was allowed to warm to ambient temperature and stir for 1 h. The reaction mixture was cooled to 4° C. and quenched carefully with sodium methoxide (93 mL, 5.4 M solution in methanol, 500 mmol). The mixture was allowed to warm to ambient temperature overnight and neutralized with glacial acetic acid (30 mL, 500 mmol) to pH 6. The mixture was concentrated and the residue triturated with water (2×400 mL). The aqueous layer was decanted and the residue dried in vacuo. The residue was taken in ethyl acetate (250 mL) and boiled to reflux and filtered through a fluted filter paper. The residue was boiled with ethyl acetate (2×100 mL) and filtered (the residue left behind is unwanted compound and doesn't move in TLC analysis 50% ethyl acetate in hexane). The filtrates were combined concentrated in vacuo to 250 mL and kept in refrigerator overnight. The brown crystals obtained was collected by filtration washed with ice cold ethylacetate/hexane (2×100 mL) and dried in vacuo to furnish 6-Methoxy-N-(benzyloxymethyl)-9-deazahypoxanthine (27e) (46.64 g, 43%) as an orange brown solid. An analytical sample was prepared by recrystallization from ethyl acetate; MP 123-127° C.; $^1$H NMR (DMSO-$d_6$) δ 8.44 (s, 1H), 7.86 (d, J=3.1 Hz, 1 H), 7.31-7.22 (m, 5 H), 6.62 (d, J=3.6 Hz, 1 H), 5.75 (s, 2 H), 4.49 (s, 2 H), 4.05 (s, 3 H); $^{13}$C-NMR (DMSO-$d_6$) 156.11, 151.59, 150.09, 137.82, 134.80, 128.53, 127.87, 127.77, 114.99, 103.08, 77.55, 69.95, 53.73; IR (KBr) 1602 cm$^{-1}$; MS (ES+) 269.97 (M+1); Analysis:

Calculated for $C_{15}H_{15}N_3O_2$: C, 66.90; H, 5.61; N, 15.60; Found: C, 67.09; H, 5.60; N, 15.60.

Step 6: Preparation of 6-Methoxy-N-(benzyloxymethyl)-9-bromo-9-deazahypoxanthine (27f)

To a solution of 6-Methoxy-N-(benzyloxymethyl)-9-deazahypoxanthine (27e) (59.81 g, 222 mmol) in dichloromethane (225 mL) under $N_2$ cooled to 4° C. (homogenous reaction mixture) was added NBS (40.3 g, 224 mol, 1.01 eq) in portions over 30 min such that the reaction temperature remained below 15° C. The mixture was stirred at 0° C. for 15 mins and allowed to warm to room temperature over 15 mins (TLC analysis 50% ethyl acetate in hexane). The reaction mixture was vacuum filtered to remove insoluble succinimide. The filtrate was washed with water (2×250 mL) and brine (200 mL), dried ($Na_2SO_4$), filtered and concentrated in vacuo to furnish product as a light brown solid. The solid was dissolved by boiling in ethyl acetate (200 mL) and diluted with hexane (200 mL). The solution was boiled to reflux and filtered hot very quickly (to avoid solid crystallizing out). The filtrate was then boiled and added hexane in increments of 200 mL (total volume of hexane 1600 mL). The hot solution was decanted if needed to remove insoluble residues (the product is soluble in hot 10% ethyl acetate in hexane). The hot filtrate was allowed to cool to room temperature and then kept in freezer overnight. The solid obtained was collected by filtration and washed with hexane and dried in vacuo at room temperature to furnish 6-methoxy-N-(benzyloxymethyl)-9-bromo-9-deazahypoxanthine (27f) (59.6 g, 77%), as a light yellow solid: MP 103-108° C.; $^1$H NMR (DMSO-$d_6$) δ 8.51 (s, 1H), 8.12 (s, 1H), 7.31-7.22 (m, 5H), 5.74 (s, 2H), 4.52 (s, 2H), 4.07 (s, 3H). $^{13}$C-NMR (DMSO-$d_6$) 156.19, 150.66, 148.14, 137.59, 133.45, 128.38, 127.80, 127.67, 115.02, 90.90, 77.79, 70.25, 54.07; IR (KBr) 3078, 1602, 1542 $cm^{-1}$; MS (ES+) 348.27 (100%), 350.28 (98%); Analysis: Calculated for $C_{15}H_{14}N_3O_2Br$: C, 51.74; H, 4.05; N, 12.07; Found: C, 51.72; H, 4.04; N, 12.06.

Example 2

(S)-((2R,3R,4S,5S)-5-(4-amino-5H-pyrrolo[3,2-d]pyrimidin-7-yl)-3,4-dihydroxypyrrolidin-2-yl)methyl 2-amino-3-methylbutanoate Hydrochloride (30f)

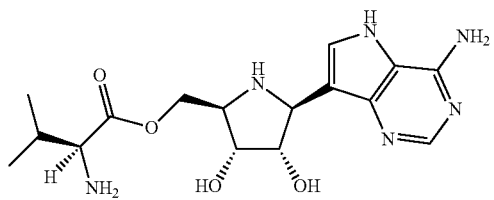

30f

Method A:

To a solution of (3aS,4S,6R,6aR)-tert-butyl 4-(4-amino-5H-pyrrolo[3,2-d]pyrimidin-7-yl)-6-(((2-((tert-butoxycarbonyl)amino)-3-methylbutanoyl)oxy)methyl)-2,2-dimethyl-dihydro-3aH-[1,3]dioxolo[4,5-c]pyrrole-5(4H)-carboxylate (30e) (600 mg, 1 mmol) in TFA (10 mL) was stirred at room temperature for 1 h and concentrated in vacuum to dryness. The residue was dissolved in 10 mL of AcOH and added a solution of $BCl_3$ (3.6 mL, 3.6 mmol, 1 M in dichloromethane), stirred at room temperature for 4 min and quenched with water (5 mL). The reaction mixture was concentrated to dryness. The residue was freeze-dried to afford (S)-((2R,3R,4S,5S)-5-(4-amino-5H-pyrrolo[3,2-d]pyrimidin-7-yl)-3,4-dihydroxypyrrolidin-2-yl)methyl 2-amino-3-methylbutanoate Hydrochloride (30f) (400 mg, 76%) as a white solid; $^1$H NMR (300 MHz, DMSO-$d_6$/$D_2O$) δ 8.64 (s, 1H), 8.21 (s, 1H), 4.83 (d, J=8.4 Hz, 1H), 4.63-4.49 (m, 3H), 4.27-4.19 (m, 1H), 3.94 (d, J=4.8 Hz, 1H), 3.82-3.70 (m, 1H), 2.33-2.18 (m, 1H), 0.99 (d, J=6.9 Hz, 6H); MS (ES+) 365.1 (M+1); Analysis: Calculated for $C_{16}H_{27}Cl_3N_6O_4$.3HCl.2.5$H_2O$: C, 37.17; H, 6.07; Cl, 20.16; N, 16.09; Found: C, 37.04; H, 6.22; Cl, 20.50; N, 16.20.

Method B:

To a solution of (3aS,4S,6R,6aR)-tert-butyl 4-(4-amino-5H-pyrrolo[3,2-d]pyrimidin-7-yl)-6-(((2-((tert-butoxycarbonyl)amino)-3-methylbutanoyl)oxy)methyl)-2,2-dimethyl-dihydro-3aH-[1,3]dioxolo[4,5-c]pyrrole-5(4H)-carboxylate (30e) (0.151 g, 0.25 mmol) in acetone (2 mL) was added conc sulfuric acid (18 N, 0.139 mL, 2.5 mmol) and stirred at room temperature overnight. The reaction mixture was decanted and to the residue was added acetone (10 mL) boiled and cooled to room temperature. The solid obtained was collected by filtration to furnish ((2R,3R,4S,5S)-5-(4-amino-5H-pyrrolo[3,2-d]pyrimidin-7-yl)-3,4-dihydroxypyrrolidin-2-yl)methyl 2-amino-3-methylbutanoate sulfate (30f) as a white solid; $^1$H NMR (300 MHz, $D_2O$) δ 8.42 (s, 1H), 8.04 (s, 1H), 5.05 (d, J=8.1 Hz, 1H), 4.79 (d, J=4.9 Hz, 1H), 4.62 (dd, J=12.6, 7.5 Hz, 1H), 4.55 (t, J=5.2 Hz, 1H), 4.20-4.08 (m, 3H), 2.45-2.28 (m, 1H), 1.06 (t, J=7.3 Hz, 6H).

Method C:

To a solution of (3aS,4S,6R,6aR)-tert-butyl 4-(4-amino-5H-pyrrolo[3,2-d]pyrimidin-7-yl)-6-(((2-((tert-butoxycarbonyl)amino)-3-methylbutanoyl)oxy)methyl)-2,2-dimethyl-dihydro-3aH-[1,3]dioxolo[4,5-c]pyrrole-5(4H)-carboxylate (30e) (0.302 g, 0.5 mmol) in MTBE (2.5 mL) was added water (0.046 mL) and conc sulfuric acid (0.138 mL, 5.00 mmol) followed by MTBE (2.5 mL) after 15 mins and stirred at room temperature for 4 h. Decant TBDME add water (0.5 mL) and stir to dissolve the solid then add ethanol (9.5 mL) and stir vigorously for 2 h. The fine solid obtained was collected by filtration washed with ethanol to give ((2R,3R,4S,5S)-5-(4-amino-5H-pyrrolo[3,2-d]pyrimidin-7-yl)-3,4-dihydroxypyrrolidin-2-yl)methyl 2-amino-3-methylbutanoate sulfate (30f) (0.288 g, 103% yield) as a white solid; $^1$H NMR (300 MHz, DMSO-$d_6$/$D_2O$) δ 8.26 (s, 1H), 7.81 (s, 1H), 4.67 (d, J=6.7 Hz, 1H), 4.59-4.41 (m, 3H), 4.27 (t, J=5.6 Hz, 1H), 3.91 (d, J=4.6 Hz, 1H), 3.81-3.69 (m, 1H), 2.28-2.10 (m, 1H), 0.97 (d, J=6.9 Hz, 6H).

Method D:

To a solution of (3aS,4S,6R,6aR)-tert-butyl 4-(4-amino-5H-pyrrolo[3,2-d]pyrimidin-7-yl)-6-(((2-((tert-butoxycarbonyl)amino)-3-methylbutanoyl)oxy)methyl)-2,2-dimethyl-dihydro-3aH-[1,3]dioxolo[4,5-c]pyrrole-5 (4H)-carboxylate (30e) (0.302 g, 0.5 mmol) in MTBE (2.5 mL) was added water (0.138 mL) and conc sulfuric acid (0.138 mL, 5.00 mmol) followed by MTBE (2.5 mL) after 15 mins and stirred at room temperature for 4 h. Decant TBDME add ethanol (9.5 mL) and stir for 2 h, collect solid by filtration dried in vacuum to furnish a white solid of ((2R,3R,4S,5S)-5-(4-amino-5H-pyrrolo[3,2-d]pyrimidin-7-yl)-3,4-dihydroxypyrrolidin-2-yl)methyl 2-amino-3-methylbutanoate sulfate (30f) (0.160 g, 0.285 mmol, 57.1% yield).

Preparation of (3aS,4S,6R,6aR)-tert-butyl 4-(4-amino-5H-pyrrolo[3,2-d]pyrimidin-7-yl)-6-(((2-((tert-butoxycarbonyl)amino)-3-methylbutanoyl)oxy)methyl)-2,2-dimethyldihydro-3aH-[1,3]dioxolo[4,5-c]pyrrole-5(4H)-carboxylate (30e)

Step 1: Preparation of (2S,3S,4R,5R)-tert-butyl 2-(4-chloro-5H-pyrrolo[3,2-d]pyrimidin-7-yl)-3,4-dihydroxy-5-(hydroxymethyl)pyrrolidine-1-carboxylate (30a)

To a solution of (2R,3R,4S,5S)-2-(acetoxymethyl)-1-(tert-butoxycarbonyl)-5-(4-chloro-5H-pyrrolo[3,2-d]pyrimidin-7-yl)pyrrolidine-3,4-diyl diacetate (28c) (25.8 g, 50.5 mmol) dissolved in methanol (200 mL) and was added sodium methoxide 25% wt in methanol (3.6 mL, 16.66 mmol) at room temperature. The reaction mixture was stirred at room temperature overnight. The reaction mixture was concentrated to dryness and purified with a 600 g column, to afford (2S,3S,4R,5S)-tert-butyl 2-(4-chloro-5H-pyrrolo[3,2-d]pyrimidin-7-yl)-3,4-dihydroxy-5-(hydroxymethyl)pyrrolidine-1-carboxylate (30a) (17.7 g, 46 mmol, 91% yield) as colorless foam; $^1$H NMR (300 MHz, DMSO-d$_6$) δ 12.34 (s, 1H), 8.62 (s, 1H), 7.94 (s, 1H), 5.40-5.02 (m, 2H), 4.96-4.70 (m, 2H), 4.41-4.25 (m, 1H), 4.13-3.93 (m, 2H), 3.69-3.51 (m, 2H), 1.35 (s, 3H), 1.01 (s, 6H); MS (ES+) 384.9 (M+1), 792.6 (2M+Na); (ES−) 382.6 (M−1).

Step 2: Preparation of (3aS,4S,6R,6aR)-tert-butyl 4-(4-chloro-5H-pyrrolo[3,2-d]pyrimidin-7-yl)-6-(hydroxymethyl)-2,2-dimethyldihydro-3aH-[1,3]dioxolo[4,5-c]pyrrole-5(4H)-carboxylate (30b)

To a solution of (2S,3S,4R,5R)-tert-butyl 2-(4-chloro-5H-pyrrolo[3,2-d]pyrimidin-7-yl)-3,4-dihydroxy-5-(hydroxymethyl)pyrrolidine-1-carboxylate (30a) (16.3 g, 42.4 mmol) in acetone (400 mL) was added 2,2-dimethoxypropane (11.17 mL, 89 mmol) and 4-methylbenzenesulfonic acid hydrate (0.41 g, 2.12 mmol). The reaction was stirred at room temperature overnight. The reaction mixture was quenched with TEA (590 μL, 4.24 mmol) and concentrated to dryness. The residue was purified by flash column chromatography (silica gel 500 g) to give (3aS,4S,6R,6aR)-tert-butyl 4-(4-chloro-5H-pyrrolo[3,2-d]pyrimidin-7-yl)-6-(hydroxymethyl)-2,2-dimethyldihydro-3aH-[1,3]dioxolo[4,5-c]pyrrole-5(4H)-carboxylate (30b) (10.7 g, 25.2 mmol, 59.5% yield) as a colorless foam; $^1$H NMR (300 MHz, DMSO-d$_6$) δ 12.45 (s, 1H), 8.67 (s, 1H), 7.81 (s, 1H), 5.09 (d, J=36.7 Hz, 3H), 4.82 (d, J=5.7 Hz, 1H), 4.00 (s, 1H), 3.53 (s, 1H), 3.34 (s, 1H), 1.47 (s, 3H), 1.40 (bs, 4H), 1.29 (bs, 4H), 1.20 (bs, 4H); MS (ES+) 426.9 (M+1); 422.6 (M−1).

Step 3: Preparation of (3aS,4S,6S,6aR)-tert-butyl 4-(4-azido-5H-pyrrolo[3,2-d]pyrimidin-7-yl)-6-(hydroxymethyl)-2,2-dimethyldihydro-3aH-[1,3]dioxolo[4,5-c]pyrrole-5(4H)-carboxylate (30c)

To the solution of (3aS,4S,6R,6aR)-tert-butyl 4-(4-chloro-5H-pyrrolo[3,2-d]pyrimidin-7-yl)-6-(hydroxymethyl)-2,2-dimethyldihydro-3aH-[1,3]dioxolo[4,5-c]pyrrole-5(4H)-carboxylate (30b) (5.1 g, 12 mmol) in DMF (30 mL) was added sodium azide (3.9 g, 60 mmol), the resulting solution was stirred at 80° C. for 4 h. The reaction mixture was concentrated in vacuum to remove most of DMF and the residue obtained was dissolved in chloroform. The organic layer was washed with water, dried with MgSO$_4$ and concentrated in vacuum to give (3aS,4S,6R,6aR)-tert-butyl 4-(4-azido-5H-pyrrolo[3,2-d]pyrimidin-7-yl)-6-(hydroxymethyl)-2,2-dimethyldihydro-3aH-[1,3]dioxolo[4,5-c]pyrrole-5 (4H)-carboxylate (30c) (5 g, 97%); $^1$H NMR (300 MHz, DMSO-d$_6$) δ 13.22 (bs, 1H), 9.87 (s, 1H), 7.69-7.47 (m, 1H), 5.28 (m, 1H), 5.05 (m, 2H), 4.81 (d, J=5.9, 1H), 4.06-3.91 (m, 1H), 3.57 (m, 1H), 3.51-3.38 (m, 1H), 1.48 (s, 3H), 1.41-1.23 (bs, 9H), 1.30 (s, 3H); MS (ES+) 454 (M+Na), 863.1 (2M+1), 885.2 (2M+Na); (ES−) 429.7 (M−1).

Step 4: Preparation of (3aS,4S,6R,6aR)-tert-butyl 4-(4-azido-5H-pyrrolo[3,2-d]pyrimidin-7-yl)-6-(((((S)-2-((tert-butoxycarbonyl)amino)-3-methylbutanoyl)oxy)methyl)-2,2-dimethyldihydro-3aH-[1,3]dioxolo[4,5-c]pyrrole-5(4H)-carboxylate (30d)

To a solution of (3aS,4S,6R,6aR)-tert-butyl 4-(4-azido-5H-pyrrolo[3,2-d]pyrimidin-7-yl)-6-(hydroxymethyl)-2,2-dimethyldihydro-3aH-[1,3]dioxolo[4,5-c]pyrrole-5(4H)-carboxylate (30c) (1.088 g, 2.5 mmol) and (S)-2-((tert-butoxycarbonyl)amino)-3-methylbutanoic acid (L-Boc valine, 0.543 g, 2.5 mmol) in DMF (20 mL) was added EDCI (1.198 g, 6.25 mmol) and DMAP (92 mg, 0.75 mmol). The reaction mixture was stirred at room temperature for 10 days and quenched with water (60 mL) extracted with ethyl acetate (3×50 mL). The organic layers were combined washed with water (2×50 mL), brine, dried and concentrated in vacuum. The residue obtained was purified twice by flash column chromatography to afford (3aS,4S,6R,6aR)-tert-butyl 4-(4-azido-5H-pyrrolo[3,2-d]pyrimidin-7-yl)-6-(((((S)-2-((tert-butoxycarbonyl)amino)-3-methylbutanoyl)oxy)methyl)-2,2-dimethyldihydro-3aH-[1,3]dioxolo[4,5-c]pyrrole-5(4H)-carboxylate (30d) (0.75 g, 47%) as a white solid; $^1$H NMR (300 MHz, DMSO-d$_6$) δ 13.30 (s, 1H), 9.88 (s, 1H), 7.60 (s, 1H), 7.10 (s, 1H), 5.34 (s, 1H), 5.20 (dd, J=5.7, 1.5 Hz, 1H), 4.82 (d, J=5.8 Hz, 1H), 4.34-4.14 (m, 2H), 3.80 (dd, J=8.0, 5.9 Hz, 1H), 3.34 (s, 1H), 1.97-1.84 (m, 1H), 1.47 (s, 3H), 1.43-1.31 (m, 21H), 0.80 (dd, J=6.9, 5.2 Hz, 6H); MS (ES−) 629.1 (M−1); IR (KBr) 2315 cm$^{-1}$.

Step 5: Preparation of (3aS,4S,6R,6aR)-tert-butyl 4-(4-amino-5H-pyrrolo[3,2-d]pyrimidin-7-yl)-6-(((((S)-2-((tert-butoxycarbonyl)amino)-3-methylbutanoyl)oxy)methyl)-2,2-dimethyldihydro-3aH-[1,3]dioxolo[4,5-c]pyrrole-5(4H)-carboxylate (30e)

To a solution of (3aS,4S,6R,6aR)-tert-butyl 4-(4-azido-5H-pyrrolo[3,2-d]pyrimidin-7-yl)-6-(((((S)-2-((tert-butoxycarbonyl)amino)-3-methylbutanoyl)oxy)methyl)-2,2-dimethyldihydro-3aH-[1,3]dioxolo[4,5-c]pyrrole-5(4H)-carboxylate (30d) (0.72 g, 1.19 mmol) in methanol (20 mL) was added Pd/C (200 mg, 5% wt on C) and hydrogenated under hydrogen atmosphere for 2 h. The catalyst was removed by filtration through Celite and the filtrate was concentrated in vacuum. The residue obtained was purified with column to furnish (3aS,4S,6R,6aR)-tert-butyl 4-(4-amino-5H-pyrrolo[3,2-d]pyrimidin-7-yl)-6-(4(S)-2-((tert-butoxycarbonyl)amino)-3-methylbutanoyl)oxy)methyl)-2,2-dimethyldihydro-3aH-[1,3]dioxolo[4,5-c]pyrrole-5(4H)-carboxylate (30e) (600 mg, 83%) as a white solid. $^1$H NMR (300 MHz, DMSO-d$_6$) δ 11.97 (s, 1H), 10.87 (s, 1H), 8.09 (s, 1H), 7.36 (s, 1H), 6.78 (s, 2H), 5.30-5.22 (m, 1H), 5.19-5.07 (m, 1H), 4.88 (d, J=5.9 Hz, 1H), 4.18-4.07 (m, 2H), 3.87-3.79 (m, 1H), 3.44 (qd, J=7.0, 5.1 Hz, 1H), 2.01-1.92 (m, 1H), 1.44-1.32 (m, 21H), 1.28 (s, 3H), 0.82 (d, J=6.7 Hz, 6H); MS (ES+) 605.1 (M+1).

Example 3

(2S,3S)-((2R,3R,4S,5S)-5-(4-amino-5H-pyrrolo[3,2-d]pyrimidin-7-yl)-3,4-dihydroxypyrrolidin-2-yl)methyl 2-amino-3-methylpentanoate Hydrochloride (31c)

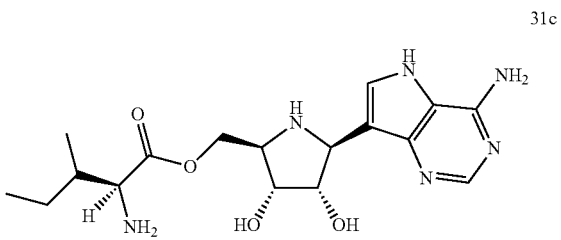 [SMILES: CCC(C)[C@H](N)C(=O)OC[C@H]1N[C@@H](c2c[nH]c3c(N)ncnc23)[C@H](O)[C@@H]1O]

31c

A solution of (3aS,4S,6R,6aR)-tert-butyl 4-(4-amino-5H-pyrrolo[3,2-d]pyrimidin-7-yl)-6-((((2S,3S)-2-((tert-butoxycarbonyl)amino)-3-methylpentanoyl)oxy)methyl)-2,2-dimethyldihydro-3aH-[1,3]dioxolo[4,5-c]pyrrole-5(4H)-carboxylate (31b) (0.398 g, 0.643 mmol) in trifluoroacetic acid (10 mL) was stirred at room temperature for 1 h and concentrated in vacuum to dryness. The residue was triturated with toluene (20 mL) concentrated in vacuum to dryness. The residue obtained was dissolved in AcOH (10 mL) and to this was added a solution of trichloroborane (2.32 mL, 2.32 mmol), stirred at room temperature for 4 min and quenched with water (5 mL). The reaction mixture was concentrated in vacuum to dryness. The gummy solid obtained was dissolved water (5 mL) and filtered. The filtrate was freeze-dried to afford (2S,3S)-((2R,3R,4S,5S)-5-(4-amino-5H-pyrrolo[3,2-d]pyrimidin-7-yl)-3,4-dihydroxypyrrolidin-2-yl)methyl 2-amino-3-methylpentanoate (31c) (0.275 g, 88% yield) as a white solid.

$^1$H NMR (300 MHz, D$_2$O) δ 8.24 (s, 1H), 7.87 (s, 1H), 4.89 (d, J=8.0 Hz, 1H), 4.61-4.43 (m, 3H), 4.41 (t, J=5.0 Hz, 1H), 4.04 (d, J=3.9 Hz, 1H), 3.98 (dt, J=6.7, 4.2 Hz, 1H), 2.00-1.88 (m, 1H), 1.41-1.10 (m, 2H), 0.88 (d, J=7.0 Hz, 3H), 0.79 (t, J=7.4 Hz, 3H); $^1$H NMR (300 MHz, DMSO-d$_6$/D$_2$O) δ 8.61 (s, 1H), 8.17 (s, 1H), 4.85 (d, J=8.3 Hz, 1H), 4.62 (dd, J=12.2, 4.2 Hz, 1H), 4.57-4.46 (m, 2H), 4.24 (t, J=5.0 Hz, 1H), 4.01 (d, J=4.1 Hz, 1H), 2.01-1.94 (m, 1H), 1.56-1.39 (m, 1H), 1.36-1.22 (m, 1H), 0.96 (d, J=6.9 Hz, 3H), 0.90 (t, J=7.3 Hz, 3H); MS (ES+) 379.1 (M+1), (ES−) 412.5 (M+Cl); HPLC [Restek Pinnacle DB C18, 150×4.6 mm, 5 μm, Flow Rate: 1.0 mL per minute at 40° C. "A" buffer=Dissolve 4.3 g of sodium 1-octane sulfonic acid monohydrate in 900 mL of HPLC grade water. Add 10 mL of acetic acid and 100 mL acetonitrile. "B" buffer=Dissolve 4.3 g of sodium 1-octane sulfonic acid monohydrate in 600 mL of HPLC grade water. Add 10 mL of acetic acid and 400 mL of acetonitrile, UV absorbance=260 nM; (A:B, 85/15 (0 min) to A:B 0/100 (25 min) to A:B 0/100 (40 min) to A:B 85/15 (50 min)) Rt=22.79 (97.26%)]; Analysis: Calculated for C$_{17}$H$_{26}$N$_6$O$_4$.3HCl.2.25H$_2$O.2B(OH)$_3$: C, 31.84; H, 6.21; Cl, 16.59; N, 13.11; Found: C, 31.99; H, 6.13; Cl, 16.33; N, 12.80.

Preparation of (3aS,4S,6R,6aR)-tert-butyl 4-(4-amino-5H-pyrrolo[3,2-d]pyrimidin-7-yl)-6-((((2S,3S)-2-((tert-butoxycarbonyl)amino)-3-methylpentanoyl)oxy)methyl)-2,2-dimethyldihydro-3aH-[1,3]dioxolo[4,5-c]pyrrole-5(4H)-carboxylate (31b)

Step 1: Preparation of (3aS,4S,6R,6aR)-tert-butyl 4-(4-azido-5H-pyrrolo[3,2-d]pyrimidin-7-yl)-6-((((2S,3S)-2-((tert-butoxycarbonyl)amino)-3-methylpentanoyl)oxy)methyl)-2,2-dimethyldihydro-3aH-[1,3]dioxolo[4,5-c]pyrrole-5(4H)-carboxylate (31a)

To a solution of (3aS,4S,6R,6aR)-tert-butyl 4-(4-azido-5H-pyrrolo[3,2-d]pyrimidin-7-yl)-6-(hydroxymethyl)-2,2-dimethyldihydro-3aH-[1,3]dioxolo[4,5-c]pyrrole-5(4H)-carboxylate (30c) (1.079 g, 2.5 mmol), (2S,3S)-2-((tert-butoxycarbonyl)amino)-3-methylpentanoic acid (Boc-L-isoleucine) (0.578 g, 2.5 mmol) in DMF (20 mL) was added N1-((ethylimino)methylene)-N3,N3-dimethylpropane-1,3-diamine hydrochloride (EDCI, 1.20 g, 6.25 mmol) and N,N-dimethylpyridin-4-amine (DMAP, 0.092 g, 0.75 mmol). The reaction mixture was stirred at room temperature for 5 days, quenched with 1 N aq. HCl (5.00 mL) and water (60 mL). The reaction mixture was extracted with ethyl acetate (3×50 mL). The organic layers were combined, washed with water (2×25 mL), brine, dried and concentrated in vacuum The residue obtained was purified by flash column chromatography (silica gel, 25 g, eluting with ethyl acetate in hexanes from 0-100%) to afford (3aS,4S,6R,6aR)-tert-butyl 4-(4-azido-5H-pyrrolo[3,2-d]pyrimidin-7-yl)-6-((((2S,3S)-2-((tert-butoxycarbonyl)amino)-3-methylpentanoyl)oxy)methyl)-2,2-dimethyldihydro-3aH-[1,3]dioxolo[4,5-c]pyrrole-5(4H)-carboxylate (31a) (0.683 g, 42% yield) as a white solid; $^1$H NMR (300 MHz, DMSO-d6) δ 13.29 (s, 1H, D$_2$O exchangeable), 9.86 (s, 1H), 7.59 (s, 1H), 7.11 (d, J=7.0 Hz, 1H), 5.32 (s, 1H), 5.20 (d, J=5.8 Hz, 1H), 4.81 (d, J=5.7 Hz, 1H), 4.28 (bs, 2H), 4.08-3.93 (m, 1H), 3.90-3.77 (m, 1H), 1.62 (s, 1H), 1.52-1.21 (m, 26H), 0.84-0.66 (m, 6H); MS (ES+) 645.2 (M+1), 667.2 (M+Na), (ES−) 643.1 (M−1).

Step 2: Preparation of (3aS,4S,6R,6aR)-tert-butyl 4-(4-amino-5H-pyrrolo[3,2-d]pyrimidin-7-yl)-6-((((2S,3S)-2-((tert-butoxycarbonyl)amino)-3-methylpentanoyl)oxy)methyl)-2,2-dimethyldihydro-3aH-[1,3]dioxolo[4,5-c]pyrrole-5(4H)-carboxylate (31b)

To a solution of (3aS,4S,6R,6aR)-tert-butyl 4-(4-azido-5H-pyrrolo[3,2-d]pyrimidin-7-yl)-6-((((2S,3S)-2-((tert-butoxycarbonyl)amino)-3-methylpentanoyl)oxy)methyl)-2,2-dimethyldihydro-3aH-[1,3]dioxolo[4,5-c]pyrrole-5(4H)-carboxylate (31a) (0.625 g, 0.969 mmol) in methanol (20 mL) was added (10%) palladium on carbon (206 mg) and hydrogenated at 60 psi for 3.5 h. TLC analysis shows (ethylacetate/methanol (9:1) in 1:1 hexanes) reaction was complete. The catalyst was removed by filtration through Celite and the filtrate was concentrated in vacuum. The residue obtained was purified by flash column chromatography (silica gel 12 g, eluting with ethyl acetate/methanol (9:1) in hexanes from 0-100%) to furnish (3aS,4S,6R,6aR)-tert-butyl 4-(4-amino-5H-pyrrolo[3,2-d]pyrimidin-7-yl)-6-((((2S,3S)-2-((tert-butoxycarbonyl)amino)-3-methylpentanoyl)oxy)methyl)-2,2-dimethyldihydro-3aH-[1,3]dioxolo[4,5-c]pyrrole-5(4H)-carboxylate (31b) (0.418 g, 70% yield) as a white solid; $^1$H NMR (300 MHz, DMSO-d6) δ 10.86 (bs, 1H, D$_2$O exchangeable), 8.09 (s, 1H), 7.36 (d, J=2.8 Hz, 1H), 7.14 (s, 1H), 6.77 (s, 2H), 5.25 (s, 1H), 5.14 (bs, 1H), 4.88 (d, J=5.9 Hz, 1H), 4.18 (s, 1H), 4.05 (s, 3H), 3.90 (s, 1H), 1.68 (bs, 1H), 1.42 (s, 3H), 1.38 (s, 18H), 1.28 (s, 3H), 1.17 (s, 1H), 0.78 (m, 6H); MS (ES+) 619.2 (M+1), (ES−) 653.2 (M+Cl); Analysis: Calculated for $C_{30}H_{46}N_6O_8 \cdot 0.25H_2O$: C, 57.82; H, 7.52; N, 13.48; Found: C, 57.56; H, 7.42; N, 13.40.

Example 4

(S)-((2R,3R,4S,5S)-5-(4-amino-5H-pyrrolo[3,2-d]pyrimidin-7-yl)-3,4-dihydroxypyrrolidin-2-yl)methyl 2-amino-4-methylpentanoate Hydrochloride (32c)

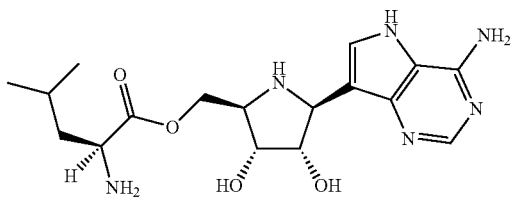

32c

To a solution of (3aS,4S,6R,6aR)-tert-butyl 4-(4-amino-5H-pyrrolo[3,2-d]pyrimidin-7-yl)-6-((((S)-2-((tert-butoxycarbonyl)amino)-4-methylpentanoyl)oxy)methyl)-2,2-dimethyldihydro-3aH-[1,3]dioxolo[4,5-c]pyrrole-5(4H)-carboxylate (32b) (0.243 g, 0.393 mmol) in trifluoroacetic acid (10 mL) was stirred at room temperature for 1 h and concentrated in vacuum to dryness. The residue was triturated with toluene (20 mL) and concentrated in vacuum to dryness. The residue was dissolved in AcOH (10 mL) and added a solution of trichloroborane (1.4 mL, 1.4 mmol), stirred at room temperature for 4 min and quenched with water (5 mL). The reaction mixture was concentrated to dryness. The gummy solid was dissolved with water (5 mL) and filtered. The filtrate was freeze dried to obtain solid (201 mg). The solid was dissolved in 0.37 mL of water and heated gently until clear solution was formed, again 0.13 mL of water was added, then diluted with 9.0 mL of 2-propanol (IPA) then added 0.25 mL of water (now total was 0.75 mL), the solution was decanted to remove the insoluble mass. At this stage solution was clear, heated and added 5.5 mL of IPA, the solution become turbid and allowed to stand for 1 h. The solid obtained was collected by filtration to afford (S)-((2R,3R,4S,5S)-5-(4-amino-5H -pyrrolo[3,2-d]pyrimidin-7-yl)-3,4-dihydroxypyrrolidin-2-yl)methyl 2-amino-4-methylpentanoate Hydrochloride (32c) (73 mg, 49% yield) as a white solid; $^1$H NMR (300 MHz, DMSO-d6) δ 8.47 (s, 1H), 8.03 (s, 1H), 4.77 (d, J=7.5 Hz, 1H), 4.60-4.45 (m, 3H), 4.29 (t, J=5.0 Hz, 1H), 4.03 (t, J=6.4 Hz, 1H), 3.80-3.71 (m, 1H), 1.83-1.58 (m, 3H), 0.90 (d, J=5.2 Hz, 6H); MS (ES+) 379.1 (M+1), (ES−) 412.7 (M+Cl); HPLC [Restek Pinnacle DB C18, 150×4.6 mm, 5 μm column, Flow Rate: 1.0 mL per minute at 40° C. "A" buffer=Dissolve 4.3 g of sodium 1-octane sulfonic acid monohydrate in 900 mL of HPLC grade water. Add 10 mL of acetic acid and 100 mL acetonitrile. "B" buffer=Dissolve 4.3 g of sodium 1-octane sulfonic acid monohydrate in 600 mL of HPLC grade water. Add 10 mL of acetic acid and 400 mL of acetonitrile, UV absorbance=260 nM; (A:B, 85/15 (0 min) to A:B 0/100 (25 min) to A:B 0/100 (40 min) to A:B 85/15 (50 min)) Rt=22.79 (96.3027%)]; Analysis: Calculated for $C_{17}H_{26}N_6O_4 \cdot 2.75H_2O \cdot 2.5HCl$: C, 39.33; H, 6.60; Cl, 17.07; N, 16.19; Found: C, 39.04; H, 6.32; Cl, 17.46; N, 15.96.

Preparation of (3aS,4S,6R,6aR)-tert-butyl 4-(4-amino-5H-pyrrolo[3,2-d]pyrimidin-7-yl)-6-((((S)-2-((tert-butoxycarbonyl)amino)-4-methylpentanoyl)oxy)methyl)-2,2-dimethyldihydro-3aH-[1,3]dioxolo [4,5-c]pyrrole-5(4H)-carboxylate (32b)

Step 1: preparation of (3aS,4S,6R,6aR)-tert-butyl 4-(4-azido-5H-pyrrolo[3,2-d]pyrimidin-7-yl)-6-((((S)-2-((tert-butoxycarbonyl)amino)-4-methylpentanoyl)oxy)methyl)-2,2-dimethyldihydro-3aH-[1,3]dioxolo[4,5-c]pyrrole-5(4H)-carboxylate (32a)

To a solution of (3aS,4S,6R,6aR)-tert-butyl 4-(4-azido-5H-pyrrolo[3,2-d]pyrimidin-7-yl)-6-(hydroxymethyl)-2,2-dimethyldihydro-3aH-[1,3]dioxolo[4,5-c]pyrrole-5(4H)-carboxylate (30c) (1.088 g, 2.52 mmol) and (S)-2-((tert-butoxycarbonyl)amino)-4-methylpentanoic acid (Boc-L-leucine) (0.583 g, 2.52 mmol) in DMF (20 mL) was added N1-((ethylimino)methylene)-N3,N3-dimethylpropane-1,3-diamine hydrochloride (EDCI, 1.21 g, 6.30 mmol) and N,N-dimethylpyridin-4-amine (DMAP, 0.092 g, 0.757 mmol). The reaction mixture was stirred at room temperature for 96 h, quenched with water (60 mL) and extracted with EtOAc (3×50 mL). The combined organic layers were washed with water (2×50 mL), brine (50 mL), dried over $MgSO_4$ and concentrated to dryness in vacuum. The residue obtained was purified by flash column chromatography (silica gel 25 g) to furnish (3aS,4S,6R,6aR)-tert-butyl 4-(4-azido-5H-pyrrolo[3,2-d]pyrimidin-7-yl)-6-((((S)-2-((tert-butoxycarbonyl)amino)-4-methylpentanoyl)oxy)methyl)-2,2-dimethyldihydro-3aH-[1,3]dioxolo[4,5-c]pyrrole-5(4H)-carboxylate (32a) (633 mg, 39% yield) as a white foam; $^1$H NMR (300 MHz, DMSO-d6) δ 13.28 (s, 1H), 9.86 (s, 1H), 7.56 (s, 1H), 7.19 (d, J=7.4 Hz, 1H), 5.31 (s, 1H), 5.16 (d, J=6.8 Hz, 1H), 4.80 (d, J=5.8 Hz, 1H), 4.23 (s, 2H), 3.86 (t, J=11.4 Hz, 1H), 1.39 (m, 27H), 0.86 (dd, J=11.7, 6.0 Hz, 1H), 0.75 (dd, J=13.6, 6.5 Hz, 6H); MS (ES+) 645.19 (M+1), 667.17 (M+Na); (ES−) 643.20 (M−1), 679.18 (M+Cl).

Step 2: (3aS,4S,6R,6aR)-tert-butyl 4-(4-amino-5H-pyrrolo[3,2-d]pyrimidin-7-yl)-6-((((S)-2-((tert-butoxycarbonyl)amino)-4-methylpentanoyl)oxy)methyl)-2,2-dimethyldihydro-3aH-[1,3]dioxolo[4,5-c]pyrrole-5(4H)-carboxylate (32b)

To a solution of (3aS,4S,6R,6aR)-tert-butyl 4-(4-azido-5H-pyrrolo[3,2-d]pyrimidin-7-yl)-6-((((S)-2-((tert-butoxycarbonyl)amino)-4-methylpentanoyl)oxy)methyl)-2,2-dimethyldihydro-3aH-[1,3]dioxolo[4,5-c]pyrrole-5(4H)-carboxylate (32a) (584 mg, 0.91 mmol) in methanol (20 mL) was added 10% Palladium on carbon (193 mg) and hydrogenated at 50 psi for 2 h. The catalyst was filtered through a pad of Celite, and the filtrate was concentrated in vacuum. The residue obtained was purified by flash column chromatography (silica gel, 4 g) to furnish (3aS,4S,6R,6aR)-tert-butyl 4-(4-amino-5H -pyrrolo[3,2-d]pyrimidin-7-yl)-6-((((S)-2-((tert-butoxycarbonyl)amino)-4-methylpentanoyl)oxy)methyl)-2,2-dimethyldihydro-3aH-[1,3]dioxolo[4,5-c] pyrrole-5(4H) -carboxylate (32b) (300 mg, 53.5% yield) as a white solid; $^1$H NMR (300 MHz, DMSO-d6) δ 10.86 (s, 1H, exchangeable), 8.09 (d, J=5.0 Hz, 1H), 7.34 (d, J=2.4 Hz, 1H), 7.22 (s, 1H), 6.78 (s, 2H, exchangeable), 5.23 (d, J=5.3 Hz, 1H), 5.14 (s, 1H), 4.87 (d, J=5.7 Hz, 1H), 4.22-4.05 (m, 3H), 3.99-3.86 (m, 1H), 3.17 (d, J=5.2 Hz, 1H), 1.55 (dd, J=12.5, 6.0 Hz, 1H), 1.46-1.34 (m, 22H), 1.28 (s, 3H), 0.81 (dd, J=9.1, 6.7 Hz, 6H); MS (ES+) 619.13

(M+1), 642.15 (M+Na); (ES−) 617.18 (M−1), 653.27 (M+Cl); Analysis: Calculated for $C_{30}H_{44}N_8O_8 \cdot 0.5H_2O$: C, 57.40; H, 7.55; N, 13.39; Found: C, 57.46; H, 7.53; N, 13.13.

Example 5

(2S,2'S)-(2S,3S,4R,5R)-2-(4-amino-5H-pyrrolo[3,2-d]pyrimidin-7-yl)-5-(hydroxymethyl)pyrrolidine-3,4-diylbis(2-amino-3-methylbutanoate) (38c)

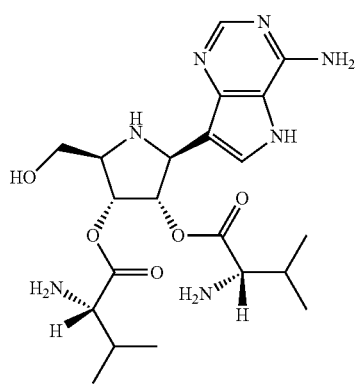

To a solution of (2S,2'S)-(2S,3S,4R,5R)-2-(4-amino-5H-pyrrolo[3,2-d]pyrimidin-7-yl)-1-(tert-butoxycarbonyl)-5-((trityloxy)methyl)pyrrolidine-3,4-diylbis(2-((tert -butoxycarbonyl)amino)-3-methylbutanoate) (38b) (715 mg, 0.711 mmol) in acetone (25 mL) was added 9 M sulfuric acid (0.395 mL, 3.55 mmol) and stirred at room temperature overnight. The acetone layer was decanted and the residue was treated with acetone and decanted (3 times). The residue obtained was purified by flash column chromatography (silica gel 12 g, eluting with 0-100% CMA-50 in CMA-80) to furnish (2S,2'S)-(2S,3S,4R,5R)-2-(4-amino-5H-pyrrolo[3,2-d]pyrimidin-7-yl)-5-(hydroxymethyl)pyrrolidine-3,4-diylbis(2-amino-3-methylbutanoate) (38c) (188 mg, 57%) as a white solid; $^1$H NMR (300 MHz, DMSO-d$_6$) δ 10.84 (bs, 1H, D$_2$O exchangeable), 8.06 (s, 1H), 7.51 (d, J=2.3 Hz, 1H), 6.77 (s, 2H, D$_2$O exchangeable), 5.33 (dd, J=7.6, 5.6 Hz, 1H), 5.24 (dd, J=5.7, 3.8 Hz, 1H), 4.39 (d, J=7.6 Hz, 1H), 3.64-3.51 (m, 2H), 3.17 (dd, J=4.5, 2.9 Hz, 2H), 3.06 (d, J=4.9 Hz, 1H), 2.01-1.88 (m, 1H), 1.87-1.75 (m, 1H), 0.91 (d, J=6.8 Hz, 3H), 0.84 (d, J=6.7 Hz, 3H), 0.79 (d, J=6.8 Hz, 3H), 0.73 (d, J=6.8 Hz, 3H); MS (ES+) 928.2 (2M+1); (ES−) 462.0 (M−1), 925.1 (2M−1).

Preparation of (2S,2'S)-(2S,3S,4R,5R)-2-(4-amino-5H-pyrrolo[3,2-d]pyrimidin-7-yl)-1-(tert-butoxycarbonyl)-5-((trityloxy)methyl)pyrrolidine-3,4-diylbis(2-((tert-butoxycarbonyl)amino)-3-methylbutanoate) (38b)

Step 1: (2S,3S,4R,5R)-tert-butyl 2-(4-chloro-5H-pyrrolo[3,2-d]pyrimidin-7-yl)-3,4-dihydroxy-5-(hydroxymethyl)pyrrolidine-1-carboxylate (34a)

To a solution of (2R,3R,4S,5S)-2-(acetoxymethyl)-1-(tert-butoxycarbonyl)-5-(4-chloro-5H-pyrrolo[3,2-d]pyrimidin-7-yl)pyrrolidine-3,4-diyl diacetate (28c) (25.8 g, 50.5 mmol) in methanol (200 mL) and was added sodium methoxide 25% wt in methanol (3.6 mL, 16.66 mmol) at room temperature. The reaction mixture was stirred at room temperature overnight. The reaction mixture was concentrated in vacuum to dryness and purified by flash column chromatography (silica gel 600 g) to furnish (2S,3S,4R,5R)-tert -butyl 2-(4-chloro-5H-pyrrolo[3,2-d]pyrimidin-7-yl)-3,4-dihydroxy-5-(hydroxymethyl)pyrrolidine-1-carboxylate (34a) (17.7 g, 91% yield) as colorless foam; $^1$H NMR (300 MHz, DMSO-d$_6$) δ 12.34 (s, 1H), 8.62 (s, 1H), 7.94 (s, 1H), 5.40-5.02 (m, 2H), 4.96-4.70 (m, 2H), 4.41-4.25 (m, 1H), 4.13-3.93 (m, 2H), 3.69-3.51 (m, 2H), 1.35 (s, 3H), 1.01 (s, 6H); MS (ES+) 384.9 (M+1), 792.6 (2M+Na); (ES−) 382.6 (M−1).

Step 2: Preparation of (2S,3S,4R,5R)-tert-butyl 2-(4-azido-5H-pyrrolo[3,2-d]pyrimidin-7-yl)-3,4-dihydroxy-5-(hydroxymethyl)pyrrolidine-1-carboxylate (34b)

To a solution of (2S,3S,4R,5R)-tert-butyl 2-(4-chloro-5H-pyrrolo[3,2-d]pyrimidin-7-yl)-3,4-dihydroxy-5-(hydroxymethyl)pyrrolidine-1-carboxylate (34a) (4 g, 10.39 mmol) in DMF (80 mL) was added sodium azide (3.38 g, 52.0 mmol) and heated with stirring at 80° C. for 10 h. The reaction was cooled to 25° C., dumped in ice and extracted with ethyl acetate. The ethyl acetate layer was separated washed with water, brine, dried, filtered and concentrated in vacuum to dryness (water bath 50° C.). The crude residue obtained was purified by flash column chromatography (silica gel 120 g, eluting with methanol in chloroform from 0-100%) to furnish (2S,3S,4R,5R)-tert-butyl 2-(4-azido-5H-pyrrolo[3,2-d]pyrimidin-7-yl)-3,4-dihydroxy-5-(hydroxymethyl)pyrrolidine-1-carboxylate (34b) (1.28 g, 31% yield) as a white solid; $^1$H NMR (300 MHz, DMSO-d$_6$) δ 13.05 (bs, 1H, D$_2$O exchangeable), 9.84 (s, 1H), 7.81 (m, 1H), 5.13 (m, 1H), 5.05-4.83 (m, 3H, D$_2$O exchangeable), 4.24 (m, 1H), 4.09 (m, 1H), 4.03 (m, 1H), 3.59 (m, 2H), 1.38 (s, 4H for Boc) and 1.05 (s, 5H for Boc); MS (ES+) 782.8 (2M+1), (ES−) 389.6 (M−1).

Step 3: Preparation of (2S,3S,4R,5R)-tert-butyl 2-(4-azido-5H-pyrrolo[3,2-d]pyrimidin-7-yl)-3,4-dihydroxy-5-((trityloxy)methyl)pyrrolidine-1-carboxylate (35a)

To a solution of (2S,3S,4R,5R)-tert-butyl 2-(4-azido-5H-pyrrolo[3,2-d]pyrimidin-7-yl)-3,4-dihydroxy-5-(hydroxymethyl)pyrrolidine-1-carboxylate (34b) (1.0 g, 2.55 mmol) in pyridine (5.0 mL, 62.06 mmol) was added chlorotriphenylmethane (0.85 g, 3.07 mmol). The resulting mixture was stirred at 50° C. for 4 h at which time the reaction has gone to completion (TLC in 9:1 chloroform:methanol). The reaction mixture was cooled to 25° C., dumped in ice water (80 mL) and extracted with ethyl acetate (100 mL, 2×60 mL). The organic layers were combined washed with water, brine, dried, filtered and concentrated in vacuum to yield an off-white solid The solid was triturated with 5% EtOAc in n-hexane and collected by filtration to furnish (2S,3S,4R,5R)-tert-butyl 2-(4-azido-5H-pyrrolo[3,2-d]pyrimidin-7-yl)-3,4-dihydroxy-5-((trityloxy)methyl)pyrrolidine-1-carboxylate (35a) (1.47 g, 90.74% yield) as a pale yellow solid; $^1$H NMR (300 MHz, DMSO-d$_6$, 370 K) δ 12.82 (s, 1H), 9.48 (s, 1H), 7.44 (s, 1H), 7.36 (d, J=8.0 Hz, 5H), 7.29-7.19 (m, 9H), 4.96 (d, J=4.6 Hz, 1H), 4.72 (d, J=5.3 Hz, 1H), 4.59 (d, J=5.0 Hz, 1H), 4.54-4.46 (m, 1H), 4.38-4.30 (m, 1H), 4.08-3.99 (m, 1H), 3.93-3.84 (m, 1H), 3.46 (dd, J=9.1, 6.4

Hz, 1H), 3.37 (dd, J=9.2, 4.2 Hz, 1H), 1.19 (s, 9H); MS (ES+) 655.85 (M+Na), (ES−) 632.55 (M−1). IR (KBr) 2133 cm$^{-1}$.

Step 4: Preparation of (2S,3S,4R,5R)-tert-butyl 2-(4-azido-5H-pyrrolo[3,2-d]pyrimidin-7-yl)-3-(((S)-2-((tert-butoxycarbonyl)amino)-3-methylbutanoyl)oxy)-4-hydroxy-5-((trityloxy)methyl)pyrrolidine-1-carboxylate (39a); (2S,3S,4R,5R)-tert-butyl 2-(4-azido-5H-pyrrolo[3,2-d]pyrimidin-7-yl)-4-(((S)-2-((tert-butoxycarbonyl)amino)-3-methylbutanoyl)oxy)-3-hydroxy-5-((trityloxy)methyl)pyrrolidine-1-carboxylate (39b) and (2S,2'S)-(2S,3S,4R,5R)-2-(4-azido-5H-pyrrolo[3,2-d]pyrimidin-7-yl)-1-(tert-butoxycarbonyl)-5-((trityloxy)methyl)pyrrolidine-3,4-diylbis(2-((tert-butoxycarbonyl)amino)-3-methylbutanoate) (38a)

Method 1:

To a solution of (2S,3S,4R,5R)-tert-butyl 2-(4-azido-5H-pyrrolo[3,2-d]pyrimidin-7-yl)-3,4-dihydroxy-5-((trityloxy)methyl)pyrrolidine-1-carboxylate (35a) (1 g, 1.578 mmol) and (S)-2-(tert-butoxycarbonylamino)-3-methylbutanoic acid (L-Boc valine, 0.343 g, 1.58 mmol) in DMF (10 mL) was added N1-((ethylimino)methylene)-N3,N3-dimethylpropane-1,3-diamine hydrochloride (EDCI, 0.756 g, 3.95 mmol) and N,N-dimethylpyridin-4-amine (DMAP, 0.193 g, 1.578 mmol) at room temperature. The reaction mixture was stirred at room temperature overnight. TLC analysis (10% chloroform in methanol) some unreacted (2S,3S,4R,5R)-tert-butyl 2-(4-azido-5H-pyrrolo[3,2-d]pyrimidin-7-yl)-3,4-dihydroxy-5-((trityloxy)methyl)pyrrolidine-1-carboxylate (35a). The reaction was quenched with water (50 mL) and extracted with ethyl acetate (3×100 mL). The organic layers were combined, washed with water, brine (100 mL), dried, filtered and concentrated in vacuum. The crude residue obtained was purified by flash column chromatography (silica gel 40 g) to furnish:

2-(4-azido-5H-pyrrolo[3,2-d]pyrimidin-7-yl)-3,4-dihydroxy-5-((trityloxy)methyl)pyrrolidine-1-carboxylate (35a) (196 mg, 19.6%) as a white solid;

(2S,3S,4R,5R)-tert-butyl 2-(4-azido-5H-pyrrolo[3,2-d]pyrimidin-7-yl)-3-(((S)-2-((tert-butoxycarbonyl)amino)-3-methylbutanoyl)oxy)-4-hydroxy-5-((trityloxy)methyl)pyrrolidine-1-carboxylate (39a) (511 mg, 38.9%) as a white solid; $^1$H NMR (300 MHz, DMSO-d$_6$, 370K) δ 12.86 (s, 1H), 9.39 (s, 1H), 7.47 (s, 1H), 7.38 (d, J=7.9 Hz, 6H), 7.31-7.18 (m, 9H), 6.57 (d, J=7.3 Hz, 1H), 5.46 (s, 1H), 5.05 (d, J=6.2 Hz, 1H), 4.94 (d, J=6.3 Hz, 1H), 4.78-4.69 (m, 1H), 4.13-4.05 (m, 2H), 3.53-3.36 (m, 2H), 2.19-2.04 (m, 1H), 1.42 (s, 9H), 1.17 (s, 9H), 0.92 (t, J=6.7 Hz, 6H); IR (KBr) 2133 cm$^{-1}$; MS (ES−) 831.1 (M−1);

(2S,3S,4R,5R)-tert-butyl 2-(4-azido-5H-pyrrolo[3,2-d]pyrimidin-7-yl)-4-(((S)-2-((tert-butoxycarbonyl)amino)-3-methylbutanoyl)oxy)-3-hydroxy-5-((trityloxy)methyl)pyrrolidine-1-carboxylate (39b) (250 mg, 19%) as a white solid; $^1$H NMR (300 MHz, DMSO-d$_6$, 370K) δ 12.84 (s, 1H), 9.49 (s, 1H), 7.51 (s, 1H), 7.36-7.28 (m, 6H), 7.25-7.17 (m, 9H), 6.48 (d, J=7.6 Hz, 1H), 5.81-5.71 (m, 1H), 5.22 (d, J=4.2 Hz, 1H), 5.00 (d, J=6.0 Hz, 1H), 4.71 (t, J=8.1 Hz, 1H), 3.91 (m, 2H), 3.56-3.32 (m, 2H), 2.10-2.00 (m, 1H), 1.32 (s, 9H), 1.22 (s, 9H), 0.88 (dd, J=6.6, 3.4 Hz, 6H); IR (KBr) 2134 cm$^{-1}$; MS (ES−) 831.1 (M−1); and (2S,2'S)-(2S,3S,4R,5R)-2-(4-azido-5H-pyrrolo[3,2-d]pyrimidin-7-yl)-1-(tert-butoxycarbonyl)-5-((trityloxy)methyl)pyrrolidine-3,4-diyl bis(2-((tert-butoxycarbonyl)amino)-3-methylbutanoate) (38a) (18 mg, 1.1%) as a white solid; $^1$H NMR (300 MHz, DMSO, 370K) δ 12.94 (s, 1H, N—H), 9.38 (s, 1H), 7.54 (s, 1H), 7.38-7.14 (m, 15H), 6.51 (s, 1H, N—H), 6.37 (s, 1H, N—H), 5.97 (d, J=17.2 Hz, 1H), 5.76 (s, 1H), 5.22 (t, J=11.3 Hz, 1H), 4.19-3.98 (m, 2H), 3.91 (d, J=5.3 Hz, 1H), 3.55 (d, J=18.8 Hz, 1H), 3.35 (m, 1H), 2.06 (m, 2H), 1.37 (s, 9H), 1.24 (s, 9H), 1.21 (s, 9H), 0.94-0.78 (m, 12H).

Method 2:

To a solution of (2S,3S,4R,5R)-tert-butyl 2-(4-azido-5H-pyrrolo[3,2-d]pyrimidin-7-yl)-3,4-dihydroxy-5-((trityloxy)methyl)pyrrolidine-1-carboxylate (35a) (1.0 g, 1.58 mmol) and (S)-2-(tert-butoxycarbonylamino)-3-methylbutanoic acid (L-Boc valine, 0.720 g, 3.31 mmol) in DMF (10 mL) was added N1-((ethylimino)methylene)-N3,N3-dimethylpropane-1,3-diamine hydrochloride (EDCI, 0.756 g, 3.95 mmol) and N,N-dimethylpyridin-4-amine (DMAP, 0.193 g, 1.578 mmol) at room temperature. The reaction mixture was stirred at room temperature overnight and quenched with water (30 mL). The reaction mixture was extracted with ethyl acetate (3×60 mL). The organic layers were combined washed with water, brine (50 mL), dried, filtered and concentrated in vacuum. The crude residue obtained was purified by flash column chromatography (silica gel 25 g, eluting with ethyl acetate in hexanes 0-50%) to furnish (2S,2'S)-(2S,3S,4R,5R)-2-(4-azido-5H-pyrrolo[3,2-d]pyrimidin-7-yl)-1-(tert-butoxycarbonyl)-5-((trityloxy)methyl)pyrrolidine-3,4-diylbis(2-((tert-butoxycarbonyl)amino)-3-methylbutanoate) (38a) (670 mg, 41.2% yield) as a white foam, plus mixture containing (2S,3S,4R,5R)-tert-butyl 2-(4-azido-5H-pyrrolo[3,2-d]pyrimidin-7-yl)-3-(((S)-2-((tert-butoxycarbonyl)amino)-3-methylbutanoyl)oxy)-4-hydroxy-5-((trityloxy)methyl)pyrrolidine-1-carboxylate (39a) and (2S,3S,4R,5R)-tert-butyl 2-(4-azido-5H-pyrrolo[3,2-d]pyrimidin-7-yl)-4-(((S)-2-((tert-butoxycarbonyl)amino)-3-methylbutanoyl)oxy)-3-hydroxy-5-((trityloxy)methyl)pyrrolidine-1-carboxylate (39b) (610 mg, 47.9%) as a white foam; MS (ES−) 831.5 (M−1).

Step 5: Preparation of (2S,2'S)-(2S,3S,4R,5R)-2-(4-amino-5H-pyrrolo[3,2-d]pyrimidin-7-yl)-1-(tert-butoxycarbonyl)-5-((trityloxy)methyl)pyrrolidine-3,4-diylbis(2-((tert-butoxycarbonyl)amino)-3-methylbutanoate) (38b)

To a solution of (2S,2'S)-(2S,3S,4R,5R)-2-(4-azido-5H-pyrrolo[3,2-d]pyrimidin-7-yl)-1-(tert-butoxycarbonyl)-5-((trityloxy)methyl)pyrrolidine-3,4-diyl bis(2-((tert-butoxycarbonyl)amino)-3-methylbutanoate) (38a) (964 mg, 0.934 mmol) in ethanol (25 mL) was added Pd/C (10%) (150 mg) and hydrogenated at 50 psi overnight. The catalyst was removed by filtration through a pad of Celite and the filtrate was concentrated in vacuum. The residue obtained was purified by flash column chromatography (silica gel 4 g, eluting with (ethyl acetate/methanol, 9:1) in hexane, 0-100%) to furnish (2S,2'S)-(2S,3S,4R,5R)-2-(4-amino-5H-pyrrolo[3,2-d]pyrimidin-7-yl)-1-(tert-butoxycarbonyl)-5-((trityloxy)methyl)pyrrolidine-3,4-diyl bis(2-((tert-butoxycarbonyl)amino)-3-methylbutanoate) (38b) (765 mg, 81% yield) as a white solid; $^1$H NMR (300 MHz, DMSO-d$_6$, 370K) δ 10.61 (s, 1H, N—H), 7.86 (d, J=2.2 Hz, 1H), 7.37-7.17 (m, 16H), 6.38 (m, 2H, N—H), 6.30 (s, 2H, N—H), 6.16 (t, J=5.1 Hz, 1H), 5.87 (t, J=3.8 Hz, 1H), 5.06 (d, J=5.9 Hz, 1H), 4.12-4.00 (m, 2H), 3.98-3.86 (m, 1H), 3.78 (dd, J=9.7, 6.9 Hz, 1H), 3.20 (m, 1H), 2.05 (m, 2H), 1.40 (s, 9H), 1.31 (s, 9H), 1.23 (d, J=2.0 Hz, 9H), 0.90-0.80

(m, 12H); Analysis: Calculated for $C_{55}H_{71}N_7O_{11}\cdot H_2O$: C, 64.50; H, 7.18; N, 9.57; Found: C, 64.36; H, 7.11; N, 9.38.

Example 6

Preparation of (S)-(2R,3R,4S,5S)-5-(4-amino-5H-pyrrolo[3,2-d]pyrimidin-7-yl)-4-hydroxy-2-(hydroxymethyl)pyrrolidin-3-yl 2-amino-3-methylbutanoate (35e) and (S)-(2S,3S,4R,5R)-2-(4-amino-5H-pyrrolo[3,2-d]pyrimidin-7-yl)-4-hydroxy-5-(hydroxymethyl)pyrrolidin-3-yl 2-amino-3-methylbutanoate (34f)

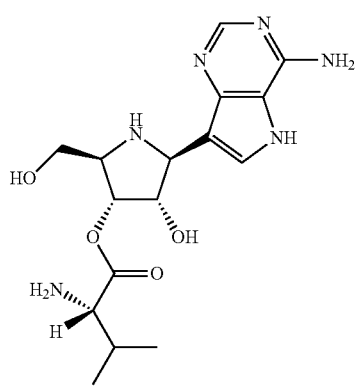

35e

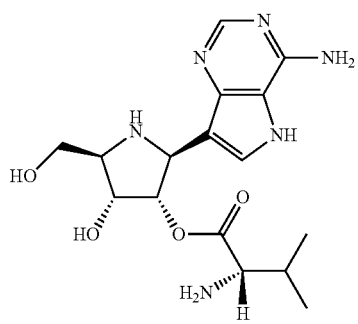

34f

Method 1:

From (2S,3S,4R,5R)-tert-butyl 2-(4-amino-5H-pyrrolo[3,2-d]pyrimidin-7-yl)-3-(((S)-2-((tert-butoxycarbonyl)amino)-3-methylbutanoyl)oxy)-4-hydroxy-5-((trityloxy)methyl)pyrrolidine-1-carboxylate (39d) and (2S,3S,4R,5R)-tert-butyl 2-(4-amino-5H-pyrrolo[3,2-d]pyrimidin-7-yl)-4-(((S)-2-((tert-butoxycarbonyl)amino)-3-methylbutanoyl)oxy)-3-hydroxy-5-((trityloxy)methyl)pyrrolidine-1-carboxylate (39e)

To a solution of (2S,3S,4R,5R)-tert-butyl 2-(4-amino-5H-pyrrolo[3,2-d]pyrimidin-7-yl)-3-(((S)-2-((tert-butoxycarbonyl)amino)-3-methylbutanoyl)oxy)-4-hydroxy-5-((trityloxy)methyl)pyrrolidine-1-carboxylate (39d) and (2S,3S,4R,5R)-tert-butyl 2-(4-amino-5H-pyrrolo[3,2-d]pyrimidin-7-yl)-4-(((S)-2-((tert-butoxycarbonyl)amino)-3-methylbutanoyl)oxy)-3-hydroxy-5-((trityloxy)methyl)pyrrolidine-1-carboxylate (39e) (744 mg, 0.922 mmol) in acetone (15 mL) was added 9 M sulfuric acid (0.512 mL, 4.61 mmol) and stirred at room temperature overnight. The solvent was decanted and the white solid was washed with acetone and stirred for 30 min before decanting again. The same procedure was repeated 3-4 times, the solid obtained was collected by filtration, washed with acetone dried under vacuum at 35° C. to give mixtures of (S)-(2R,3R,4S,5S)-5-(4-amino-5H-pyrrolo[3,2-d]pyrimidin-7-yl)-4-hydroxy-2-(hydroxymethyl)pyrrolidin-3-yl 2-amino-3-methylbutanoate (35e) and (S)-(2S,3S,4R,5R)-2-(4-amino-5H-pyrrolo[3,2-d]pyrimidin-7-yl)-4-hydroxy-5-(hydroxymethyl)pyrrolidin-3-yl 2-amino-3-methylbutanoate (34f) as a sulfate salt (500 mg, 1.081 mmol, 97% yield) as a white solid. Purification using flash column chromatography (233 mgs of sample mixture, silica gel eluting with 0-100% CMA-50 in CMA-80) afforded mixtures of (S)-(2R,3R,4S,5S)-5-(4-amino-5H-pyrrolo[3,2-d]pyrimidin-7-yl)-4-hydroxy-2-(hydroxymethyl)pyrrolidin-3-yl 2-amino-3-methylbutanoate (35e) and (S)-(2S,3S,4R,5R)-2-(4-amino-5H-pyrrolo[3,2-d]pyrimidin-7-yl)-4-hydroxy-5-(hydroxymethyl)pyrrolidin-3-yl 2-amino-3-methylbutanoate (34f) (74 mgs, 48%) as a white solid; $^1$H NMR (300 MHz, DMSO-$d_6$) δ [8.08 (s, 0.65H), 8.07 (s, 0.35H) 1H], [7.49 (s, 0.35H), 7.48 (s, 0.65H) 1H], [5.09 (t, J=6.4 Hz, 0.35H), 5.01 (dd, J=5.7, 3.7 Hz, 0.65H) 1H], [4.35 (d, J=6.7 Hz, 0.35H), 4.21 (d, J=5.6 Hz, 0.35H), 4.18 (d, J=5.7 Hz, 0.65H), 4.14-4.09 (m, 1.65H) 3H], [3.63-3.48 (m, 1H) 1H], [3.25 (d, J=5.1 Hz, 0.7H), 3.20-3.10 (m, 1.3H) 2H], [2.05-1.82 (m, 1H)], [0.93 (d, J=6.8 Hz, 1.95H), 0.88 (d, J=6.8 Hz, 1.95H), 0.81 (d, J=6.9 Hz, 1.05H), 0.77 (d, J=6.8 Hz, 1.05H) 6H]; MS (ES+) 365.0 (M+1).

Method 2:

From (6aR,8S,9S,9aR)-tert-butyl 8-(4-amino-5H-pyrrolo[3,2-d]pyrimidin-7-yl)-9-(((S)-2-((tert-butoxycarbonyl)amino)-3-methylbutanoyl)oxy)-2,2,4,4-tetraisopropyltetrahydro-[1,3,5,2,4]trioxadisilocino[7,6-b]pyrrole-7(8H)-carboxylate (34e)

To a stirred solution of (6aR,8S,9S,9aR)-tert-butyl 8-(4-amino-5H-pyrrolo[3,2-d]pyrimidin-7-yl)-9-(((S)-2-((tert-butoxycarbonyl)amino)-3-methylbutanoyl)oxy)-2,2,4,4-tetraisopropyltetrahydro-[1,3,5,2,4]trioxadisilocino[7,6-b]pyrrole-7(8H)-carboxylate (34e) (0.843 g, 1.04 mmol) in acetone (10 mL) was added conc. sulfuric acid (50% solution in water, 1.16 mL, 10.44 mmol) at room temperature and stirred for 18 h. The reaction mixture was diluted with acetone (30 mL) and stirred. Acetone was decanted and this operation was repeated twice. The solid that separated out was collected by filtration dried in vacuum to furnish mixtures of (S)-(2R,3R,4S,5S)-5-(4-amino-5H-pyrrolo[3,2-d]pyrimidin-7-yl)-4-hydroxy-2-(hydroxymethyl)pyrrolidin-3-yl 2-amino-3-methylbutanoate (35e) and (S)-(2S,3S,4R,5R)-2-(4-amino-5H-pyrrolo[3,2-d]pyrimidin-7-yl)-4-hydroxy-5-(hydroxymethyl)pyrrolidin-3-yl 2-amino-3-methylbutanoate sulfate salt (34f) (0.4 g, 68%) as a white solid. The solid was purified by flash column chromatography (silica gel 4 g eluting with 0-100% CMA-50 in CMA-80) to furnish mixtures of (S)-(2R,3R,4S,5S)-5-(4-amino-5H-pyrrolo[3,2-d]pyrimidin-7-yl)-4-hydroxy-2-(hydroxymethyl)pyrrolidin-3-yl 2-amino-3-methylbutanoate (35e) and (S)-(2S,3S,4R,5R)-2-(4-amino-5H-pyrrolo[3,2-d]pyrimidin-7-yl)-4-hydroxy-5-(hydroxymethyl)pyrrolidin-3-yl 2-amino-3-methylbutanoate (34f); NMR analysis shows mixtures of compound 35e and 34f; MS (ES+) 365.1 (M+1), (ES−) 362.9 (M−1).

115

Preparation of (2S,3S,4R,5R)-tert-butyl 2-(4-amino-5H-pyrrolo[3,2-d]pyrimidin-7-yl)-3-(((S)-2-((tert-butoxycarbonyl)amino)-3-methylbutanoyl)oxy)-4-hydroxy-5-((trityloxy)methyl)pyrrolidine-1-carboxylate (39d) and (2S,3S,4R,5R)-tert-butyl 2-(4-amino-5H-pyrrolo[3,2-d]pyrimidin-7-yl)-4-(((S)-2-((tert-butoxycarbonyl)amino)-3-methylbutanoyl)oxy)-3-hydroxy-5-((trityloxy)methyl)pyrrolidine-1-carboxylate (39e)

Method 1:

From (2S,3S,4R,5R)-tert-butyl 2-(4-azido-5H-pyrrolo[3,2-d]pyrimidin-7-yl)-3-(((S)-2-((tert-butoxycarbonyl)amino)-3-methylbutanoyl)oxy)-4-hydroxy-5-((trityloxy)methyl)pyrrolidine-1-carboxylate (39a)

To a solution of (2S,3S,4R,5R)-tert-butyl 2-(4-azido-5H-pyrrolo[3,2-d]pyrimidin-7-yl)-3-(((S)-2-((tert-butoxycarbonyl)amino)-3-methylbutanoyl)oxy)-4-hydroxy-5-((trityloxy)methyl)pyrrolidine-1-carboxylate (39a) (1.319 g, 1.584 mmol) in ethanol (50 mL) was added 10% Pd/C (200 mg) and hydrogenated at 50 psi for 8 h. The catalyst was removed by filtration of the reaction mixture through a pad of Celite. The filtrate was concentrated in vacuum and the residue obtained was purified by flash column chromatography to furnish a 3:2 mixture (analyzed by NMR) of (2S,3S,4R,5R)-tert-butyl 2-(4-amino-5H-pyrrolo[3,2-d]pyrimidin-7-yl)-3-(((S)-2-((tert-butoxycarbonyl)amino)-3-methylbutanoyl)oxy)-4-hydroxy-5-((trityloxy)methyl)pyrrolidine-1-carboxylate (39d) and (2S,3S,4R,5R)-tert-butyl 2-(4-amino-5H-pyrrolo[3,2-d]pyrimidin-7-yl)-4-(((S)-2-((tert-butoxycarbonyl)amino)-3-methylbutanoyl)oxy)-3-hydroxy-5-((trityloxy)methyl)pyrrolidine-1-carboxylate (39e) (945 mg, 1.171 mmol, 74.0% yield) as white solid; MS (ES+) 806.9 (M+1); (ES−) 805.0 (M−1), 841.2 (M+Cl).

Method 2

From (2S,3S,4R,5R)-tert-butyl 2-(4-azido-5H-pyrrolo[3,2-d]pyrimidin-7-yl)-4-(((S)-2-((tert-butoxycarbonyl)amino)-3-methylbutanoyl)oxy)-3-hydroxy-5-((trityloxy)methyl)pyrrolidine-1-carboxylate (39b)

To a solution of (2S,3S,4R,5R)-tert-butyl 2-(4-azido-5H-pyrrolo[3,2-d]pyrimidin-7-yl)-4-(((S)-2-((tert-butoxycarbonyl)amino)-3-methylbutanoyl)oxy)-3-hydroxy-5-((trityloxy)methyl)pyrrolidine-1-carboxylate (39b) (634 mg, 0.761 mmol) in ethanol (25 mL) was added 10% Pd/C (100 mg) and hydrogenated at 50 psi for 8 h. The catalyst was removed by filtration of the reaction mixture through a pad of Celite. The filtrate was concentrated in vacuum and the residue obtained was purified by flash column chromatography to furnish a 3:2 mixture of (2S,3S,4R,5R)-tert-butyl 2-(4-amino-5H-pyrrolo[3,2-d]pyrimidin-7-yl)-3-(((S)-2-((tert-butoxycarbonyl)amino)-3-methylbutanoyl)oxy)-4-hydroxy-5-((trityloxy)methyl)pyrrolidine-1-carboxylate (39d) and (2S,3S,4R,5R)-tert-butyl 2-(4-amino-5H-pyrrolo[3,2-d]pyrimidin-7-yl)-4-(((S)-2-((tert-butoxycarbonyl)amino)-3-methylbutanoyl)oxy)-3-hydroxy-5-((trityloxy)methyl)pyrrolidine-1-carboxylate (39e) (474 mg, 0.587 mmol, 77% yield) as white solid; NMR spectrum matches with the product obtained using procedure from compound 39a; MS (ES+) 806.9 (M+1); (ES−) 805.7 (M−1).

116

Preparation of (6aR,8S,9S,9aR)-tert-butyl 8-(4-amino-5H-pyrrolo[3,2-d]pyrimidin-7-yl)-9-(((S)-2-((tert-butoxycarbonyl)amino)-3-methylbutanoyl)oxy)-2,2,4,4-tetraisopropyltetrahydro-[1,3,5,2,4]trioxadisilocino[7,6-b]pyrrole-7(8H)-carboxylate (34e)

Step 1: Preparation of (6aR,8S,9S,9aR)-tert-butyl 8-(4-azido-5H-pyrrolo[3,2-d]pyrimidin-7-yl)-9-hydroxy-2,2,4,4-tetraisopropyltetrahydro-[1,3,5,2,4]trioxadisilocino[7,6-b]pyrrole-7(8H)-carboxylate (34c)

To a stirred solution of (2S,3S,4R,5R)-tert-butyl 2-(4-azido-5H-pyrrolo[3,2-d]pyrimidin-7-yl)-3,4-dihydroxy-5-(hydroxymethyl)pyrrolidine-1-carboxylate (34b) (5 g, 12.78 mmol) in DMF (25 mL) was added N,N-dimethylpyridin-4-amine (DMAP, 0.078 g, 0.639 mmol), 1H-imidazole (3.48 g, 51.1 mmol) and 1,3-dichloro-1,1,3,3-tetraisopropyldisiloxane (4.63 mL, 14.05 mmol). The reaction mixture was stirred at room temperature overnight and diluted with water (300 mL). The solid separated was collected by filtration and washed with water. The solid was purified by flash column chromatography (silica gel, eluting with ethyl acetate in hexanes 0 to 35%) to furnish (6aR,8S,9S,9aR)-tert-butyl 8-(4-azido-5H-pyrrolo[3,2-d]pyrimidin-7-yl)-9-hydroxy-2,2,4,4-tetraisopropyltetrahydro-[1,3,5,2,4]trioxadisilocino[7,6-b]pyrrole-7(8H)-carboxylate (34c) (5.02 g, 62.0% yield) as a white solid; $^1$H NMR (300 MHz, DMSO-$d_6$) δ 13.26 (s, 1H, $D_2O$ exchangeable), 9.85 (s, 1H), 7.49 (s, 1H), 5.52 (d, J=3.2 Hz, 1H, $D_2O$ exchangeable), 5.10 (s, 1H), 4.63-4.24 (m, 2H), 4.18-3.82 (m, 1H), 3.67 (dt, J=8.2, 2.9 Hz, 1H), 1.37 (d, J=45.1 Hz, 10H), 1.08-0.99 (m, 14H), 0.86 (m, 14H); MS (ES+) 633.9 (M+1); (ES−) 632.2 (M−1); Analysis: Calculated for $C_{28}H_{47}N_7O_6Si_2$: C, 53.05; H, 7.47; N, 15.47; Found: C, 53.00; H, 7.55; N, 15.15.

Step 2: Preparation of (6aR,8S,9S,9aR)-tert-butyl 8-(4-azido-5H-pyrrolo[3,2-d]pyrimidin-7-yl)-9-(((S)-2-((tert-butoxycarbonyl)amino)-3-methylbutanoyl)oxy)-2,2,4,4-tetraisopropyltetrahydro-[1,3,5,2,4]trioxadisilocino[7,6-b]pyrrole-7(8H)-carboxylate (34d)

To a stirred solution of (6aR,8S,9S,9aR)-tert-butyl 8-(4-azido-5H-pyrrolo[3,2-d]pyrimidin-7-yl)-9-hydroxy-2,2,4,4-tetraisopropyltetrahydro-[1,3,5,2,4]trioxadisilocino[7,6-b]pyrrole-7(8H)-carboxylate (34c) (2 g, 3.16 mmol) in DMF (20 mL) was added (S)-2-(tert-butoxycarbonylamino)-3-methylbutanoic acid (L-Boc Valine, 1.03 g, 4.73 mmol) and cooled to 0° C. At 0° C. N1-((ethylimino)methylene)-N3,N3-dimethylpropane-1,3-diamine hydrochloride (EDCI, 1.51 g, 7.89 mmol) and N,N -dimethylpyridin-4-amine (DMAP, 0.385 g, 3.16 mmol) was added and allowed the reaction to come to room temperature overnight. The reaction was diluted with water (100 mL) and extracted with ethyl acetate (2×100 mL). The ethyl acetate layers were combined washed with water (2×50 mL), brine (50 mL), dried, filtered and concentrated in vacuum. The residue obtained was purified by flash column chromatography (silica gel 80 g, eluting with ethyl acetate in hexanes 0 to 35%) to afford (6aR,8S,9S,9aR)-tert-butyl 8-(4-azido-5H-pyrrolo[3,2-d]pyrimidin-7-yl)-9-(((S)-2-((tert-butoxycarbonyl)amino)-3-methylbutanoyl)oxy)-2,2,4,4-tetraisopropyltetrahydro-[1,3,5,2,4]trioxadisilocino[7,6-b]pyrrole-7(8H)-carboxylate (34d) (2.1 g, 80%) as a white solid; $^1$H NMR (300 MHz, DMSO-$d_6$) δ 13.40 (s, 1H, $D_2O$ exchangeable), 9.85 (d, J=5.7 Hz, 1H), 7.57 (s, 1H), 7.23 (d, J=8.2 Hz, 1H), 5.84 (d, J=3.7 Hz, 1H), 5.24 (d, J=10.7 Hz, 1H), 4.82-4.58 (m, 1H), 4.41 (d, J=12.4 Hz, 1H), 4.03-3.93 (m, 2H), 3.67 (s, 1H), 2.08 (dt, J=13.5, 6.8 Hz, 1H), 1.49-1.33 (m, 18H), 1.15-0.67 (m, 35H); MS (ES+) 856.0 (M+Na), 832.4 (M−1). Analysis: Calculated for $C_{38}H_{64}N_8O_9Si_2$: C, 54.77; H, 7.74; N, 13.45; Found: C, 54.86; H, 7.78; N, 13.13.

Step 3: Preparation of (6aR,8S,9S,9aR)-tert-butyl 8-(4-amino-5H-pyrrolo[3,2-d]pyrimidin-7-yl)-9-(((S)-2-((tert-butoxycarbonyl)amino)-3-methylbutanoyl)oxy)-2,2,4,4-tetraisopropyltetrahydro-[1,3,5,2,4]trioxadisilocino[7,6-b]pyrrole-7(8H)-carboxylate (34e)

To a suspension of Palladium on Carbon (10%, 0.262 g) in ethanol (50 mL) was added (6aR,8S,9S,9aR)-tert-butyl 8-(4-azido-5H-pyrrolo[3,2-d]pyrimidin-7-yl)-9-(((S)-2-((tert-butoxycarbonyl)amino)-3-methylbutanoyl)oxy)-2,2,4,4-tetraisopropyltetrahydro-[1,3,5,2,4]trioxadisilocino[7,6-b]pyrrole-7(8H)-carboxylate (34d) (2.05 g, 2.46 mmol) and hydrogenated at 60 psi for 12 h. The catalyst was removed by filtration through a pad of Celite and the filtrate was concentrated in vacuum. The residue obtained was purified by flash column chromatography (silica gel 25 g, eluting with CMA 80 in chloroform 0 to 100%) to furnish (6aR, 8S,9S,9aR)-tert-butyl 8-(4-amino-5H-pyrrolo[3,2-d]pyrimidin-7-yl)-9-(((S)-2-((tert-butoxycarbonyl)amino)-3-methylbutanoyl)oxy)-2,2,4,4-tetraisopropyltetrahydro-[1,3,5,2,4]trioxadisilocino[7,6-b]pyrrole-7(8H)-carboxylate (34e) (1.9 g, 96% yield) as a colorless solid; $^1$H NMR (300 MHz, DMSO-$d_6$) δ 10.94 (s, 1H, $D_2O$ exchangeable), 8.05 (s, 1H), 7.46-7.30 (m, 1H), 7.17 (d, J=8.0 Hz, 1H), 6.82 (s, 2H, $D_2O$ exchangeable), 5.86 (d, J=4.0 Hz, 1H), 5.16 (d, J=25.0 Hz, 1H, $D_2O$ exchangeable), 5.00 (d, J=8.2 Hz, 1H), 4.17 (dd, J=12.2, 5.1 Hz, 1H), 3.98-3.88 (m, 1H), 3.61 (s, 1H), 2.16-1.92 (m, 1H), 1.41 (bs, 18H), 1.01-0.83 (m, 35H); MS (ES+) 806.921 (M+1), 830.1 (M+Na), (ES−) 805.289 (M−1), 842.0 (M+Cl).

Example 7

Pharmacokinetics of Compound 30f Following Oral Administration to Rats

Healthy 8-to-10-week-old male Sprague-Dawley rats were randomly assigned to control and experimental groups, N=4 per group. All animals were housed and fed in standard manner. On the day of the experiment, all animals were isolated and fasted approximately 15 hours prior to dose in metabolic cages. Food was returned to animals two hours post dose with control or experimental agent. Water was delivered ad libitum. Immediately prior to administration, control compound (2S,3S,4R,5R)-2-(4-amino-5H -pyrrolo[3,2-d]pyrimidin-7-yl)-5-(hydroxymethyl)pyrrolidine-3,4-diol dihydrochloride (12i) was dissolved in water to attain a concentration of 1 mg/mL. Experimental compound 30f similarly was dissolved in water to attain an equivalent concentration (1 mg/mL in terms of compound 12i). After each animal was weighed, all control animals were administered 10 mg/kg body weight of compound 12i by oral gavage at time 0, while all experimental animals were administered 10 mg/kg body weight compound 30f by oral gavage at time 0. Serial blood samples were obtained at time 0, 15 min, 30 min, 1 hr, 2 hr, 4 hr, 8 hr, 12 hr, and 24 hr. All samples were transferred to microcentrifuge tubes and centrifuged at 14,000 rpm for 3 min. Plasma from each tube was removed and transferred to a pre-labeled microcentrifuge tube and put on dry ice until samples were transferred to −80° C. freezer for storage until analysis. Individual samples were then analyzed for compound 12i. Plasma concentration-versus-time data were analyzed by non-compartmental approaches using the WinNonlin software program. Pharmacokinetic parameter $T_{max}$, $C_{max}$, $T_{1/2}$, $AUC_{(0-last)}$, $AUC_{(0-inf)}$, $MRT_{(0-inf)}$ and graphs of plasma and liver concentrations versus time profile were obtained. Results are shown in FIG. 1.

As depicted in FIG. 1, experimental and control groups showed striking differences in pharmacokinetics. While $T_{max}$ was the same for the two groups (0.5 h), $C_{max}$ for the experimental group was 527 ng/mL, while $C_{max}$ for the control group was only 123 ng/mL, and $AUC_{(0-inf)}$ for the experimental group was 1076 ng·h, while $AUC_{(0-inf)}$ for the control group was only 219 ng·h. Based on these results, compound 30f has approximately four-fold greater bioavailability than compound 12i, and plasma esterases rapidly hydrolyze compound 30f to compound 12i.

Example 8

Effects of Viral RNA Polymerase Inhibitor (Compound 12i) on Replication of Measles Virus in African Green Monkey Kidney Cells Materials and Methods: Vero-76 cells (African green monkey kidney cells) were obtained from the American Type Culture Collection (ATCC, Manassas, Va.). The cells were routinely passed in minimal essential medium (MEM with 0.15% $NaHCO_3$; Hyclone Laboratories, Logan, Utah, USA) supplemented with 5% fetal bovine serum (FBS, Hyclone). When evaluating compounds, the serum was reduced to a final concentration of 2.5%, and gentamicin was added to the test medium to a final concentration of 50 μg/mL. Measles virus (MV), strain Chicago, was obtained from the Centers for Disease Control (Atlanta, Ga.).

Antiviral Testing Procedures:
Cytopathic Effect Inhibition Assay (Visual Assay)
Cells were seeded to 96-well flat-bottomed tissue culture plates (Corning Glass Works, Corning, N.Y.), 0.2 mL/well, at the proper cell concentration, and incubated overnight at 37° C. in order to establish a cell monolayer. When the monolayer was established, the growth medium was decanted and the various dilutions of test compound were added to each well (3 wells/dilution, 0.1 mL/well). Compound diluent medium was added to cell and virus control wells (0.1 mL/well). Virus, diluted in test medium, was added to compound test wells (3 wells/dilution of compound) and to virus control wells (6 wells) at 0.1 mL/well. Virus (viral MOI=0.001) was added approximately 5 min after compound. Test medium without virus was added to all toxicity control wells (2 wells/dilution of each test compound) and to cell control wells (6 wells) at 0.1 mL/well. The plates were incubated at 37° C. in a humidified incubator with 5% $CO_2$, 95% air atmosphere until virus control wells had adequate cytopathic effect (CPE) readings (80-100% cell destruction). This was achieved from 4-11 days after virus exposure to cells, depending on the virus. Cells were then examined microscopically for CPE, this being scored from 0 (normal cells) to 4 (maximal, 100%, CPE). The cells in the toxicity control wells were observed microscopically for morphologic changes attributed to cytotoxicity. This cytotoxicity (cell destruction and/or morphology change) was also graded at 100% toxicity, 80% cytotoxicity), 60% cytotoxicity, 40% cytotoxicity, 20% cytotoxicity, and 0 (normal cells). The 50% effective dose (EC50) and 50% cytotoxic dose (IC50) were calculated by regression analysis of the virus CPE data and the toxicity control data, respectively. The selective index (SI) for each compound tested was calculated using the formula: SI=CC50/EC50.

Neutral Red (NR) Uptake Assay of CPE Inhibition NR uptake was chosen as the dye quantitation method for evaluating antiviral drugs based on the findings of Smee et al (*Virol. Methods* 2002, 106: 71-79; herein incorporated by reference in its entirety). This assay was done on the same CPE inhibition test plates described above to verify the inhibitory activity and the cytotoxicity observed by visual observation. The NR assay was performed using a modified method of Cavenaugh et al. (*Invest. New Drugs* 1990, 8:347-354; herein incorporated by reference in its entirety) as described by Barnard et al. (*Antiviral Chem. Chernother.* 2001, 12:220-231; herein incorporated by reference in its entirety). Briefly, medium was removed from each well of a plate scored for CPE from a CPE inhibition assay, 0.034% NR was added to each well of the plate and the plate incubated for 2 hr at 37° C. in the dark. The NR solution was then removed from the wells. After rinsing (sometimes cells slough from the plate causing erroneous low up of neutral red) and aspirating to dryness, the remaining dye was extracted for 30 min at room temperature in the dark from the cells using absolute ethanol buffered with Sorenson citrate buffer. Absorbances at 540 nm/405 nm are read with a microplate reader (Opsys MR™, Dynex Technologies, Chantilly, Va., USA). Absorbance values were expressed as percents of untreated controls and EC50, CC50 and SI values were calculated as described above.

Virus Yield Reduction Assay:

Virus yield reduction assays were performed using the cell culture 50% infectious dose (CCID50) assay essentially as described previously (*Antimicrob. Agents Chemother.* 1992, 3:1837-1842; herein incorporated by reference in its entirety). Briefly, supernatants from each well were serially diluted in triplicate wells of 96-well plates containing Vero-76 cells. Plates were incubated for 6 days and then checked for virus-induced CPE. Quantitation of virus yield titers was by the endpoint method of Reed and Muench (Am. J. Hyg. 1938, 27:493-498; herein incorporated by reference in its entirety). The EC90 value was calculated using linear regression to estimate the concentration necessary to inhibit virus yield by 90% or a one $\log_{10}$ decrease in virus titer.

Results and Discussion:

Measles virus was potently inhibited by compound 12i (Table 1). EC50 values against the measles virus were 0.6 and 1.4 µg/mL by visual assay and NR assay, respectively. The compound did not have any cytotoxicity in either the visual or NR assays (IC50>100). Therefore, the selective indices by both assays suggested that compound 12i was highly active against measles virus (MV). The potent inhibitory activity against MV was confirmed by a virus yield reduction assay with an EC90=0.36 µg/mL, representing a one $\log_{10}$ drop in virus produced in infected cells.

Conclusions

Compound 12i demonstrated potent and selective inhibitory activity. By virus yield reduction assay, compound 12i was also a potent inhibitor of MV (EC90=0.37 µg/mL). Thus, compound 12i has been found to be a potent inhibitor of many RNA viruses and suggests that compound 12i warrants further in vitro and in vivo evaluation as a broad-spectrum inhibitor of selected RNA viruses.

TABLE 1

Effects of a polymerase inhibitor (compound 12i) on the replication of various viruses

| | Visual CPE Assay (ng/mL) | | | Neutral Red Uptake Assay (ng/mL) | | |
|---|---|---|---|---|---|---|
| Virus | EC50 | IC50 | SI | EC50 | IC50 | SI |
| Adenovirus type 165089/Chicago (A-549 cells) | 39 | >100 | >2.6 | 43 | >100 | >2.3 |
| Dengue 2 New Guinea C (Vero cells) | 15 | 360 | 25 | 13 | 340 | 26 |
| Influenza A H1N1 CA/04/2009 (Pandemic H1N1) | 1.8 | 210 | 120 | 1.8 | 210 | 120 |
| Influenza A H3N2 Brisbane/10/2007 | 1.8 | 260 | 140 | 5.6 | 440 | 79 |
| Influenza A H5N1 VN/I203/2004 Hybrid (on H1N1 backbone) | 0.63 | >1000 | >1600 | 0.99 | 130 | 130 |
| Influenza B Florida | 1.8 | 530 | 290 | 1.8 | 50 | 38 |
| Junin Candid 1 (Vero cells) | 29 | >520 | >17 | 16 | 240 | 14 |
| Measles | 0.6 | >100 | >180 | 1.4 | >100 | >71 |
| Parainfluenza 3 14702 (MA-104 cells) | 14 | 100 | 7.1 | 10 | 52 | 52 |
| Pichinde (Vero cells) | 61 | >500 | >8.2 | 28 | 190 | 6.7 |
| Punta Toro A2 (Vero 76 cells) | 310 | >500 | >1.6 | >250 | 250 | 0 |
| Respiratory Syncytial A2 (MA-104 cells) | >100 | >100 | 0 | >100 | >100 | 0 |
| Rhinovirus 2 HGP (HeLa Ohio-1 cells) | 57 | >100 | >1.8 | 56 | >100 | >1.8 |
| Rift Valley Fever MP-12 (Vero 76 cells) | 75 | 680 | 9.1 | 64 | 420 | 6.6 |
| SARS-CoV Urbani (Vero 76 cells) | 14 | >100 | >7.1 | 16 | >100 | >6.3 |

TABLE 1-continued

Effects of a polymerase inhibitor (compound 12i) on the replication of various viruses

| Virus | Visual CPE Assay (ng/mL) | | | Neutral Red Uptake Assay (ng/mL) | | |
|---|---|---|---|---|---|---|
| | EC50 | IC50 | SI | EC50 | IC50 | SI |
| Tacaribe TRVL 11573 (Vero cells) | 29 | 320 | 4.2 | 2 | 200 | 2 |
| Venezuelan Equine Encephalitis TC83 (Vero 76 cells) | 280 | 610 | 2.2 | 170 | 230 | 1.2 |
| West Nile (Vero Cells) | >100 | >100 | 0 | 36 | >100 | 2.8 |
| Yellow Fever 17D (Vero 76 cells) | 8.3 | 360 | 43 | 8.3 | 320 | 38 |

Example 9

Effects of Viral RNA Polymerase Inhibitor (Compound 12i) on Replication of Various RNA Viruses Materials and Methods Cells and Virus African green monkey kidney cells (MA-104) were obtained from Whitaker Mass. Bioproducts, Walkersville, Md., USA). All Vero cells (African green monkey kidney cells, human carcinoma of the larynx cells (A-549), and Madin-Darby canine kidney cells were obtained from the American Type Culture Collection (ATCC, Manassas, Va.). A-549 cells were cultured in Dulbecco's minimal essential medium (DMEM) supplemented with 0.15% NaHCO$_3$ (Hyclone Laboratories, Logan, Utah, USA) and with 10% fetal bovine serum (FBS, Hyclone). The remaining cells were routinely passed in minimal essential medium (MEM with 0.15% NaHCO$_3$; Hyclone Laboratories, Logan, Utah, USA) supplemented with 5% fetal bovine serum (FBS, Hyclone).

When evaluating compounds, the serum was reduced to a final concentration of 2.5%, and gentamicin is added to the test medium to a final concentration of 50 µg/mL. Test medium for influenza assays consisted of MEM without serum, 0.18% NaHCO$_3$, 20 µg trypsin/mL, 2.0 µg EDTA/mL, and 50 µg gentamicin/mL.

For evaluation of toxicity in actively growing cells, cytotoxicity was evaluated by determining the total number of cells as reflected by a NR uptake assay after a 3-day exposure to several concentrations of compound. To quantitate cell growth at 72 h in the presence or absence of drug, plates were seeded with 1×10$^3$ MDCK cells, and after 4 h (allowed all cells to attach plate wells) were exposed to selected concentrations of drug in MEM or MEM. After 72 h the plates were treated as described above for the NR assay. Absorbance values were expressed as percent of untreated controls and CC50 values were calculated by regression analysis.

Dengue virus 2 (DV-2), strain New Guinea C, Respiratory syncytial virus (RSV) A2, Rhinovirus 2 (RV-2), strain HOP, Tacaribe virus (TCV), strain TRVL 11573, Venezuelan equine encephalitis virus (VEE), and Yellow fever virus (YFV), strain 17D, were all purchased from American Type Culture Collection (ATCC; Manassas, Va.). All influenza viruses, Measles virus (MV), strain Chicago, SARS corona virus (SARS-CoV), strain Urbani, and West Nile virus (WNV), prototypic New York 1999 isolate designated strain 996625, were obtained from the Centers for Disease Control (Atlanta, Ga.). Punta Toro virus (PTV), Adames strain, was obtained from Dr. Dominique Pifat of the U.S. Army Medical Research Institute for Infectious Diseases, Ft. Detrick (Frederick, Md.). Rift Valley fever virus (RVFV) vaccine strain, MP-12, and Junin virus (JUNV) vaccine strain, Candid 1, were kindly provided by Dr. Robert Tesh (World Reference Center for Emerging and Viruses and Arboviruses, University of Texas Medical Branch, Galveston, Tex.). Pichinde virus (PICV), strain An 4763, was provided by Dr. David Gangemi (Clemson University, Clemson, S.C.). Parainfluenza virus type 3 (PIV-3), strain 14702/5/95, was obtained from Jacquelin Boivin (Hospitale St. Justin, Montreal, Canada). Adenovirus (AV-1) type 1, strain Chicago/95, was isolated from the tracheal washings of a pediatric patient and was provided by M. F. Smaron (Department of Medicine, University of Chicago, Chicago Ill.).

Antiviral Testing Procedure:

Cytopathic Effect inhibition Assay (Visual Assay)

Cells were seeded to 96-well flat-bottomed tissue culture plates (Corning Glass Works, Corning, N.Y.), 0.2 mL/well, at the proper cell concentration, and incubated overnight at 37° C. in order to establish a cell monolayer. When the monolayer was established, the growth medium was decanted and the various dilutions of test compound were added to each well (3 wells/dilution, 0.1 mL/well). Compound diluent medium was added to cell and virus control wells (0.1 mL/well). Virus, diluted in test medium, was added to compound test wells (3 wells/dilution of compound) and to virus control wells (6 wells) at 0.1 mL/well. Virus (viral MOT=0.001) was added approximately 5 min after compound. Test medium without virus was added to all toxicity control wells (2 wells/dilution of each test compound) and to cell control wells (6 wells) at 0.1 mL/well. The plates were incubated at 37° C. in a humidified incubator with 5% CO$_2$, 95% air atmosphere until virus control wells had adequate cytopathic effect (CPE) readings (80-100% cell destruction). This was achieved from 4-11 days after virus exposure to cells, depending on the virus. Cells were then examined microscopically for CPE, this being scored from 0 (normal cells) to 4 (maximal, 100%) CPE. The cells in the toxicity control wells were observed microscopically for morphologic changes attributed to cytotoxicity. This cytotoxicity (cell destruction and/or morphology change) was also graded at 100% toxicity, 80% cytotoxicity, 60% cytotoxicity, 40% cytotoxicity, 20% cytotoxicity, and 0 (normal cells). The 50% effective dose (EC50) and 50% cytotoxic dose (IC50) were calculated by regression analysis of the virus CPE data and the toxicity control data, respectively. The selective index (SI) for each compound tested was calculated using the formula: SI=CC50/EC50.

Neutral Red (NR) Uptake Assay of CPE Inhibition and Compound Cytotoxicity

NR uptake was chosen as the dye quantitation method for evaluating antiviral drugs based on the findings of Smee et al (supra). This assay was done on the same CPE inhibition test plates described above to verify the inhibitory activity and the cytotoxicity observed by visual observation. The NR assay was performed using a modified method of Cavenaugh et al. (supra) as described by Barnard et al. (supra). Briefly, medium was removed from each well of a plate scored for CPE from a CPE inhibition assay, 0.034% NR was added to each well of the plate and the plate incubated for 2 hr at 37° C. in the dark. The NR solution was then removed from the wells. After rinsing (sometimes cells slough from the plate causing erroneous low up of neutral red) and aspirating to dryness, the remaining dye was extracted for 30 min at room temperature in the dark from the cells using absolute ethanol buffered with Sorenson citrate buffer. Absorbances at 540 nm/405 nm are read with a microplate reader (Opsys MR™, Dynex Technologies, Chantilly, Va., USA). Absorbance values were expressed as percents of untreated controls and EC50, CC50 and SI values were calculated as described above.

Other viruses that were considered significantly inhibited by compound 12i (SI>10) were DV-2 (EC50=15, 13 µg/mL), JUNV (EC50=29, 16 µg/mL), YFV (EC50=8.3, 8.3 µg/mL) (Table 1). The following viruses were slightly inhibited by compound 12i (3<SI<10): PIV-3 (EC50=7.1, 10 µg/mL), SARS-CoV (EC50=14, 16 µg/mL), PICV (EC50=61, 28 µg/mL), and RVFV (EC50=75, 64 µg/mL). Compound 12i was tested against a subset of influenza viral strains (Table 2), and exhibited broad spectrum anti-influenza activity against multiple strains.

TABLE 2

Broad spectrum anti-influenza activity of compound 12i.

| Virus | EC50 (µg/mL) |
|---|---|
| A/CA/04/2009 (Pandemic H1N1) | 1.8 |
| A/Brisbane/10/2007 (H3N2) | 5.6 |
| A/VN/1203/2004 (H5N1) | 0.99 |
| B/Florida | 1.8 |
| A/CA/27/2007 (H1N1) | 0.66 |
| A/NJ/15/2007 (H1N1 - H274Y) | 1.39 |
| A/Vic/3/75 (H3N2) | 4.0 |

Conclusions

Compound 12i demonstrated potent activity against all the influenza viruses tested. Compound 12i was found to be a potent inhibitor of influenza virus replication and suggests that compound 12i is effective as a broad-spectrum inhibitor of selected RNA viruses, including all influenza viruses.

Example 10

In Vitro Antiviral Activity of Compound 12i

Antiviral activity of compound 12i was assessed in vitro in several viruses for antiviral activity. EC50 values ranged from about 10 µg/mL to about >300 µg/mL against Marburg (filoviridae), Junin Candid 1 (arenaviridae), Pichinde (arenaviridae), Chikungunya 181/25 (togaviridae), and Vaccinia NYCBH (poxviridae).

Example 11

Synergistic Antiviral Activity of Compound 12i and Neuraminidase Inhibitor in MDCK Cells Madin Darby Canine Kidney (MDCK) cells were infected with influenza virus H3N2 (A/Victoria/3/75) virus and treated with various combinations of compound 12i and peramivir for 72 h. Cytopathic effect was determined using neutral red dye uptake assay. The data is shown in Table 3.

TABLE 3

Percent inhibition of cytopathic effect in influenza-infected cells

| | Peramivir | | |
|---|---|---|---|
| Compound 12i | 0.0 µM | 0.0 µM | 0.0 µM |
| 0.0 µM | 0 | 3.6 ± 9 | 10.8 ± 11 |
| 1.8 µM | 1.6 ± 6.1 | 22.7 ± 6.1 | 21.5 ± 4.6 |
| 7.8 µM | 25.8 ± 4.8 | 50.4 ± 7.9 | 70.3 ± 4.9 |

The experimental data were evaluated by the three dimensional analysis using Mac Synergy II™ software program (Prichard and Shipman, 1990; herein incorporated by reference in its entirety). The software calculates the theoretical additive interactions from the dose-response curves of the individual drugs. The calculated additive surface, which represents the predicted additive interactions, is then subtracted from the experimental surface to reveal regions of greater (synergy)- or less (antagonism)-than-expected interactions. Combination of peramivir and compound 12i in cell culture studies demonstrated a synergistic antiviral effect with a volume of synergy equal to 92 µM$^2$ unit %.

Example 12

Efficacy of Compound 12i Intramuscular (IM) Injection in Murine Influenza Model

BALB/c mice between 6-8 weeks old were adapted to H3N2 virus (A/Victoria/3/75). Doses of 0, 30, 100, and 300 mg/kg/d qd were given by intramuscular (IM) injection for 5 days starting 1 h prior to infection. N=50 animals. All animals were followed for 16 days. Endpoints included lethality, mean days to death, and weight loss.

Compound 12i (IM) in mouse influenza model virus results are shown in Table 4. Compound 12i given IM improved the survival and weight loss in mice infected with influenza virus.

TABLE 4

Compound 12i (IM) in mouse influenza model virus - H3N2 A/Vic/3/75

| Treatment | Dose Level (mg/kg/d) | Number of deaths | Mean day to death (Mean ± SEM) | Mean weight change (grams ± SEM) Day 8 |
|---|---|---|---|---|
| Vehicle, uninfected | 0 | 0 | >16 | 0.58 ± 0.23 |
| Vehicle, infected | 0 | 7/15 | 10.3 ± 0.3 | −4.98 ± 0.14 |
| compound 12i | 30 | 10/10* | >16 | −3.27 ± 0.37** |
| compound 12i | 100 | 10/10* | >16 | 0.78 ± 0.17** |
| compound 12i | 300 | 10/10* | >16 | 0.60 ± 0.17** |

*P < 0.001 compared to vehicle-infected group (log rank test)
**P < 0.001 compared to vehicle-infected group (t-test)

Example 13

Efficacy of Compound 12i Oral Administration in Murine Influenza Model

BALB/c mice between 6-8 weeks old were adapted to H3N2 virus (A/Victoria/3/75). Doses of 0, 30, 100, and 300 mg/kg/d qd and 100 mg/kg/d bid were given orally. N=60 animals. All animals were followed for 16 days. Endpoints included lethality, mean days to death, and weight loss. The effects of orally administered compound 12i on weight loss in mice infected with H3N2 A/Vic/3/75 influenza virus are shown in Table 5. Compound 12i given orally improved the survival and weight loss in mice infected with influenza virus.

TABLE 5

Compound 12i (Oral) in mouse influenza model virus - H3N2 A/Vic/3/75

| Treatment | Dose Level (mg/kg/d) qd | Survival/Total | Mean day to death (Mean ± SEM) | Mean weight change (grams ± SEM) Day 9 |
|---|---|---|---|---|
| Vehicle, uninfected | 0 | 0 | >16 | 1.36 ± 0.96 |
| Vehicle, infected | 0 | 7/15 | 10.5 ± 0.3 | −3.74 ± 0.23 |
| compound 12i | 30 | 10/10* | >16 | −1.58 ± 0.32** |
| compound 12i | 100 | 10/10* | >16 | 1.03 ± 0.22** |
| compound 12i | 100 (bid) | 10/10* | >16 | 0.01 + 0.27** |
| compound 12i | 300 | 10/10* | >16 | 0.66 ± 0.23** |

*P < 0.001 compared to vehicle-infected group (log rank test)
**P < 0.001 compared to vehicle-infected group (t-test)

Example 14

Pharmacokinetic Studies in Mice

Female BALB/c mice (N=30) were dosed orally with compound 12i at 100 mg/kg. Mice were bled through the retro orbital sinus at t=0.17, 0.5, 1.0, 3, 6, and 24 h (5 mice each per time point), centrifuged and plasma was stored at −80° C. Plasma drug levels were measured via LC/MS/MS analysis.

Mouse plasma levels for compound 12i after oral administration are shown in Table 6.

TABLE 6

Compound 12i plasma levels in mice following oral administration

| Time point (h) | Plasma drug levels (ng/mL) (Mean ± SEM) |
|---|---|
| 0.17 | 607.1 ± 61.0 |
| 0.5 | 910.0 ± 121.9 |

TABLE 6-continued

Compound 12i plasma levels in mice following oral administration

| Time point (h) | Plasma drug levels (ng/mL) (Mean ± SEM) |
|---|---|
| 1 | 341.6 ± 121.9 |
| 3 | 89.7 ± 8.5 |
| 5 | 94.2 ± 6.4 |
| 24 | 50.5 ± 8.9 |

Example 15

Ebola Virus Mouse Prophylaxis Study

Compound 12i was administered i.p., i.m., and orally (300 mg/kg/day, BID) to 8-12 week old C57BL/6 mice (N=10 per group, 4 groups—one saline- and three drug-treated groups). Eight days of treatment starting 4 h prior to infection. Mouse-adapted Ebola virus (Zaire) challenge was administered intraperitoneally. Mortality and weight were monitored for 14 days post-infection.

Saline-treated mice infected with Ebola virus all died by day 8. All mice treated intraperitoneally or intramuscularly with compound 12i survived at study endpoint (day 14). Eighty percent of mice treated orally with compound 12i survived at study endpoint (day 14).

Saline-treated mice infected with Ebola virus exhibited overall weight loss until day 8 (all control mice were dead by day 8). Mice treated intraperitoneally or intramuscularly with compound 12i retained greater than 95% of starting weight at day 12. Mice treated orally with compound 12i retained greater than 80% of starting weight at day 12. All drug-treated mice continued to gain weight after day 12.

Example 16

Ebola Virus Mouse Prophylaxis Study

Compound 12i was administered i.m. and orally to 8-12 week old C57BL/6 mice. The study subjects were divided into 6 groups (N=10 per group). Group 1 was a saline control, group 2 was dosed with 150 mg/kg compound 12i (p.o., BID); group 3 was dosed with 250 mg/kg compound 12i (p.o., BID); group 4 was dosed with 150 mg/kg compound 12i (i.m., BID). Group 5 was uninfected mice treated with saline (p.o., BID), and group 6 was uninfected mice treated with 250 mg/kg compound 12i (p.o., BID). Treatment was for nine days, starting 4 h prior to infection. Mouse-adapted Ebola virus (Zaire) challenge was administered intraperitoneally (1,000 pfu). Mortality and weight were monitored for 14 days post-infection.

Saline-treated mice infected with Ebola virus all died by day 8. All mice treated intramuscularly with compound 12i survived at study endpoint, indicating that the i.m. dosage of compound 12i was completely protective. Eighty percent or greater of mice treated orally with compound 12i survived at study endpoint.

Saline-treated mice infected with Ebola virus exhibited overall weight loss until day 7 (all control mice were dead by day 8). Mice treated intramuscularly with compound 12i exhibited weight gain similar to the uninfected control group at day 11. Mice treated orally with compound 12i exhibited reversible weight loss, and retained greater than 100% of starting weight at day 11.

Example 17

Yellow Fever Virus (YFV) Time Window Golden Hamster Study

Yellow fever virus (Jimenez strain) was injected i.p. into female Syrian golden hamsters (99 g) at 20 CCID50 per hamster (~6.25×LD50). Groups were divided as follows: 1) compound 12i was administered beginning −4 h (N=15); 2) compound 12i administered beginning 1 dpi (days post-infection) (N=10); 3) compound 12i administered beginning 2 dpi (N=10); 4) compound 12i administered 3 dpi (N=10); 5) compound 12i administered 4 dpi (N=10); 6) ribavirin administered beginning −4 h (N=10); 7) saline vehicle beginning −4 h (N=16); 8) uninfected hamsters administered compound 12i beginning −4 h (N=3); 9) uninfected hamsters administered saline vehicle beginning −4 h (N=3); and 10) uninfected, untreated normal controls (N=3). Treatment dose was 100 mg/kg i.p., BID for 7 days. Study endpoints were morality at 21 days, weight measured on days 0, 3, 5, and 6; serum and liver virus titers (day 4, compound 12i at −4 h, and vehicle at −4 h), and ALT and AST on day 6.

Figure 2:
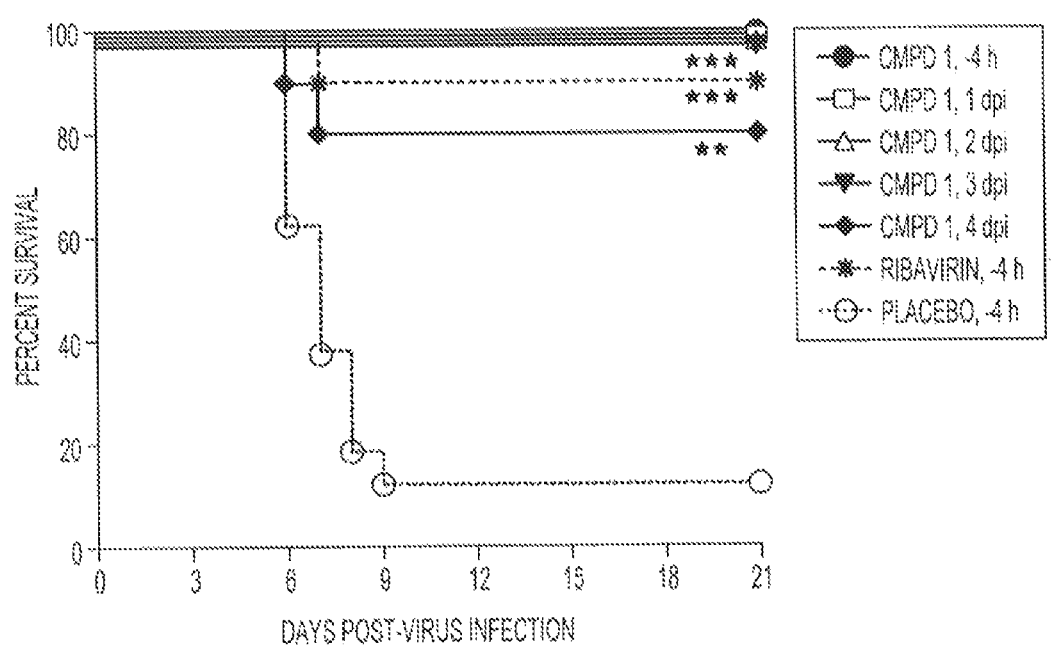
FIG. 2 is a graph depicting the effect of compound 12i (CMPD 1) on survival of hamsters infected with Yellow Fever virus. , P<0.01 compared to placebo. *, P<0.001 compared to placebo. dpi, days post infection.

The results showed enhanced survival for compound 12i with delayed treatment compared to placebo (FIG. 2). Survival of hamsters infected with YFV and treated with compound 12i twice daily for 7 days beginning with various times after virus challenge is indicated (*P<0.001, P<0.1, as compared to placebo). Survival rate was 100% for compound 12i beginning pre-infection, and delayed treatment up to 3 days post-infection. Survival rate was 80% for compound 12i beginning 4 days post-infection, indicating a significant improvement over placebo in groups with delayed treatment. In contrast, ribavirin provided 90% survival beginning pre-infection and the vehicle provided 12.5% survival beginning pre-infection. Most deaths occurred within 10 days of infection. Surviving animals will be re-challenged with YFV at 21 days post-infection.

Hamsters infected with YFV and treated with compound 12i from pre-infection to 4 days post-infection showed weight gain over placebo and ribavirin administered pre-infection.

Example 18

Marburg Virus Study for Compound 12i

Compound 12i was dosed i.m. in 10-12 week old BALB/c mice challenged (intraperitoneally) with 1000 pfu mouse-adapted MARV-Ravn. The study was divided into 10 groups (N=10 per group). Dosing regimens, routes, and doses are shown in Table 7. Compound 12i was dissolved in 0.9% saline prior to administration, and health and weight were monitored for 14 days post-infection.

TABLE 7

Study design for prophylaxis and treatment with compound 12i for Marburg virus infection

| Group | N | Treatment | Cmpd 12i Dose (mg/kg) | Cmpd 12i Dose (mg/kg/d) | Route | Regimen* |
|---|---|---|---|---|---|---|
| 1 | 10 | saline | — | — | IM | BID; Days 0-8 PI |
| 2 | 10 | Cmpd 12i | 150 | 300 | IM | BID; Days 0-8 PI |
| 3 | 10 | Cmpd 12i | 50 | 100 | IM | BID; Days 0-8 PI |
| 4 | 10 | Cmpd 12i | 15 | 30 | IM | BID; Days 0-8 PI |
| 5 | 10 | Cmpd 12i | 5 | 10 | IM | BID; Days 0-8 PI |
| 6 | 10 | Cmpd 12i | 150 | 300 | IM | BID; −1- 4 h, Days 1-8 PI |
| 7 | 10 | Cmpd 12i | 150 | 300 | IM | BID; Days 1-8 PI |
| 8 | 10 | Cmpd 12i | 150 | 300 | IM | BID; Days 2-8 PI |
| 9 | 10 | Cmpd 12i | 150 | 300 | IM | BID; Days 3-8 PI |
| 10 | 10 | Cmpd 12i | 150 | 300 | IM | BID; Days 4-8 PI |

*Day 0 treatment initiated 4 h prior to infection, except for group 6.
Group 6 treatment initiated at 4 h post-infection on day 0.
PI = post-infection.

Percent survival for the 10 groups in this study to day 12 is included in Table 8. The survival rate for mice treated with vehicle only (0.9% saline) was 60% at day 7 and 30% on days 8-12. Compound 12i was shown to increase survival to at least 90% at day 7, and at least 80% on days 8-12 at all doses.

TABLE 8

Percent survival rate for prophylaxis and treatment with compound 12i for Marburg virus infection

| Grp | Treatment | Percent Survival (Day) | | | | | | | | | | | | |
|---|---|---|---|---|---|---|---|---|---|---|---|---|---|---|
| | | 0 | 1 | 2 | 3 | 4 | 5 | 6 | 7 | 8 | 9 | 10 | 11 | 12 |
| 1 | 0.9% saline | 100 | 100 | 100 | 100 | 100 | 100 | 100 | 60 | 30 | 30 | 30 | 30 | 30 |
| 2 | Cmpd. 12i (150 mg/kg) | 100 | 100 | 100 | 100 | 100 | 100 | 100 | 100 | 100 | 100 | 100 | 100 | 100 |

TABLE 8-continued

Percent survival rate for prophylaxis and treatment with compound 12i for Marburg virus infection

| Grp | Treatment | Percent Survival (Day) | | | | | | | | | | | | |
|---|---|---|---|---|---|---|---|---|---|---|---|---|---|---|
| | | 0 | 1 | 2 | 3 | 4 | 5 | 6 | 7 | 8 | 9 | 10 | 11 | 12 |
| 3 | Cmpd. 12i (50 mg/kg) | 100 | 100 | 100 | 100 | 100 | 100 | 100 | 100 | 100 | 100 | 100 | 100 | 100 |
| 4 | Cmpd. 12i (15 mg/kg) | 100 | 100 | 100 | 100 | 100 | 90 | 90 | 90 | 90 | 90 | 90 | 90 | 90 |
| 5 | Cmpd. 12i (5 mg/kg) | 100 | 100 | 100 | 100 | 100 | 100 | 100 | 100 | 100 | 100 | 100 | 100 | 100 |
| 6 | Cmpd.12i (150 mg/kg) +4 h | 100 | 100 | 100 | 100 | 100 | 100 | 100 | 100 | 90 | 90 | 90 | 90 | 90 |
| 7 | Cmpd. 12i (150 mg/kg) +24 h | 100 | 100 | 100 | 90 | 90 | 90 | 90 | 80 | 80 | 80 | 80 | 80 | 80 |
| 8 | Cmpd. 12i (150 mg/kg) +48 h | 100 | 100 | 100 | 100 | 100 | 100 | 100 | 90 | 90 | 90 | 90 | 90 | 90 |
| 9 | Cmpd. 12i (150 mg/kg) +72 h | 100 | 100 | 100 | 100 | 90 | 90 | 90 | 90 | 80 | 80 | 80 | 80 | 80 |
| 10 | Cmpd. 12i (150 mg/kg) +96 h | 100 | 100 | 100 | 100 | 100 | 100 | 100 | 100 | 100 | 90 | 90 | 90 | 90 |

Example 19

Pharmaceutical Dosage Forms

The following illustrate representative pharmaceutical dosage forms, containing a compound of the invention ('Compound X'), for therapeutic or prophylactic use in humans.

| (i) Tablet 1 | mg/tablet |
|---|---|
| Compound X | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| Compound X (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/mL |
|---|---|
| Compound X (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| Compound X | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

We claim:
1. A compound represented by Formula (I), or a pharmaceutically acceptable salt thereof:

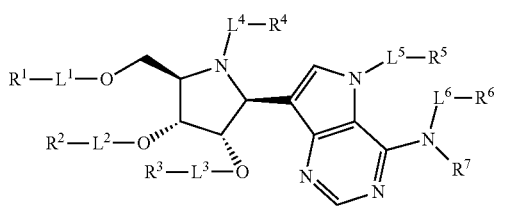

(I)

wherein:
- $L^1$, $L^2$, and $L^3$, each independently, are a bond or —C(R⁰)₂—O—;
  - wherein when $L^1$, $L^2$, or $L^3$ is —C(R⁰)₂—O—, the —C(R⁰)₂— moiety of the —C(R⁰)₂—O— group is attached to the oxygen on the pyrrolidine ring and the —O— atom of the —C(R⁰)₂—O— group is attached to $R^1$, $R^2$, or $R^3$, respectively;
- $L^4$, $L^5$, and $L^6$ are each a bond;
- $R^0$, independently for each occurrence, is H or ($C_1$-$C_6$) alkyl;
- $R^1$, $R^2$, and $R^3$, each independently, are selected from the group consisting of H, aminoacyl, aminothionyl, acyl, $R^{10}$OC(O)—, phosphoryl, and aminophosphoryl;
- or $R^1$ and $R^2$, taken together, or $R^2$ and $R^3$, taken together, may be selected from the group consisting of carbonyl, thiocarbonyl, phosphoryl, and ($C_1$-$C_6$)alkylphosphoryl;
- $R^4$, $R^5$, and $R^6$ are each H;
- $R^7$ is H;
- $R^{10}$, independently for each occurrence, is selected from the group consisting of H, ($C_1$-$C_6$)alkyl, aryl, heteroaryl, aralkyl, and heteroaralkyl;
- provided that the compound represented by Formula (I) is not

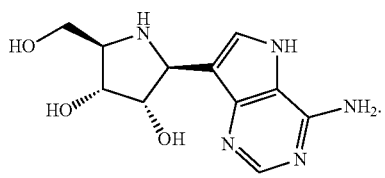 [SMILES: Nc1ncnc2c([C@@H]3N[C@H](CO)[C@@H](O)[C@H]3O)c[nH]c12]

2. The compound of claim 1, wherein $L^1$-$R^1$ and $L^2$-$R^2$ are identical, $L^2$-$R^2$ and $L^3$-$R^3$ are identical, or $L^1$-$R^1$ and $L^3$-$R^3$ are identical.
3. The compound of claim 2, wherein $L^3$-$R^3$ is H.
4. The compound of claim 2, wherein $L^1$-$R^1$ is H.
5. The compound of claim 2, wherein $L^2$-$R^2$ is H.
6. The compound of claim 1, wherein $L^1$-$R^1$, $L^2$-$R^2$, and $L^3$-$R^3$ are identical.
7. The compound of claim 1, wherein independently for each occurrence aminoacyl is —C(=O)CH(NH₂)(CH₂)ₙCHR³⁰R³¹, wherein n is 0 or 1; and
$R^{30}$ and $R^{31}$ each independently are selected from the group consisting of H, ($C_1$-$C_6$)alkyl, aryl, heteroaryl, aralkyl, and heteroaralkyl.

8. The compound of claim 1, wherein independently for each occurrence aminothionyl is —C(=S)CH(NH₂)(CH₂)ₙCHR³⁰R³¹, wherein
n is 0 or 1; and
$R^{30}$ and $R^{31}$ each independently are selected from the group consisting of H, ($C_1$-$C_6$)alkyl, aryl, heteroaryl, aralkyl, and heteroaralkyl.

9. The compound of claim 1, wherein independently for each occurrence acyl is —C(=O)R⁴⁰, wherein $R^{40}$ is selected from the group consisting of H, ($C_1$-$C_6$)alkyl, aryl, heteroaryl, aralkyl, and heteroaralkyl.

10. The compound of claim 1, wherein independently for each occurrence aminophosphoryl is —P(=O)(OR⁵⁰)NR⁵¹R⁵², wherein
$R^{50}$ is selected from the group consisting of H, ($C_1$-$C_6$) alkyl, aryl, arylalkyl, heteroaryl, heteroaralkyl, and -(CH₂)ₘSC(=O)C(CH₃)₂CH₂OH;
m is 1 or 2;
$R^{51}$ is H or ($C_1$-$C_6$)alkyl; and
$R^{52}$ is selected from the group consisting of H, ($C_1$-$C_6$) alkyl, aryl, aralkyl, heteroaryl, heteroaralkyl, and —CR⁶⁰R⁶¹C(=O)OR⁶², wherein
$R^{60}$ and $R^{61}$ each independently are H or ($C_1$-$C_6$)alkyl; and
$R^{62}$ is selected from the group consisting of H, ($C_1$-$C_6$) alkyl, aryl, aralkyl, heteroaryl, heteroaralkyl.

11. The compound of claim 10, wherein $R^{52}$ is —CR⁶⁰R⁶¹C(=O)OR⁶².

12. The compound of claim 11, wherein $R^{60}$ is H; $R^{61}$ is ($C_1$-$C_6$)alkyl; and $R^{62}$ is ($C_1$-$C_6$)alkyl.

13. The compound of claim 1, selected from the group consisting of:

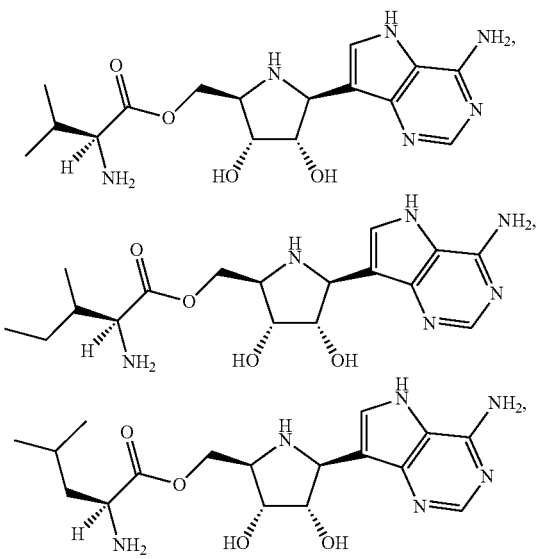

-continued

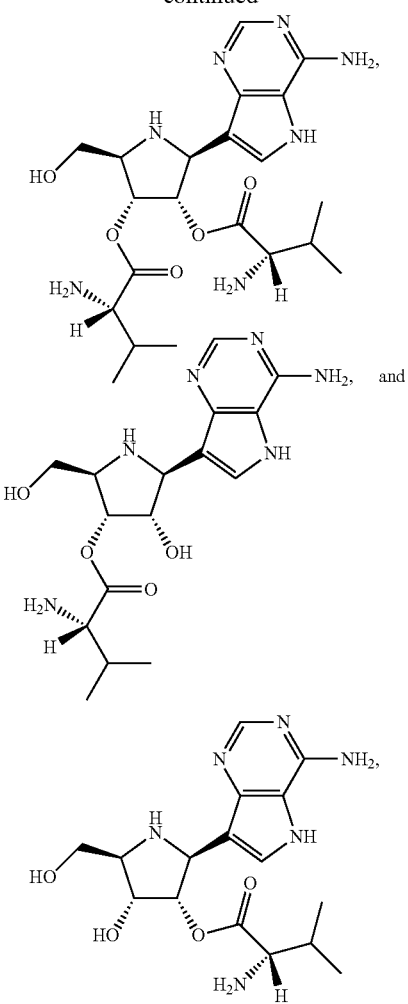

and pharmaceutically acceptable salts thereof.

14. The compound of claim 1 represented by

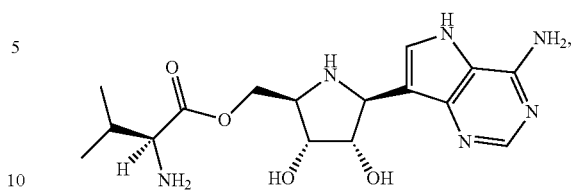

or a pharmaceutically acceptable salt thereof.

15. The compound of claim 1, selected from the group consisting of:
  (S)-((2R,3R,4S,5S)-5-(4-amino-5H-pyrrolo[3,2-d]pyrimidin-7-yl)-3,4-dihydroxypyrrolidin-2-yl)methyl 2-amino-3-methylbutanoate;
  (2S,3S)-((2R,3R,4S,5S)-5-(4-amino-5H-pyrrolo[3,2-d]pyrimidin-7-yl)-3,4-dihydroxypyrrolidin-2-yl)methyl 2-amino-3-methylpentanoate;
  (S)-((2R,3R,4S,5S)-5-(4-amino-5H-pyrrolo[3,2-d]pyrimidin-7-yl)-3,4-dihydroxypyrrolidin-2-yl)methyl 2-amino-4-methylpentanoate;
  (2S,2'S)-(2S,3S,4R,5R)-2-(4-amino-5H-pyrrolo[3,2-d]pyrimidin-7-yl)-5-(hydroxymethyl)pyrrolidine-3,4-diyl bis(2-amino-3-methylbutanoate);
  (S)-(2R,3R,4S,5S)-5-(4-amino-5H-pyrrolo[3,2-d]pyrimidin-7-yl)-4-hydroxy-2-(hydroxymethyl)pyrrolidin-3-yl 2-amino-3-methylbutanoate;
  (S)-(2S,3S,4R,5R)-2-(4-amino-5H-pyrrolo[3,2-d]pyrimidin-7-yl)-4-hydroxy-5-(hydroxymethyl)pyrrolidin-3-yl 2-amino-3-methylbutanoate; and
  pharmaceutically acceptable salts thereof.

16. A pharmaceutical composition, comprising a compound of claim 1, or a pharmaceutically acceptable salt thereof, and a pharmaceutically acceptable carrier.

* * * * *